(12) United States Patent
Ashrafi

(10) Patent No.: US 10,209,192 B2
(45) Date of Patent: Feb. 19, 2019

(54) SPECTROSCOPY WITH CORRELATION MATRICES, RATIOS AND GLYCATION

(71) Applicant: NxGen Partners IP, LLC, Dallas, TX (US)

(72) Inventor: Solyman Ashrafi, Plano, TX (US)

(73) Assignee: NXGEN PARTNERS IP, LLC, Dallas, TX (US)

( * ) Notice: Subject to any disclaimer, the term of this patent is extended or adjusted under 35 U.S.C. 154(b) by 0 days.

(21) Appl. No.: 16/006,090

(22) Filed: Jun. 12, 2018

(65) Prior Publication Data

US 2018/0306723 A1    Oct. 25, 2018

Related U.S. Application Data

(63) Continuation-in-part of application No. 15/405,974, filed on Jan. 13, 2017, now Pat. No. 10,006,859, and (Continued)

(51) Int. Cl.
| | | |
|---|---|---|
| *G01J 3/44* | (2006.01) | |
| *G01N 21/65* | (2006.01) | |
| *G01N 21/64* | (2006.01) | |
| *G01N 21/35* | (2014.01) | |
| *G01N 21/55* | (2014.01) | |
| *G01N 33/49* | (2006.01) | |

(52) U.S. Cl.
CPC .............. *G01N 21/65* (2013.01); *G01N 21/35* (2013.01); *G01N 21/55* (2013.01); *G01N 21/6428* (2013.01); *G01N 33/49* (2013.01)

(58) Field of Classification Search
CPC ... G01J 3/02; G01J 3/44; G01N 21/64; G01N 21/65; G01N 21/31; G01N 21/35; G01N 21/55; G01N 33/49; G01N 21/723
See application file for complete search history.

(56) References Cited

U.S. PATENT DOCUMENTS

| | | |
|---|---|---|
| 3,459,466 A | 8/1969 | Giordmaine |
| 3,614,722 A | 10/1971 | Jones |

(Continued)

OTHER PUBLICATIONS

Vasnetsov, M. V., Pasko, V.A. & Soskin, M.S.; Analysis of orbital angular momentum of a misaligned optical beam; New Journal of Physics 7, 46 (2005).

(Continued)

*Primary Examiner* — Abdullahi Nur

(57) ABSTRACT

A system and method for detecting glycation levels within hemoglobin generates a first correlation matrix using a first light beam at a first wavelength passing through a hemoglobin sample. A second correlation matrix is generated using a second light beam at a second wavelength passing through the hemoglobin sample. The first correlation matrix is multiplied by an inverse of the second correlation matrix to obtain a third matrix. A fourth matrix is generated by taking a singular value decomposition of the third matrix. The fourth matrix comprises a unique biomarker for a level of glycation within the hemoglobin sample. The level of glycation within the hemoglobin sample is determined responsive to the fourth matrix and an indicator identifying the determined level of glycation is output.

23 Claims, 69 Drawing Sheets

Related U.S. Application Data a continuation-in-part of application No. 14/875,507, filed on Oct. 5, 2015, now Pat. No. 9,784,724, and a continuation-in-part of application No. 15/348,608, filed on Nov. 10, 2016, now Pat. No. 9,645,083, and a continuation-in-part of application No. 15/049,594, filed on Feb. 22, 2016, now Pat. No. 9,714,902.

(60) Provisional application No. 62/522,154, filed on Jun. 20, 2017, provisional application No. 62/278,186, filed on Jan. 13, 2016, provisional application No. 62/322,507, filed on Apr. 14, 2016, provisional application No. 62/365,486, filed on Jul. 22, 2016.

(56) References Cited

U.S. PATENT DOCUMENTS

| | | |
|---|---|---|
| 4,379,409 A | 4/1983 | Primbsch et al. |
| 4,503,336 A | 3/1985 | Hutchin et al. |
| 4,584,883 A | 4/1986 | Miyoshi et al. |
| 4,736,463 A | 4/1988 | Chavez |
| 4,862,115 A | 8/1989 | Lee et al. |
| 5,051,754 A | 9/1991 | Newberg |
| 5,220,163 A | 6/1993 | Toughlian et al. |
| 5,222,071 A | 6/1993 | Pezeshki et al. |
| 5,272,484 A | 12/1993 | Labaar |
| 5,543,805 A | 8/1996 | Thaniyavarn |
| 5,555,530 A | 9/1996 | Meehan |
| 6,337,659 B1 | 1/2002 | Kim |
| 6,992,829 B1 | 1/2006 | Jennings et al. |
| 7,577,165 B1 | 8/2009 | Barrett |
| 7,729,572 B1 | 6/2010 | Pepper et al. |
| 7,792,431 B2 | 9/2010 | Jennings et al. |
| 8,432,884 B1 | 4/2013 | Ashrafi |
| 8,503,546 B1 | 8/2013 | Ashrafi |
| 8,559,823 B2 | 10/2013 | Izadpanah et al. |
| 8,811,366 B2 | 8/2014 | Ashrafi |
| 9,077,577 B1 | 7/2015 | Ashrafi |
| 9,391,375 B1 | 7/2016 | Bales |
| 2005/0254826 A1 | 11/2005 | Jennings et al. |
| 2005/0259914 A1 | 11/2005 | Padgett et al. |
| 2010/0013696 A1 | 1/2010 | Schmitt et al. |
| 2010/0317959 A1 | 12/2010 | Eigort et al. |
| 2011/0069309 A1 | 3/2011 | Newbury et al. |
| 2012/0207470 A1 | 8/2012 | Djordevic et al. |
| 2013/0027774 A1 | 1/2013 | Bovino et al. |
| 2013/0235744 A1 | 9/2013 | Chen et al. |
| 2013/0321801 A1 | 12/2013 | Lewis et al. |
| 2014/0070102 A1 | 3/2014 | Glopus et al. |
| 2014/0349337 A1* | 11/2014 | Dasari ................ G01N 33/49 435/40.5 |
| 2014/0355624 A1 | 12/2014 | Li et al. |
| 2015/0098697 A1 | 4/2015 | Marom et al. |
| 2016/0061810 A1* | 3/2016 | Kim .................... G01N 33/49 250/340 |
| 2016/0109361 A1 | 4/2016 | Wang et al. |
| 2016/0231274 A1 | 8/2016 | Tirapu et al. |

OTHER PUBLICATIONS

Byun, S.H., Haji, G.A. & Young, L.E.; Development and application of GPS signal multipath simulator; Radio Science, vol. 37, No. 6, 1098 (2002).

Tamburini, Fabrizio; Encoding many channels on the same frequency through radio vorticity: first experimental test; New Journal of Physics 14, 033001 (2012).

Gibson, G. et al., Free-space information transfer using light beans carrying orbital angular momentum; Optical Express 12, 5448-5456 (2004).

Yan, Y. et al.; High-capacity millimetre-wave communications with orbital angular momentum multiplexing; Nature Communications; 5, 4876 (2014).

Hur, Sooyoung et at.; Millimeter Wave Beamforming for Wireless Backhaul and Access in Small Cell Networks. IEEE Transactions on Communications, vol. 61, 4391-4402 (2013).

Allen, L., Beijersbergen, M., Spreeuw, R.J.C., and Woerdman, J.P.; Orbital Angular Momentum of Light and the Transformation of Laguerre-Gaussian Laser Modes; Physical Review A, vol. 45, No. 11; 8185-8189 (1992).

Anderson, Jorgen Bach; Rappaport, Theodore S.; Yoshida, Susumu; Propagation Measurements and Models for Wireless Communications Channels; 33 42-49 (1995).

Iskander, Magdy F.; Propagation Prediction Models for Wireless Communication Systems; IEEE Transactions on Microwave Theory and Techniques, vol. 50., No. 3, 662-673 (2002).

Wang, Jian, et al.; Terabit free-space data transmission employing orbital angular momentum multiplexing. Nature Photonics; 6, 488-496 (2012).

Katayama, Y., et al.; Wireless Data Center Networking with Steered-Beam mmWave Links; IEEE Wireless communication Network Conference; 2011, 2179-2184 (2011).

Molina-Terriza, G., et al.; Management of the Angular Momentum of Light: Preparation of Photons in Multidimensional Vector States of Angular Momentum; Physical Review Letters; vol. 88, No. 1; 77, 01360111-4 (2002).

Rapport, T.S.; Millimeter Wave Mobile Communications for 5G Cellular: It Will Work!; IEEE Access, 1, 335-349 (2013).

Huang, Hao et. al.; Crosstalk mitigation in a free-space orbital angular momentum multiplexed communication link using 4×4 MIMO equalization; Optics Letters, vol. 39, No. 15; 4360-4363; (2014).

Time-resolved orbital angular momentum spectroscopy, published by the American Institute of Physics, Appl. Phys. Lett. 107, 032406 (2015) by Loyan et al.

Solyman Ashrafi, Channeling Radiation of Electrons in Crystal Lattices, Essays on Classical and Quantum Dynamics, Gordon and Breach Science Publishers, 1991.

Solyman Ashrafi, Solar Flux Forecasting Using Mutual Information with an Optimal Delay, Advances in the Astronautical Sciences, American Astronautical Society, vol. 84 Part II, 1993.

Solyman Ashrafi, PCS system design issues in the presence of microwave OFS, Electromagnetic Wave Interactions, Series on Stability, Vibration and Control of Systems, World Scientific, Jan. 1996.

Solyman Ashrafi, Performance Metrics and Design Parameters for an FSO Communications Link Based on Multiplexing of Multiple Orbital-Angular-Momentum Beams, IEEE Globecom 2014, paper 1570005079, Austin, TX, Dec. 2014(IEEE, Piscataway, NJ, 2014).

Solyman Ashrafi, Optical Communications Using Orbital Angular Momentum Beams, Adv. Opt. Photon. 7, 66-106, Advances in Optics and Photonic, 2015.

Solyman Ashrafi, Performance Enhancement of an Orbital-Angular-Momentum based Free-space Optical Communications Link Through Beam Divergence Controlling, IEEE/OSA Conference on Optical Fiber communications (OFC) and National Fiber Optics Engineers Conference (NFOEC),paper M2F.6, Los Angeles, CA, Mar. 2015 (Optical Society of America, Washington, D.C., 2015).

Solyman Ashrafi, Experimental demonstration of enhanced spectral efficiency of 1.18 symbols/s/Hz using multiple-layer-overlay modulation for QPSK over a 14-km fiber link. OSA Technical Digest (online), paper JTh2A.63. The Optical Society, 2014.

Solyman Ashrafi, Link Analysis of Using Hermite-Gaussian Modes for Transmitting Multiple Channels in a Free-Space Optical Communication System, The Optical Society, vol. 2, No. 4, Apr. 2015.

Solyman Ashrafi, Performance Metrics and Design Considerations for a Free-Space Optical Orbital-Angular-Momentum Multiplexed Communication Link, The Optical Society, vol. 2, No. 4, Apr. 2015.

Solyman Ashrafi, Demonstration of Distance Emulation for an Orbital-Angular-Momentum Beam. OSA Technical Digest (online), paper STh1F.6. The Optical Society, 2015.

Solyman Ashrafi, Free-Space Optical Communications Using Orbital-Angular-Momentum Multiplexing Combined with MIMO-Based Spatial Multiplexing. Optics Letters, vol. 40, No. 18, Sep. 4, 2015.

Solyman Ashrafi, Enhanced Spectral Efficiency of 2.36 bits/s/Hz Using Multiple Layer Overlay Modulation for QPSK over a 14-km

(56) References Cited

OTHER PUBLICATIONS

Single Mode Fiber Link. OSA Technical Digest (online), paper SW1M.6. The Optical Society, 2015.
Solyman Ashrafi, Experimental Demonstration of a 400-Gbit/s Free Space Optical Link Using Multiple Orbital-4ngular-Momentum Beams with Higher Order Radial Indices. OSA Technical Digest (online), paper SW4M.5. The Optical Society, 2015.
Solyman Ashrafi, Experimental Demonstration of 16-Gbit/s Millimeter-Wave Communications Link using Thin Metamaterial Plates to Generate Data-Carrying Orbital-Angular-Momentum Beams, ICC 2015, London, UK, 2014.
Solyman Ashrafi, Experimental Demonstration of Using Multi-Layer-Overlay Technique for Increasing Spectral Efficiency to 1.18 bits/s/Hz in a 3 Gbit/s Signal over 4-km Multimode Fiber. OSA Technical Digest (online), paper JTh2A.63. The Optical Society, 2015.
Solyman Ashrafi, Experimental Measurements of Multipath-Induced Intra- and Inter-Channel Crosstalk Effects in a Millimeter-wave Communications Link using Orbital-Angular-Momentum Multiplexing, IEEE International communication Conference(ICC) 2015, paper1570038347, London, UK, Jun. 2015(IEEE, Piscataway, NJ, 2015).
Solyman Ashrafi, Performance Metrics for a Free-Space Communication Link Based on Multiplexing of Multiple Orbital Angular Momentum Beams with Higher Order Radial Indice. OSA Technical Digest (online), paper JTh2A.62. The Optical Society, 2015.
Solyman Ashrafi, 400-Gbit/s Free Space Optical Communications Link Over 120-meter using Multiplexing of 4 Collocated Orbital-Angular-Momentum Beams, IEEE/OSA Conference on Optical Fiber Communications (OFC) and National Fiber Optics Engineers Conference (NFOEC),paper M2F.1, Los Angeles, CA, Mar. 2015 (Optical Society of America, Washington, D.C., 2015).
Solyman Ashrafi, Experimental Demonstration of Two-Mode 16-Gbit/s Free-Space mm-Wave Communications Link Using Thin Metamaterial Plates to Generate Orbital Angular Momentum Beams, Optica, vol. 1, No. 6, Dec. 2014.
Solyman Ashrafi, Demonstration of an Obstruction-Tolerant Millimeter-Wave Free-Space Communications Link of Two 1-Gbaud 16-qam Channels using Bessel Beams Containing Orbital Angular Momentum, Third International conference on Optical Angular Momentum (ICOAM), Aug. 4-7, 2015, New York USA.
Solyman Ashrafi, An Information Theoretic Framework to Increase Spectral Efficiency, IEEE Transactions on Information Theory, vol. XX, No. Y, Oct. 2014, Dallas, Texas.
Solyman Ashrafi, Acoustically induced stresses in elastic cylinders and their visualization, The Journal of the Acoustical Society of America 82(4):1378-1385, Sep. 1987.
Solyman Ashrafi, Splitting of channeling-radiation peaks in strained-layer superlattices, Journal of the Optical Society of America B 8(12), Nov. 1991.
Solyman Ashrafi, Experimental Characterization of a 400 Gbit/s Orbital Angular Momentum Multiplexed Free-space Optical Link over 120-meters, Optics Letters, vol. 41, No. 3, pp. 622-625, 2016.
Solyman Ashrafi, Orbital-Angular-Momentum-Multiplexed Free-Space Optical Communication Link Using Transmitter Lenses, Applied Optics, vol. 55, No. 8, pp. 2098-2103, 2016.
Solyman Ashrafi, 32 Gbit/s 60 GHz Millimeter-Wave Wireless Communications using Orbital-Angular-Momentum and Polarization Mulitplexing, IEEE International Communication Conference (ICC) 2016, paper 1570226040, Kuala Lumpur, Malaysia, May 2016 (IEEE, Piscataway, NJ, 2016).
Solyman Ashrafi, Tunable Generation and Angular Steering of a Millimeter-Wave Orbital-Angular-Momentum Seam using Differential Time Delays in a Circular Antenna Array, IEEE International Communication Conference (ICC) 2016, paper 1570225424, Kuala Lumpur, Malaysia, May 2016 (IEEE, Piscataway, NJ, 2016).
Solyman Ashrafi, A Dual-Channel 60 GHz Communications Link Using Patch Antenna Arrays to Generate Data-marrying Orbital-Angular-Momentum Beams, IEEE International Communication Conference (ICC) 2016, paper 1570224643, Kuala Lumpur, Malaysia, May 2016 (IEEE, Piscataway, NJ, 2016).
Solyman Ashrafi, Demonstration of OAM-based MIMO FSO link using spatial diversity and Mimo equalization for turbulence mitigation, IEEE/OSA Conference on Optical Fiber Communications (OFC), paper Th1H.2, Anaheim, CA, Mar. 2016 (Optical Society of America, Washington, D.C., 2016).
Solyman Ashrafi, Dividing and Multiplying the Mode Order for Orbital-Angular-Momentum Beams, European Conference on Optical Communications (ECOC), paper Th.4.5.1, Valencia, Spain, Sep. 2015.
Solyman Ashrafi, Exploiting the Unique Intensity Gradient of an Orbital-Angular-Momentum Beam for Accurate Receiver Alignment Monitoring in a Free-Space Communication Link, European Conference on Optical communications (ECOC), paper We.3.6.2, Valencia, Spain, Sep. 2015.
Solyman Ashrafi, Experimental Demonstration of a 400-Gbit/s Free Space Optical Link using Multiple Orbital-Angular-Momentum Beams with Higher Order Radial Indices, APS/IEEE/OSA Conference on Lasers and Electro-Optics (CLEO), paper SW4M.5, San Jose, CA, May 2015 (OSA, Wash., D.C., 2015).
Solyman Ashrafi, Spurious Resonances and Modelling of Composite Resonators, 37th Annual Symposium on Frequency Control, 1983.
Solyman Ashrafi, Splitting and contrary motion of coherent bremsstrahlung peaks in strained-layer superlattices, Journal of Applied Physics 70:4190-4193, Dec. 1990.
Solyman Ashrafi, Nonlinear Techniques for Forecasting Solar Activity Directly From its Time Series, Proceedings of Flight Mechanics/Estimation Theory Symposium, National Aeronautics and Space Administration, May 1992.
Solyman Ashrafi, Demonstration of using Passive Integrated Phase Masks to Generate Orbital-Angular-Momentum Beams in a Communications Link, APS/IEEE/OSA Conference on Lasers and Electro-Optics (CLEO), paper 2480002, San Jose, CA, Jun. 2016 (OSA, Wash., D.C., 2016).
Solyman Ashrafi, Combining Schatten's Solar Activity Prediction Model with a Chaotic Prediction Model, National Aeronautics and Space Administration, Nov. 1991.
Solyman Ashrafi, Detecting and Disentangling Nonlinear Structure from Solar Flux Time Series, 43rd Congress of be International Astronautical Federation, Aug. 1992.
Solyman Ashrafi, Physical Phaseplate for the Generation of a Millimeter-Wave Hermite-Gaussian Beam, IEEE Antennas and Wireless Propagation Letters, RWS 2016; pp. 234-237.
Solyman Ashrafi, Future Mission Studies: Forecasting Solar Flux Directly From Its Chaotic Time Series, Computer Sciences Corp., Dec. 1991.
Solyman Ashrafi, CMA Equalization for a 2 Gb/s Orbital Angular Momentum Multiplexed Optical Underwater Link through Thermally Induced Refractive Index Inhomogeneity, APS/IEEE/OSA Conference on Lasers and Electro-Dptics (CLEO), paper 2479987, San Jose, CA, Jun. 2016 (OSA, Wash., D.C., 2016).
Solyman Ashrafi, 4 Gbit/s Underwater Transmission Using OAM Multiplexing and Directly Modulated Green Laser, APS/IEEE/OSA Conference on Lasers and Electro-Optics (CLEO), paper 2477374, San Jose, CA, Jun. 2016 (OSA, Wash., D.C., 2016).
Solyman Ashrafi, Evidence of Chaotic Pattern in Solar Flux Through a Reproducible Sequence of Period-Doubling-Type Bifurcations; Computer Sciences Corporation (CSC); Flight Mechanics/Estimation Theory Symposium; NASA Goddard Space Flight Center; Greenbelt, Maryland; May 21-23, 1991.
Solyman Ashrafi; Future Mission Studies: Preliminary Comparisons of Solar Flux Models; NASA Goddard Space light Center Flight Dynamics Division; Flight Dynamics Division Code 550; Greenbelt, Maryland; Dec. 1991.
H. Yao et al.; Patch Antenna Array for the Generation of Millimeter-wave Hermite-Gaussian Beams, IEEE Antennas and Wireless Propagation Letters; 2016.
Yongxiong Ren et al.; Experimental Investigation of Data Transmission Over a Graded-index Multimode Fiber Using the Basis of Orbital Angular Momentum Modes.

(56) References Cited

OTHER PUBLICATIONS

Ren, Y. et al.; Experimental Demonstration of 16 Gbit/s millimeter-wave Communications using MIMO Processing of 2 OAM Modes on Each of Two Transmitter/Receiver Antenna Apertures. In Proc. IEEE GLobal TElecom. Conf. 3821-3826 (2014).
Li, X. et al.; Investigation of interference in multiple-input multiple-output wireless transmission at W band for an optical wireless integration system. Optics Letters 38, 742-744 (2013).
Padgett, Miles J. et al., Divergence of an orbital-angular-momentum-carrying beam upon propagation. New Journal of Physics 17, 023011 (2015).
Mahmouli, F.E. & Walker, D. 4-Gbps Uncompressed Video Transmission over a 60-GHz Orbital Angular Momentum Wireless Channel. IEEE Wireless Communications Letters, vol. 2, No. 2, 223-226 (Apr. 2013).

\* cited by examiner

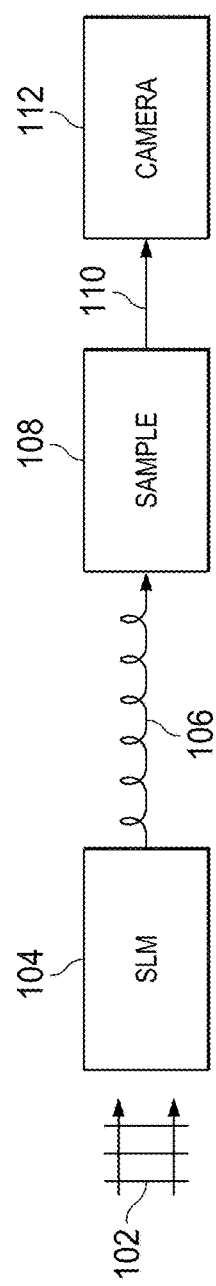
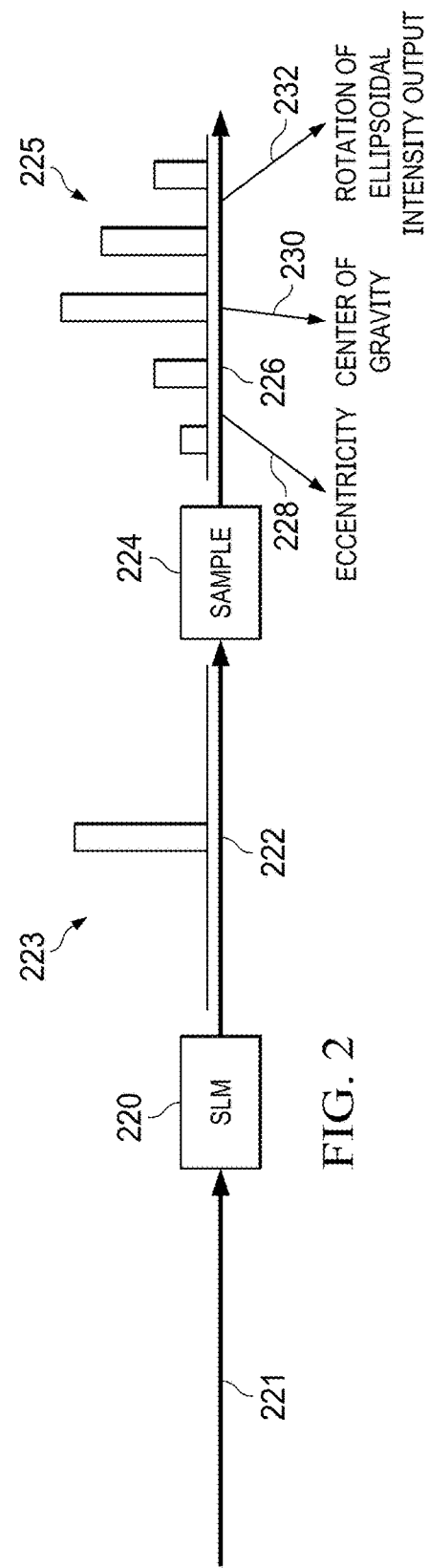

$$\Delta h = \frac{\ell \lambda}{n-1}$$

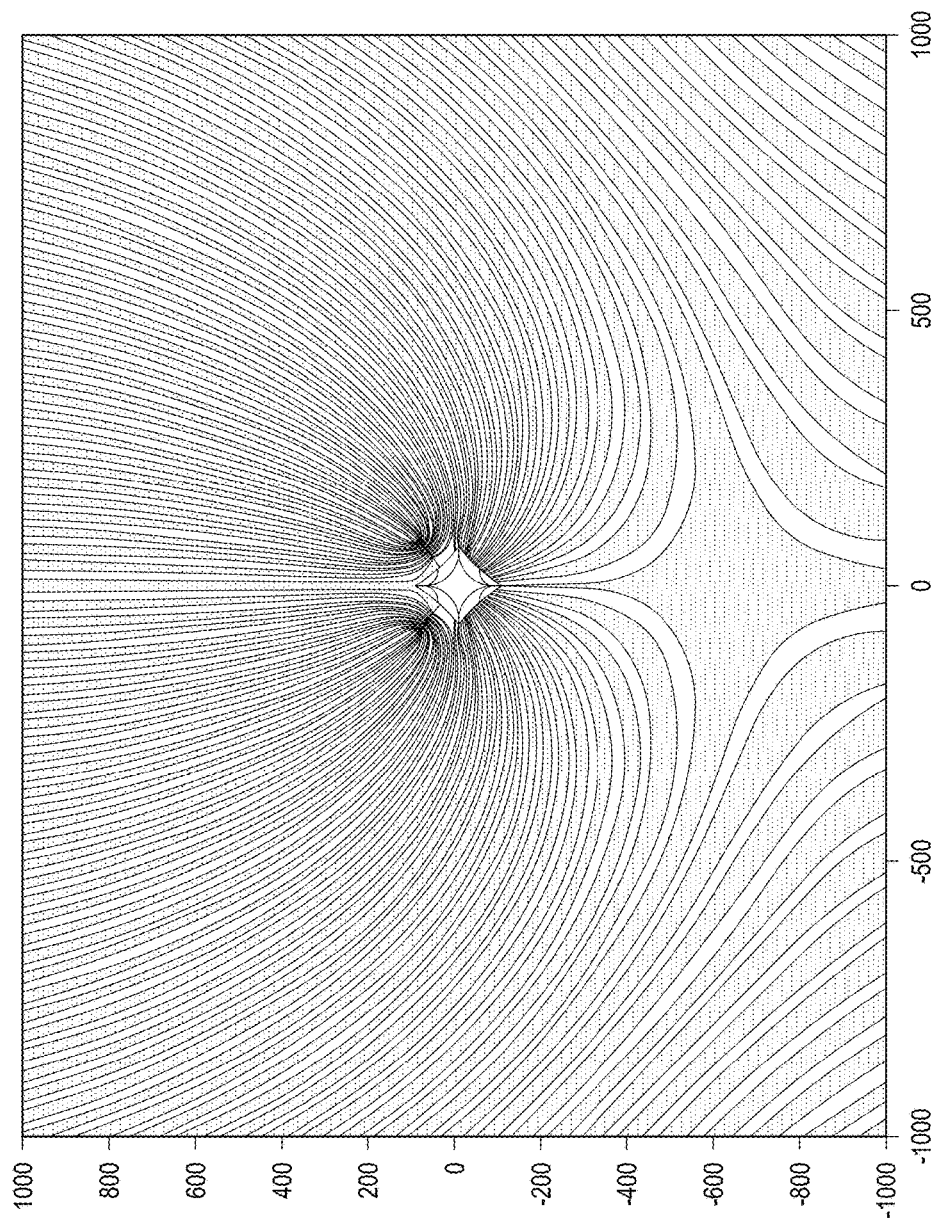

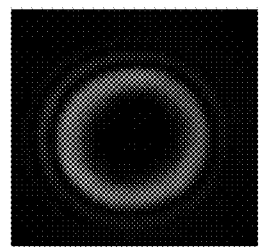
FIG. 37A (WATER)
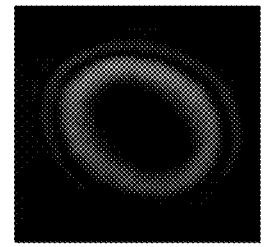
FIG. 37B (15% GLUCOSE IN WATER)
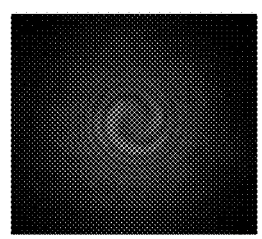
FIG. 38A (WATER)
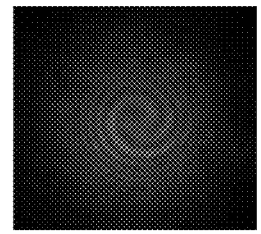
FIG. 38B (15% GLUCOSE IN WATER)
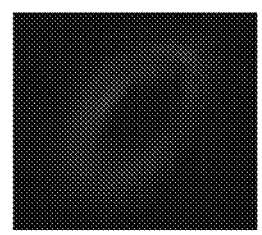
FIG. 39 (AMPLITUDE)
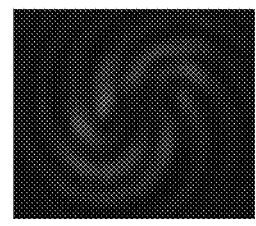
FIG. 40 (PHASE)

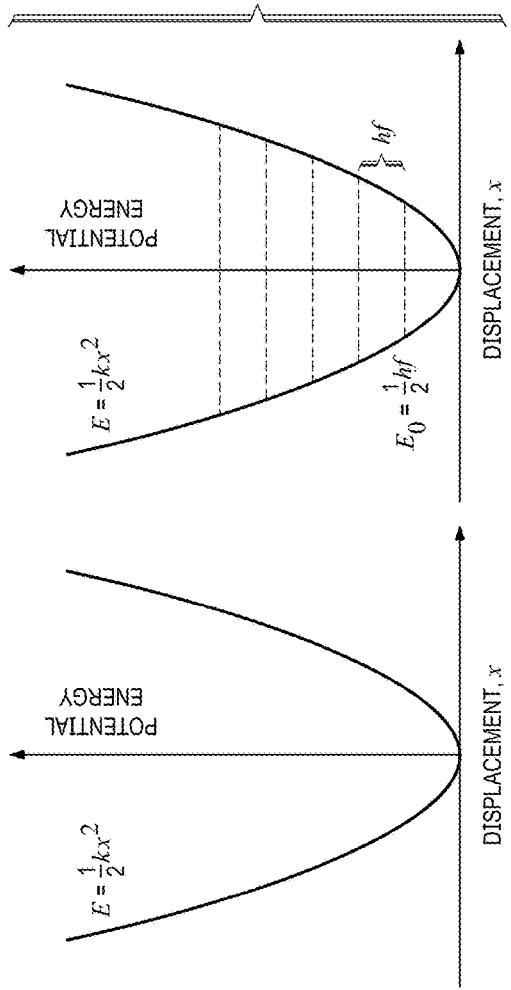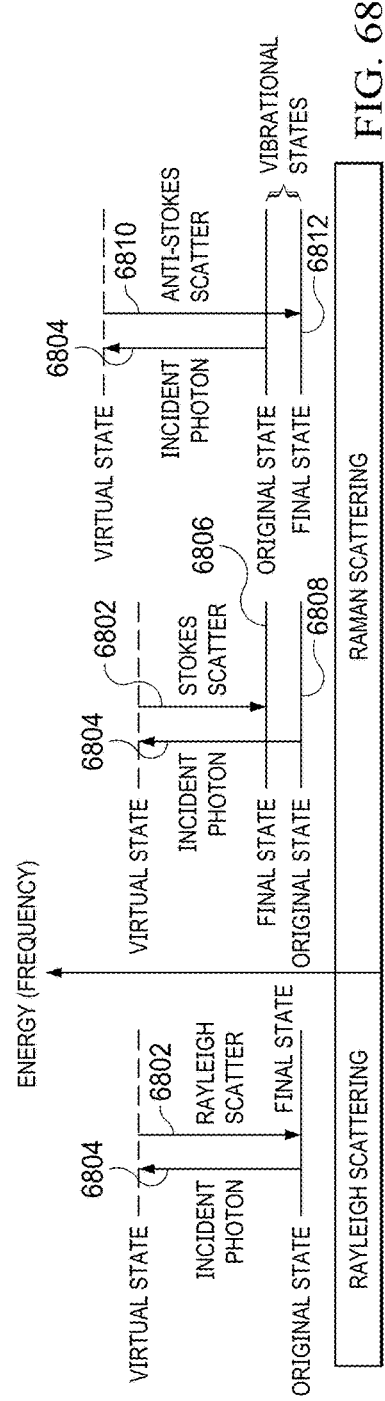

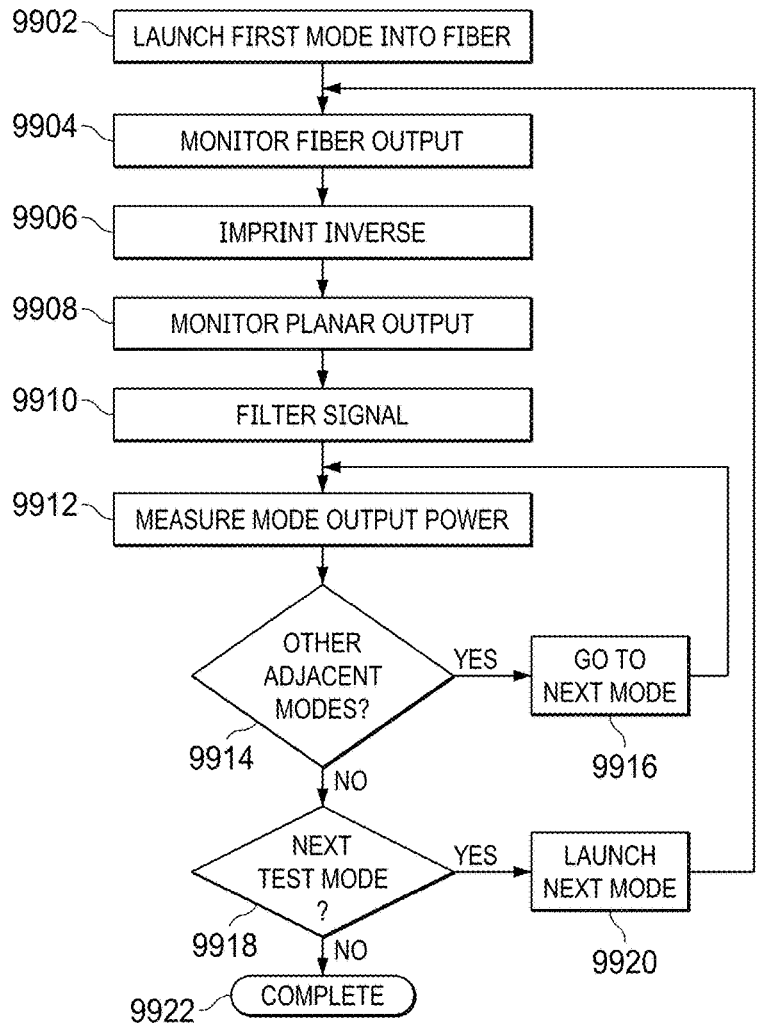

$A_{325}=$

| | $LG_1$ | $LG_2$ | $LG_3$ | $LG_4$ | $LG_5$ | $LG_6$ | $LG_7$ | $LG_8$ | $LG_9$ | $LG_{10}$ |
|---|---|---|---|---|---|---|---|---|---|---|
| $LG_{10}$ | $a_{101}$ | $a_{102}$ | $a_{103}$ | $a_{104}$ | $a_{105}$ | $a_{106}$ | $a_{107}$ | $a_{108}$ | $a_{109}$ | $\mathbf{a_{1010}}$ |
| $LG_9$ | $a_{91}$ | $a_{92}$ | $a_{93}$ | $a_{94}$ | $a_{95}$ | $a_{96}$ | $a_{97}$ | $a_{98}$ | $\mathbf{a_{99}}$ | $a_{910}$ |
| $LG_8$ | $a_{81}$ | $a_{82}$ | $a_{83}$ | $a_{84}$ | $a_{85}$ | $a_{86}$ | $a_{87}$ | $\mathbf{a_{88}}$ | $a_{89}$ | $a_{810}$ |
| $LG_7$ | $a_{71}$ | $a_{72}$ | $a_{73}$ | $a_{74}$ | $a_{75}$ | $a_{76}$ | $\mathbf{a_{77}}$ | $a_{78}$ | $a_{79}$ | $a_{710}$ |
| $LG_6$ | $a_{61}$ | $a_{62}$ | $a_{63}$ | $a_{64}$ | $a_{65}$ | $\mathbf{a_{66}}$ | $a_{67}$ | $a_{68}$ | $a_{69}$ | $a_{610}$ |
| $LG_5$ | $a_{51}$ | $a_{52}$ | $a_{53}$ | $a_{54}$ | $\mathbf{a_{55}}$ | $a_{56}$ | $a_{57}$ | $a_{58}$ | $a_{59}$ | $a_{510}$ |
| $LG_4$ | $a_{41}$ | $a_{42}$ | $a_{43}$ | $\mathbf{a_{44}}$ | $a_{45}$ | $a_{46}$ | $a_{47}$ | $a_{48}$ | $a_{49}$ | $a_{410}$ |
| $LG_3$ | $a_{31}$ | $a_{32}$ | $\mathbf{a_{33}}$ | $a_{34}$ | $a_{35}$ | $a_{36}$ | $a_{37}$ | $a_{38}$ | $a_{39}$ | $a_{310}$ |
| $LG_2$ | $a_{21}$ | $\mathbf{a_{22}}$ | $a_{23}$ | $a_{24}$ | $a_{25}$ | $a_{26}$ | $a_{27}$ | $a_{28}$ | $a_{29}$ | $a_{210}$ |
| $LG_1$ | $\mathbf{a_{11}}$ | $a_{12}$ | $a_{13}$ | $a_{14}$ | $a_{15}$ | $a_{16}$ | $a_{17}$ | $a_{18}$ | $a_{19}$ | $a_{110}$ |

FIG. 108

$$B_{355} = \begin{array}{|c|c|c|c|c|c|c|c|c|c|c|}
\hline
LG_{10} & a_{101} & a_{102} & a_{103} & a_{104} & a_{105} & a_{106} & a_{107} & a_{108} & a_{109} & \mathbf{a_{1010}} \\
\hline
LG_9 & a_{91} & a_{92} & a_{93} & a_{94} & a_{95} & a_{96} & a_{97} & a_{98} & \mathbf{a_{99}} & a_{910} \\
\hline
LG_8 & a_{81} & a_{82} & a_{83} & a_{84} & a_{85} & a_{86} & a_{87} & \mathbf{a_{88}} & a_{89} & a_{810} \\
\hline
LG_7 & a_{71} & a_{72} & a_{73} & a_{74} & a_{75} & a_{76} & \mathbf{a_{77}} & a_{78} & a_{79} & a_{710} \\
\hline
LG_6 & a_{61} & a_{62} & a_{63} & a_{64} & a_{65} & \mathbf{a_{66}} & a_{67} & a_{68} & a_{69} & a_{610} \\
\hline
LG_5 & a_{51} & a_{52} & a_{53} & a_{54} & \mathbf{a_{55}} & a_{56} & a_{57} & a_{58} & a_{59} & a_{510} \\
\hline
LG_4 & a_{41} & a_{42} & a_{43} & \mathbf{a_{44}} & a_{45} & a_{46} & a_{47} & a_{48} & a_{49} & a_{410} \\
\hline
LG_3 & a_{31} & a_{32} & \mathbf{a_{33}} & a_{34} & a_{35} & a_{36} & a_{37} & a_{38} & a_{39} & a_{310} \\
\hline
LG_2 & a_{21} & \mathbf{a_{22}} & a_{23} & a_{24} & a_{25} & a_{26} & a_{27} & a_{28} & a_{29} & a_{210} \\
\hline
LG_1 & \mathbf{a_{11}} & a_{12} & a_{13} & a_{14} & a_{15} & a_{16} & a_{17} & a_{18} & a_{19} & a_{110} \\
\hline
 & LG_1 & LG_2 & LG_3 & LG_4 & LG_5 & LG_6 & LG_7 & LG_8 & LG_9 & LG_{10} \\
\hline
\end{array}$$

| Σ | | | | | | | | | | |
|---|---|---|---|---|---|---|---|---|---|---|
| | $\sigma_{11}$ | 0 | 0 | 0 | 0 | 0 | 0 | 0 | 0 | 0 |
| | 0 | $\sigma_{22}$ | 0 | 0 | 0 | 0 | 0 | 0 | 0 | 0 |
| | 0 | 0 | $\sigma_{33}$ | 0 | 0 | 0 | 0 | 0 | 0 | 0 |
| | 0 | 0 | 0 | $\sigma_{44}$ | 0 | 0 | 0 | 0 | 0 | 0 |
| | 0 | 0 | 0 | 0 | $\sigma_{55}$ | 0 | 0 | 0 | 0 | 0 |
| | 0 | 0 | 0 | 0 | 0 | $\sigma_{66}$ | 0 | 0 | 0 | 0 |
| | 0 | 0 | 0 | 0 | 0 | 0 | $\sigma_{77}$ | 0 | 0 | 0 |
| | 0 | 0 | 0 | 0 | 0 | 0 | 0 | $\sigma_{88}$ | 0 | 0 |
| | 0 | 0 | 0 | 0 | 0 | 0 | 0 | 0 | $\sigma_{99}$ | 0 |
| | 0 | 0 | 0 | 0 | 0 | 0 | 0 | 0 | 0 | $\sigma_{1010}$ |

D =

SPECTROSCOPY WITH CORRELATION MATRICES, RATIOS AND GLYCATION

CROSS-REFERENCE TO RELATED APPLICATIONS

This application claims the benefit of U.S. Provisional Application Ser. No. 62/522,154, filed Jun. 20, 2017, and entitled SPECTROSCOPY WITH CORRELATION MATRICES, RATIOS AND GLYCATION, which is incorporated by reference herein in its entirety.

This application is also a Continuation-in-Part of U.S. application Ser. No. 15/405,974, filed Jan. 13, 2017, and entitled SYSTEM AND METHOD FOR MULTI-PARAMETER SPECTROSCOPY, now U.S. Pat. No. 10,006,859 issued Jun. 7, 2018. U.S. patent application Ser. No. 15/405,974 claims the benefit of U.S. Provisional Application No. 62/278,186, filed Jan. 13, 2016 and entitled MULTI-PARAMETER SPECTROSCOPY and claims the benefit of U.S. Provisional Application No. 62/322,507, filed Apr. 14, 2016 and entitled RAMAN SPECTROSCOPY WITH ORBITAL ANGULAR MOMENTUM and claims the benefit of U.S. Provisional Application No. 62/365,486, filed Jul. 22, 2016 and entitled INCE-GAUSSIAN SPECTROSCOPY, each of which is incorporated by reference herein in its entirety.

U.S. patent application Ser. No. 15/405,974 is also a Continuation-in-Part of U.S. application Ser. No. 14/875,507 filed Oct. 5, 2015 and entitled SYSTEM AND METHOD FOR EARLY DETECTION OF ALZHEIMERS BY DETECTING AMYLOID-BETA USING ORBITAL ANGULAR MOMENTUM, now U.S. Pat. No. 9,784,724 issued Oct. 10, 2017, and it is also a Continuation-in-Part of U.S. application Ser. No. 15/348,608 filed Nov. 10, 2016 and entitled SYSTEM AND METHOD USING OAM SPECTROSCOPY LEVERAGING FRACTIONAL ORBITAL ANGULAR MOMENTUM AS SIGNATURE TO DETECT MATERIALS, now U.S. Pat. No. 9,645,083 issued May 9, 2017, and it is also a Continuation-in-Part of U.S. application Ser. No. 15/049,594 filed Feb. 22, 2016 and entitled SYSTEM AND METHOD FOR MAKING CONCENTRATION MEASUREMENTS WITHIN A SAMPLE MATERIAL USING ORBITAL ANGULAR MOMENTUM, now U.S. Pat. No. 9,714,902 issued Jul. 25, 2017. U.S. application Ser. Nos. 14/875,507; 15/348,608; 15/049,594; and U.S. Pat. Nos. 9,784,724; 9,645,083; and 9,714,902 are incorporated by reference herein in their entirety.

TECHNICAL FIELD

The present invention relates to the detection of glycation within a sample, and more particularly, to the detection of glycation within a sample using correlation matrices.

BACKGROUND

Concentration measurements and detection of the presence of organic and non-organic materials is of great interest in a number of applications. In one example, detection of materials within human tissue is an increasingly important aspect of healthcare for individuals. The development of non-invasive measurement techniques for monitoring biological and metabolic agents within human tissue is an important aspect of diagnosis therapy of various human diseases and may play a key role in the proper management of diseases. The development of non-invasive measurement techniques for monitoring biological and metabolic agents within human tissue is an important aspect of diagnosis therapy of various human diseases and may play a key role in the proper management of diseases. One such material relevant to Alzheimer's is amyloid-beta.

Another example of a biological agent that may be monitored for within human tissue is glucose. Glucose ($C_6H_{12}O_6$) is a monosaccharide sugar and is one of the most important carbohydrate nutrient sources. Glucose is fundamental to almost all biological processes and is required for the production of ATP adenosine triphosphate and other essential cellular components. The normal range of glucose concentration within human blood is 70-160 mg/dl depending on the time of the last meal, the extent of physical tolerance and other factors. Freely circulating glucose molecules stimulate the release of insulin from the pancreas. Insulin helps glucose molecules to penetrate the cell wall by binding two specific receptors within cell membranes which are normally impermeable to glucose.

One disease associated with issues related to glucose concentrations is diabetes. Diabetes is a disorder caused by the decreased production of insulin, or by a decreased ability to utilize insulin and transport the glucose across cell membranes. As a result, a high potentially dangerous concentration of glucose can accumulate within the blood (hyperglycemia) during the disease. Therefore, it is of great importance to maintain blood glucose concentration within a normal range in order to prevent possible severe physiological complications.

One significant role of physiological glucose monitoring is the diagnosis and management of several metabolic diseases, such as diabetes mellitus (or simply diabetes). There are a number of invasive and non-invasive techniques presently used for glucose monitoring. The problem with existing non-invasive glucose monitoring techniques is that a clinically acceptable process has not yet been determined. Standard techniques from the analysis of blood currently involve an individual puncturing a finger and subsequent analysis of collected blood samples from the finger. In recent decades, non-invasive blood glucose monitoring has become an increasingly important topic of investigation in the realm of biomedical engineering. In particular, the introduction of optical approaches has caused some advances within the field. Advances in optics have led to a focused interest in optical imaging technologies and the development of non-invasive imaging systems. The application of optical methods to monitoring in cancer diagnostics and treatment is also a growing field due to the simplicity and low risk of optical detection methods. In addition to the medical field, the detection of various types of materials in a variety of other environments would be readily apparent.

Many optical techniques for sensing different tissue metabolites and glucose in living tissue have been in development over the last 50 years. These methods have been based upon florescent, near infrared and mid-infrared spectroscopy, Raman spectroscopy, photoacoustics, optical coherence tomography and other techniques. However, none of these techniques that have been tried have proved completely satisfactory.

Another organic component lending itself to optical material concentration sensing involves is human skin. The defense mechanisms of human skin are based on the action of antioxidant substances such as carotenoids, vitamins and enzymes. Beta carotene and lycopene represent more than 70% of the carotenoids in the human organism. The topical or systematic application of beta carotene and lycopene is a general strategy for improving the defense system of the human body. The evaluation and optimization of this treatment requires the measurement of the b-carotene and lycopene concentrations in human tissue, especially in the human skin as the barrier to the environment.

Thus, an improved non-invasive technique enabling the detection of concentrations and presence of various materials within a human body or other types of samples would have a number of applications within the medical field.

SUMMARY

The present invention, as disclosed and described herein, in one aspect thereof, comprise a system and method for detecting glycation levels within hemoglobin generates a first correlation matrix using a first light beam at a first wavelength passing through a hemoglobin sample. A second correlation matrix is generated using a second light beam at a second wavelength passing through the hemoglobin sample. The first correlation matrix is multiplied by an inverse of the second correlation matrix to obtain a third matrix. A fourth matrix is generated by taking a singular value decomposition of the third matrix. The fourth matrix comprises a unique biomarker for a level of glycation within the hemoglobin sample. The level of glycation within the hemoglobin sample is determined responsive to the fourth matrix and an indicator identifying the determined level of glycation is output.

BRIEF DESCRIPTION OF THE DRAWINGS

For a more complete understanding, reference is now made to the following description taken in conjunction with the accompanying drawings in which:

FIG. 1 illustrates the manner for using an Orbital Angular Momentum signature to detect the presence of a material within a sample;

FIG. 2 illustrates the manner in which an OAM generator generates an OAM twisted beam;

FIGS. 15A-15D illustrate various holograms for use in applying an orbital angular momentum to a plane wave signal;

FIG. 37A illustrates an OAM signature of a sample consisting only of water;

FIG. 37B illustrates an OAM signature of a sample of 15% glucose in water;

FIG. 38A illustrates an interferogram of a sample consisting only of water;

FIG. 38B illustrates an interferogram of a sample of 15% glucose in water;

FIG. 39 shows the amplitude of an OAM beam;

FIG. 40 shows the phase of an OAM beam;

FIG. 67 illustrates the energy curve for a vibrating spring and quantized energy level;

FIG. 68 illustrates Rayleigh scattering and Ramen scattering by Stokes and anti-Stokes resonance;

FIG. 99 illustrates a flow diagram of the process for performing the measurement technique using a mode crosstalk matrix;

FIG. 100 illustrates a generated single row of the mode crosstalk matrix;

FIG. 108 illustrates a first correlation matrix generated at a first wavelength;

FIG. 109 illustrates a second correlation matrix generated at a second wavelength; and FIG. 110 illustrates a biomarker signature matrix illustrating glycation level in hemoglobin.

DETAILED DESCRIPTION

Figure 3:
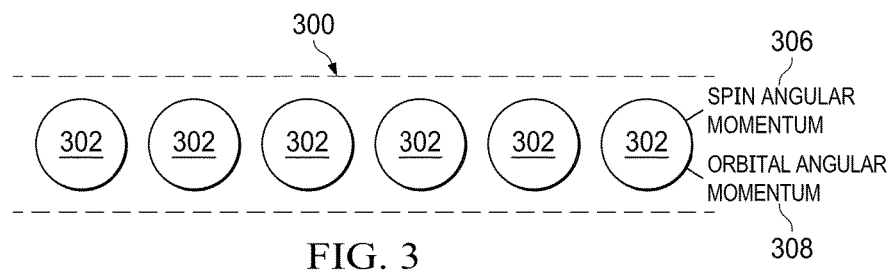
FIG. 3 illustrates a light beam having orbital angular momentum imparted thereto.

Referring now to the drawings, wherein like reference numbers are used herein to designate like elements throughout, the various views and embodiments of a system and method for detecting materials using orbital angular momentum signatures are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to the drawings, and more particularly to FIG. 1, there is illustrated the manner for detecting the presence of a particular material within a sample based upon the unique orbital angular momentum signature imparted to a signal passing through the sample. An optical signal 102 having a series of plane waves therein is applied to a device for applying an orbital angular momentum (OAM) signal to the optical signal 102 such as a spatial light modulator (SLM) 104. While the present embodiment envisions the use of an optical signal 102, other types of signals having orbital angular momentum or other orthogonal signals therein may be utilized in alternative embodiments. The SLM 104 generates an output signal 106 having a known OAM twist applied to the signal. The OAM twist has known characteristics that act as a baseline prior to the application of the output signal 106 to a sample 108. The sample 108 may comprise a material contained within a holding container, such as a cuvette, or may be a material in its natural state, such as the eye or body of a patient or its naturally occurring location in nature. The sample 108 only indicates that a particular material or item of interest is being detected by the describe system. While passing through the sample 108, the output signal 106 has a unique OAM signature applied thereto that is provided as an OAM distinct signature signal 110. OAM beams have been observed to exhibit unique topological evolution upon interacting with chiral solutions. While it has been seen that chiral molecules create unique OAM signatures when an OAM beam is passed through a sample of the chiral material, the generation of unique OAM signatures from signals passing through non-chiral molecules/material may also be provided. Given these unique topological features one can detect the existence of a molecule in a given solution with specific signatures in both the amplitude and phase measurements. This distinct signature signal 110 may then be examined using for example a camera 112 in order to detect the unique signal characteristics applied thereto and determine the material within the sample based upon this unique signature. Application of multi-parameter spectroscopy for the detection of different molecules can be applied to different industries including, but not limited to, food (identification of food spoilage), Nanoscale Material development for defense and national security, chemical industries, pharma and medical industries for testing where non-invasive solutions are critical, medical and dental industry for identification of infections, cancer cells, organic compounds and many others. The determination of the particular material indicated by the unique signature may be determined in one embodiment by comparison of the signature to a unique database of signatures that include known signatures that are associated with a particular material or concentration. The manner of creating such a database would be known to one skilled in the art.

Referring now to FIG. 2 illustrates the manner in which an OAM generator 220 may generate an OAM twisted beam 222. The OAM generator 210 may use any number of devices to generate the twisted beam 222 including holograms with an amplitude mask, holograms with a phase mask, Spatial Light Modulators (SLMs) or Digital Light Processors (DLPs). The OAM generator 220 receives a light beam 221 (for example from a laser) that includes a series of plane waves. The OAM generator 220 applies an orbital angular momentum to the beam 222. The beam 222 includes a single OAM mode as illustrated by the intensity diagram 223. The OAM twisted beam 222 is passed through a sample 224 including material that is being detected. As mentioned previously the sample 224 may be in a container or its naturally occurring location. The presence of the material within the sample 224 will create new OAM mode levels within the intensity diagram 225. Once the beam 222 passes through the sample 224, the output beam 226 will have three distinct signatures associated therewith based on a detection of a particular material at a particular concentration. These signatures include a change in eccentricity 228 of the intensity pattern, a shift or translation 230 in the center of gravity of the intensity pattern and a rotation 232 in three general directions ($\alpha, \beta, \gamma$) of the ellipsoidal intensity pattern output. Each of these distinct signature indications may occur in any configuration and each distinct signature will provide a unique indication of the presence of particular materials and the concentrations of these detected materials. These three distinct signatures will appear when a molecule under measurement is detected and the manner of change of these signatures represents concentration levels. The detection of the helicity spectrums from the beam passing through the sample 224 involves detecting the helical wave scatters (forward and backward) from the sample material.

The use of the OAM of light for the metrology of glucose, amyloid beta and other chiral materials has been demonstrated using the above-described configurations. OAM beams are observed to exhibit unique topological evolution upon interacting with chiral solutions within 3 cm optical path links. It should be realized that unique topological evolution may also be provided from non-chiral materials. Chiral solution, such as Amyloid-beta, glucose and others, have been observed to cause orbital angular momentum (OAM) beams to exhibit unique topological evolution when interacting therewith. OAM is not typically carried by naturally scattered photons which make use of the twisted beams more accurate when identifying the helicities of chiral molecules because OAM does not have ambient light scattering (noise) in its detection. Thus, the unique OAM signatures imparted by a material is not interfered with by ambient light scattering (noise) that does not carry OAM in naturally scattered photons making detection much more accurate. Given these unique topological features one can detect the amyloid-beta presence and concentration within a given sample based upon a specific signature in both amplitude and phase measurements. Molecular chirality signifies a structural handedness associated with variance under spatial inversion or a combination of inversion and rotation, equivalent to the usual criteria of a lack of any proper axes of rotation. Something is chiral when something cannot be made identical to its reflection. Chiral molecules that are not superimposable on their mirror image are known as Enantiomers. Traditionally, engages circularly polarized light, even in the case of optical rotation, interpretation of the phenomenon commonly requires the plane polarized state to be understood as a superposition of circular polarizations with opposite handedness. For circularly polarized light, the left and right forms designate the sign of intrinsic spin angular momentum, $\pm h$ and also the helicity of the locus described by the associated electromagnetic field vectors. For this reason its interactions with matter are enantiomerically specific.

The continuous symmetry measure (CSM) is used to evaluate the degree of symmetry of a molecule, or the chirality. This value ranges from 0 to 100. The higher the symmetry value of a molecule the more symmetry distorted the molecule and the more chiral the molecule. The measurement is based on the minimal distance between the chiral molecule and the nearest achiral molecule.

The continuous symmetry measure may be achieved according to the equation:

$$S(G) = 100 \times \min \frac{1}{Nd^2} \sum_{k=1}^{N} |Q_k - \hat{Q}_k|^2$$

$Q_k$: The original structure
$\hat{Q}_k$: The symmetry-operated structure
N: Number of vertices
d: Size normalization factor
*The scale is 0-1 (0-100):
The larger S(G) is, the higher is the deviation from G-symmetry SG as a continuous chirality measure may be determined according to:

$$S(G) = 100 \times \min \frac{1}{Nd^2} \sum_{k=1}^{N} |Q_k - \hat{Q}_k|^2$$

G: The achiral symmetry point group which minimizes S(G)
Achiral molecule: S(G)=0
An achiral molecule has a value of S(G)=0. The more chiral a molecule is the higher the value of S(G).

The considerable interest in orbital angular momentum has been enhanced through realization of the possibility to engineer optical vortices. Here, helicity is present in the wave-front surface of the electromagnetic fields and the associated angular momentum is termed "orbital". The radiation itself is commonly referred to as a 'twisted' or 'helical' beam. Mostly, optical vortices have been studied only in their interactions with achiral matter—the only apparent exception is some recent work on liquid crystals. It is timely and of interest to assess what new features, if any, can be expected if such beams are used to interrogate any system whose optical response is associated with enantiomerically specific molecules.

First the criteria for manifestations of chirality in optical interactions are constructed in generalized form. For simplicity, materials with a unique enantiomeric specificity are assumed—signifying a chirality that is intrinsic and common to all molecular components (or chromophores) involved in the optical response. Results for systems of this kind will also apply to single molecule studies. Longer range translation/rotation order can also produce chirality, as for example in twisted nematic crystals, but such mesoscopic chirality cannot directly engender enantiomerically specific interactions. The only exception is where optical waves probe two or more electronically distinct, dissymmetrically oriented but intrinsically achiral molecules or chromophores.

Chiroptical interactions can be distinguished by their electromagnetic origins: for molecular systems in their usual singlet electronic ground state, they involve the spatial variation of the electric and magnetic fields associated with the input of optical radiation. This variation over space can be understood to engage chirality either through its coupling with di-symmetrically placed, neighboring chromophore groups (Kirkwood's two-group model, of limited application) or more generally through the coupling of its associated electric and magnetic fields with individual groups. As chirality signifies a local breaking of parity it permits an interference of electric and magnetic interactions. Even in the two group case, the paired electric interactions of the system correspond to electric and magnetic interactions of the single entity which the two groups comprise. Thus, for convenience, the term 'chiral center' is used in the following to denote either chromophore or molecule.

With the advent of the laser, the Gaussian beam solution to the wave equation came into common engineering parlance, and its extension two higher order laser modes, Hermite Gaussian for Cartesian symmetry; Laguerre Gaussian for cylindrical symmetry, etc., entered laboratory optics operations. Higher order Laguerre Gaussian beam modes exhibit spiral, or helical phase fronts. Thus, the propagation vector, or the eikonal of the beam, and hence the beams momentum, includes in addition to a spin angular momentum, an orbital angular momentum, i.e. a wobble around the sea axis. This phenomenon is often referred to as vorticity. The expression for a Laguerre Gaussian beam is given in cylindrical coordinates:

$$u(r, \theta, z) = \sqrt{\frac{2pl}{1 + \delta_{0,m}\pi(m+p)!}} \frac{1}{w(z)}$$
$$\exp[j(2p + m + 1)(\psi(z) - \psi_0)]\left(\frac{\sqrt{2}\,r}{w(z)}\right)L_p^m\left(\frac{2r^2}{w(z)^2}\right)\exp\left[-jk\frac{r^2}{2q(z)} + im\theta\right]$$

Here, w (x) is the beam spot size, q(c) is the complex beam parameter comprising the evolution of the spherical wave front and the spot size. Integers p and m are the radial and azimuthal modes, respectively. The exp(imθ) term describes the spiral phase fronts.

Referring now also to FIG. 3, there is illustrated one embodiment of a beam for use with the system. A light beam 300 consists of a stream of photons 302 within the light beam 300. Each photon has an energy ±ℏω and a linear momentum of ±ℏk which is directed along the light beam axis 304 perpendicular to the wavefront. Independent of the frequency, each photon 302 within the light beam has a spin angular momentum 306 of ±ℏ aligned parallel or antiparallel to the direction of light beam propagation. Alignment of all of the photons 302 spins gives rise to a circularly polarized light beam. In addition to the circular polarization, the light beams also may carry an orbital angular momentum 308 which does not depend on the circular polarization and thus is not related to photon spin.

Figure 4:
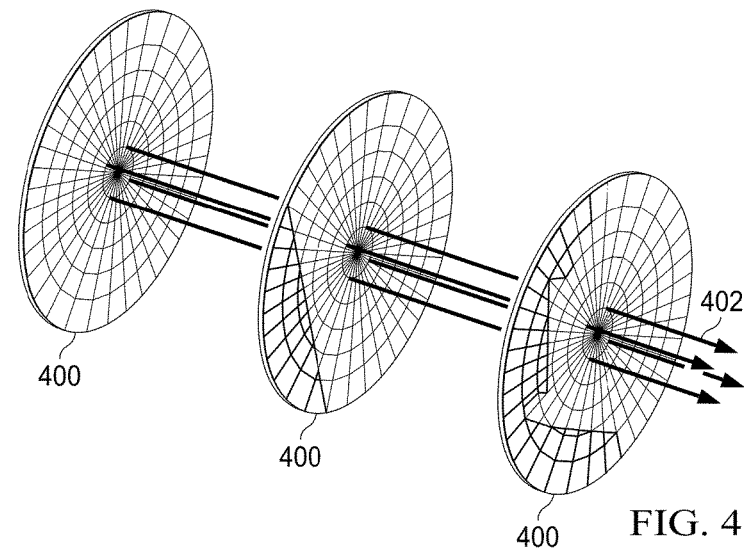
FIG. 4 illustrates a series of parallel wavefronts.

Lasers are widely used in optical experiments as the source of well-behaved light beams of a defined frequency. A laser may be used for providing the light beam 300. The energy flux in any light beam 300 is given by the Poynting vector which may be calculated from the vector product of the electric and magnetic fields within the light beam. In a vacuum or any isotropic material, the Poynting vector is parallel to the wave vector and perpendicular to the wavefront of the light beam. In a normal laser light, the wavefronts 400 are parallel as illustrated in FIG. 4. The wave vector and linear momentum of the photons are directed along the axis in a z direction 402. The field distributions of such light beams are paraxial solutions to Maxwell's wave equation but although these simple beams are the most common, other possibilities exist.

Figure 5:
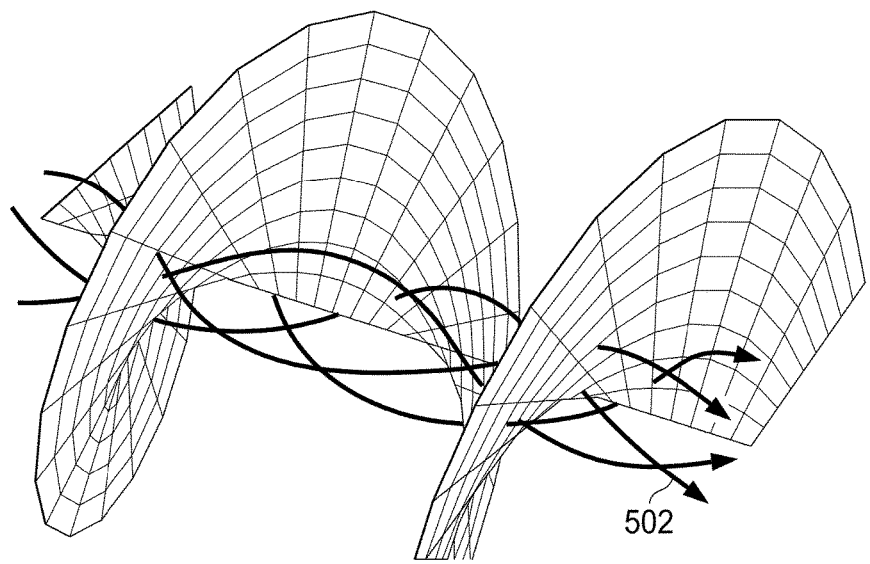
FIG. 5 illustrates a wavefront having a Poynting vector spiraling around a direction of propagation of the wavefront.

For example, beams that have 1 intertwined helical fronts are also solutions of the wave equation. The structure of these complicated beams is difficult to visualize, but their form is familiar from the 1=3 fusilli pasta. Most importantly, the wavefront has a Poynting vector and a wave vector that spirals around the light beam axis direction of propagation as illustrated in FIG. 5 at 502.

A Poynting vector has an azimuthal component on the wave front and a non-zero resultant when integrated over the beam cross-section. The spin angular momentum of circularly polarized light may be interpreted in a similar way. A beam with a circularly polarized planer wave front, even though it has no orbital angular momentum, has an azimuthal component of the Poynting vector proportional to the radial intensity gradient. This integrates over the cross-section of the light beam to a finite value. When the beam is linearly polarized, there is no azimuthal component to the Poynting vector and thus no spin angular momentum.

Thus, the momentum of each photon 302 within the light beam 300 has an azimuthal component. A detailed calculation of the momentum involves all of the electric fields and magnetic fields within the light beam, particularly those electric and magnetic fields in the direction of propagation of the beam. For points within the beam, the ratio between the azimuthal components and the z components of the momentum is found to be 1/kr. (where 1=the helicity or orbital angular momentum; k=wave number $2\pi/\lambda$; r=the radius vector.) The linear momentum of each photon 302 within the light beam 300 is given by $\hbar k$, so if we take the cross product of the azimuthal component within a radius vector, r, we obtain an orbital momentum for a photon 602 of $1\hbar$. Note also that the azimuthal component of the wave vectors is 1/r and independent of the wavelength.

Figure 6:
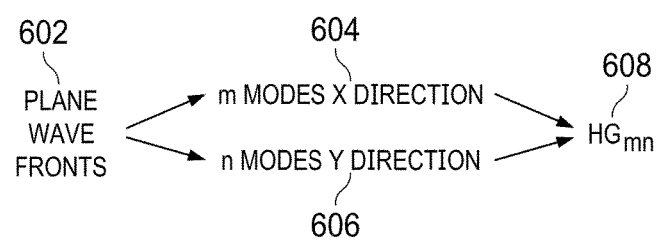
FIG. 6 illustrates a plane wavefront.
Figure 7:
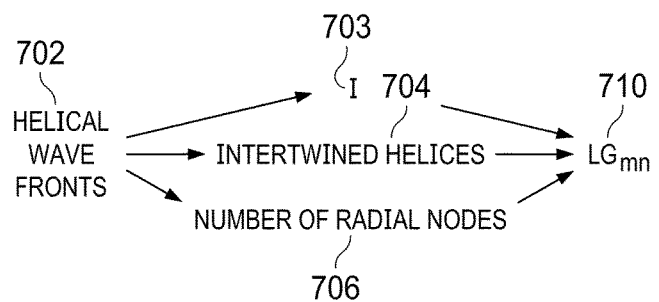
FIG. 7 illustrates a helical wavefront.

Referring now to FIGS. 6 and 7, there are illustrated plane wavefronts and helical wavefronts. Ordinarily, laser beams with plane wavefronts 602 are characterized in terms of Hermite-Gaussian modes. These modes have a rectangular symmetry and are described by two mode indices m 604 and n 606. There are m nodes in the x direction and n nodes in the y direction. Together, the combined modes in the x and y direction are labeled HGmn 608. In contrast, as shown in FIG. 7, beams with helical wavefronts 702 are best characterized in terms of Laguerre-Gaussian modes which are described by indices I 703, the number of intertwined helices 704, and p, the number of radial nodes 706. The Laguerre-Gaussian modes are labeled LGmn 710. For 1≠0, the phase singularity on a light beam 300 results in 0 on axis intensity. When a light beam 300 with a helical wavefront is also circularly polarized, the angular momentum has orbital and spin components, and the total angular momentum of the light beam is $(1\pm\hbar)$ per photon.

Using the orbital angular momentum state of the transmitted energy signals, physical information can be embedded within the electromagnetic radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x) \text{the}$$

where $\nabla$ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3x(|E|^2 + c^2|B|^2)$$

$$\frac{dU^{mech}}{dt} + \frac{dU^{em}}{dt} + \oint_{s'} d^2x'\hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3x(E \times B)$$

$$\frac{dp^{mech}}{dt} + \frac{dp^{em}}{dt} + \oint_{s'} d^2x'\hat{n}' \cdot T = 0$$

The conservation of system center of energy is represented by the equation:

$$R = \frac{1}{H}\sum_i (x_i - x_0)m_i\gamma_i c^2 + \frac{\varepsilon_0}{2H} \int d^3x(x - x_0)(|E|^2 + c^2|B|^2)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2x'\hat{n}' \cdot M = 0$$

For radiation beams in free space, the EM field angular momentum Jem can be separated into two parts:

$$J^{em} = \varepsilon_0 \int_V d^3x'(E \times A) + \varepsilon_0 \int_V d^3x' E_i[(x'-x_0) \times \nabla]A_i$$

For each singular Fourier mode in real valued representation:

$$J^{em} = -i\frac{\varepsilon_0}{2\omega}\int_{V'} d^3x'(E^* \times E) - i\frac{\varepsilon_0}{2\omega}\int_{V'} d^3x' E_i[(x'-x_0) \times \nabla]E_i$$

The first part is the EM spin angular momentum Sem, its classical manifestation is wave polarization. And the second part is the EM orbital angular momentum Lem its classical manifestation is wave helicity. In general, both EM linear momentum Pem, and EM angular momentum Jem=Lem+Sem are radiated all the way to the far field.

By using Poynting theorem, the optical vorticity of the signals may be determined according to the optical velocity equation:

$$\frac{\partial U}{\partial t} + \nabla \cdot S = 0$$

where S is the Poynting vector $$S = \frac{1}{4}(E \times H^* + E^* \times H)$$

and U is the energy density $$U = \frac{1}{4}(\varepsilon|E|^2 + \mu_0|H|^2)$$

with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left(\frac{E \times H^* + E^* \times H}{\varepsilon|E|^2 + \mu_0|H|^2}\right)$$

Figure 8:
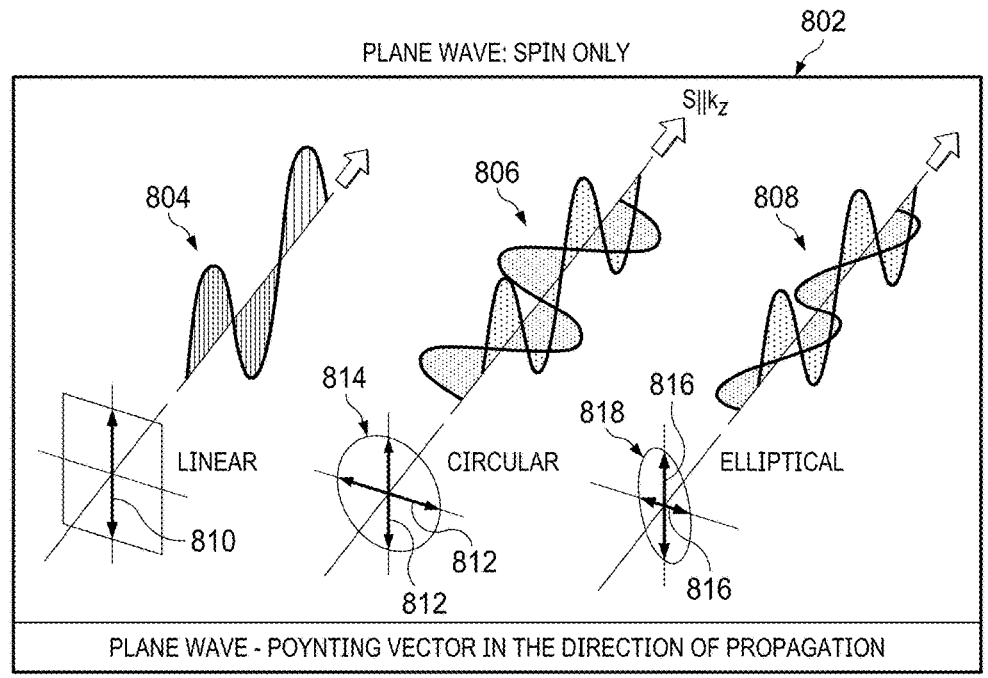
FIG. 8 illustrates a plane wave having only variations in the spin vector.
Figure 9:
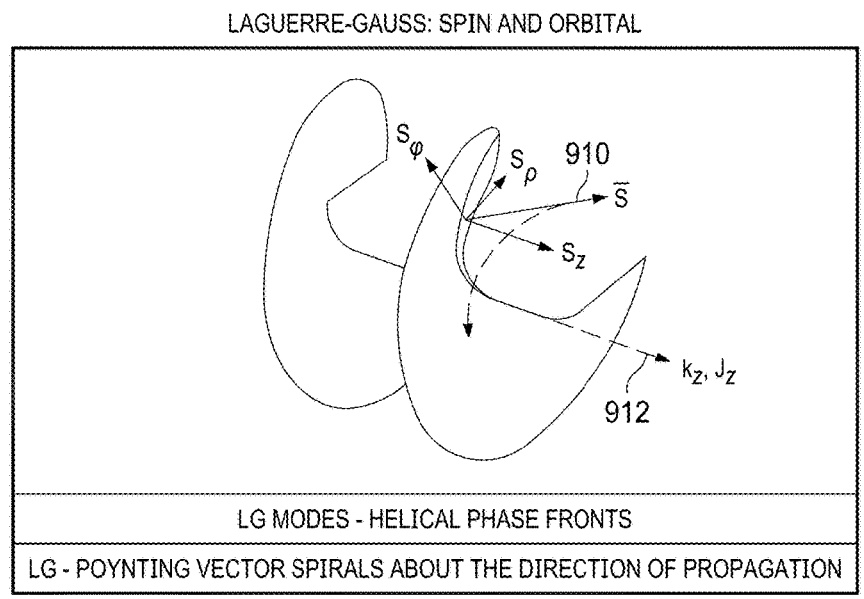
FIG. 9 illustrates the application of a unique orbital angular momentum to a wave.

Referring now to FIGS. 8 and 9, there are illustrated the manner in which a signal and an associated Poynting vector of the signal vary in a plane wave situation (FIG. 8) where only the spin vector is altered, and in a situation wherein the spin and orbital vectors are altered in a manner to cause the Poynting vector to spiral about the direction of propagation (FIG. 9).

In the plane wave situation, illustrated in FIG. 8, when only the spin vector of the plane wave is altered, the transmitted signal may take on one of three configurations. When the spin vectors are in the same direction, a linear signal is provided as illustrated generally at 804. It should be noted that while 804 illustrates the spin vectors being altered only in the x direction to provide a linear signal, the spin vectors can also be altered in the y direction to provide a linear signal that appears similar to that illustrated at 804 but in a perpendicular orientation to the signal illustrated at 804. In linear polarization such as that illustrated at 804, the vectors for the signal are in the same direction and have a same magnitude.

Within a circular polarization as illustrated at 806, the signal vectors 812 are 90 degrees to each other but have the same magnitude. This causes the signal to propagate as illustrated at 806 and provide the circular polarization 814 illustrated in FIG. 8. Within an elliptical polarization 808, the signal vectors 816 are also 90 degrees to each other but have differing magnitudes. This provides the elliptical polarizations 818 illustrated for the signal propagation 408. For the plane waves illustrated in FIG. 8, the Poynting vector is maintained in a constant direction for the various signal configurations illustrated therein.

The situation in FIG. 9 illustrates when a unique orbital angular momentum is applied to a signal. When this occurs, Poynting vector S 910 will spiral around the general direction of propagation 912 of the signal. The Poynting vector 910 has three axial components $S\varphi$, Sp and Sz which vary causing the vector to spiral about the direction of propagation 912 of the signal. The changing values of the various vectors comprising the Poynting vector 910 may cause the spiral of the Poynting vector to be varied in order to enable signals to be transmitted on a same wavelength or frequency as will be more fully described herein. Additionally, the values of the orbital angular momentum indicated by the Poynting vector 910 may be measured to determine the presence of particular materials and the concentrations associated with particular materials being processed by a scanning mechanism.

Figure 10A:
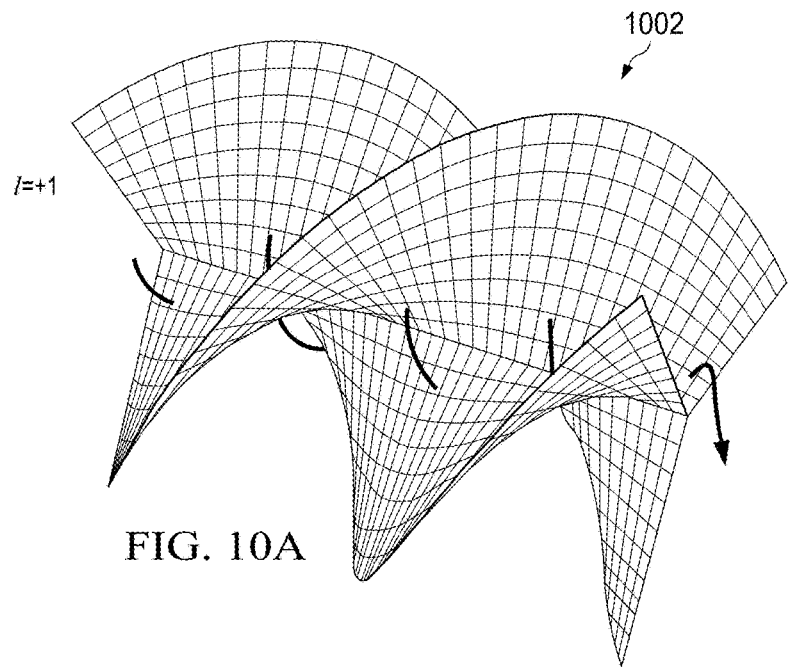
FIGS. 10A-10C illustrate the differences between signals having different orbital angular momentum applied thereto.
Figure 10B:
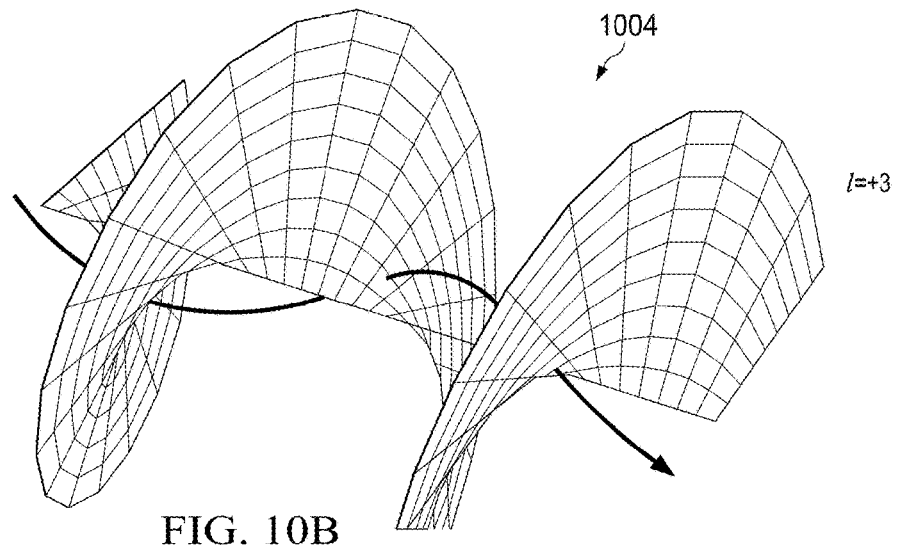
Figure 10C:
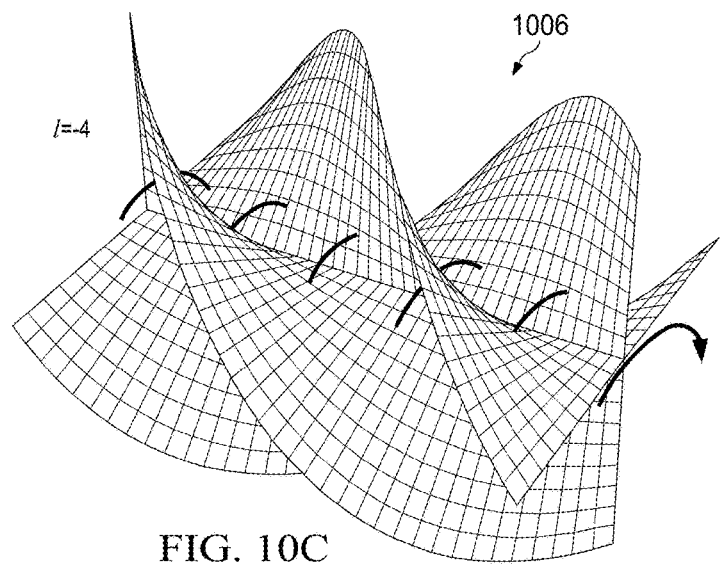

FIGS. 10A-10C illustrate the differences in signals having a different helicity (i.e., orbital angular momentum applied thereto). The differing helicities would be indicative of differing materials and concentration of materials within a sample that a beam was being passed through. By determining the particular orbital angular momentum signature associated with a signal, the particular material and concentration amounts of the material could be determined. Each of the spiraling Poynting vectors associated with a signal 1002, 1004 and 1006 provides a different-shaped signal. Signal 1002 has an orbital angular momentum of +1, signal 1004 has an orbital angular momentum of +3 and signal 1006 has an orbital angular momentum of −4. Each signal has a distinct orbital angular momentum and associated Poynting vector enabling the signal to be indicative of a particular material and concentration of material that is associated with the detected orbital angular momentum. This allows determinations of materials and concentrations of various types of materials to be determined from a signal since the orbital angular momentums are separately detectable and provide a unique indication of the particular material and the concentration of the particular material that has affected the orbital angular momentum of the signal transmitted through the sample material.

Figure 11A:
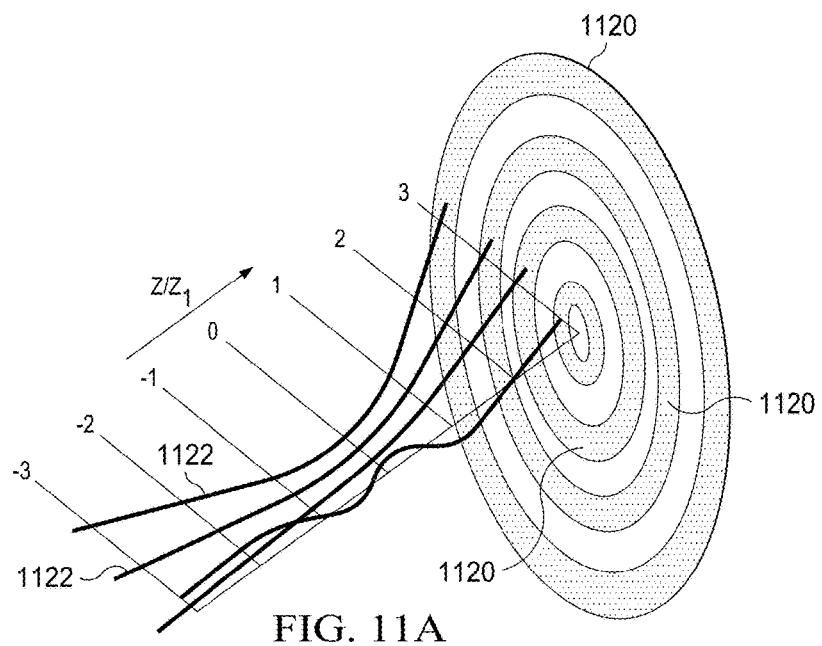
FIG. 11A illustrates the propagation of Poynting vectors for various eigenmodes.

FIG. 11A illustrates the propagation of Poynting vectors for various Eigen modes. Each of the rings 1120 represents a different Eigen mode or twist representing a different orbital angular momentum. Each of the different orbital angular momentums is associated with particular material and a particular concentration of the particular material. Detection of orbital angular momentums provides an indication of the a presence of an associated material and a concentration of the material that is being detected by the apparatus. Each of the rings 1120 represents a different material and/or concentration of a selected material that is being monitored. Each of the Eigen modes has a Poynting vector 1122 for generating the rings indicating different materials and material concentrations.

Topological charge may be multiplexed to the frequency for either linear or circular polarization. In case of linear polarizations, topological charge would be multiplexed on vertical and horizontal polarization. In case of circular polarization, topological charge would multiplex on left hand and right hand circular polarizations. The topological charge is another name for the helicity index "l" or the amount of twist or OAM applied to the signal. The helicity index may be positive or negative.

Figure 11B:
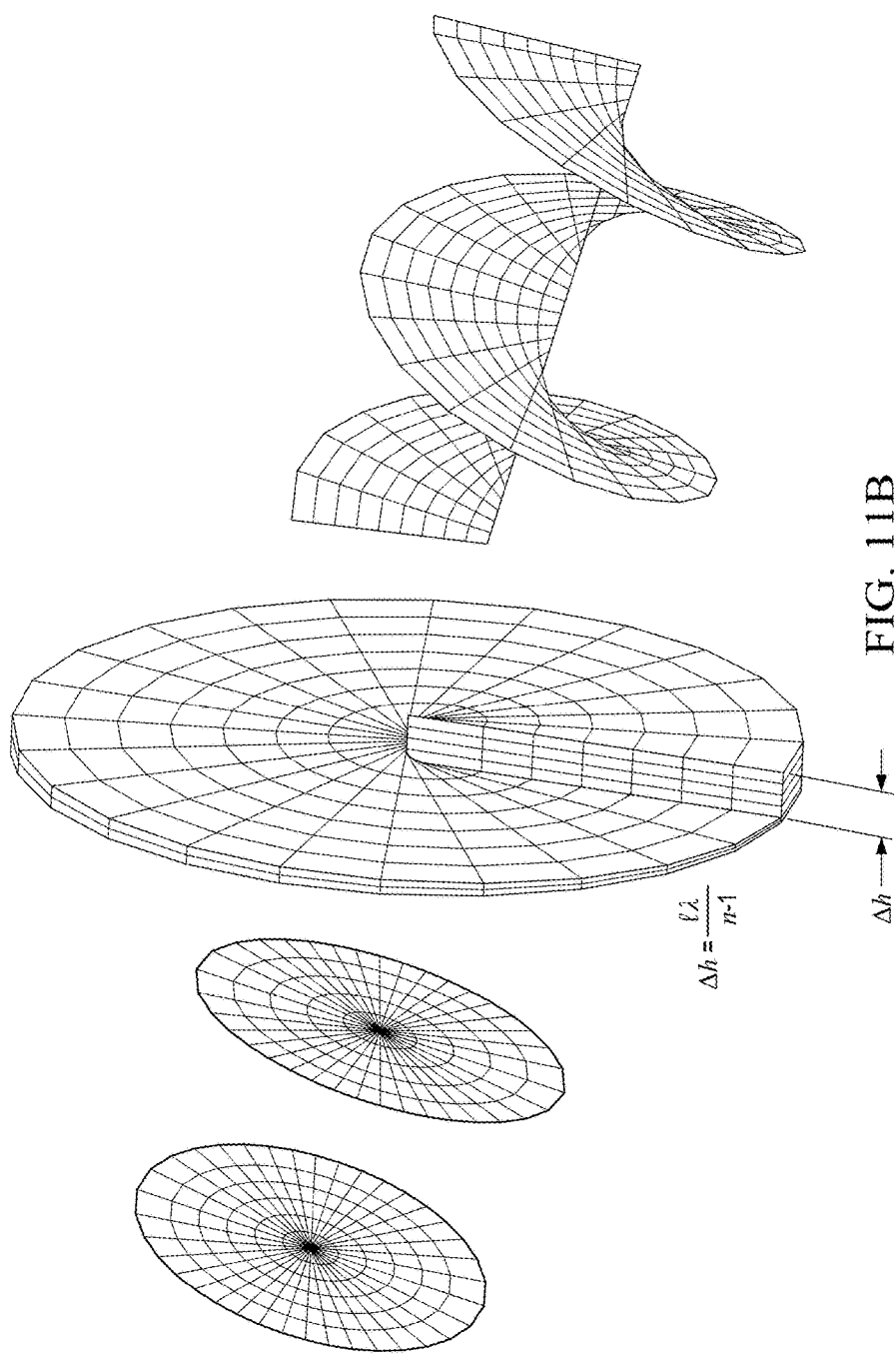
FIG. 11B illustrates a spiral phase plate.

The topological charges 1 s can be created using Spiral Phase Plates (SPPs) as shown in FIG. 11B using a proper material with specific index of refraction and ability to machine shop or phase mask, holograms created of new materials. Spiral Phase plates can transform a RF plane wave (1=0) to a twisted wave of a specific helicity (i.e. 1=+1).

Figure 12:
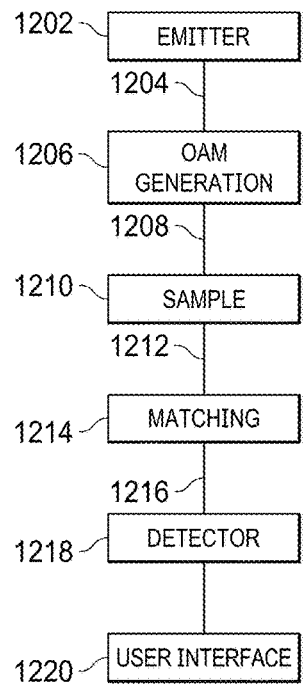
FIG. 12 illustrates a block diagram of an apparatus for providing concentration measurements and presence detection of various materials using orbital angular momentum.

Referring now to FIG. 12, there is illustrated a block diagram of the apparatus for providing detection of the presence of a material and concentration measurements of various materials responsive to the orbital angular momentum detected by the apparatus in accordance with the principles described herein above. An emitter 1202 transmits wave energy 1204 that comprises a series of plane waves. The emitter 1202 may provide a series of plane waves such as those describes previously with respect to FIG. 7. The orbital angular momentum generation circuitry 1206 generates a series of waves having an orbital angular momentum applied to the waves 1208 in a known manner. The orbital angular momentum generation circuitry 1206 may utilize holograms or some other type of orbital angular momentum generation process as will be more fully described herein below. The OAM generation circuitry 1206 may be generated by transmitting plane waves through a spatial light modulator (SLM), an amplitude mask or a phase mask. The orbital angular momentum twisted waves 1208 are applied to a sample material 1210 under test. The sample material 1210 contains a material, and the presence and concentration of the material is determined via a detection apparatus in accordance with the process described herein. The sample material 1210 may be located in a container or at its naturally occurring location in nature such as an individual's body.

A series of output waves 1212 from the sample material 1210 exit the sample and have a particular orbital angular momentum imparted thereto as a result of the material and the concentration of the particular material under study within the sample material 1210. The output waves 1212 are applied to a matching module 1214 that includes a mapping aperture for amplifying a particular orbital angular momentum generated by the specific material under study. The matching module 1214 will amplify the orbital angular momentums associated with the particular material and concentration of material that is detected by the apparatus. The amplified OAM waves 1216 are provided to a detector 1218. The detector 1218 detects OAM waves relating to the material and the concentration of a material within the sample and provides this information to a user interface 1220. The detector 1218 may utilize a camera to detect distinct topological features from the beam passing through the sample. The user interface 1220 interprets the information and provides relevant material type and concentration indication to an individual or a recording device.

Figure 13:
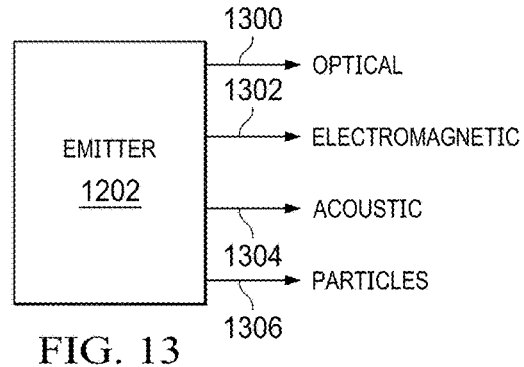
FIG. 13 illustrates an emitter of the system of FIG. 11.

Referring now to FIG. 13, there is more particularly illustrated the emitter 1202. The emitter 1202 may emit a number of types of energy waves 1204 to the OAM generation module 1206. The emitter 1202 may emit optical waves 1300, electromagnetic waves 1302, acoustic waves 1304 or any other type of particle waves 1306. The emitted waves 1204 are plane waves such as those illustrated in FIG. 4 having no orbital angular momentum applied thereto and may come from a variety of types of emission devices and have information included therein. In one embodiment, the emission device may comprise a laser. Plane waves have wavefronts that are parallel to each other having no twist or helicity applied thereto, and the orbital angular momentum of the wave is equal to 0. The Poynting vector within a plane wave is completely in line with the direction of propagation of the wave.

Figure 14:
FIG. 14 illustrates a fixed orbital angular momentum generator of the system of FIG. 11.
Figure 15A:
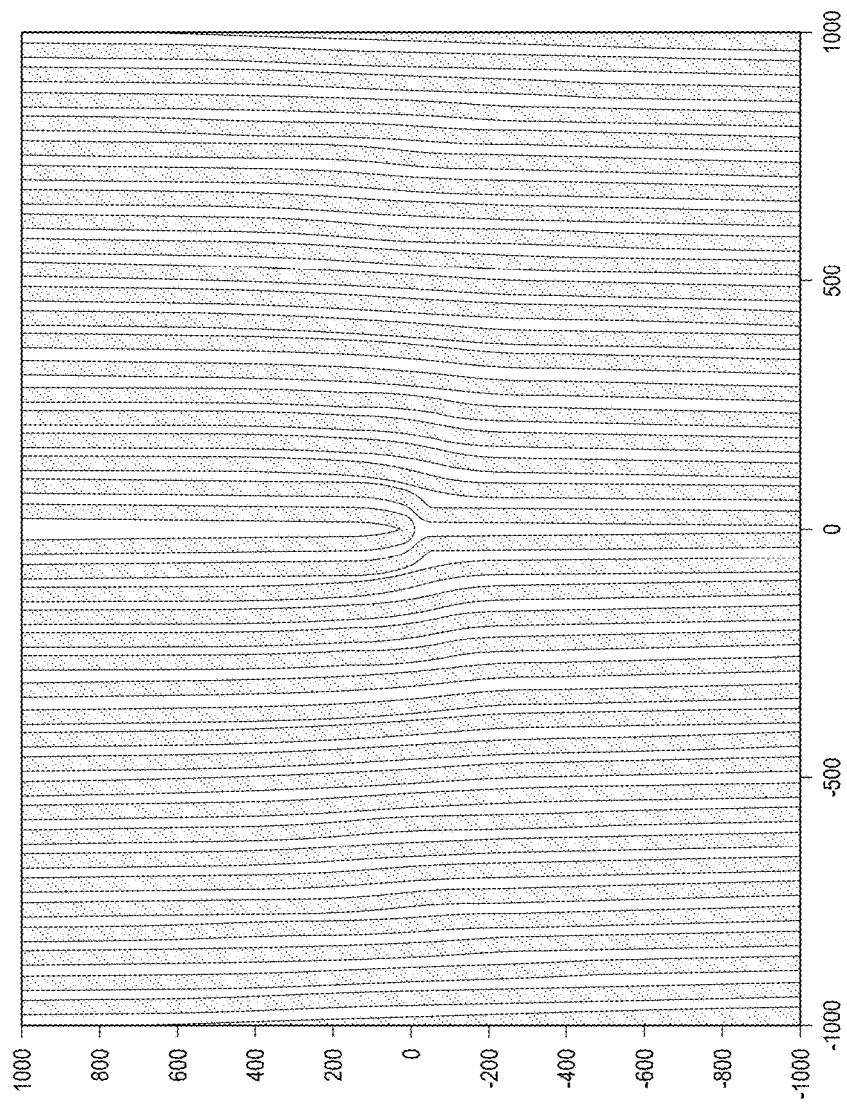
Figure 15B:
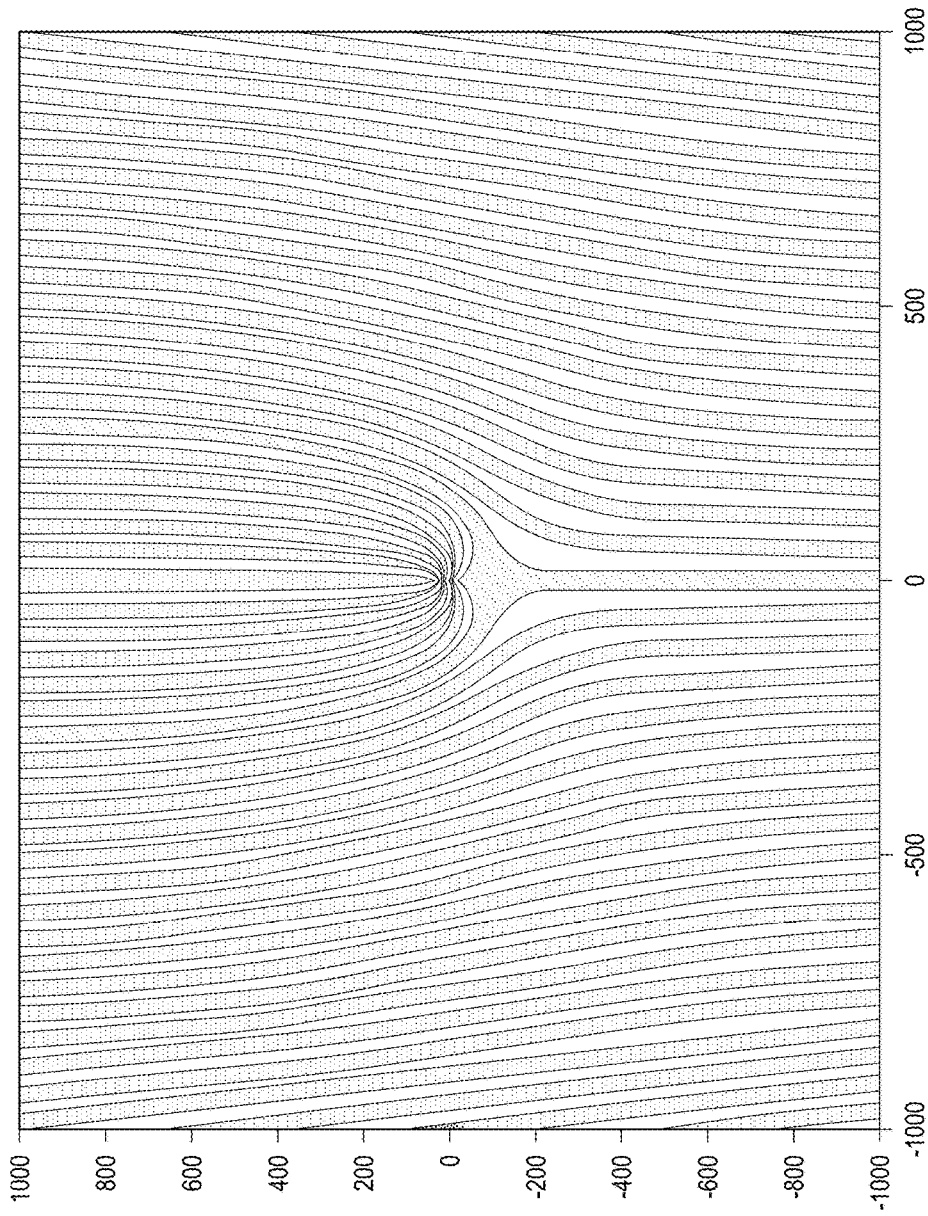
Figure 15C:
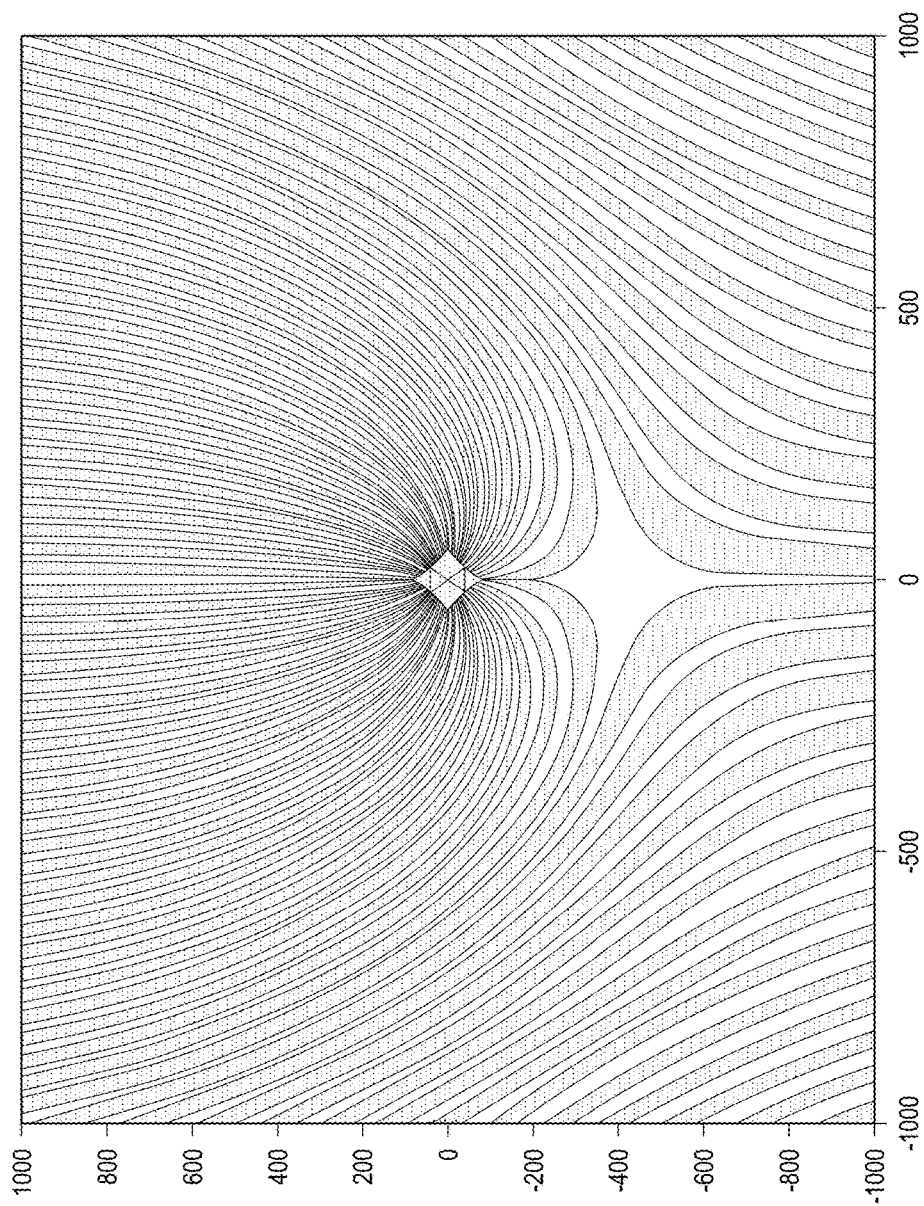

The OAM generation module 1206 processes the incoming plane wave 1204 and imparts a known orbital angular momentum onto the plane waves 1204 provided from the emitter 1202. The OAM generation module 1206 generates twisted or helical electromagnetic, optic, acoustic or other types of particle waves from the plane waves of the emitter 1202. A helical wave 1208 is not aligned with the direction of propagation of the wave but has a procession around direction of propagation as shown in FIG. 14. The OAM generation module 1206 may comprise in one embodiment a fixed orbital angular momentum generator 1402 as illustrated in FIG. 14. The fixed orbital angular momentum generator 1402 receives the plane waves 1204 from the emitter 1202 and generates an output wave 1404 having a fixed orbital angular momentum applied thereto.

The fixed orbital angular momentum generator 1402 may in one embodiment comprise a holographic image for applying the fixed orbital angular momentum to the plane wave 1204 in order to generate the OAM twisted wave 1404. Various types of holographic images may be generated in order to create the desired orbital angular momentum twist to an optical signal that is being applied to the orbital angular momentum generator 1402. Various examples of these holographic images are illustrated in FIG. 15A-15D. In one embodiment, the conversion of the plane wave signals transmitted from the emitter 1202 by the orbital angular momentum generation circuitry 1206 may be achieved using holographic images.

Figure 16:
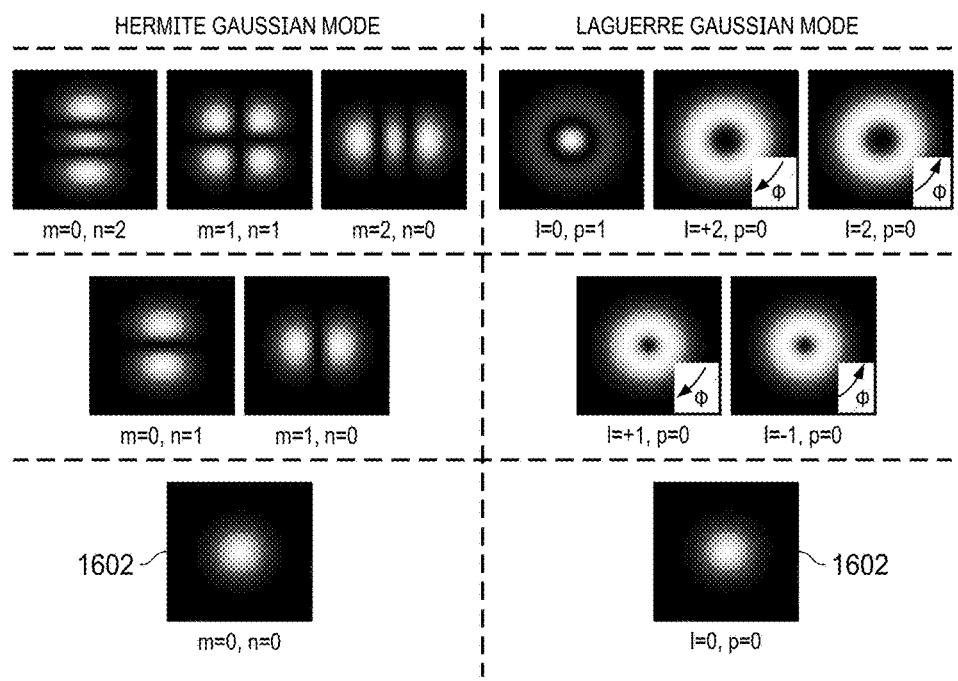
FIG. 16 illustrates the relationship between Hermite-Gaussian modes and Laguerre-Gaussian modes.

Most commercial lasers emit an HG00 (Hermite-Gaussian) mode 1602 (FIG. 16) with a planar wave front and a transverse intensity described by a Gaussian function. Although a number of different methods have been used to successfully transform an HG00 Hermite-Gaussian mode 1602 into a Laguerre-Gaussian mode 1604, the simplest to understand is the use of a hologram.

The cylindrical symmetric solution upl (r,φ,z) which describes Laguerre-Gaussian beams, is given by the equation:

$$u_{pl}(r, \phi, z) = \frac{C}{(1+z^2/z_R^2)^{1/2}} \left[\frac{r\sqrt{2}}{w(z)}\right]^l L_p^l\left[\frac{2r^2}{w^2(z)}\right] \exp\left[\frac{-r^2}{w^2(z)}\right]$$

$$\exp\left[\frac{-ikr^2z}{2(z^2+z_R^2)}\right] \exp(-il\phi) \times \exp\left[i(2p+l+1)\tan^{-1}\frac{z}{z_R}\right]$$

Where $z_R$ is the Rayleigh range, w(z) is the radius of the beam, $L_p$ is the Laguerre polynomial, C is a constant, and the beam waist is at z=0.

In its simplest form, a computer generated hologram is produced from the calculated interference pattern that results when the desired beam intersects the beam of a conventional laser at a small angle. The calculated pattern is transferred to a high resolution holographic film. When the developed hologram is placed in the original laser beam, a diffraction pattern results. The first order of which has a desired amplitude and phase distribution. This is one manner for implementing the OAM generation module 1206. A number of examples of holographic images for use within a OAM generation module are illustrated with respect to FIGS. 15A-15D.

There are various levels of sophistication in hologram design. Holograms that comprise only black and white areas with no grayscale are referred to as binary holograms. Within binary holograms, the relative intensities of the two interfering beams play no role and the transmission of the hologram is set to be zero for a calculated phase difference between zero and π, or unity for a phase difference between π and 2π. A limitation of binary holograms is that very little of the incident power ends up in the first order diffracted spot, although this can be partly overcome by blazing the grating. When mode purity is of particular importance, it is also possible to create more sophisticated holograms where the contrast of the pattern is varied as a function of radius such that the diffracted beam has the required radial profile.

A plane wave shining through the holographic images 1502 will have a predetermined orbital angular momentum shift applied thereto after passing through the holographic image 1502. OAM generator 1202 is fixed in the sense that a same image is used and applied to the beam being passed through the holographic image. Since the holographic image 1502 does not change, the same orbital angular momentum is always applied to the beam being passed through the holographic image 1502. While FIGS. 15A-15D illustrate a number of embodiments of various holographic images that might be utilized within the orbital angular momentum generator 1202, it will be realized that any type of holographic image 1502 may be utilized in order to achieve the desired orbital angular momentum within an beam being shined through the image 1502.

Figure 17:
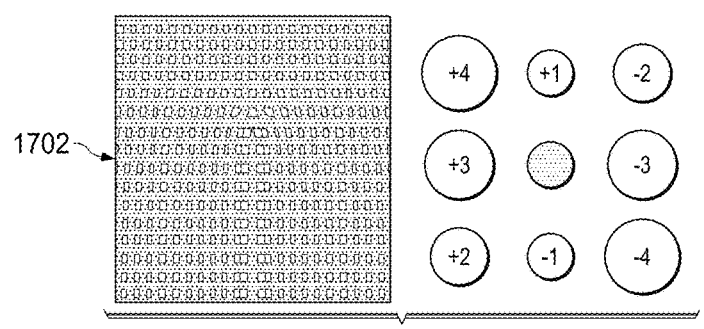
FIG. 17 illustrates super-imposed holograms for applying orbital angular momentum to a signal.

In another example of a holographic image illustrated in FIG. 17, there is illustrated a hologram that utilizes two separate holograms that are gridded together to produce a rich number of orbital angular momentum (l). The superimposed holograms of FIG. 17 have an orbital angular momentum of l=1 and l=3 which are superimposed upon each other to compose the composite vortex grid 1702. The holograms utilized may also be built in a manner that the two holograms are gridded together to produce a varied number of orbital angular momentums (l) not just on a line (l=+1, l=0, l=−1) but on a square which is able to identify the many variables more easily. Thus, in the example in FIG. 17, the orbital angular momentums along the top edge vary from +4 to +1 to −2 and on the bottom edge from +2 to −1 to −4. Similarly, along the left edge the orbital angular momentums vary from +4 to +3 to +2 and on the right edge from −2 to −3 to −4. Across the horizontal center of the hologram the orbital angular momentums provided vary from +3 to 0 to −3 and along the vertical axis vary from +1 to 0 to −1. Thus, depending upon the portion of the grid a beam may pass through, varying orbital angular momentum may be achieved.

Figure 18:
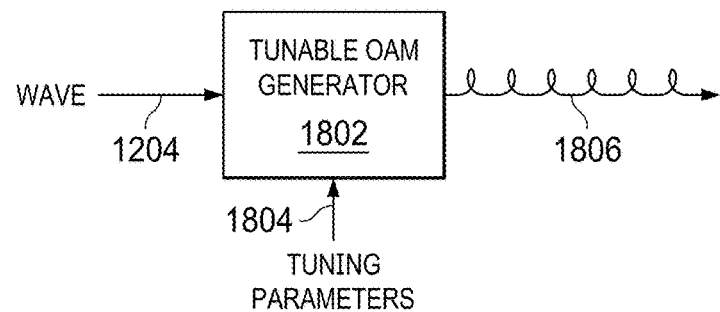
FIG. 18 illustrates a tunable orbital angular momentum generator for use in the system of FIG. 11.

Referring now to FIG. 18, in addition to a fixed orbital angular momentum generator, the orbital angular momentum generation circuitry 1206 may also comprise a tunable orbital angular momentum generator circuitry 1802. The tunable orbital angular momentum generator 1802 receives the input plane wave 1204 but additionally receives one or more tuning parameters 1804. The tuning parameters 1804 tune the tunable OAM generator 1802 to apply a selected orbital angular momentum so that the tuned OAM wave 1806 that is output from the OAM generator 1802 has a selected orbital angular momentum value applied thereto.

This may be achieved in any number of fashions. In one embodiment, illustrated in FIG. 22, the tunable orbital angular momentum generator 1802 may include multiple hologram images 2202 within the tunable OAM generator 1802. The tuning parameters 1804 enable selection of one of the holographic images 2206 in order to provide the desired OAM wave twisted output signal 1806 through a selector circuit 2204. Alternatively, the gridded holographic image such as that described in FIG. 16 may be utilized and the beam shined on a portion of the gridded image to provide the desired OAM output. The tunable OAM generator 1802 has the advantage of being controlled to apply a particular orbital angular momentum to the output orbital angular momentum wave 1806 depending upon the provided input parameter 1804. This enables the presence and concentrations of a variety of different materials to be monitored, or alternatively, for various different concentrations of the same material to be monitored.

Figure 19:
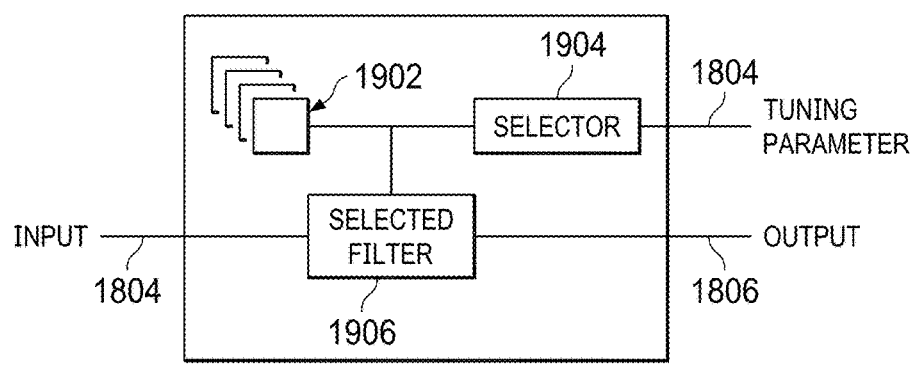
FIG. 19 illustrates a block diagram of a tunable orbital angular momentum generator including multiple hologram images therein.

Referring now to FIG. 19, there is more particularly implemented a block diagram of a tunable orbital angular momentum generator 1802. The generator 1802 includes a plurality of holographic images 1902 for providing orbital angular momentums of various types to a provided light signal. These holographic images 1902 are selected responsive to a selector circuitry 1904 that is responsive to the input tuning parameters 1804. The selected filter 1906 comprises the holographic image that has been selected responsive to the selector controller 1904 and receives the input plane waves 1204 to provide the tuned orbital angular momentum wave output 1206. In this manner, signals having a desired orbital angular momentum may be output from the OAM generation circuitry 1206.

Figure 20:
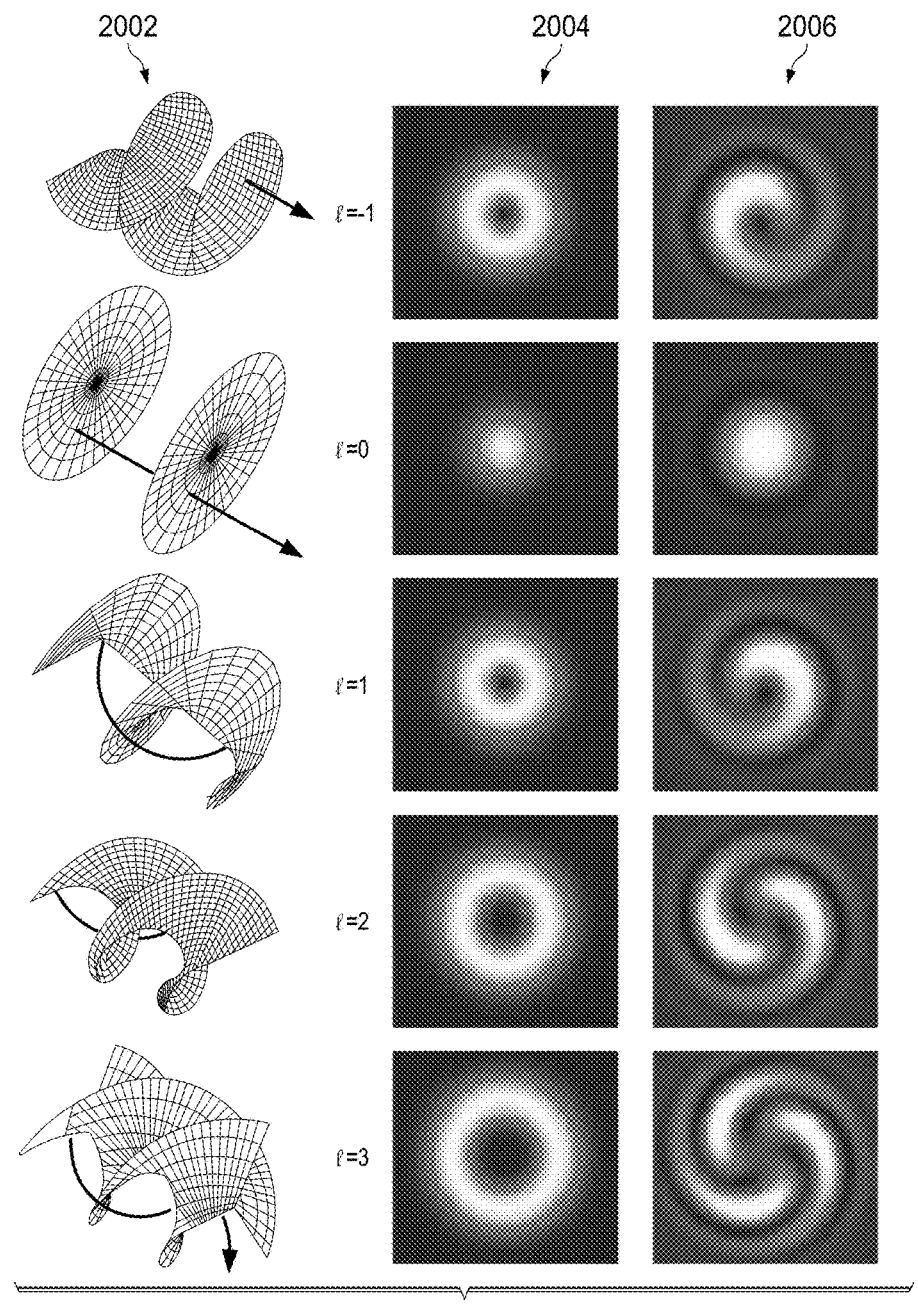
FIG. 20 illustrates the manner in which the output of the OAM generator may be varied by applying different orbital angular momentums thereto.

Referring now to FIG. 20, there is illustrated the manner in which the output of the OAM generator 1206 may vary a signal by applying different orbital angular momentums thereto. FIG. 20 illustrates helical phase fronts in which the Poynting vector is no longer parallel to the beam axis and thus has an orbital angular momentum applied thereto. In any fixed radius within the beam, the Poynting vector follows a spiral trajectory around the axis. Rows are labeled by 1, the orbital angular momentum quantum number, L=lℏ is the beams orbital angular momentum per photon within the output signal. For each l, the left column 2002 is the light beam's instantaneous phase. The center column 2004 comprises the angular intensity profiles and the right column 2006 illustrates what occurs when such a beam interferes with a plane wave and produces a spiral intensity pattern. This is illustrated for orbital angular momentums of −1, 0, 1, 2 and 3 within the various rows of FIG. 23.

Figure 21:
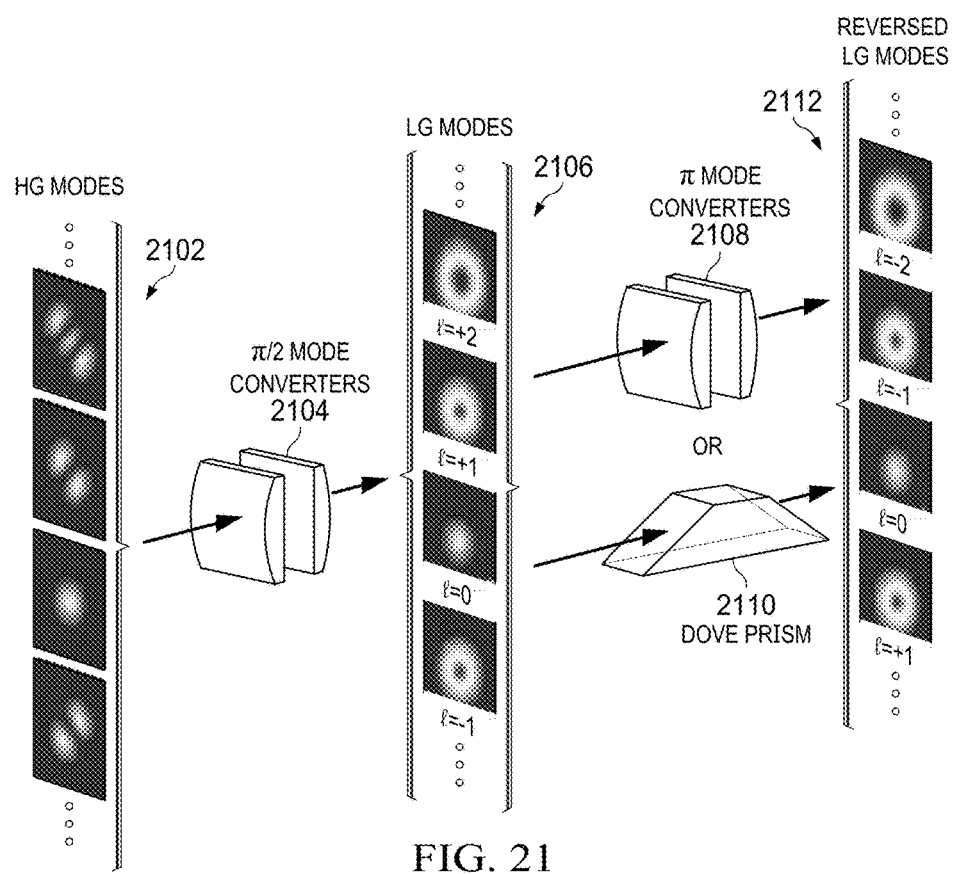
FIG. 21 illustrates an alternative manner in which the OAM generator may convert a Hermite-Gaussian beam to a Laguerre-Gaussian beam.

Referring now to FIG. 21, there is illustrated an alternative manner in which the OAM generator 1206 may convert a Hermite-Gaussian beam output from an emitter 1202 to a Laguerre-Gaussian beams having imparted therein an orbital angular momentum using mode converters 2104 and a Dove prism 2110. The Hermite-Gaussian mode plane waves 2102 are provided to a π/2 mode convertor 2104. The π/2 mode convertor 2104 produce beams in the Laguerre-Gaussian modes 2106. The Laguerre-Gaussian modes beams 2106 are applied to either a π mode convertor 2108 or a dove prism 2110 that reverses the mode to create a reverse Laguerre-Gaussian mode signal 2112.

Figure 22:
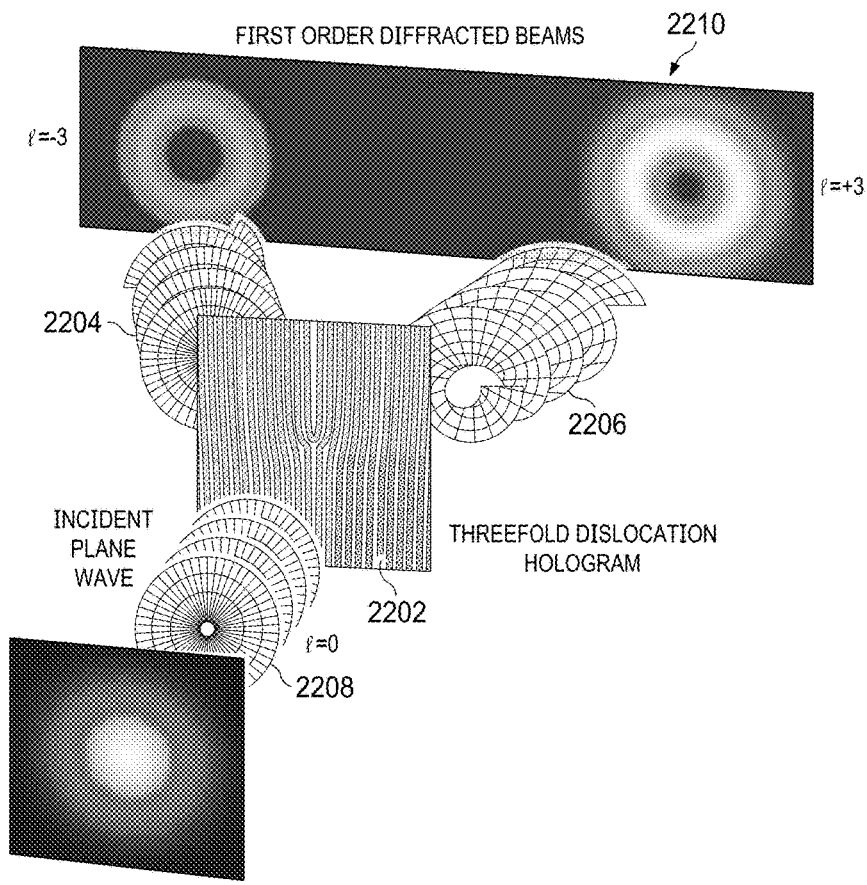
FIG. 22 illustrates the manner in which holograms within an OAM generator may twist a beam of light.

Referring now to FIG. 22, there is illustrated the manner in which holograms within the OAM generator 1206 generate a twisted light beam. A hologram 2202 can produce light beam 2204 and light beam 2206 having helical wave fronts and associated orbital angular momentum lh per photon. The appropriate hologram 2202 can be calculated or generated from the interference pattern between the desired beam form 2204, 2206 and a plane wave 2208. The resulting holographic pattern within the hologram 2202 resembles a diffraction grating, but has a 1-pronged dislocation at the beam axis. When the hologram is illuminated with the plane wave 2208, the first-order diffracted beams 2204 and 2206 have the desired helical wave fronts to provide the desired first ordered diffracted beam display 2210.

Figure 23:
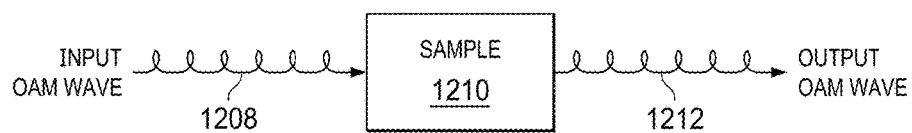
FIG. 23 illustrates the manner in which a sample receives an OAM twisted wave and provides an output wave having a particular OAM signature.

Referring now to FIG. 23, there is more particularly illustrated the manner in which the sample 1210 receives the input OAM twisted wave 1208 provided from the OAM generator 1206 and provides an output OAM wave 1212 having a particular OAM signature associated therewith that depends upon the material or the concentration of a particular monitored material within the sample 1210. The sample 1210 may comprise any sample that is under study and may be in a solid form, liquid form or gas form. The sample material 1210 that may be detected using the system described herein may comprise a variety of different materials. As stated previously, the material may comprise liquids such as blood, water, oil or chemicals. The various types of carbon bondings such as C—H, C—O, C—P, C—S or C—N may be provided for detection. The system may also detect various types of bondings between carbon atoms such as a single bond (methane or Isooctane), dual bond items (butadiene and benzene) or triple bond carbon items such as acetylene.

The sample 1210 may include detectable items such as organic compounds including carbohydrates, lipids (cylcerol and fatty acids), nucleic acids (C,H,O,N,P) (RNA and DNA) or various types of proteins such as polyour of amino $NH_2$ and carboxyl COOH or aminos such as tryptophan, tyrosine and phenylalanine. Various chains within the samples 1210 may also be detected such as monomers, isomers and polymers. Enzymes such as ATP and ADP within the samples may be detected. Substances produced or released by glands of the body may be in the sample and detected. These include items released by the exocrine glands via tube/ducts, endocrine glands released directly into blood samples or hormones. Various types of glands that may have their secretions detected within a sample 1210 include the hypothalamus, pineal and pituitary glands, the parathyroid and thyroid and thymus, the adrenal and pancreas glands of the torso and the hormones released by the ovaries or testes of a male or female.

The sample 1210 may also be used for detecting various types of biochemical markers within the blood and urine of an individual such as melanocytes and keratinocytes. The sample 1210 may include various parts of the body to detect defense substances therein. For example, with respect to the skin, the sample 1210 may be used to detect carotenoids, vitamins, enzymes, b-carotene and lycopene. With respect to the eye pigment, the melanin/eumelanin, dihydroxyindole or carboxylic may be detected. The system may also detect various types of materials within the body's biosynthetic pathways within the sample 1210 including hemoglobin, myoglobin, cytochromes, and porphyrin molecules such as protoporphyrin, coporphyrin, uroporphyrin and nematoporphyrin. The sample 1210 may also contain various bacterial to be detected such as propion bacterium, acnes. Also various types of dental plaque bacteria may be detected such as porphyromonos gingivitis, prevotella intremedi and prevotella nigrescens. The sample 1210 may also be used for the detection of glucose in insulin within a blood sample 1210. The sample 1210 may also include amyloid-beta detection. Detection of amyloid-beta within the sample may then be used for determinations of early onset Alzheimer's. Higher levels of amyloid-beta may provide an indication of the early stages of Alzheimer's. The sample 1210 may comprise any material that is desired to be detected that provides a unique OAM twist to a signal passing through the sample.

Figure 24:
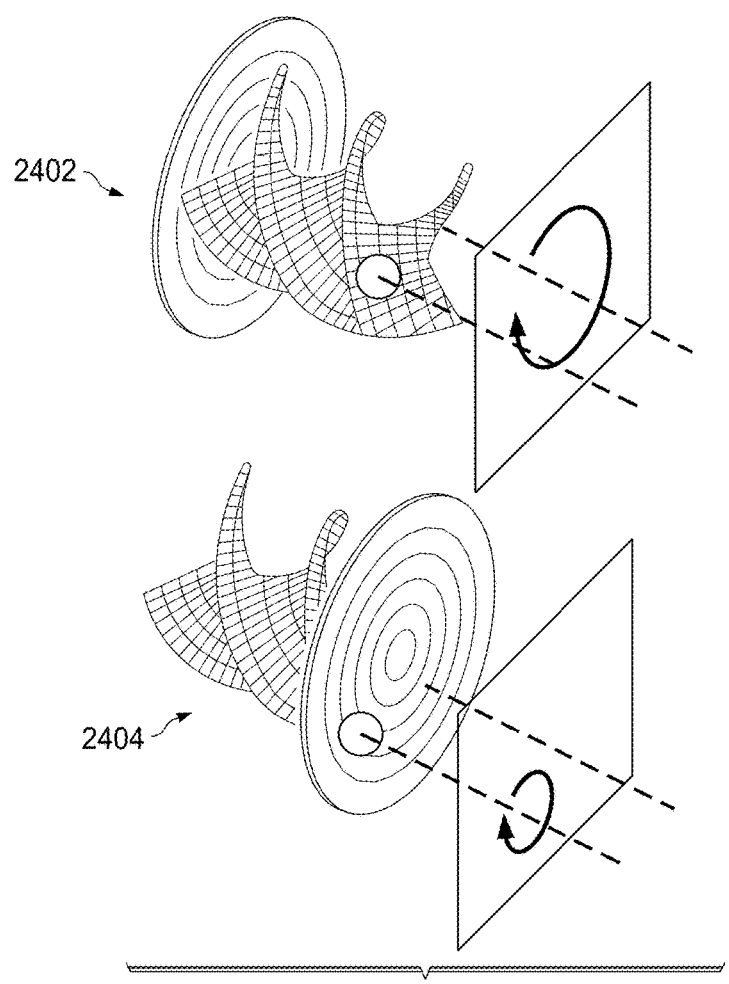
FIG. 24 illustrates the manner in which orbital angular momentum interacts with a molecule around its beam axis.

The orbital angular momentum within the beams provided within the sample 1210 may be transferred from light to matter molecules depending upon the rotation of the matter molecules. When a circularly polarized laser beam with a helical wave front traps a molecule in an angular ring of light around the beam axis, one can observe the transfer of both orbital and spin angular momentum. The trapping is a form of optical tweezing accomplished without mechanical constraints by the ring's intensity gradient. The orbital angular momentum transferred to the molecule makes it orbit around the beam axis as illustrated at 2402 of FIG. 24. The spin angular momentum sets the molecule spinning on its own axis as illustrated at 2404.

The output OAM wave 1212 from the sample 1210 will have an orbital angular momentum associated therewith that is different from the orbital angular momentum provided on the input OAM wave 1208. The difference in the output OAM wave 1212 will depend upon the material contained within the sample 1210 and the concentration of these materials within the sample 1210. Differing materials of differing concentration will have unique orbital angular momentums associated therewith. Thus, by analyzing the particular orbital angular momentum signature associated with the output OAM wave 1212, determinations may be made as to the materials present within the sample 1210 and the concentration of these materials within the sample may also be determined.

Figure 25:
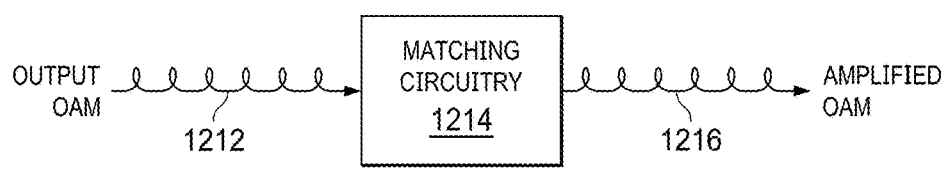
FIG. 25 illustrates a block diagram of the matching circuitry for amplifying a received orbital angular momentum signal.

Referring now to FIG. 25, the matching module 1214 receives the output orbital angular momentum wave 1212 from the sample 1210 that has a particular signature associated therewith based upon the orbital angular momentum imparted to the waves passing through the sample 1210. The matching module 1214 amplifies the particular orbital angular momentum of interest in order to provide an amplified wave having the desired orbital angular momentum of interest 1216 amplified. The matching module 1214 may comprise a matching aperture that amplifies the detection orbital angular momentum associated with a specific material or characteristic that is under study. The matching module 1214 may in one embodiment comprise a holographic filter such as that described with respect to FIGS. 15A-15D in order to amplify the desired orbital angular momentum wave of interest. The matching module 1214 is established based upon a specific material of interest that is trying to be detected by the system. The matching module 1214 may comprise a fixed module using holograms as illustrated in FIGS. 15A-15D or a tunable module in a manner similar to that discussed with respect to the OAM generation module 1206. In this case, a number of different orbital angular momentums could be amplified by the matching module in order to detect differing materials or differing concentrations of materials within the sample 1210. Other examples of components for the matching module 1214 include the use of quantum dots, nanomaterials or metamaterials in order to amplify any desired orbital angular momentum values within a received wave form from the sample 1210.

Figure 26:
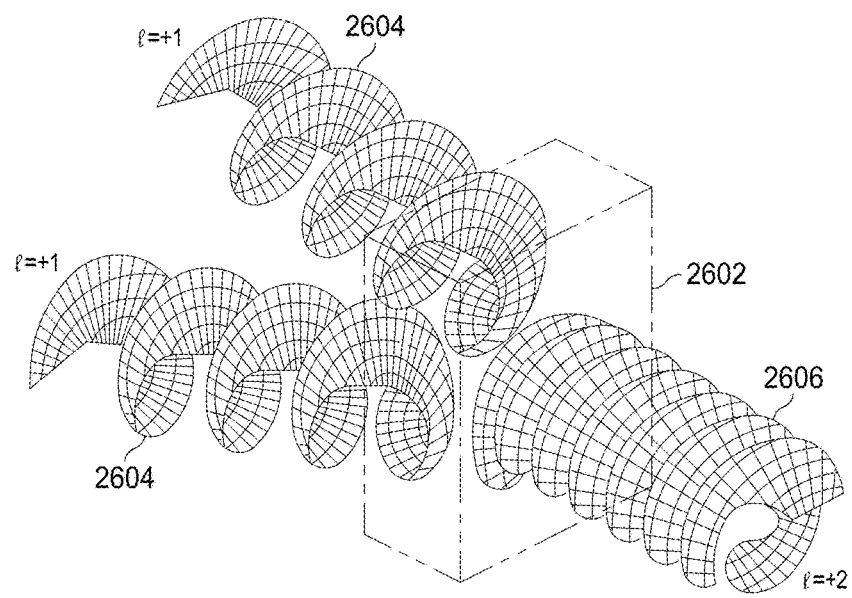
FIG. 26 illustrates the manner in which the matching module may use non-linear crystals in order to generate a higher order orbital angular momentum light beam.

Referring now to FIG. 26, the matching module 1214 rather than using holographic images in order to amplify the desired orbital angular momentum signals may use non-linear crystals in order to generate higher orbital angular momentum light beams. Using a non-linear crystal 2602, a first harmonic orbital angular momentum beam 2604 may be applied to a non-linear crystal 2602. The non-linear crystal 2602 will create a second order harmonic signal 2606.

Figure 27:
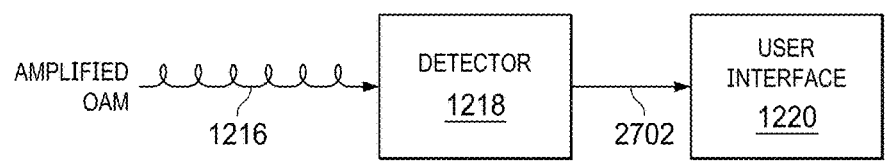
FIG. 27 illustrates a block diagram of an orbital angular momentum detector and user interface.

Referring now to FIG. 27, there is more particularly illustrated the detector 1218 to which the amplified orbital angular momentum wave 1216 from the matching circuit 1214 in order that the detector 1218 may extract desired OAM measurements 2602. The detector 1218 receives the amplified OAM waves 1216 and detects and measures observable changes within the orbital angular momentum of the emitted waves due to the presence of a particular material and the concentration of a particular material under study within the sample 1210. The detector 1218 is able to measure observable changes within the emitted amplified OAM wave 1216 from the state of the input OAM wave 1208 applied to the sample 1210. The extracted OAM measurements 2702 are applied to the user interface 1220. The detector 618 includes an orbital angular momentum detector 2104 for determining a profile of orbital angular momentum states of the orbital angular momentum within the orbital angular momentum signal 616 and a processor 2106 for determining the material within the sample responsive to the detected profile of the orbital angular momentum states of the orbital angular momentum. The manner in which the detector 1218 may detect differences within the orbital angular momentum is more particularly illustrates with respect to FIG. 28-30.

Figure 28:
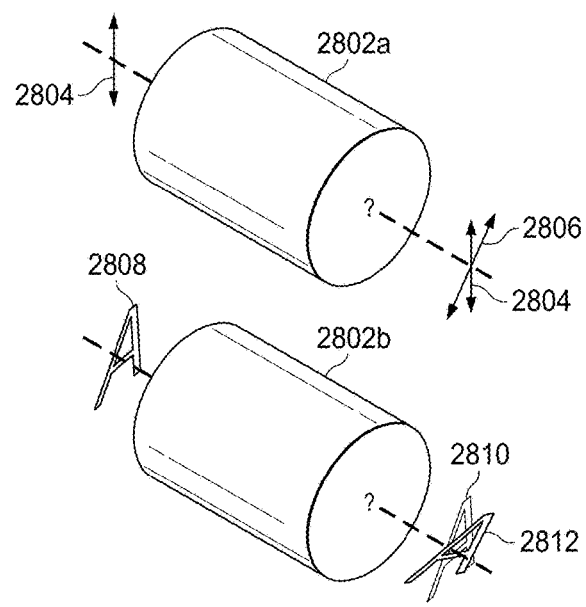
FIG. 28 illustrates the effect of sample concentrations upon the spin angular polarization and orbital angular polarization of a light beam passing through a sample.

FIG. 28 illustrates the difference in impact between spin angular polarization and orbital angular polarization due to passing of a beam of light through a sample 2802. In sample 2802a, there is illustrated the manner in which spin angular polarization is altered responsive to a beam passing through the sample 2802a. The polarization of a wave having a particular spin angular momentum 2804 passing through the sample 2802a will rotate from a position 2804 to a new position 2806. The rotation occurs within the same plane of polarization. In a similar manner, as illustrated with respect to sample 2802b, an image appears as illustrated generally at 2808 before it passes through the sample 2802b. Upon passing the image through the sample 2802b the image will rotate from the position illustrated at 2810 to a rotated position illustrated at 2812. The amount of rotation is dependent upon the presence of the material being detected and the level of concentration of the material being detected within the sample 2802. Thus, as can be seen with respect to the sample 2802 of FIG. 28, both the spin angular polarization and the orbital angular momentum will change based upon the presence and concentration of materials within the sample 2802. By measuring the amount of rotation of the image caused by the change in orbital angular momentum, the presence and concentration of a particular material may be determined.

Figure 29:
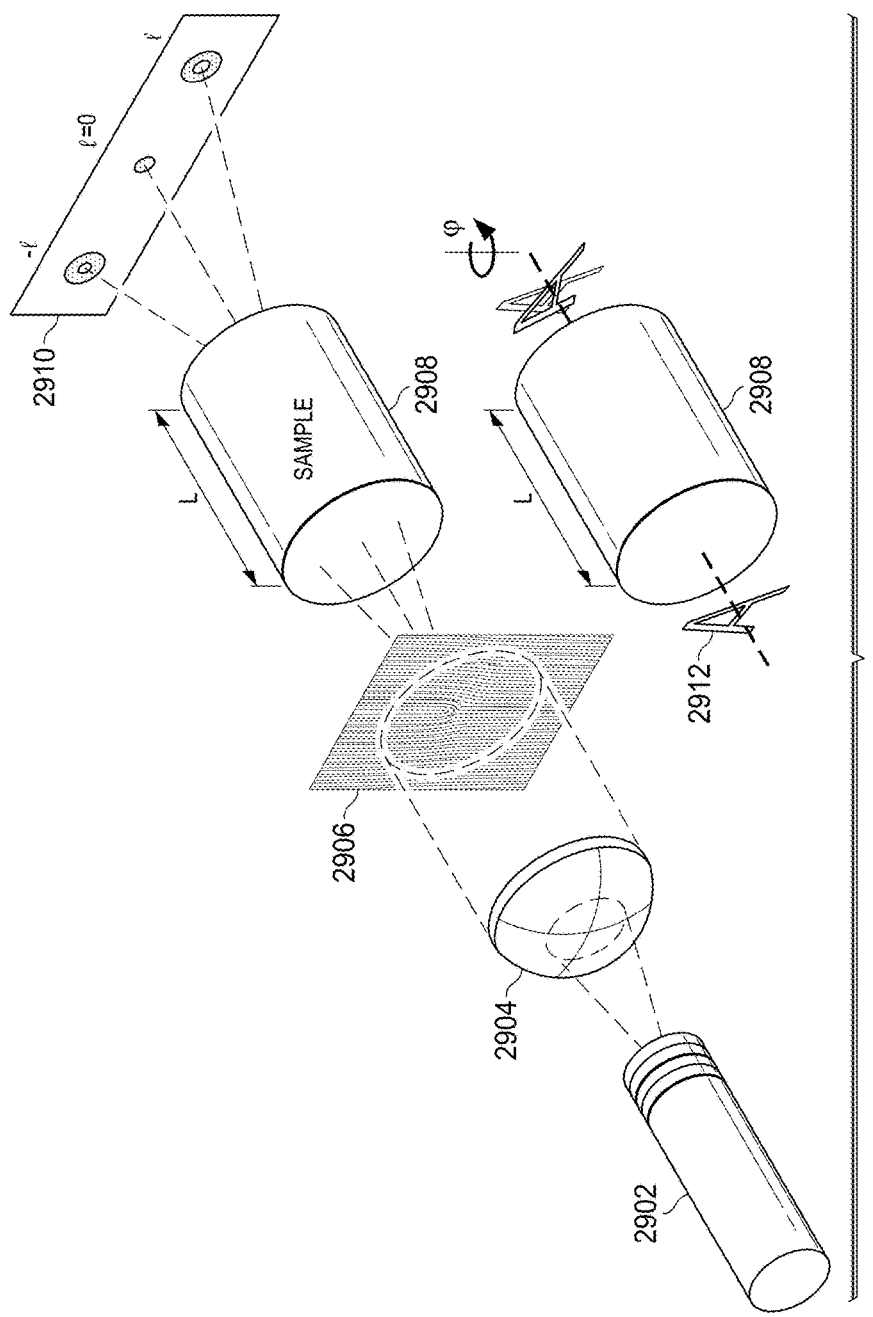
FIG. 29 more particularly illustrates the process that alters the orbital angular momentum polarization of a light beam passing through a sample.

This overall process can be more particularly illustrated in FIG. 29. A light source 2902 shines a light beam through expanding optics 2904. The expanded light beam is applied through a metalab generated hologram 2906 that imparts an orbital angular momentum to the beam. The twisted beam from the hologram 2906 is shined through a sample 2908 having a particular length L. As mentioned previously, the sample 2908 may be located in a container or in its naturally occurring state. This causes the generation of a twisted beam on the output side of the sample 2908 to create a number of detectable waves having various orbital angular momentums 2910 associated therewith. The image 2912 associated with the light beam that is applied to sample 2908 will rotate an angle $\varphi$ depending upon the presence and concentration of the material within the sample 2908. The rotation $\varphi$ of the image 2912 is different for each value orbital angular momentum $-1$ or $+1$. The change in rotation of the image $\Delta\varphi$ may be described according to the equation:

$$\Delta\varphi = \varphi_1 - \varphi_{-1} = f(l, L, C)$$

Where l is orbital angular momentum number, L is the path length of the sample and C is the concentration of the material being detected.

Thus, since the length of the sample L is known and the orbital angular momentum may be determined using the process described herein, these two pieces of information may be able to calculate a concentration of the material within the provided sample.

Figure 30:
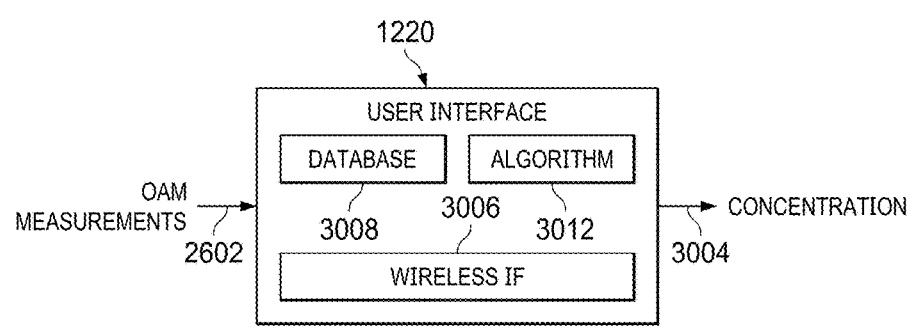
FIG. 30 provides a block diagram of a user interface of the system of FIG. 12.

The above equation may be utilized within the user interface more particularly illustrated in FIG. 30. The user interface 1220 processes the OAM measurements 3002 using an internal algorithm 3002 that provides for the generation of material and/or concentration information 3004 that may be displayed in some type of user display. The algorithm would in one embodiment utilize that equation described herein above in order to determine the material and/or concentration based upon the length of a sample and the detected variation in orbital angular momentum. The process for calculating the material and/or concentration may be done in a laboratory setting where the information is transmitted wirelessly to the lab or the user interface can be associated with a wearable device connected to a meter or cell phone running an application on the cell phone connected via a local area network or wide area network to a personal or public cloud. The user interface 3020 of the device can either have a wired or wireless connection utilizing Bluetooth, ZigBee or other wireless protocols.

Figure 31:
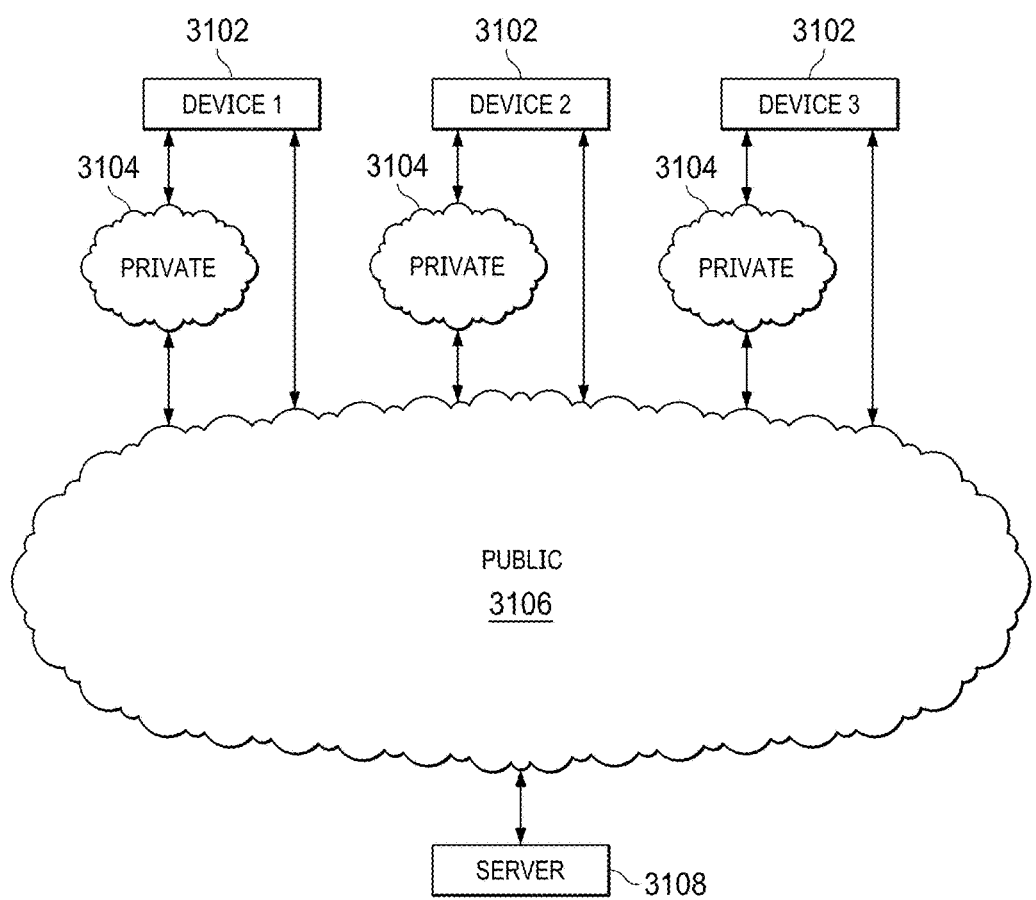
FIG. 31 illustrates a network configuration for passing around data collected via devices such as that illustrated in FIG. 15.

Referring now to FIG. 31, there is illustrated the manner in which the various data accumulated within the user interface 1220 that has been collected in the manner described herein above may be stored and utilized for higher level analysis. Various devices 3102 for collecting data as described herein above may communicate via private network clouds 3104 or with a public cloud 3106. When communicating with a private cloud 3104, the devices 3102 merely store information that is associated with a particular user device that is for use with respect to analysis of the user associated with that user device. Thus, an individual user could be monitoring and storing information with respect to their present glucose concentrations in order to monitor and maintain their diabetes.

Alternatively, when information is compiled from multiple devices 3102 within the public cloud 3106, this information may be provided directly to the public cloud 3106 from the individual devices 3102 or through the private clouds 3104 of the associated network devices 3102. Utilizing this information within the public cloud 3106 large databases may be established within servers 3108 associated with the public cloud 3106 to enable large scale analysis of various health related issues associated with the information processed from each of the individual devices 3102. This information may be used for analyzing public health issues.

Thus, the user interface 1220 in addition to including the algorithm 3002 for determining material and/or concentration information 3004 will include a wireless interface 3006 enabling the collected information to be wirelessly transmitted over the public or private cloud as described with respect to FIG. 31. Alternatively, the user interface may comprise a storage database 3008 enabling the collected information to be locally stored rather than transmitted wirelessly to a remote location.

Figure 32:
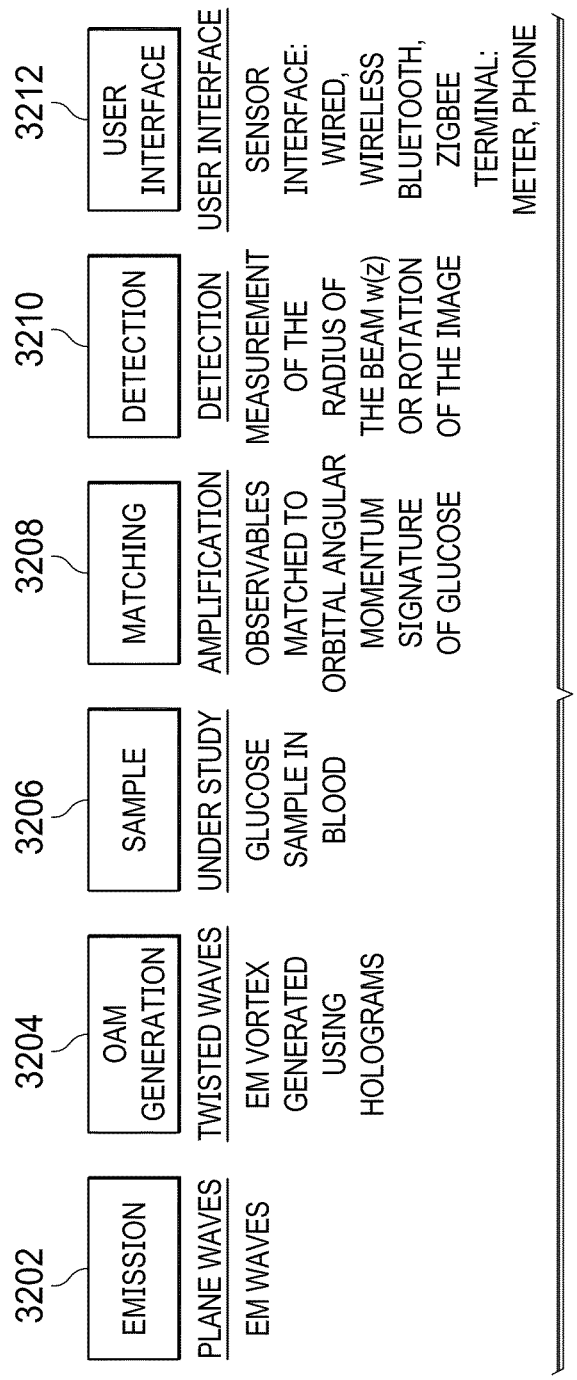
FIG. 32 provides a block diagram of a more particular embodiment of an apparatus for measuring the concentration and presence of glucose using orbital angular momentum.

Referring now to FIG. 32, there is illustrated a particular example of a block diagram of a particular apparatus for measuring the presence an concentration of glucose using the orbital angular momentum of photons of a light beam shined through a glucose sample. While the present example is with respect to the detection of glucose, one skilled in the art would realize that the example would be applicable to the detection of the presence and concentration of any material. The process creates a second-order harmonic with helical light beam using a non-linear crystal such as that described with respect to FIG. 25. The emission module 2402 generates plane electromagnetic waves that are provided to an OAM generation module 3204. The OAM generation module 3204 generates light waves having an orbital angular momentum applied thereto using holograms to create a wave having an electromagnetic vortex. The OAM twisted waves are applied to the sample 3206 that is under study in order to detect the glucose and glucose concentration within a sample. A rotated signature exits the sample 3206 in the manner described previously with respect to FIGS. 28-29 and is provided to the matching module 3208. The matching module 3208 will amplify the orbital angular momentum such that the observed concentrations may be calculated from the orbital momentum of the signature of the glucose. These amplified signals are provided to detection module 3210 which measures the radius of the beam w(z) or the rotation of the image provided to the sample via the light beam. This detected information is provided to the user interface that includes a sensor interface wired or wireless Bluetooth or ZigBee connection to enable the provision of the material to a reading meter or a user phone for the display of concentration information with respect to the sample. In this manner concentrations of various types of material as describe herein may be determined utilizing the orbital angular momentum signatures of the samples under study and the detection of these materials or their concentrations within the sample determine as described.

Provided the orthogonality of Laguerre polynomials, Laguerre Gaussian beams exhibiting orbital angular momentum (OAM) have been determined as a basis for spatial division multiplexing (SDM) in communication applications using for example a mux-demux optical element design. OAM beams are also of interest in quantum informatics. OAM also enables the probing of solutions of chiral and non-chiral molecules.

Figure 33:
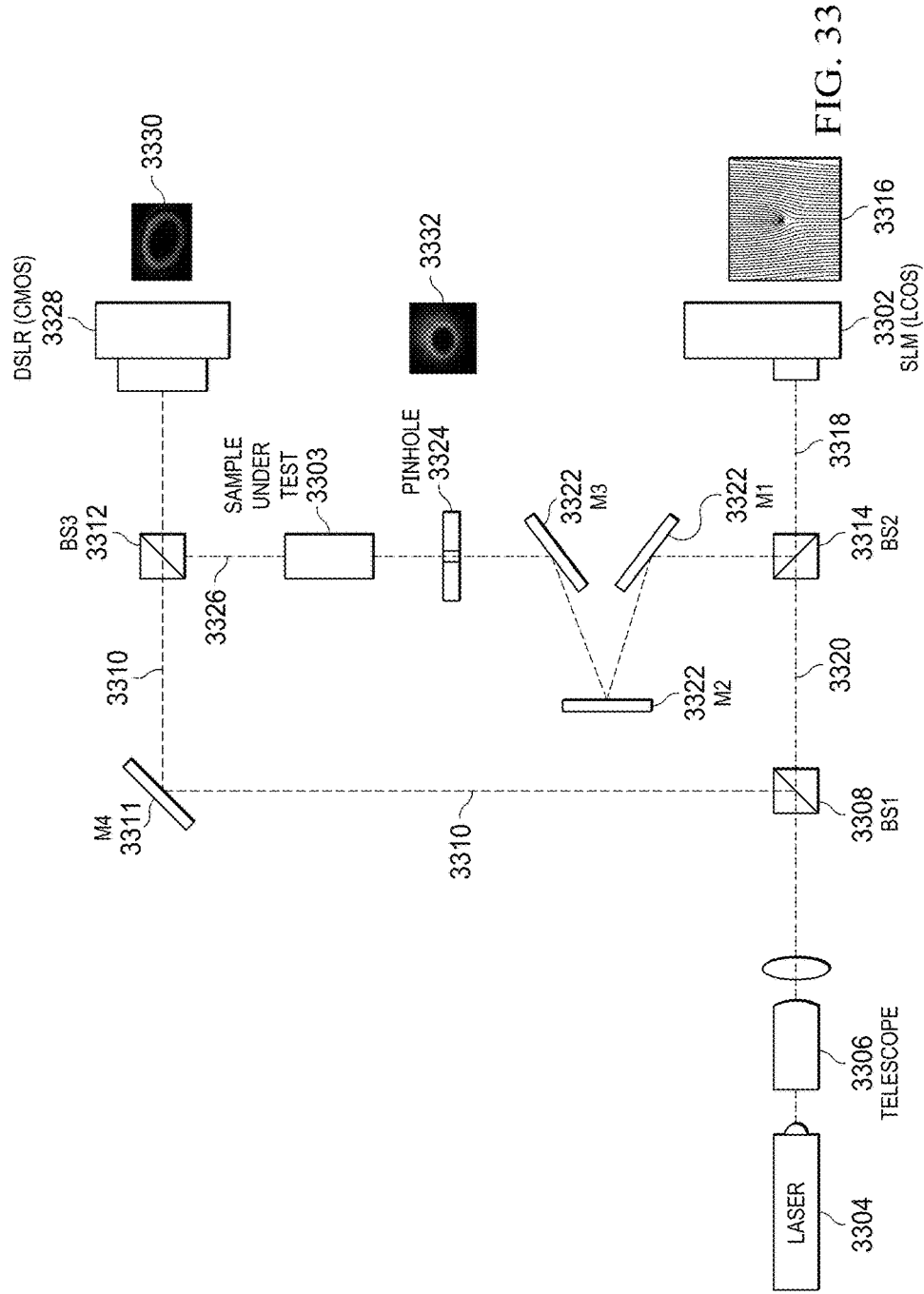
FIG. 33 illustrates an optical system for detecting a unique OAM signature of a signal passing through a sample under test.

FIG. 33 illustrates a further optical configuration for transmitting and detecting information. The twisted nematic LCOS SLM 3302 implements a 1024×768 array with 9 μm pitch and 8-bit resolution covering the visible wavelength range (430-650 nm) and readily interfaced via a VGA connection. A programmable SLM 3302 allows for the generation of a variety of engineered beams. A twisted nematic (TN) liquid crystal on silicon (LCOS) SLM is particularly useful in realizing the holograms that modulate the phase front of the input plane wave 102 (FIG. 1) or Gaussian beam. An SLM is computer addressable using common software packages such as Matlab or Mathematica to define an arbitrary two-dimensional phase shift imprinted onto the beam input using, for example, a hologram.

A collimated input beam is reflected off of a display appropriately encoded by a phase retarding forked gratings, or hologram. The generating equation for the forked gratings may be written as a Fourier series:

$$T(r,\varphi) = \sum_{m=-\infty}^{\infty} t_m \exp\left[-im\left(\frac{2\pi}{D}r\cos\varphi - l\varphi\right)\right]$$

Where r and φ are the coordinates, l is the order of the vorticity and D is the period of the rectilinear grating far from the forked pole. The weights, $t_m$, of the Fourier components of the phase grating may be written in terms of Bessel functions of integer order:

$$t_m = (-i)^m J_m(k\beta)\exp(ik\alpha).$$

Where kα and kβ bias and modulate the phase of the forked grating, respectively. Typically only a handful of terms of this series are needed to generate the OAM beams. For example, success has been had with the transfer pattern:

$$T(r,\varphi) = \frac{1}{2} - \frac{1}{2}\sin\left(\frac{2\pi}{D}r\cos\varphi - l\varphi\right)$$

Referring now back to FIG. 33, there is illustrated the optical configuration for detecting a unique signature of a signal passing through a sample under test 3303. The sample 3303 may be in a container or in its naturally occurring state. At a high-level, the instrument comprises a Mach Zehnder interferometer. One arm of the interferometer propagates a reference beam 3310. The reference beam 3310 is created by a laser 3304 generating a light beam including a plurality of plane waves that is transmitted through a telescope 3306. The plane wave light beam from the telescope 3306 passes through a first beam splitter 3308. The beam splitter 3308 generates the reference beam 3310 that is reflected from a mirror 3311 to an interfering circuit 3312. The reference beam 3310 may be a plane wave or, with the addition of a lens, a spherical wavefront may be implemented. This arm is blocked for amplitude only measurements.

In a second arm, the split plane wave beam from the beam splitter 3308 is combined at a beam combiner 3314 with the beam provided from the spatial light modulator 3302. The spatial light modulator 3302 provides a light beam including the forked hologram 3316. The beam combiner 3314 combines the forked hologram beam 3318 from the SLM 3302 and a plane wave beam 3320 from the laser 3304 to generate an OAM or other orthogonal function twisted beam of a known signature. This beam is reflected through a series of mirrors 3322 and focused on a pinhole aperture 3324 before passing the beam having the known orbital angular momentum through the sample under test 3303.

The sample twisted beam 3326 has been interfered at the signal combiner 3312 with the reference beam 3310. This interfered image may then be recorded by a camera or recording device 3328. This provides a unique OAM signature 3330 that may be analyzed in order to detect materials within the sample under test 3303. As can be seen, the unique OAM signature 3330 is different from the signature 3332 of the transmitted beam. The manner in which the signature is altered will be more fully described herein below.

In the second arm, the LCOS SLM 3302 is used to transform a collimated plane wave input beam 3320 into an OAM encoded beam. The SLM 3302 is driven by a Matlab programs on an extended laptop display to provide a display of a forked hologram of any l or ρ. Following the SLM 3302, the beam is reflected through three mirrors 3322 to provide a sufficient distance for the separation of the diffracted OAM modes such that a pinhole iris aperture 3324 may select the desired mode to pass through a sample under test 3303.

Several materials of interest may be detected with OAM signatures using the setup of FIG. 33. Examples of these materials include acetone, isopropyl alcohol, sucrose, amyloid-beta, and glucose in steam distilled water. Spectroscopic grade soda lime glass cuvettes (1 cm×2.5 cm×3 cm)

or larger custom-made circular cuvettes having BK7 cover glass in caps may be utilized for containing the sample under test 3303.

The sample under test 3303 is mounted on a translation stage arranged to allow quick and repeatable positioning in and out of the beam path either by movement of the sample or movement of the beam projection apparatus. Additionally, back reflections from the sample services are monitored carefully and blocked by irises so no spurious, secondary interactions occur. The optical power through samples is low (less than 25 μW) to avoid any refractive index dependent thermal gradients in the solution.

The insertion of wave plates, variable retarders and polarizers before and after the sample under test has not revealed any remarkable results. While glucose is well-known to have a polarimetric response at these wavelengths, the concentration path length product is too small to produce a notable shift in the state of polarization. This suggests that the OAM and glucose is a more pronounced response then polarimetry of the molecule.

Images 3330 of the beam at the output of the instrument are recorded using the high-resolution DSLR camera 3328 that is securely mounted perpendicular to the beam propagation direction and remotely triggered to prevent vibration or shift in the instrument. Measurement of ellipticity is performed using Photoshop and Matlab or similar types of image measuring and processing software or applications.

With this instrument, the change to an OAM state imparted on the input beam by a sample under test 3303 can be quantified in both intensity and phase. A series of experiments has been performed using primarily aqueous glucose solutions. A 15% stock solution was diluted to a variety of desired concentrations. Because the different isomers of the sugar interact with each other before attaining equilibrium, a settling time is required for a new or altered solution. Solutions were allowed to equilibrate overnight (approximately 15 hours), a time much longer than the recommended 2 hours, in a Cuvette that was capped to prevent evaporation.

Figure 34:
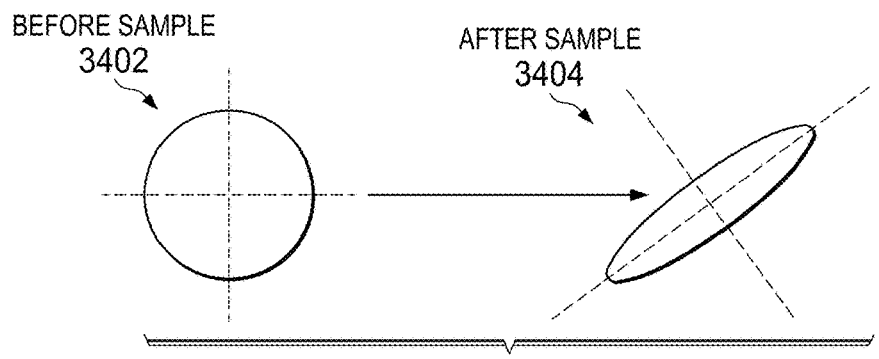
FIG. 34 illustrates the manner in which the ellipticity of an OAM intensity diagram changes after passing through a sample.
Figure 35:
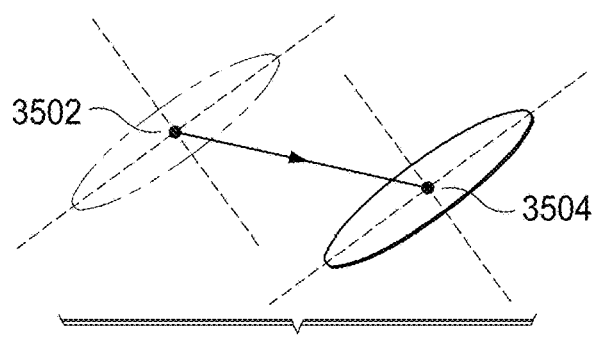
FIG. 35 illustrates the manner in which a center of gravity of an intensity diagram shifts after passing through a sample.
Figure 36:
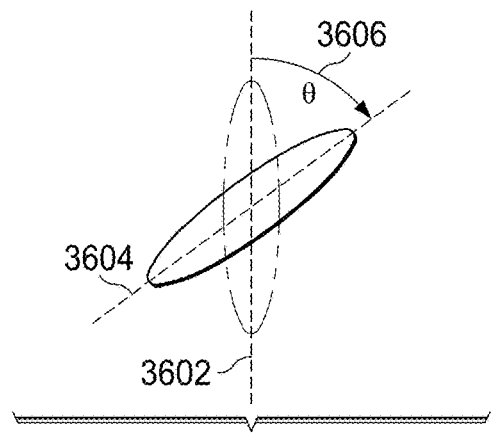
FIG. 36 illustrates the manner in which an axis of the intensity diagram shifts after passing through a sample.

As mentioned previously with respect to FIG. 1, passing through the sample 3303 causes a unique OAM signature to be imparted to the light beam passing through the sample. This unique OAM signature provides an identification of the presence of a material within the sample and of the concentration of the material within the sample. This unique OAM signature includes a number of differences from the OAM signal signature that is input to the sample 3303. The unique OAM signature characteristics are illustrated in FIGS. 34-36. FIG. 34 illustrates the manner in which the ellipticity of the OAM intensity diagram changes after passing through the sample 3303. Initially, as illustrated at 3402, the intensity diagram has a substantially circular shape from the plane wave OAM beam before passing through the sample 3303. After passing through the sample 3303, the intensity diagram has a much more elliptical shape as illustrated generally at 3404. This elliptical shape is a unique characteristic that is different depending upon a material being detected and the concentration of the substance being detected. By detecting the ellipticity of the intensity diagram, a determination may be made of the presence of a particular material within the sample.

FIG. 35 illustrates a further characteristic of the OAM signature that may be altered by passing through a sample 3303. In this case, the center of gravity of the intensity diagram has been shifted. Position 3502 illustrates the initial position of the center of gravity of the intensity diagram before passing through a sample 3303. After passing through the sample 3303, the center of gravity moves to location 3504 that is a noticeable shift from the original position prior to passing through the sample. The shift is uniquely affected by different materials. Thus, the shift in center of gravity may also be used as an OAM distinct signature characteristic with the center of gravity shift indicating the presence of a particular material and the concentration of the material. Based upon an analysis of the shift in the center of gravity of the intensity diagram, a determination of the presence and/or concentration of a material may be made.

A final distinct OAM signature characteristic is illustrated in FIG. 36. In this case, the major axis 3602 of the intensity diagram ellipse shifts from a first position 3602 to a second position 3604 over an angle θ 3606. The major axis of the intensity diagram ellipse rotates from a position 3602 to position 3604 based upon the material being detected. The angle θ is uniquely associated with a particular substance and concentration of the substance being detected. Thus, a material may be detected based upon a determined angle θ within the intensity diagram.

A mathematical model may be used to represent the unique OAM signatures provided by each of changes in eccentricity, shift or translation of the center of gravity in rotation of the axis. The change in eccentricity may be represented by:

$$\text{circle} \Rightarrow x^2 + y^2 + z^2 \Rightarrow [x \ y \ z] \begin{bmatrix} x \\ y \\ z \end{bmatrix}$$

$$\text{3-dimensional ellipse} \Rightarrow [x \ y \ z] \begin{bmatrix} \frac{1}{a^2} & 0 & 0 \\ 0 & \frac{1}{b^2} & 0 \\ 0 & 0 & \frac{1}{c^2} \end{bmatrix} \begin{bmatrix} x \\ y \\ z \end{bmatrix}$$

Where a, b, c are dimensions of the ellipse.

The change in the center of gravity may be represented by a shift or translation in space of a vector v according to the matrix:

$$\text{translation} \Rightarrow \begin{bmatrix} 1 & 0 & v_x \\ 0 & 1 & v_y \\ 0 & 0 & v_z \end{bmatrix}$$

The rotations of the axis may be represented by a series of matrices showing rotations in 3-different orientations:

$$\begin{bmatrix} 1 & 0 & 0 \\ 0 & \cos\alpha & -\sin\alpha \\ 0 & \sin\alpha & \cos\alpha \end{bmatrix} \begin{bmatrix} \cos\beta & 0 & \sin\beta \\ 0 & 1 & 0 \\ -\sin\beta & 0 & \cos\beta \end{bmatrix} \begin{bmatrix} \cos\gamma & -\sin\gamma & 0 \\ \sin\gamma & \cos\gamma & 0 \\ 0 & 0 & 1 \end{bmatrix}$$

Rotation by α  Rotation by β  Rotation by γ

In an example illustrated in FIGS. 37A and 37B there is shown the application of an OAM beam to a sample consisting only of water (FIG. 37A) and of water including a 15% glucose concentration (FIG. 37B). An l=7 OAM beam at 543 nm is propagated through a 3 cm Cuvette of only water to provide the intensity diagram illustrated in FIG. 37A. The intensity diagram illustrated in FIG. 37B is provided when the l=7 OAM beam passes through a 15% glucose solution in water. The OAM signature manifests itself as an induced ellipticity on the ordinary circular beam amplitude illustrated in the intensity diagram of FIG. 37A. The distinct signature effect may also be observed in phase diagrams such as that illustrated in FIGS. 38A and 38B. FIGS. 38A and 38B illustrate interferograms of an l=2 OAM beam at 633 nm propagating through a 3 cm cuvette of water (FIG. 38A) and a 3 cm cuvette of 15% glucose in water (FIG. 38B). In this particular interferance, the reference beams have the same spherical wave fronts. This is why essentially spiral pattern is observed in the phase measurements. Note in particular, the torsional shift in one of the 2 spirals of the phase front of the sample propagating through the glucose solution. The shift in the spiral pattern is the signature of the interaction in this experiment.

An unperturbed OAM mode propagates through several meters of free space. Glucose samples appear to impart a phase perturbation on an OAM beam causing the OAM mode to topologically be involved in the propagation direction. This effect allows for more sensitive metrology. FIG. 39 shows the amplitude of an OAM beam and FIG. 40 shows the phase of an OAM beam. The beam is an OAM l=beam and is perturbed when passing through a 3 cm Cuvette of a 5% glucose solution and a plane four meters beyond the Cuvette. The ellipticity of the beam is much more pronounced in both amplitude and phase measurements.

Figure 41:
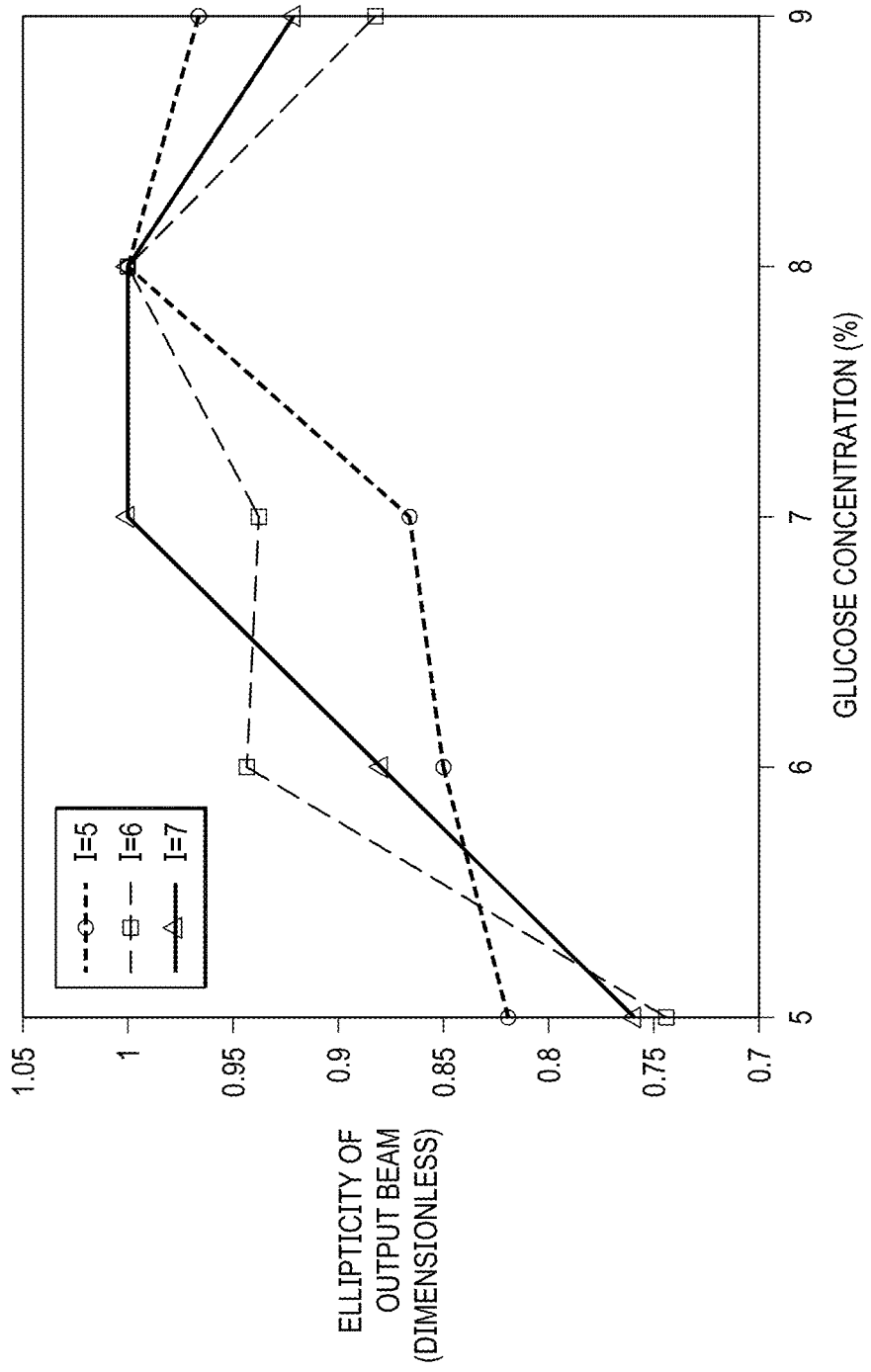
FIG. 41 is a chart illustrating the ellipticity of a beam on the output of a Cuvette for three different OAM modes.

The OAM signature is nonlinear with respect to glucose concentrations and under some conditions, appears to be somewhat periodic with concentration. The ellipticity as a function of glucose concentration is plotted in FIG. 41 using a 3 cm Cuvette, OAM modes l=5, 6, 7, for concentrations of glucose between 5% and 9% in water. Though the preliminary data is noisy, the trend persists over several OAM modes.

There is a broad absorption band for glucose centered at approximately 750 nm, with a FWHM (Full Width Half Maximum), as understood by a person of skill in the art, of approximately 250 nm. Given that the 543 nm absorbance of glucose is 4 times smaller than that for 633 nm, it is interesting that the formal wavelength provides a stronger OAM response. This suggests the interaction is based on the real part of the susceptibility, $\chi'$, rather than its imaginary part, $\chi''$. We note as well that in a separate polarimetry characterization of glucose, using sample cells as long as 20 cm, we measured a 50% larger specific rotation at 543 nm than at 633 nm. In the OAM work, however, we found no discernable change in the effect with polarization, nor did we observe a change in the state of polarization of the beam through the 3 cm samples. This is in keeping with the previous polarization studies of OAM with chiral molecules.

Figure 42A:
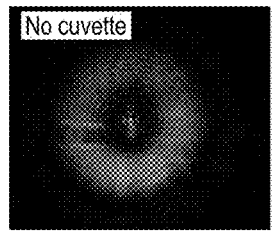
FIGS. 42A-42C illustrates the propagation due to and annulus shaped beam for a Cuvette, water and glucose.
Figure 42B:
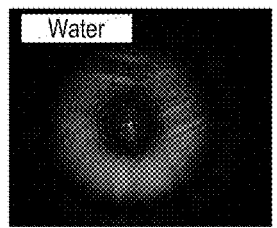
Figure 42C:
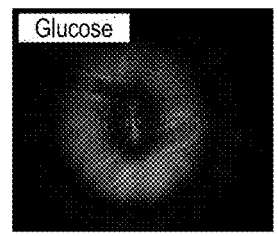

As a check for whether the vorticity of the OAM beam was important for the effect, and annulus was used to project a simple ring of light through a glucose sample. The annulus pattern was printed on a traditional plastic transparency sheet and illuminated with a magnified and collimated 543 nm laser beam. As can be seen in FIGS. 42A-42C, no distortion or signature was observed through Cuvette's of water (FIG. 42B) or Glucose (FIG. 42C) solution. Varying the ring diameter did not change these no results, even for diameters larger than the typical OAM beam. When the annulus diameter was larger than the Cuvette, obvious clipping was observed. The power level of the beams in this test was as much in order of magnitude higher than in the OAM experiments. Thus, any thermal effects would have been accentuated.

Since aqueous solutions of glucose were used in the experiments, the study of propagation of OAM in water is relevant. Steam distilled water, the solvent used in dilution, was placed in clean new cells of the variety of links and cross-sections and propagation of a variety of OAM beams through this medium was measured. No discernible differences were observed among an OAM mode propagated through a dry cell, a sample of path length 0.5 cm and a sample of 8 cm of water.

Figure 43:
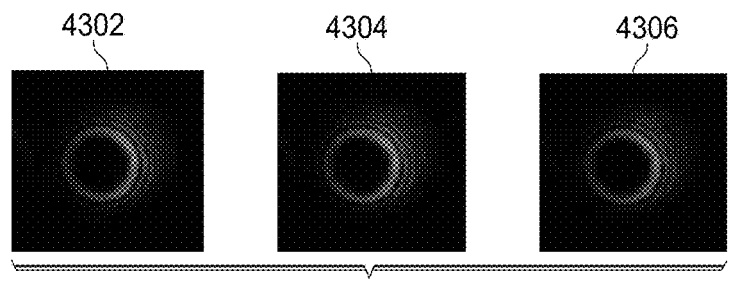
FIG. 43 illustrates OAM propagation through water for differing drive voltages.

Another null result was observed in an experiment were in an OAM beam was propagated through a liquid crystal that variable retarder. In FIG. 43, reference Nos. 4302, 4304 and 4306 show an l=7 OAM mode at the output of a variable wave plate for differing drive voltages between 0.1 V and 6 V.

Figure 44:
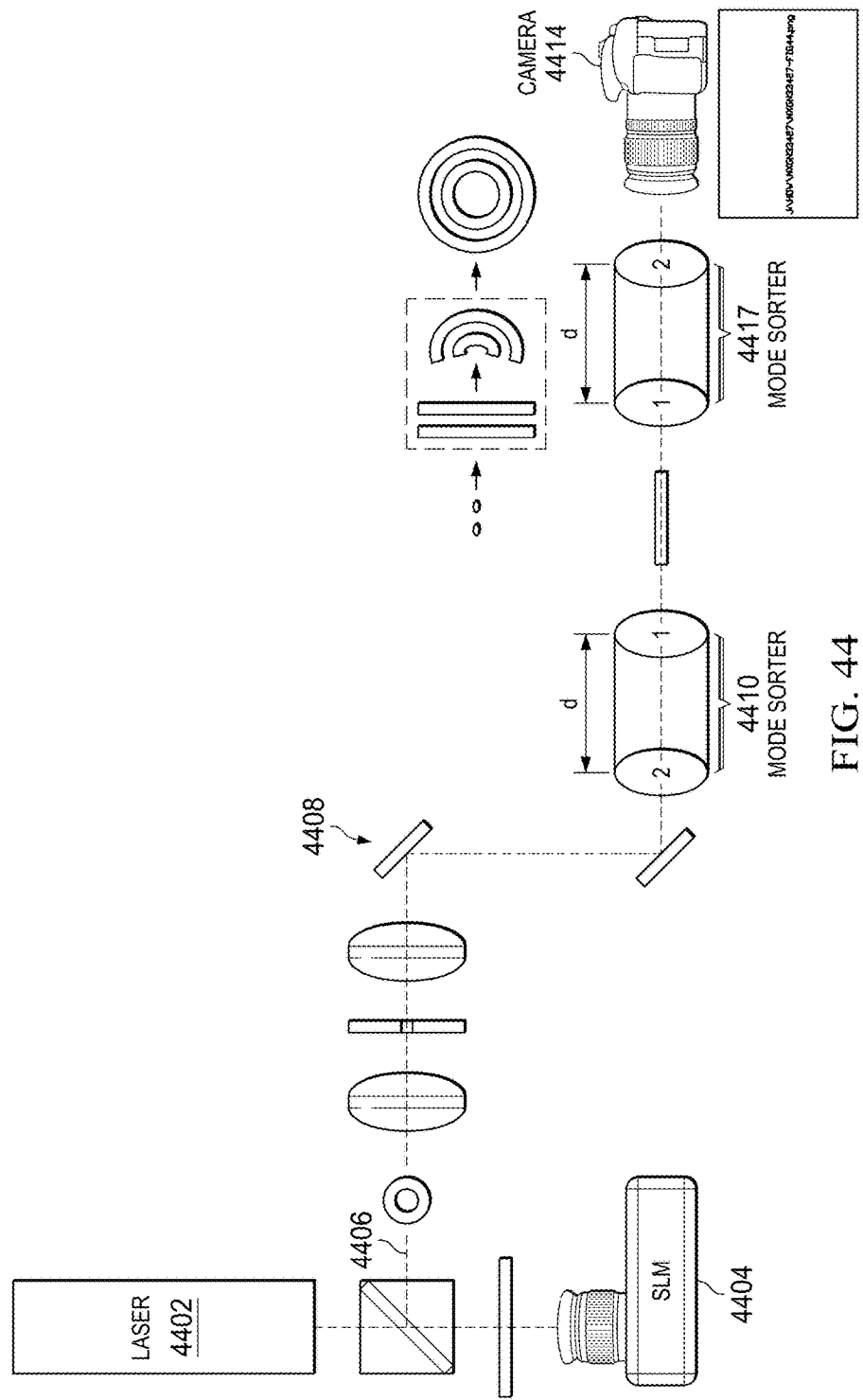
FIG. 44 illustrates an example of a light beam that is altered by a hologram to produce an OAM twisted beam.

It is been noted that the eccentricities of the intensity images produced by shining orthogonal function processed beam through a sample can have variances due to a number of differing factors. FIG. 44 illustrates an example wherein a light beam produced by a laser 4402 is altered by a hologram provided by an SLM 4404 to generate an OAM twisted beam 4406. The OAM twisted beam in addition to being altered by OAM functions may also be processed using Hermite Gaussian functions, Laguerre Gaussian functions or any other type of orthogonal function. The OAM twisted beam is focused through a system 4408 of lenses and mirrors to direct the beam through a mode sorter 4410. The beam is separated into its different modes when regenerated at mode sorter 4412 and the intensity images may be registered by a camera 4414.

Figure 45:
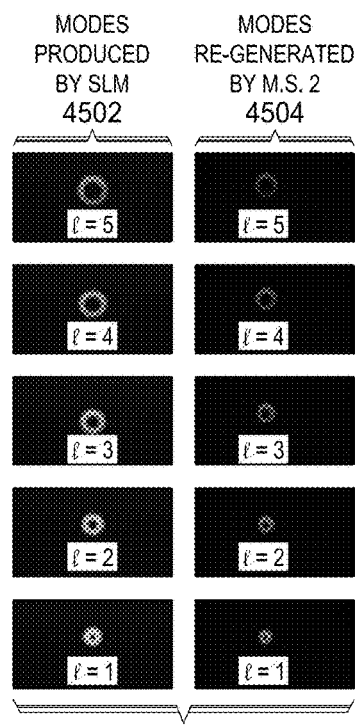
FIG. 45 illustrates various OAM modes produced by a spatial light modulator.

The beam from the laser 4402 has an inherent eccentricity of approximately 0.15. As illustrated in FIG. 45, there are illustrated various OAM modes produced by the SLM in column 4502 for l=5, 4, 3, 2, 1. As can be seen, there are differences between the eccentricity of the modes produced by the SLM, and the eccentricity of the modes regenerated by the second mode sorter 4412.

Figure 46:
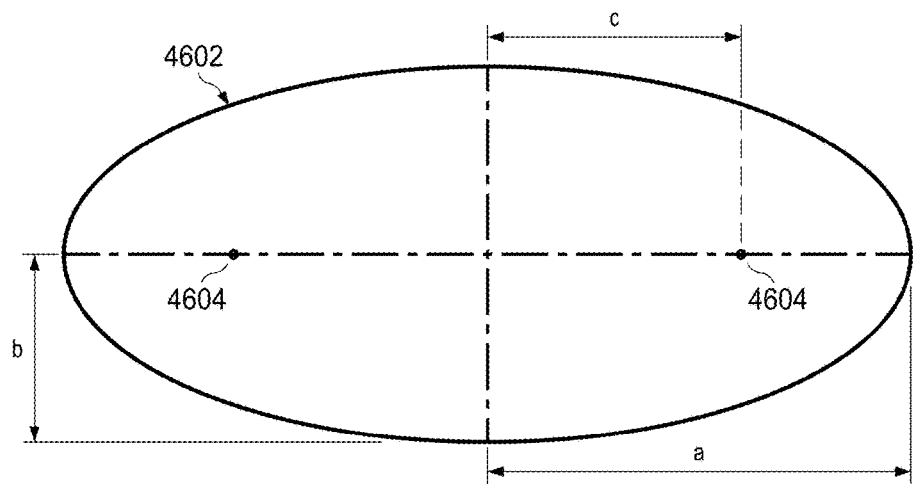
FIG. 46 illustrates an ellipse.

Measurements of eccentricity are performed using Photoshop and Matlab to identify the specific signatures. Referring now to FIG. 46, there is illustrated an example of an ellipse 4602 having a radius "a" along its long axis, a radius "b" along a short axis and a distance "c" to the foci 4604 of the ellipse. The eccentricity of the ellipse is represented by the equation eccentricity=c/a. The eccentricity varies from 0 to 1 with 0 representing a circle and 1 representing a line. The eccentricity equation is calculated according to the following equations:

$$U_{xx} = \frac{1}{N}\sum_{i=1}^{N} x_i^2 + \frac{1}{12}$$

$$U_{yy} = \frac{1}{N}\sum_{i=1}^{N} y_i^2 + \frac{1}{12}$$

$$U_{xy} = \frac{1}{N}\sum_{i=1}^{N} y_i x_i$$

$$common = \sqrt{(U_{xx} - U_{yy})^2 + 4U_{xy}^2}$$

$$2a = 2\sqrt{2}\sqrt{U_{xx}U_{yy} + common}$$

$$2b = 2\sqrt{2}\sqrt{U_{xx}U_{yy} - common}$$

$$c = \sqrt{a^2 - b^2}$$

-continued $$\text{Eccentricity} = \frac{c}{a}$$

where $x_i$ is the x location of the pixels in the ellipse; $y_i$ is the y locations of the pixels in the ellipse; and N is the number of pixels in the ellipse.

It is been found that the eccentricity is greater than 0 when no sample is present within the cuvette. A number of factors contribute to the nonzero eccentricity. OAM twisted signals have been found to provide different eccentricities based upon a number of different factors that may affect the index of refraction. These factors include things such as the sample distribution of the material within the cuvette due to gravity, the distance of the camera from the spatial light modulator and the camera angle of the camera from the spatial light modulator. Other factors affecting the eccentricity are the cuvette positioning, the index of refraction changes do to the sample, the cuvette shape and the beam incidence and exit angle from the cuvette.

Several image processing factors have also been determined not to cause changes that are outside the margin of error. Changes based on software processing errors, a circular mask that is not OAM, the sample sitting time or the sample interaction with the glass or plastic comprising the sample container may provide eccentricity changes, but the changes are not due to optical impairments caused by the cuvette orientation, camera alignment, etc. These factors do produce some changes in eccentricity, but they are within the margin of error and the majority of the eccentricity change is based on the signature of the molecule being detected.

Figure 47:
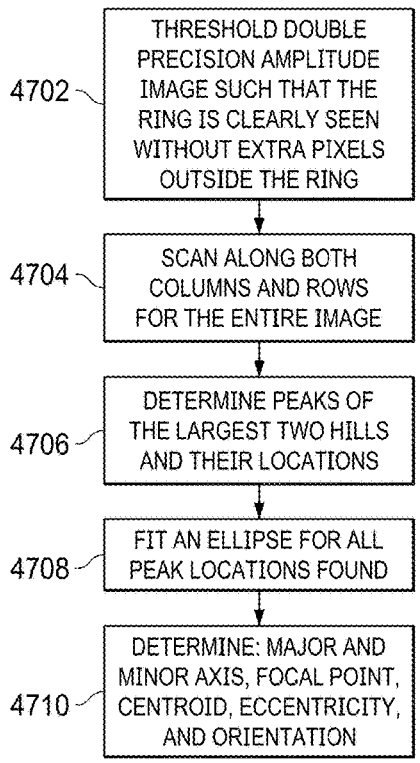
FIG. 47 is a flow diagram illustrating a process for analyzing intensity images.

Referring now to FIG. 47, there is illustrated a flow diagram for analyzing intensity images taken by the camera 4414. The intensity image has applied thereto threshold double precision amplitude to enable the ring to be clearly seen without extra pixels outside of the ring at step 4702. Next at step 4701, both columns and rows are scanned along for the entire image. The peaks of the two largest hills and their locations are determined at step 4706. An ellipse is fit at step 4008 for all peak locations found. Finally, at step 4710, a determination is made of the major and minor axis of the ellipse, the focal point of the ellipse, the centroid, eccentricity and orientation of the ellipse.

Figure 48:
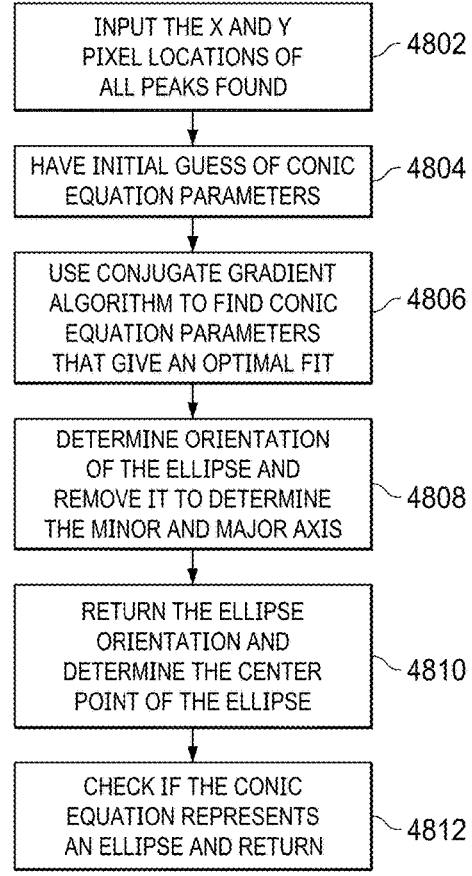
FIG. 48 illustrates an ellipse fitting algorithm.

FIG. 48 illustrates an ellipse fitting algorithm flowchart. The X and Y pixel locations are input at step 4802 for all peaks that are found. An initial guess is provided at step 4804 for the conic equation parameters. The conic equation parameters comprise parameters A, B, C, D and E for the equation $Ax^2+By^2+Cx+Dy+E=0$. The conjugate gradient algorithm is used at step 4806 to find conic equation parameters that provide an optimal fit. An orientation of the ellipse is determined at step 4808 and moved to determine the major and minor axis. The determination of step 4808 is determined according to the equation $$\phi = \frac{1}{2}\tan^{-1}\frac{B}{C-A}$$

The ellipse orientation is returned at step 4810 to determine the central point of the ellipse. Finally, at step 4812, a determination is made if the conic equation represents an ellipse. For an ellipse parameters A and B will exist and have the same sign but will not be equal. Based upon this analysis it is been determined that lateral shift of up to 1 mm can cause significant changes in the measured eccentricity due to clipping of up to 0.2.

Fractional OAM Signals

Molecular spectroscopy using OAM twisted beams can leverage fractional OAM states as a molecular signature along with other intensity signatures (i.e. eccentricity, shift of center of mass and rotation of the elliptical intensity) as well as phase signatures (i.e. changes in the phase of the scattered beam) and specific formation of publicity distributed spectrum. The method of optical orientation of electronics been by circularly polarized photons has been heavily used to study spin angular momentum in solid state materials. The process relies on spin-orbit coupling to transfer angular momentum from the spin of protons to the spin of electrons and has been Incorporated into pump-probe Kerr and Faraday rotation experiments to study the dynamics of optically excited spends. By enabling the study is spin decoherence, transport and interactions, this strategy has played a role in the development of semiconductor spintronics.

The proposed spectroscopy technique focuses instead on localized orbital angular momentum (OAM) and solids. Specifically, one can distinguish between delocalized OAM associated with the envelope wave function which may be macroscopic in spatial extent, and local OAM associated with atomic sites, which typically is incorporated into the effect of spin and associated electronic states. The former type of angular momentum is a fundamental interest to orbital fleet coherent systems, for example, quantum Hall layers, superconductors and topological insulators. Techniques to study non-equilibrium delocalized OAM in these and other systems create opportunities to improve understanding of scattering and quantum coherence of chiral electronic states, with potential implications for materials discovery.

The interaction of light with glucose in beta amyloid and the spectroscopy applications of OAM with respect to these. Additionally the transfer of OAM between acoustic and photonic modes in an elliptical fiber, the generation of Rahman sideband carrying OAM, OAM using a pleasant Monica lens, the study of optically coherent OAM in excite ons using for wave mixing in the application of linearly polarized light to create a 2-D pleasant Monica analog to OAM light in patterned sin metallic film, and the possibility of OAM light producing spin polarized vote till electronics for efficient semiconductors may also find application in these techniques.

Figure 49:
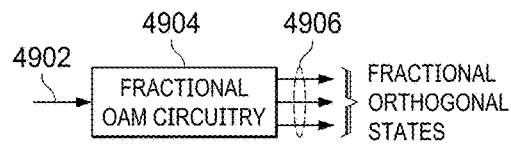
FIG. 49 illustrates the generation of fractional orthogonal states.

Referring now to FIG. 49, one manner for using nested fractional OAM states to alleviate the problems associated with integer OAM states and to enable the use of stable states of fractional OAM for similar purposes as those described herein above. In this case the input signals 4902 are provided to fractional OAM generation circuitry 4904. The fractional OAM generation circuitry 4904 generates output signals 4906 having fractional orthogonal states which may then be further applied or detected as discussed herein.

The orbital angular momentum of light beams is a consequence of their azimuthal phase structure. Light beams have a phase factor $\exp(im\varphi)$, where m is an integer and $\varphi$ is the azimuthal angle, and carry orbital angular momentum (OAM) of $m\hbar$ per photon along the beam axis. These light beams can be generated in the laboratory by optical devices, such as spiral phase plates or holograms, which manipulate the phase of the beam. In cases where such a device generates an light beam with an integer value of m, the resulting phase structure has the form of |m| intertwined helices of equal phase. For integer values of m, the chosen height of the phase step generated by the optical device is equal to the mean value of the OAM in the resulting beam.

Recently, spiral phase steps with fractional step height as well as spatial holograms have been used to generate light beams with fractional OAM states. In these implementations, the generating optical device imposes a phase change of exp(iMφ) where M is not restricted to integer values. The phase structure of such beams shows a far more complex pattern. A series of optical vortices with alternating charge is created in a dark line across the direction of the phase discontinuity imprinted by the optical device. In order to obtain the mean value of the orbital angular momentum of these beams, one has to average over the vortex pattern. This mean value coincides with the phase step only for the integer and half integer values. There are certainly more connections between optics and quantum theory to represent beams with fractional OAM as quantum states.

The theoretical description of light modes with fractional OAM is based on the generating optical device. For integer OAM values, a theoretical description may exist which provides the way to treat the angle itself as quantum mechanical Hermitian operator. The description can provide the underlying theory for a secure quantum communication system and give form to the uncertainty relation for angle and angular momentum. The theory may be generalized for fractional values of M thereby creating a quantum mechanical description of fractional OAM. Such a rigorous formulation is of particular interest is the use of half integer spiral phase plates have been used to study high dimensional entanglement. Fractional OAM states are characterized not only by the height of the phase step, but also by the orientation of the phase dislocation α. For half odd integer values of M, M mod 1=½, states with the same M but a π difference in α are orthogonal. In light of recent applications of integer OAM in quantum key distribution in the conversion of spin to orbital angular momentum in an optical medium, a rigorous formulation is important for possible applications of fractional OAM to quantum communication.

The component of the OAM in the propagation direction Lz and the azimuthal rotation angle form a pair of conjugate variables (just like time-frequency or space-momentum). Unlike linear position and momentum, which are both defined on an unbound and continuous state space, the state spaces for OAM and the rotation angle are different in nature. The OAM eigenstates form a discrete set of states with m taking on all integer values. Eigenstates of the angle operator are restricted to a $2\pi$ radian interval since it is physically impossible to distinguish between rotation angles differing by less than $2\pi$ radians. The properties of the angle operator are rigorously derived in an arbitrarily large, yet finite state space of 2 L+1 dimensions. This space is spanned by the angular momentum states |m⟩ with m ranging from $-L, -L+1, \ldots, L$. Accordingly, the $2\pi$ radian interval [θ0, θ0+2π) is spanned by 2 L+1 orthogonal angle states |θn⟩ with θn=θ0+2πn/(2L+1). Here, $\theta_0$ determines the starting point of the interval and with it a particular angle operator φ^θ. Only after physical results have been calculated within this state space is L allowed to tend to infinity, which recovers the result of an infinite but countable number of basis states for the OAM and a dense set of angle states within a $2\pi$ radian interval.

A quantum state with fractional OAM is denoted by |M⟩, where M=m+µ and m is the integer part and µ∈[0, 1) is the fractional part. The state |M⟩ is decomposed in angle states according to:

$$|M\rangle = (2L+1)^{-\frac{1}{2}} \sum_{n=0}^{2L} \exp(iM\theta_n)|\theta_n\rangle$$

$$|M\rangle = (2L+1)^{-\frac{1}{2}} \sum_{n=0}^{2L} \exp(im\theta_n)\exp(i\mu\theta_n)|\theta_n\rangle$$

It is important to note that α is bounded by 0≤α<2π, so that the orientation of the discontinuity is always understood as measured from $\theta_0$. With this construction the fractional state |M⟩ can be written as:

$$|M(\alpha)\rangle = (2L+1)^{-\frac{1}{2}} \exp(i\mu\alpha) \sum_{n=0}^{2L} \exp(iM\theta_n)\exp[i2\pi\mu f_\alpha(\theta_n)]|\theta_n\rangle$$

Figure 50:
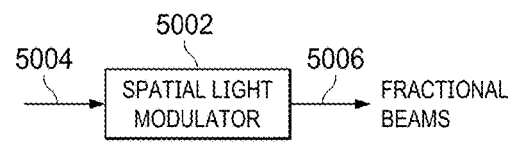
FIG. 50 illustrates the use of a spatial light modulator for the generation of fractional OAM beams.

In integer based OAM generation applications light beams may be generated using a spiral phase plate. However, light beams generated using a spiral phase plate with a non-integer phase step are unstable on propagation. However, one can generate light carrying fractional orbital angular momentum beams not with a phase step of a spiral phase plate but by a synthesis of Laguerre-Gaussian modes. This may be accomplished as illustrated in FIG. 50 using a spatial light modulator 5002. Input signals 5004 are provided to the spatial light modulator 5002 and used for the generation of fractional OAM beams 5006. The spatial light modulator 5002 synthesizes Laguerre Gaussian modes rather than using a phase step of a spiral phase plate. By limiting the number of Gouy phases in the superposition, one can produce a light beam from the SLM 5002 which is well characterized in terms of its propagation. The structural stability of these fractional OAM light beams from an SLM make them ideal for communications using fractional OAM states. Additionally as will be described herein below the beams would be useful for concentration measurements of various organic materials.

Figure 51:
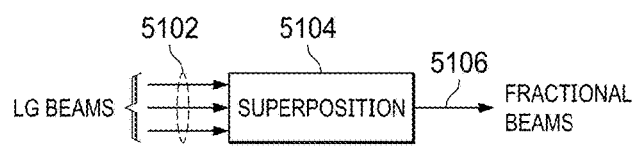
FIG. 51 illustrates one manner for the generation of fractional OAM beam using superimposed Laguerre Gaussian beams.
Figure 52:
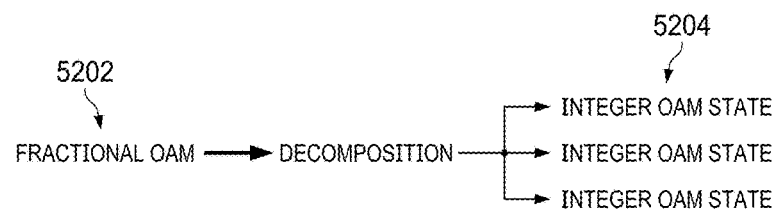
FIG. 52 illustrates the decomposition of a fractional OAM beam into integer OAM states.

Using the spatial light modulator 5002, a light beam with fractional OAM may be produced as a generic superposition of light modes with different values of m. As illustrated in FIG. 51, various Laguerre-Gaussian beam modes 5102 may have a superposition process 5104 applied thereto by the spatial light modulator 5002 in order to generate the fractional beam outputs 5106. Using the correspondence between optics and quantum theory, OAM can be represented as a quantum state. This quantum state 5202 can be decomposed into a basis of integer OAM states 5204 as generally illustrated in FIG. 52. The decomposition only determines the OAM index m which in a superposition of LG beams leaves the index for the number of concentric rings unspecified. Therefore, one can make use of this flexibility to find a representation of a fractional OAM state in terms of superimposed LG beams with a minimal number of Gouy phases to increase propagation stability. One can produce these beams using the spatial light modulator 5002 and study their propagation and vortex structure. Light beams constructed in this manner are in excellent realization of non-integer OAM states and are more stable on propagation and light emerging from fractional faced steps of a spiral phase plate.

Figure 53:
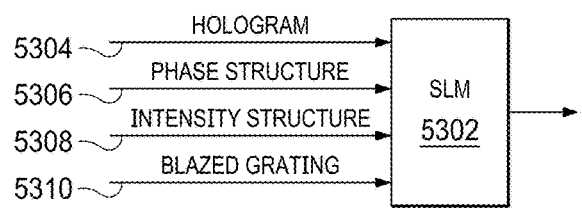
FIG. 53 illustrates the manner in which a spatial light modulator may generate a hologram for providing fractional OAM beams.

Referring now to FIG. 53, there is illustrated the manner in which an SLM may be programmed to provide fractional OAM beams. Rather than using multiple optical elements to generate each Laguerre Gaussian mode separately a single SLM 5302 may be programmed with a hologram 5304 that sets the phase structure 5306 and intensity structure 5308 for generating the superposition. A blazed grating 5310 is also included in the hologram 5304 to separate angularly the first fractional order. The formula for the resulting phase distribution of the hologram 5304 and rectilinear coordinates $\Phi(x,y)_{holo}$ is given by:

$$\Phi(x,y)_{holo} = [\Phi(x,y)_{beam} + \Phi(x,\Lambda)_{grating} \bmod 2\pi - \pi] \sin c^2[(1-I(x,y)_{beam})\pi] + \pi$$

In this equation $\Phi(x,y)$ beam is the phase profile of the superposition at the beam waist for z=0 and $\Phi(x,\Lambda)$ grating is the phase profile of the blazed grating which depends on the period of the grating $\Lambda$. The two phase distributions are added to modulo $2\pi$ and, after subtraction of $\pi$ are multiplied by an intensity mask. In regions of low intensity the intensity mask reduces the effect of the blazed grating 5310, which in turn leads to reduced intensity in the first diffraction order. The mapping between the phase depth and the desired intensity is not linear but rather given by the trigonometric sin c function.

Figure 54:
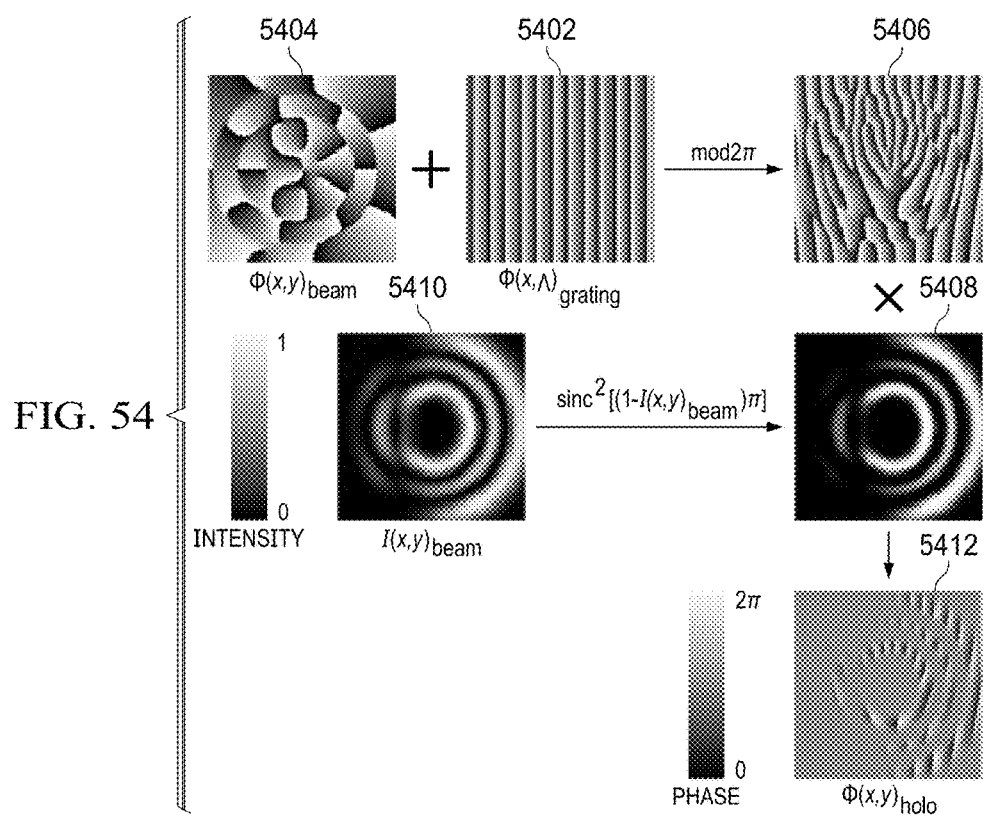
FIG. 54 illustrates the generation of a hologram to produce non-integer OAM beams.
Figure 55:
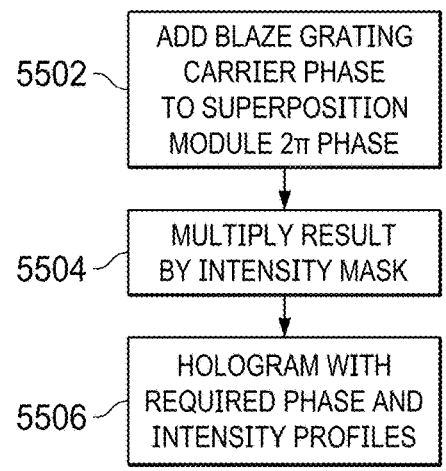
FIG. 55 is a flow diagram illustrating the generation of a hologram for producing non-integer OAM beams.

Referring now to FIG. 54 and FIG. 55, there are illustrated the steps necessary to generate a hologram for producing a non-integer OAM beam. Initially, at step 5502 a carrier phase representing a blazed grating 5402 is added to the phase 5404 of the superposition modulo $2\pi$. This combined phase 5406 is multiplied at step 5504 by an intensity mask 5408 which takes account of the correct mapping between the phase depth and diffraction intensity 3010. The resulting hologram 5412 at step 5506 is a hologram containing the required phase and intensity profiles for the desired non-integer OAM beam.

Figure 56:
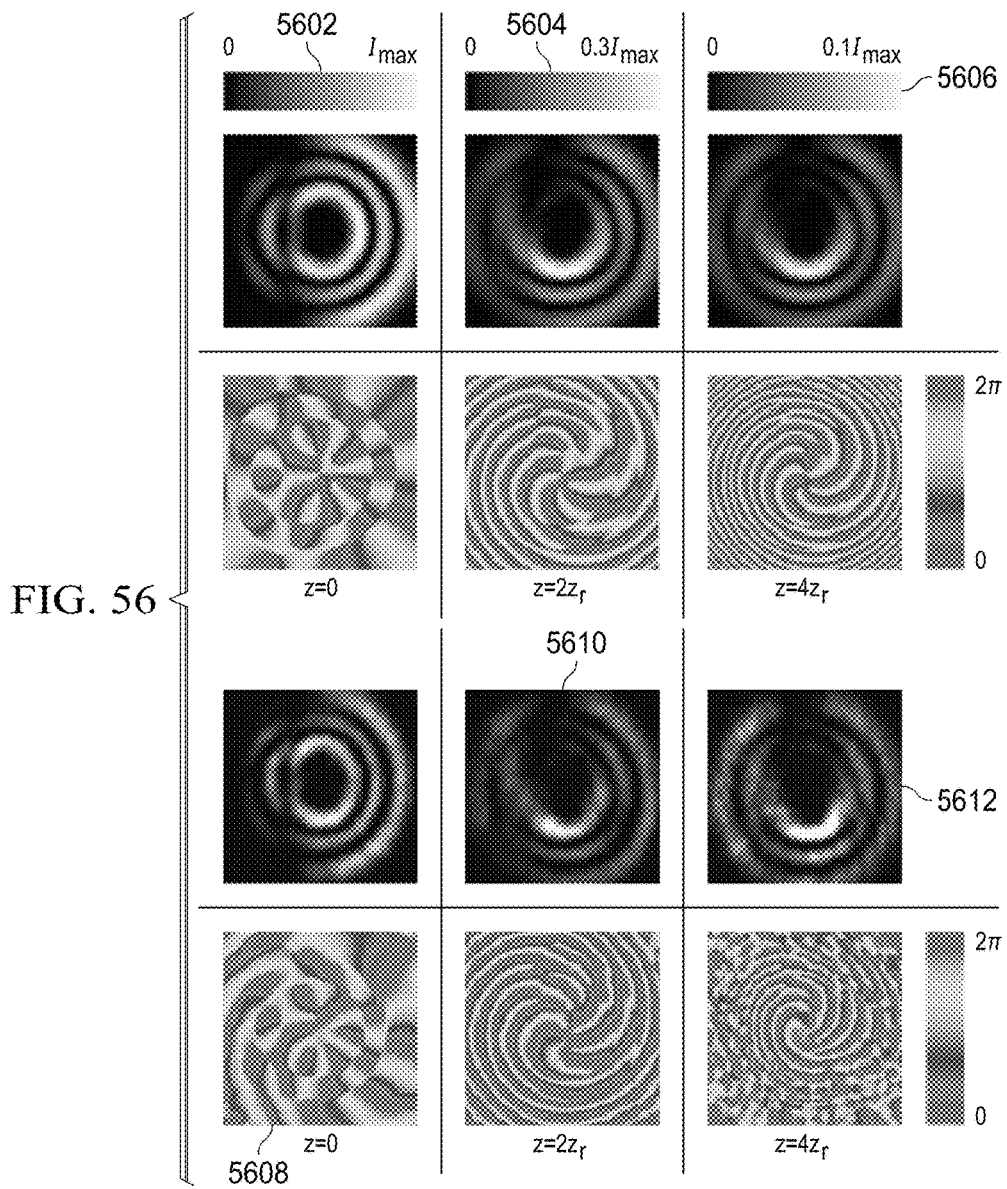
FIG. 56 illustrates the intensity and phase profiles for noninteger OAM beams.

Referring now to FIG. 56, there are illustrated the intensity and phase profiles on propagation for a superposition of 10 modes and M=6.5. Intensity and phase profiles 5602, 5604 and 5606 show a sequence of numerical plots for three different propagation distances of z=0, z=2zR and z=4zR show the changes in the phase and intensity on propagation from the waist plane into the far field. The various cross-sections are plotted over a range of ±3w(z) for each value of z. Profiles 5608, 5610 and 5612 show the corresponding experimental profiles.

Figure 57:
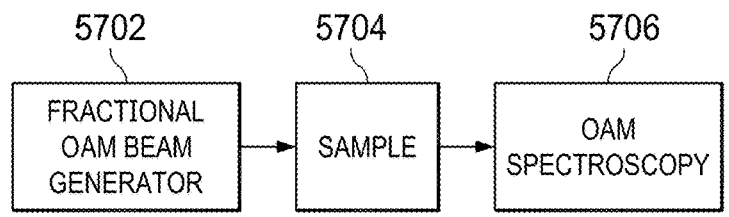
FIG. 57 is a block diagram illustrating fractional OAM beams for OAM spectroscopy analysis.

The use of fractional OAM beams may be used in a number of fashions. In one embodiment, as illustrated in FIG. 57, fractional OAM beams may be generated from a fractional OAM beam generator 5702. These fractional OAM beams are then shown through a sample 5704 in a manner similar to that discussed herein above. OAM spectroscopy detection circuitry 5706 may then be used to detect certain OAM fraction state profiles caused by the OAM beam shining through the sample 5704. Particular OAM fraction states will have a particular fractional OAM state characteristics caused by the sample 5704. This process would work in the same manner as that described herein above.

Figure 58:
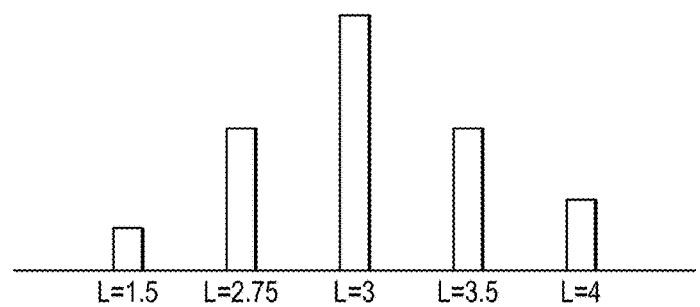
FIG. 58 illustrates an example of an OAM state profile.

FIG. 58 illustrates one example of a OAM state profile that may be used to identify a particular material within a sample. In this case, the highest number of OAM states is illustrated at L=3. Additional state levels are also illustrated at L=1.5; L=2.75; L=3.5 and L=4. This particular OAM state profile would be uniquely associated with a particular material and could be used to identify the material within a sample when the profile was detected. The interaction of Laguerre Gaussian light beams with glucose and beta amyloid have been the initial spectroscopy application of OAM to sample types.

The transfer of OAM between the acoustic and photonic modes in an optical fiber, the generation of Raman side bands carrying OAM, OAM using a plasmonic lens, the study of optically coherent OAM in excitons using four-wave mixing, the application of linearly polarized light to create a 2-D plasmonic analog to OAM light in a patterned thin metallic film and the possibility of OAM light producing spin polarized photoelectrons for efficient semiconductors are other potential spectroscopy applications.

Other means of generation and detection of OAM state profiles may also be utilized. For example a pump-probe magneto-orbital approach may be used. In this embodiment Laguerre-Gaussian optical pump pulses impart orbital angular momentum to the electronic states of a material and subsequent dynamics are studied with femto second time resolution. The excitation uses vortex modes that distribute angular momentum over a macroscopic area determined by the spot size, and the optical probe studies the chiral imbalance of vortex modes reflected off of a sample. There will be transients that evolve on timescales distinctly different from population and spin relaxation but with large lifetimes.

Multi-Parameter Spectroscopy

Figure 59:
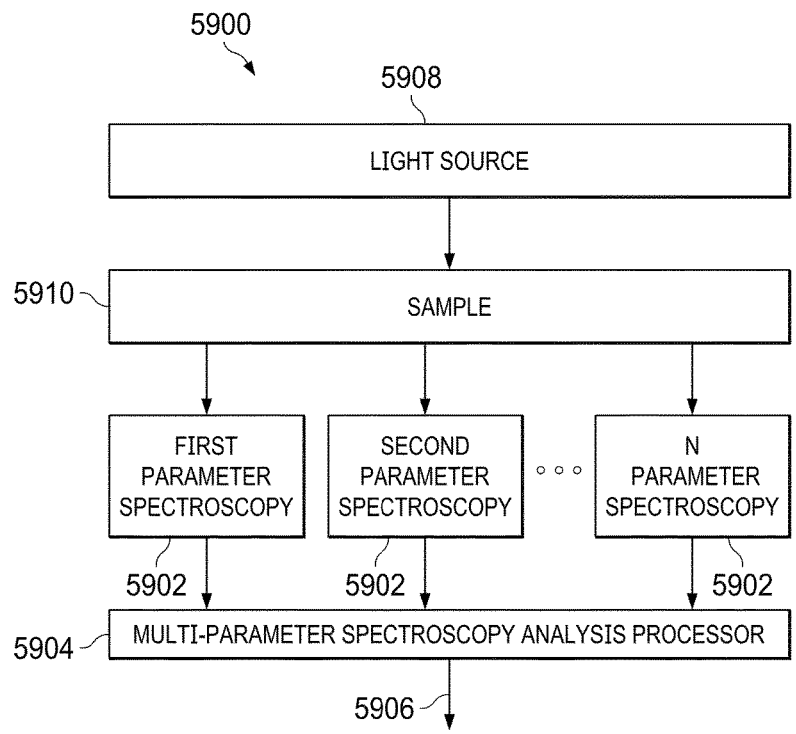
FIG. 59 illustrates the manner for combining multiple varied spectroscopy techniques to provide multiparameter spectroscopy analysis.

A further application of the OAM spectroscopy may be further refined by identifying items using a number of different types of spectroscopy to provide a more definitive analysis. Referring now to FIG. 59, there is generally illustrated a multi-parameter spectroscopy system 5900. A plurality of different spectroscopy parameters 5902 may be tracked and analyzed individually. The group of parameters is then analyzed together using multi-parameter spectroscopy analysis processor or system 5904 to determine and identify a sample with output 5906. The different spectroscopic techniques receive a light beam generated from a light source 5908, for example a laser, that has passed through a sample 5910 that a material or concentration of material therein that is being detected. While the light source of FIG. 59 illustrates a single laser and light beam, multiple light sources may provide multiple light beams or a single source may be used to provide multiple light beams. In one example, development of a single optical spectroscopy system to fully characterize the physical and electronic properties of small samples in real time may be accomplished using the polarization, wavelength, and orbital angular momentum (OAM) of light. A polarized optical source is used to characterize the atomic and molecular structure of the sample. The wavelength of the source characterizes the atomic and molecular electronic properties of the sample including their degree of polarizability. OAM properties of the source are principally used to characterize the molecular chirality, but such new techniques are not limited to chiral molecules or samples and can be applied to non-chiral molecules or samples. These three spectroscopy dimensions combine to greatly improve the process of identifying the composition of materials. Integrated into a compact hand-held spectrometer, 3D or multi-parameter spectroscopy empowers consumers with numerous applications including useful real time chemical and biological information. Combined with other pump-probe spectroscopy techniques, 3D/multi-parameter spectroscopy promises new possibilities in ultrafast, highly-selective molecular spectroscopy. While the following description discusses a number of different spectroscopy techniques that may be implemented in multi-parameter spectroscopy system 5900, it should be realized that other spectroscopy techniques may be combined to provide the multi-spectroscopy analysis system of the present disclosure.

Optical Spectroscopy

Spectroscopy is the measurement of the interaction of light with various materials. The light may either be absorbed or emitted by the material. By analyzing the amount of light absorbed or emitted, a materials composition and quantity may be determined.

Some of the light's energy is absorbed by the material. Light of a given wavelength interacting with a material may be emitted at a different wavelength. This occurs in phenomena like fluorescence, luminescence, and phosphorescence. The effect of light on a material depends on the wavelength and intensity of the light as well as its physical interaction with the molecules and atoms.

Figure 60:
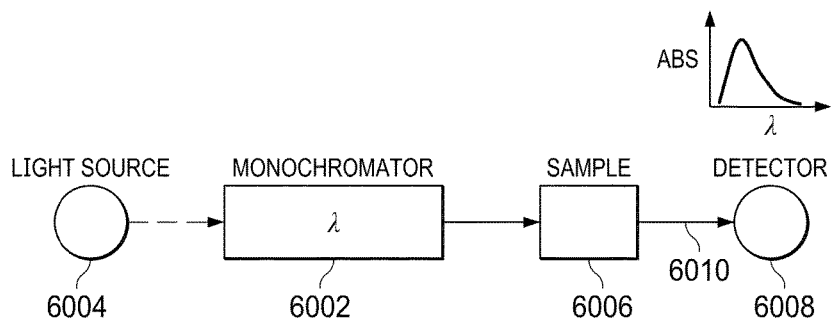
FIG. 60 illustrates a schematic drawing of a spec parameter for making relative measurements in an optical spectrum.

A schematic of a spectrometer which makes relative measurements in the optical spectral region of the electromagnetic spectrum uses light that is spectrally dispersed by a dispersing element is shown in FIG. 60. In particular, a device 6002, such as a monochromator, polychromator, or interferometer, selects a specific wavelength from a light source 6004. This single-wavelength light interacts with a sample 6006. A detector 6008 is used to measure the spectrum of light resulting from this interaction. A change in the absorbance or intensity of the resulting light 6010 is measured as the detector 6008 sweeps across a range of wavelengths. A range of different spectroscopic techniques, based on these fundamental measurements, have been developed such as those discussed in A. Hind, "Agilent 101: An Introduction to Optical Spectroscopy," 2011. (http://www.agilent.com/labs/features/2011_101_spectroscopy.html) which is incorporated herein by reference in its entirety. Here, attention is given to molecular spectroscopy techniques including infrared, Raman, terahertz, fluorescence, and orbital angular momentum spectroscopy.

Molecular Spectroscopy

Infrared Spectroscopy

Various types of molecular spectroscopy techniques may also be used in the multi-parameter spectroscopy system. These techniques include infrared spectroscopy and others.

Figure 61:
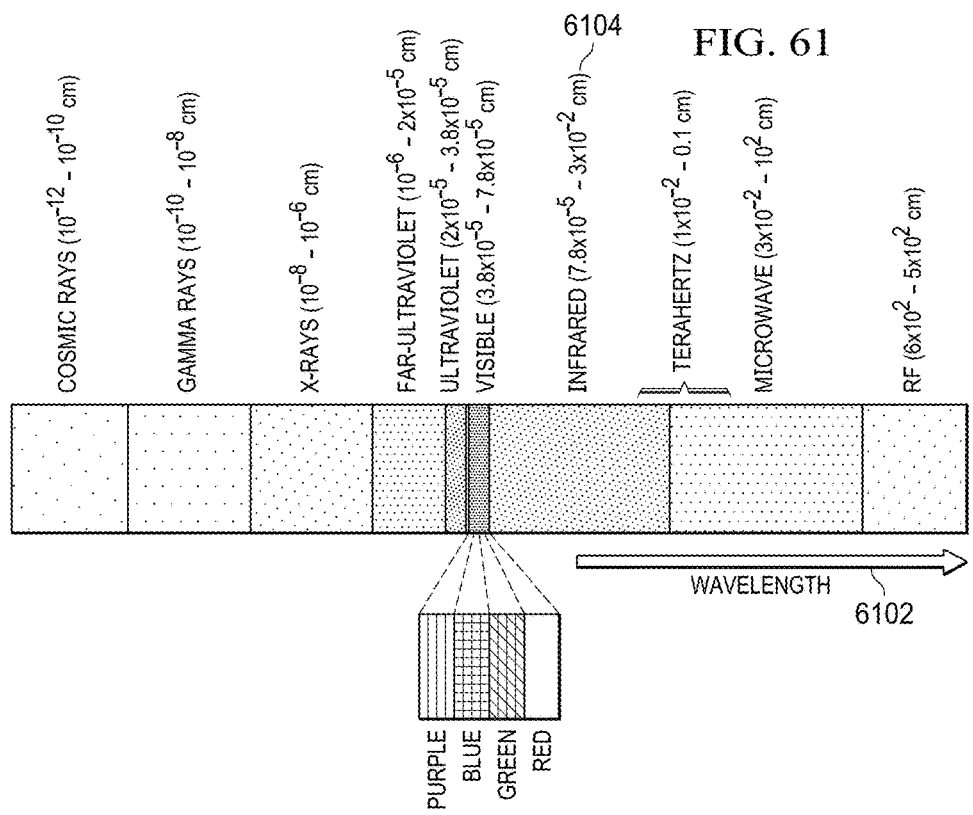
FIG. 61 illustrates an electromagnetic spectrum.

Infrared frequencies occur between the visible and microwave regions of the electromagnetic spectrum as shown in FIG. 61. The frequency, $v$, measured in Hertz (Hz), and wavelength, $\lambda$, 6102 typically measured in centimeters (cm) are inversely related according to the equations:

$$v = \frac{c}{\lambda} \text{ and } \lambda = \frac{c}{v}$$

where c is the speed of light ($3 \times 10^{10}$ cm/sec).

The energy of the light is related to $\lambda$ and $v$ by $$E = hv = \frac{hc}{\lambda}$$

where h is Planck's constant ($h = 6.6 \times 10^{-34}$ J·s).

The infrared (IR) spectrum 6104 is divided into three regions: the near-, mid-, and far-IR. The mid IR region includes wavelengths between $3 \times 10^{-4}$ and $3 \times 10^{-3}$ cm.

In the process of infrared spectroscopy, IR radiation is absorbed by organic molecules. Molecular vibrations occur when the infrared energy matches the energy of specific molecular vibration modes. At these frequencies, photons are absorbed by the material while photons at other frequencies are transmitted through the material.

Figure 62:
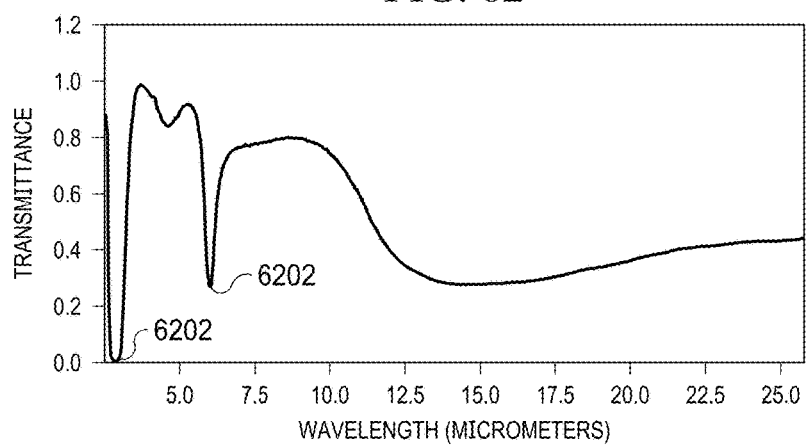
FIG. 62 illustrates the infrared spectrum of water vapor.

The IR spectrum of different materials typically includes unique transmittance, T, peaks and absorbance troughs occurring at different frequencies such as the measured IR spectrum of water vapor shown in FIG. 62.

The absorbance, A, is related to the transmittance by $$A = \log_{10}(1/T).$$

Each material exhibits a unique infrared spectral fingerprint, or signature, determined by its unique molecular vibration modes which permit identification of the material's composition by IR spectroscopy. In the case of water vapor (FIG. 62), for example, the water molecules absorb energy within two narrow infrared wavelengths bands that appear as absorbance troughs 6202.

Molecular Vibrations

Figure 63:
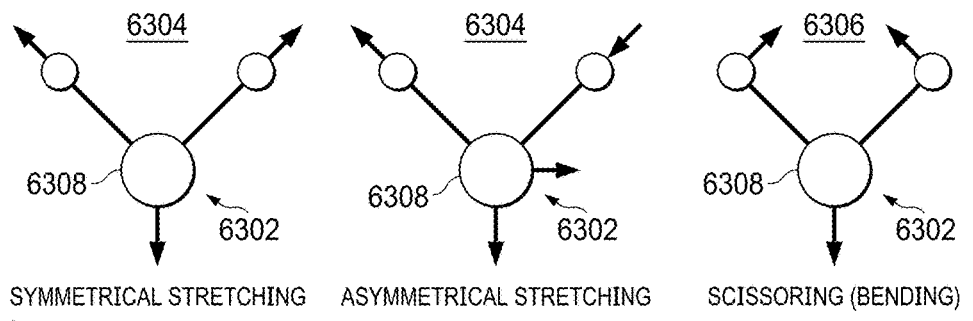
FIG. 63 illustrates the stretching and bending vibrational modes of water.

Referring now to FIG. 63, water molecules exhibit two types of molecular vibrations: stretching and bending. A molecule 6302 consisting of n atoms 6308 has 3n degrees of freedom. In a nonlinear molecule like water, three of these degrees are rotational, three are translational, and the remaining correspond to fundamental vibrations. In a linear molecule 6302, two degrees are rotational and three are translational. The net number of fundamental vibrations for nonlinear and linear molecules is therefore, 3n−6 and 3n−5, respectively.

For water vapor, there are two strong absorbance troughs 6202 (FIG. 62) occurring at approximately 2.7 µm and 6.3 µm as a result of the two stretching vibrational modes 6304 of water vapor and its bending mode 6306, respectively. In particular, the symmetric and asymmetric stretching modes 6304 absorb at frequencies in very close proximity to each other (2.734 µm and 2.662 µm, respectively) and appear as a single, broader absorbance band in FIG. 62 between the troughs 6202.

Figure 64:
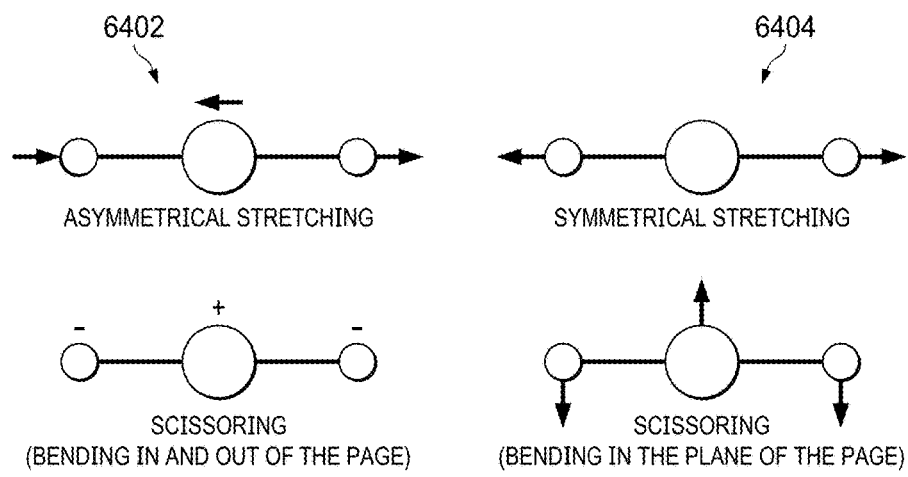
FIG. 64 illustrates the stretching and bending vibrational modes for CO2.
Figure 65:
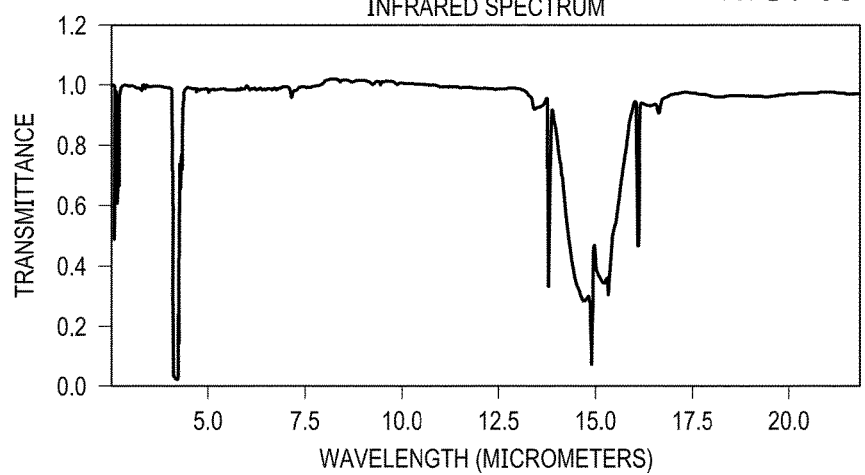
FIG. 65 illustrates the infrared spectrum of carbon dioxide.

Carbon dioxide, $CO_2$, exhibits two scissoring and bending vibrations 6402, 6404 (FIG. 64) that are equivalent and therefore, have the same degenerate frequency. This degeneracy appears in the infrared spectrum of FIG. 65 at $\lambda = 15$ µm. The symmetrical stretching vibrational mode 6404 of $CO_2$ is inactive in the infrared because it doesn't perturb its molecular dipole moment. However, the asymmetrical stretching vibration mode 6402 of $CO_2$ does perturb the molecule's dipole moment and causes an absorbance in $CO_2$ at 4.3 µm as shown in FIG. 65.

Both molecular stretching and bending vibration modes of molecules (FIGS. 63 and 64) can be predicted to useful theoretical approximation using simple classical mechanics models.

Stretching Vibrations

The stretching frequency of a molecular bond may be approximated by Hooke's Law when treated as a simple classical harmonic oscillator consisting of two equal masses bound by a spring $$v = \frac{1}{2\pi}\sqrt{\frac{k}{m}}$$

where k is the force constant of the spring and m is the mass of an atom.

In the classical harmonic oscillator, the energy depends on the extent to which the spring is stretched or compressed, $$E = \frac{1}{2}kx^2 = hv$$

where x is the displacement of the spring. The classical model of Hooke's Law, however, is inconsistent with the absorbance of energy by molecules as it would suggest that energy of any frequency is absorbed. In real molecules, vibrational motion is quantized and appropriately modeled by the quantum mechanical expression, $$E_n = \left(n + \frac{1}{2}\right)hv$$

where n is the principal quantum number (n=0, 1, 2, 3 . . . ) characteristic of each permitted energy level.

The lowest energy level is $E_0=\frac{1}{2}$ hv followed by $E_1=3/2$ hv. Only transitions to the next energy level are allowed according to the selection rule. Subsequently, molecules absorb photonic energy in integer increments of hv. For photon absorption energies of 2 hv or 3 hv, however, the resulting absorbance bands are called overtones of the infrared spectrum and are of lesser intensity than fundamental vibrational bands.

Figure 66:
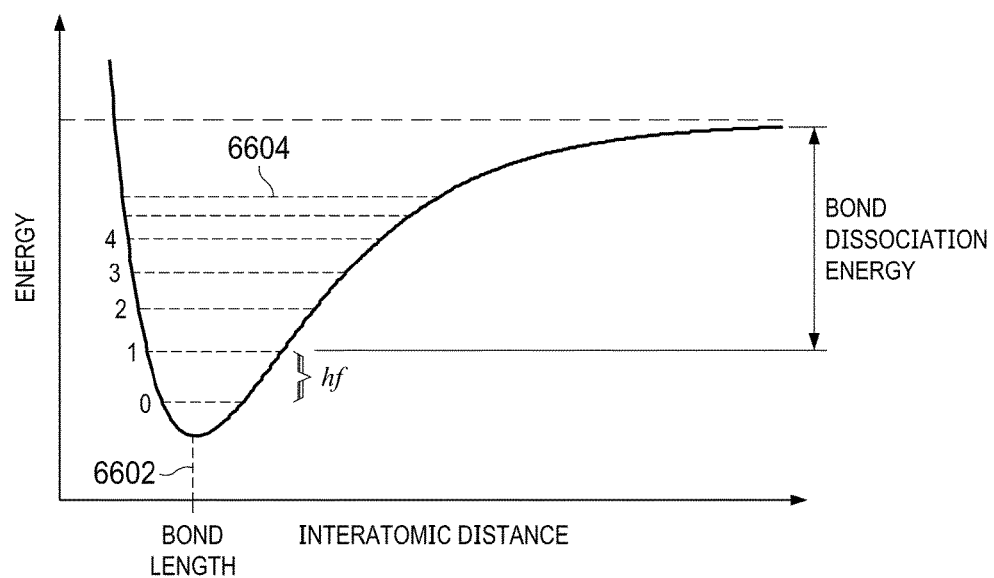
FIG. 66 illustrates the energy of an anharmonic oscillator as a function of the interatomic distance.

Atomic bonds within molecules may come apart if stretched too far and cannot be compressed beyond a certain point. As such, molecules are actually anharmonic oscillators. The energy of an anharmonic oscillator as a function of the interatomic distance is shown in FIG. 66 with an energy minimum occurs at the normal bond length 6602 (equivalent to a relaxed classical mechanical spring). As the interatomic distance increases the quantized energy levels 6604 become more closely spaced and the energy reaches a maximum. The allowed transitions, hv become smaller in magnitude which gives lower overtone energies than would otherwise be predicted using the simply harmonic oscillator theory depicted in FIG. 67.

Though this mathematical framework represents a useful, if not simple, approximation, the vibrational activity between two atoms in a large molecule cannot be isolated from the vibrational behavior of other atoms in the molecule. Vibrations of two bonds within a molecule may be coupled in such a manner that one contracts or expands while the other contracts as in either asymmetrical or symmetrical stretching vibrations. When this occurs different absorbance frequency bands are observed instead of superimposed, or degenerate, bands as observed when two identical atoms in a bond vibrate with an identical force constant.

Infrared spectroscopy is used to identify material species by their unique vibrational and rotational optical signatures. A complementary spectroscopy technique, Raman spectroscopy is used to identify materials by their unique light-scattering signatures as discussed in the next section.

Raman Spectroscopy

Since Raman spectroscopy is a technique used to characterize a material by the amount of light it scatters. Raman spectroscopy complements infrared spectroscopy which instead measures the amount of light absorbed by a material. Raman and infrared spectroscopy may further be used in conjunctions with OAM and polarization spectroscopy to further improve analysis results. When light interacts with matter, changes in the dipole moment of its molecules yield infrared absorption bands while changes in their polarizability produce Raman bands. The sequence of observed energy bands arises from specific molecular vibrations which collectively produce a unique spectral signature indicative of each type of molecule. Certain vibrational modes occurring in Raman spectroscopy are forbidden in infrared spectroscopy while other vibrational modes may be observed using both techniques or a multi-parameter technique using OAM. When these latter modes are common to both techniques, their intensities differ significantly.

The most frequent interaction of photons with molecules results in Rayleigh scattering in which photons are elastically scattered as the result of excited electrons that decay to their original energy level. Consequently, Rayleigh scattered photons have the same energy as incident photons.

With the discovery of inelastic photonic scattering phenomena in 1928 by C. V. Raman and K. S. Krishnan, Raman spectroscopy was established as a practical chemical analysis method useful to characterize a wide variety of chemical species including solid, liquid, and gaseous samples. Solid crystal lattice vibrations are typically active in Raman spectroscopy and their spectra appear in polymeric and semiconductor samples. Gaseous samples exhibit rotational structures that may be characterized by vibrational transitions.

Approximately one percent of incident photons scatter inelastically, and yield lower energy photons. Raman scattering results from changes in the vibrational, rotational, or electronic energy of a molecule. The vibrational energy of the scattering molecule is equivalent to the difference between incident and Raman scattered photons. When an incident photon interacts with the electric dipole of a molecule, this form of vibronic spectroscopy is often classically viewed as a perturbation of the molecule's electric field. Quantum mechanically, however, the scattering event is described as an excitation to a virtual energy state lower in energy than a real electronic transition with nearly coincident decay and change in vibrational energy. Such spectroscopy can work in conjunction with incident photons that carry OAM. In Raman spectroscopy, incident photons excite electrons to a different final energy level than its original energy level (FIG. 68).

Since the intensity of Raman scattering is low, heat produced by the dissipation of vibrational energy does not yield an appreciable rise in material temperature. Such Raman spectroscopy can work in conjunction with incident photons that carry OAM. At room temperature, the population of vibrationally excited states is small. Stokes-shifted scattering events shown in FIG. 68 are typically observed in Raman spectroscopy since at room temperature the excited vibrational states are low and the electron originates in the ground state. The inelastic Raman scattered photon 6802 has lower energy than the incident photon 6804 as the electron decays to an energy level 6806 higher than the original ground state 6808. Anti-Stokes shifted scattering events 6810 result from a small fraction of molecules originally in vibrationally excited states (FIG. 68) which leave them in the ground state 6812 and results in Raman scattered photons with higher energy. At room temperature, anti-Stokes shifted Raman spectra are always weaker than Stokes-shifted spectrum since the Stokes and anti-Stokes spectra contain the same frequency information. Most Raman spectroscopy focuses exclusively on Stokes-shifted scattering phenomena for this reason.

The force constant by which the vibrational mode energy may be modeled is affected by molecular structure including atomic mass, molecular species, bond order, and the geometric arrangement of molecules. However, Raman scattering occurs when the polarizability of molecules may be affected.

The polarizability, $\alpha$, of a molecule appears as a proportionality constant between the electric field and the induced dipole moment, $$P=\alpha E.$$

The induced dipole scatters a photon at the frequency of the incident photon (Rayleigh scattering). Molecular vibration, however, may change the polarizability and give rise to inelastic Raman scattering of photons. Changes in polarizability may be expressed by $$\frac{\partial \alpha}{\partial Q} \neq 0$$

where Q is in a direction normal to the vibration, and is considered a selection rule for Raman-active vibrations.

Raman-active vibrations are non-existent in the infrared for molecules having a center of symmetry while the existence of a perturbed symmetry center (e.g. permanent dipole moment) indicates the absence of infrared-active vibrations.

The intensity of a Raman band is proportional to the square of the spatial change of polarizability, or the induced dipole moment, $$I_{Raman} \propto \left(\frac{\partial \alpha}{\partial Q}\right)^2.$$

Hence, incident photons that slightly induce a dipole moment will yield a Raman band with a very small intensity. Stronger Raman scattering systems are those with higher values of α such as molecules having double carbon bonds which exhibit more broadly distributed electrons susceptible to polarization. Subsequently, the range of chemical concentrations measurable by Raman spectroscopy is considerably wide given that the scattering intensity is directly proportional to concentration.

Raman spectroscopy exhibits several advantages over other spectroscopy techniques. Raman bands exhibit good signal-to-noise ratios owing to its detection of fundamental vibrational modes. Hence, the Raman signature of measured samples is typically more pronounced and definitive.

Raman spectroscopy is more useful for analyzing aqueous solutions than infrared spectroscopy since the Raman spectrum of water is weak and unobtrusive while the infrared spectrum of water is very strong and more complex. In organic and inorganic chemistries, the existence of covalent bonds yields a unique Raman signature. A Raman spectroscopy setup only requires an appropriate laser source incident on a material and a detector to collect scattered photons which minimizes the need for elaborate sample preparation. Raman spectroscopy is non-destructive as the material is merely illuminated with a laser. Because the Raman effect is weak, the efficiency and optimization of a Raman spectroscopy instrument is critically important to providing measurements of the slightest molecular concentrations within the shortest possible time.

Spontaneous Raman Spectroscopy

The intensity of spontaneous Raman scattering is linearly dependent on the incident intensity of light but of several orders of magnitude less intense. Treating the light-matter interaction quantum mechanically, the total Hamiltonian may be expressed in terms of the energy associated with the vibrational modes of the molecule, H_v, the light, H_γ, and their interaction, H_vγ.

$$H=H\_v+H\_\gamma+H\_v\gamma.$$

In this framework $$H\_v=\tfrac{1}{2}m(p^2+\omega\_0^2 q^2)$$

with vibrational frequency ω_0 and the normal mode amplitude q which may be expressed in terms of creation and annihilation operators of the molecular vibrations, $$q=\sqrt{(2\pi\hbar/(8\pi^2\mu\omega\_0))}[b^\dagger+b]$$

with the electric dipole moment μ. This leaves $$H\_v=\hbar\omega\_0(b^\dagger b+\tfrac{1}{2}).$$

Using creation and annihilation operators for light, a^† and a, field quantization is obtained, $$E\_\lambda=\sqrt{((2\pi h\nu\_L)/(\varepsilon V\_{int}))}\Sigma\_(k\_\lambda) \llbracket e\_(k\_\lambda)i [ak\_\lambda^\dagger-ak\_\lambda] \rrbracket$$

where e_(k_λ) is the field polarization unit vector field and V_int the interaction volume. The Hamiltonian for the light is then $$H\_\gamma=\Sigma\_(k\_\lambda) \llbracket \hbar\omega\_(k\_\lambda)(a\_(k\_\lambda)^\dagger a\_(k\_\lambda)+\tfrac{1}{2}) \rrbracket.$$

Using the first order perturbation of the electric dipole approximation the interaction Hamiltonian may be obtained in terms of the molecule's polarizability, α, $$(H\_{int}\&=\&``E"\cdot\alpha\cdot``E"@\&=\&``E"\cdot\alpha\_0\cdot``E"+(\partial\alpha/\partial q)\_0``E"\cdot q\cdot``E"+\ldots)$$

within the local coordinate system, q. The first term characterizes Rayleigh scattering. The remaining first order Raman scattering term is needed to characterize spontaneous Raman scattering including the coherent laser field, "E"_L, in addition to the Stokes and anti-Stokes fields, "E"_S and "E"_AS, respectively. Substituting q and E_γ into this expression yields $$\blacksquare(H\_{int}\&=\&H\_\gamma S+H\_\gamma AS@\&\sim\&(\partial\alpha/\partial q)\_0\Sigma\_{(k\_Sk\_L)} \llbracket \sqrt{((2\omega\_L\omega\_s)/\omega\_0)}(e\_(k\_L)``\cdot"e\_(k\_s))(a\_(k\_S)^\dagger b^\dagger a\_(k\_L)``+"a\_(k\_S)ba\_(k\_L)^\dagger)\delta(k\_L``-"k\_S``-"k\_v) \rrbracket )+(\partial\alpha/\partial q)\_0\Sigma\_{(k\_ASk\_L)} \llbracket \sqrt{(((2\omega\_L\omega\_{AS}))/(\omega\_0))}(e\_(k\_L)``\cdot"e\_(k\_{AS}))(a\_(k\_{AS})^\dagger ba\_(k\_L)``+"a\_(k\_{AS})b^\dagger a\_(k\_L)^\dagger)\delta(k\_L``-"k\_{AS}``+"k\_v) \rrbracket$$

where H_γS and H_γAS are the interaction Hamiltonians of the Stokes and anti-Stokes branches, respectively.

The steady state transition rate between the initial, |i⟩, and final, |f⟩ states is given according to Fermi's golden rule, $$W\_(i\to f)=2\pi/\hbar|\langle f|H\_{int}|i\rangle|^2\rho(\hbar\omega\_f).$$

In the simple harmonic oscillator picture, the eigenstates, |n_v⟩ with excitation quanta n_v are acted upon by creation and annihilation operators to yield the Stokes and anti-Stokes transition rates $$W\_(n\_v)\to n\_v+1,\text{"and"} W\_(n\_v)\to n\_v-1\sim n\_v.$$

Hence, it is easy to determine n_v from the Raman signal intensity given a linear dependence.

Raman intensities from each vibrational level are used to identify unique vibrational molecular modes and characterize the material's composition The integrated anti-Stokes intensity of a Raman mode is proportional to the average vibrational quantum number of the mode, ⟨n_v⟩, $$I\_{AS}=A(E\_R/(h\nu\_R))=A\langle n\_v\rangle$$

where A is the Raman cross section. Normalizing I_AS with respect to the room temperature Stokes signal of the same mode in addition to using the Boltzmann distribution, $$\langle n\_v\rangle\_0=(E\_R^0)/(h\nu\_R)=1/(e^{((h\nu\_R)/(kT\_0))}-1)$$

where $E\_R^0$ is the room temperature ($T\_0$) energy of the Raman mode. Generally, $hv\_R \gg kT\_0$. so $\langle n\_v \rangle\_0 = 0$, and the normalized anti-Stokes signal is approximately $\langle n\_v \rangle$, $$I\_norm = I\_AS/(I\_R^0) = A\langle n\_v \rangle/A(1+\langle n\_v \rangle\_0) \approx \langle n\_v \rangle.$$

By comparing the normalized scattering intensities associated with different vibrational moved, the distribution of energy over different molecular modes after infrared excitation may be obtained.

Stimulated Raman Spectroscopy

Stimulated Raman intensity is nonlinearly dependent on the incident intensity of photons but of similar magnitude. Inelastic scattering of a photon with an optical phonon originating from a finite response time of the third order nonlinear polarization of a material is characteristic of Raman scattering. Monochromatic light propagating in an optical material yields spontaneous Raman scattering in which some photons are transitioned to new frequencies. The polarization of scattered photons may be parallel or orthogonal if the pump beam is linearly polarized. Stimulated Raman scattering occurs when the scattering intensity of photons at shifted frequencies is enhanced by existing photons already present at these shifted frequencies. Consequently, in stimulated Raman scattering, a coincident photon at a downshifted frequency receives a gain which may be exploited in Raman amplifiers, for example, or usefully employed in molecular spectroscopy.

Stimulated Raman scattering (SRS) has been observed in glass fibers and Raman gain has been measured in single mode fibers. Raman amplification became a mature technology with the availability of sufficiently high-power pump lasers.

Within a classical electromagnetic framework, the stimulated Raman scattered signal intensity increases proportionally with the pump and signal intensities $$(dI\_s)/dz = g\_R I\_P I\_S$$

and the Raman-gain coefficient, $g\_R$, which is related to the spontaneous Raman scattering cross section. Hence, the probability of Raman scattering is directly related to the photon density in the pump wave and the Raman cross section.

The Stokes and pump waves must overlap spatially and temporally to generate stimulated emission. Since, the Raman process involves vibrational modes of molecules within a material; its intensity spectrum determines the material composition. In amorphous materials, for example, the vibrational energy levels tend to merge and form bands and the pump frequency may differ from the Stokes frequency over a wide range. In crystalline materials, however, the intensity peaks tend to be well-separated as they have narrow bandwidths.

The coupled wave equations for forward Raman scattering include $$(dI\_S)/dz = g\_R I\_p I\_S - \alpha\_S I\_S$$

for Stokes intensities with $\alpha\_S$ the Stokes attenuation coefficient, and $$(dI\_P)/dz = -\omega\_P/\omega\_S g\_R I\_p I\_s - \alpha\_P I\_P$$

for pump wave intensities where $\omega\_P$ and $\omega\_S$ are pump and Stokes frequencies, respectively. For backward scattering, $dI\_S/dz \rightarrow -dI\_S/dz$. In the absence of loss, these expressions reduce to $$d/dz(I\_S/\omega\_s + I\_P/\omega\_P) = 0$$

which embodies the conservation of photon number in Stokes and pump waves during stimulated Raman scattering processes.

Stimulated scattering intensity increases when the stimulated gain exceeds the linear loss which is the source of the threshold power which must be overcome to initiate stimulated Raman scattering. In a material system in which forward and backward scattering occurs, a beat frequency drives molecular oscillations responsible for increasing the scattered wave amplitude. In turn, the increasing wave amplitude enhances the molecular oscillations as part of a positive feedback loop that results in the stimulated Raman scattering effect. For forward scattering processes, the pump depletion term is removed, $$(dI\_P)/dz = -\alpha\_p I\_P.$$

Solving this equation yields $I\_P(z) = I\_0\, e^{(-\alpha\_P z)}$ giving the stimulated Stokes scattering intensity $$I\_S(L) = I\_S(0) e^{(g\_R I\_{oL}\_{eff} - \alpha\_P L)}$$

where the effective optical path length is given by $$L\_{eff} = (1 - e^{(-\alpha\_p L)})/\alpha\_P.$$

Stimulated Raman scattering intensifies from scattering events occurring throughout the optical path length in the material, making it a useful molecular spectroscopy technology.

Resonance Raman Spectroscopy

The Raman effect in classical Raman spectroscopy depends only on the frequency of incident light with scattered intensity dependence on $v\_0^4$ as discussed earlier. If the vibrational mode of a molecular absorption transition precisely matches the energy of incident light, the observed scattered intensity may be as intense as $\sim v\_0^6$. This resonance Raman effect permits highly sensitive spectroscopic discrimination of a molecular species within a complex material medium such as chromophores within proteins embedded in a biological membrane.

In resonance Raman spectroscopy, only a small fraction of molecular vibrational modes are enhanced. In the simplest scenario, only one electronic state may be resonant. In this case, the resonant Raman signal is the result of nuclear motion resulting from distortions of the molecule while transitioning between the ground state and the excited state in which resonance is induced by incident light.

The functional component of most biological chromophores consist of atoms conjugated with the particular electronic transition to which resonance Raman spectroscopy is selectively sensitive. The frequency of measured resonance Raman bands yields information about the vibrational structure of the electronic states involved in the transition used for inducing the resonance. The scattering intensities provide information about the nature of mode coupling with the electronic transition.

Raman Effect in Vortex Light

A molecule in vibronic state m subjected to a plane-polarized incident light of frequency $v\_0$ and intensity $I\_0$ is perturbed into a new vibronic state n. This interaction causes the frequency of light to shift by $v\_{mn} = v\_m - v\_n$ and scatter with a frequency $v\_0 + v\_{mn}$ through a solid angle $4\pi$. The scattering intensity during the transition from m to n is given by $$I\_{mn} = (2^6 \pi^4)/(3c^3)(v\_0 + v\_{mn})^4 |\mathcal{E}\_{mn}|^2$$

in which the amplitude $\mathcal{E}\_mn$ of the electric field is given by $$\mathcal{E}\_mn = 1/\hbar \Sigma\_r \left( (M\_m(M\_mr \mathcal{U}))/(v\_rm - v\_0) + (M\_mr(M\_rn \mathcal{U}))/(v\_rn + v\_0) \right)$$

where, m, r and n are quantum numbers of the initial, intermediate and final energy states $E\_m$, $E\_r$, $E\_n$, respectively.

Between the amplitude $\mathcal{U}$ of the electric field strength $$\mathcal{E} = \mathcal{U} e\_{}^{\wedge}(-2\pi i v\_0 t) + \mathcal{U}^{\wedge *} e^{\wedge}(2\pi i v\_0 t)$$

and its amplitude $\mathcal{E}\_mn$ associated with the shifted scattered radiation induced torque, $$M\_mn = \mathcal{E}\_mne^{\wedge}(-2\pi i(v\_0 + v\_mn)t) + \mathcal{E}\_mn^{\wedge *} e^{\wedge} 2\pi i(v\_0 + v\_mn)t$$

is a tensor relation that may be expressed in terms of scattering tensor $A\_mn = (\alpha\_\rho\sigma)\_mn$ in the form $$\mathcal{E}\_mn = A\_mn \mathcal{U}$$

or in component representation,)

$$(\mathcal{E}\_\rho)\_mn = \Sigma\_\sigma \llbracket (\alpha\_\rho\sigma)\_mn \mathcal{U}\_\sigma \rrbracket$$

while the scattering tensor $A\_mn$ may be expressed as $$A\_mn = 1/\hbar \Sigma\_r \llbracket ((M\_rnM\_mr)/(v\_rm - v\_o) + (M\_mrM\_rn)/(v\_rn + v\_0)) \rrbracket,$$

Since $\mathcal{E}\_mn$ written in terms dyadic components of the tensor $A\_mn$ includes $M\_rn\, M\_mr$, each $\rho\sigma$th matrix element of the polarizability tensor, $\alpha$, for a transition from m to n, may be written in terms of intermediate vibronic states $$(\alpha\_\rho\sigma)\_mn = 1/2\pi\hbar \Sigma\_r \llbracket (((M\_\rho)\_rn(M\_\sigma)\_mr)/(v\_rm - v\_0) + ((M\_\rho)\_mr(M\_\sigma)\_rn)/(v\_rn + v\_0)) \rrbracket,$$

Where $(M\_\rho)\_mn$ is the transition matrix between vibrational levels m and n in the presence of the radiation operator $m^{\wedge}\_\rho$, $$(M\_\rho)\_mn = \int \Psi\_r^{\wedge *} m^{\wedge}\_\rho \Psi\_m d\tau$$

Herein, $(M\_l)\_rn(M\_\sigma)\_mr$ are ordinary products of scalar vector components) $(M\_l)\_rn$ and $(M\_\alpha)\_mr$ of a unit vector $\alpha\_\sigma$. In the three mutually perpendicular directions spatially fixed l, $\sigma = 1, 2, 3$ as follows $$|\mathcal{E}\_mn|^2 = \Sigma\_\rho \llbracket (\mathcal{E}\_l)\_mn^2 = \Sigma\_\rho \llbracket |\Sigma\_\sigma \llbracket (\alpha\_\rho\sigma)\_mn \mathcal{U}\_\sigma \rrbracket |^2 = A^2 \Sigma\_\rho |\Sigma\_\sigma \llbracket (\alpha\_\rho\sigma)\_mn\alpha\_\sigma \rrbracket |^2 \rrbracket$$

With an incident intensity, $I\_0 = (c/2\pi)A^2$, then, $$I\_mn = (2^{\wedge}6\pi^{\wedge}4A^2)/(3c^{\wedge}3)(v\_0 + v\_mn)^{\wedge}4 \Sigma\_\rho \llbracket |\Sigma\_\sigma \llbracket (\alpha\_\rho\alpha)\_mn\alpha\_\sigma \rrbracket |^2 = (2^{\wedge}7\pi^{\wedge}5)/(3c^{\wedge}3)I\_0 (v\_0 + v\_mn)^{\wedge}4 \Sigma\_\rho \llbracket |\Sigma\_\sigma \llbracket (\alpha\_\rho\sigma)\_mn\alpha\_\sigma \rrbracket |^2 \rrbracket.$$

The total scattering intensity is therefore dependent on the state of polarization of the exciting light. By averaging over all positions of a, or averaging over all modes of the scattering molecule at a fixed incident wave direction and polarization, $$(|\Sigma\_\sigma \llbracket (\alpha\_\rho\sigma)\_mn\alpha\_\sigma \rrbracket |^2)^- = 1/3 \Sigma\_\sigma |(\alpha\_\rho\sigma)|^2.$$

Finally, for an electron transition from $m \to n$ per molecule an average total intensity of the scattered radiation is obtained $$I\_mn = (2^{\wedge}7\pi^{\wedge}5)/(3^{\wedge}2c^{\wedge}4) I\_0 (v\_0 + v\_mn)^{\wedge}4 \Sigma\_(\rho,\sigma) |(\alpha\_\rho\sigma)\_mn|^2$$

in which $\rho = x, y, z$ and $\sigma = x', y', z'$ are independently the fixed coordinate systems of the molecule for incident and scattered photons, respectively.

Selection Rules for Raman Effect Using Vortex Light

Of interest to studies of the Raman effect using vortex light is a particular set of solutions of Maxwell's equations in a paraxial approximation. Laguerre–Gaussian functions may mathematically characterize a beam of vortex light in terms of generalized Laguerre polynomials, $L\_p^{\wedge}l\hbar (x)$, with a Gaussian envelope. In the Lorentz-gauge, the vector potential of a Laguerre-Gaussian beam is $$A\_(l,p) = A\_0(\alpha e^{\wedge}\_x + \beta e^{\wedge}\_y) \sqrt{(2p!/\pi(|l| + p)!)} w\_0/w(z) L\_LP^{\wedge}|l|((2\rho^{\wedge}2)/(w^{\wedge}2(z)))((\sqrt{2}\rho)/w(z))^{\wedge}|l| e^{\wedge}(il\phi - i\omega t + ikz)$$

in a $(\rho, \phi, z)$ coordinate system in which $w(z)$ is the beam waist (radius) at which the radial field amplitude goes to $1/e$. For simplicity, only $p = 0$ is typically chosen. In the dipole approximation, the term, $e^{\wedge}ikz$ is negligible, so the radiation operator of a Laguerre-Gaussian beam may be expressed as $$m^{\wedge}\_\rho = [A\_0(\alpha e^{\wedge}\_x + \beta e^{\wedge}\_y) \sqrt{(1/\pi!|l|!)} w\_0/w(z) L\_0^{\wedge}i\hbar ((2\rho^{\wedge}2)/w^{\wedge}2(z))((\sqrt{2}\rho)/w(z))^{\wedge} i\hbar e^{\wedge}(i1\phi - i\omega t)] \cdot p + c \cdot c$$

Here, $e^{\wedge}i\omega t$ is associated with photon emission and $e^{\wedge}(-i\omega t)$ is associated with photon absorption.

The following generalized framework for developing a set of selection rules to measure unique OAM Raman signatures of different materials applies to the intensity profiles associated with both stimulated and spontaneous Raman spectroscopy.

The relationship among irreducible representations of the phonon, the incident photon, and the scattering photon, $\Gamma\_\alpha$, $\Gamma\_\rho$, and $\Gamma\_\sigma$, required to ensure non-vanishing matrix elements of $A\_(l,p)$ is $$\Gamma\_\alpha \otimes \Gamma\_\rho \otimes \Gamma\_\sigma \ni \Gamma\_1$$

such that $h\_(e,s)^{\wedge}a$, $(M\_\rho)\_(g,e)$, and $(M\_\sigma)\_(g,s)$ are non-zero. Introducing the Raman tensor $P\_\alpha\beta\gamma\delta(\Gamma\_j^{\wedge}\sigma)$ having index $\Gamma\_j^{\wedge}\sigma$ to denote the jth branch of the $\sigma$th phonon to replace the single index $\alpha$, we similarly replace the incident photon index, $\rho$, with $(\alpha, \beta)$ and the scattered photon index, $\sigma$ with $(\gamma, \delta)$.

As the interaction of light with matter in Raman scattering processes leaves the orbital angular momentum of photons unperturbed the incident and scattered photons may be expressed in the following respective forms, $$(\rho \cdot \in\_1) \rho^{\wedge} l e^{\wedge} i l \phi \text{ "and" } (\rho \cdot \in\_s) \rho^{\wedge} l e^{\wedge}(-i l \phi).$$

Then $P\_\alpha\beta\gamma\delta (\Gamma\_j^{\wedge}\sigma)$ may be determined by the Clebsch-Gordan coefficients for all three representations $$P\_(z, \in\_s, \in\_I, z)(\Gamma\_j^{\wedge}\sigma) = (\rho \cdot \in\_S) \rho^{\wedge} l e^{\wedge}(-i l \phi) \otimes (\rho \cdot \in\_I) \rho^{\wedge} l e^{\wedge} i l \phi \otimes \phi\_\sigma j$$

For crystalline materials, the special case of forward scattering reduces $3 \times 3$ Raman tensors to $2 \times 2$. In this case, the Raman tensors for $l \geq 2$ excitations all have the same form. So from symmetry considerations, the l-dependence vanishes for $l \geq 2$. Since the constants a, b, c, d, and e depend on l and the symmetry of the crystal, non-zero OAM yields a $\Gamma_2$ phonon for $l \geq 2$ photon excitation and decouples the two Raman tensors for the $\Gamma_3$ phonon for $l \geq 1$ photon excitation.

OAM Raman spectroscopy exhibits the capacity to characterize the atomic and molecular composition of a crystalline material. More complicated selection rules are needed to fully obtain an OAM Raman signature of chiral materials which present their own unique atomic and molecular symmetry properties.

In the highly symmetric case of crystalline materials, for example, the approach is rather straightforward. Given a periodic lattice potential, electrons in crystal solids may be expressed as Bloch waves $$\psi\_(n,k)(r) = e^{\wedge}(ik \cdot r) u\_nk(r)$$

such that the electron transition moment connecting the ground state, $\psi_{(g,k)}$, to the excited state, $\psi_{(e,k)}$, may be written $$M_{(g,e)} = \Sigma_k \int [\psi_{(e,k)}^*(r)[A_0(\rho^l e^{il\phi}) \cdot p] \omega_{(g,k)}(r)dr].$$

The first order Taylor expansion with l=0 is then $$(M^\wedge \rho)_{(g,e)} = (M^\wedge \rho)_{(g,e)}{}^\wedge 0 + \Sigma_{(\alpha,S)} \int [(h\_es^\wedge \alpha Q\_\alpha)/(\Delta E_{(e,S)})(M^\wedge \rho)_{(g,e)}{}^\wedge 0].$$

Since $h_{(e,S)}{}^\wedge \alpha$, $Q_\alpha$, and $\Delta E_{es}$ depend only on the properties of the crystal and not l, only M affects scattering intensities when using vortex light. Subsequently, the electronic wavefunction and l are left as relative values of $M(l \neq 0)$ with respect to $M(l=0)$ for the Raman effect with vortex light interactions with crystal solids.

Raman scattering intensity enhancements may be identified by selecting appropriate values of l such as in the case of zinc blende crystals, for example, in which a maximum was reported for l=30 based on symmetry considerations using the approach presented above. In practice, focusing a laser producing vortex light has little impact on the intensity enhancement of M given its similarity to focusing light in an ordinary Raman scattering measurement.

Polarized Raman Spectroscopy

Given that the polarizability of molecules varies spatially with respect to the distribution of molecules in a sample, a plane-polarized Raman source may be used to characterize the atomic structure of crystals and molecular structure of polymeric films, crystals, and liquid crystals.

Figure 69:
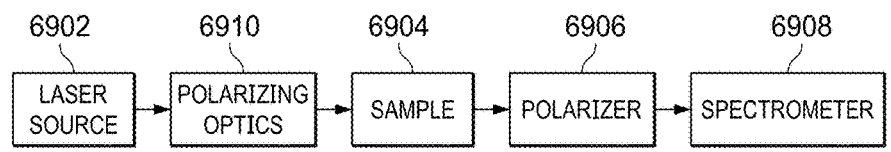
FIG. 69 illustrates circuits for carrying out polarized Rahman techniques.

Referring now to FIG. 69, polarized Raman techniques involve a polarizer 6906 between the sample 6904 and the spectrometer 6908 oriented either parallel (∥) or perpendicular (⊥) to the polarization state of the laser source 6902. As well, polarizing optics 6910 may be inserted between the laser 6902 and sample 6904 to select an appropriate state of polarization incident on the sample.

The symmetry properties of bond vibrations in a molecule are characterized by polarized Raman spectroscopy by evaluating the depolarization, $\rho$, of particular intensity peaks, $$\rho = \frac{I_\perp}{I_\parallel}$$

where $I\_\perp$ and $I\_\parallel$ are the Raman spectral band intensities with polarizations perpendicular and parallel, respectively, to the state of polarization of the laser source 6902.

Figure 70:
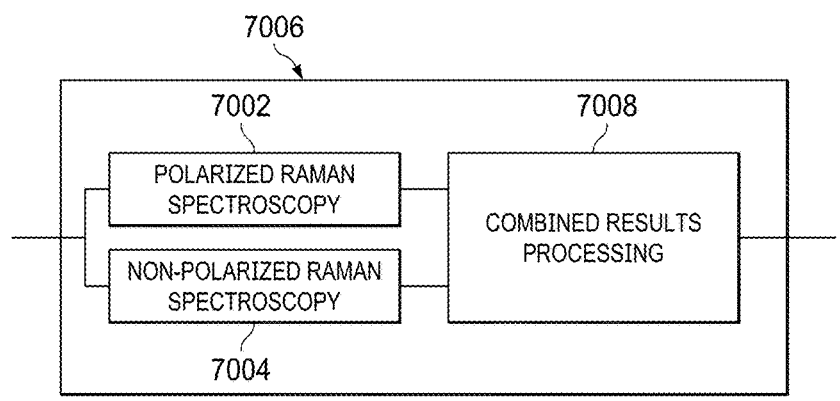
FIG. 70 illustrates circuitry for combining polarized and non-polarized Rahman spectroscopy.

As shown in FIG. 70, information gained by polarized Raman spectroscopy 7002 can be used to supplement atomic and molecular information gained by non-polarized Raman spectroscopy 7004. A single integrated spectroscopy unit 7006 exploiting both polarized and non-polarized Raman effects using combined results processing 7008 that improves overall quality and amount of information gained by spectroscopically processing data from a sample using multiple types of spectroscopic analysis.

Raman Spectroscopy with Optical Vortices

The typical Raman source is a Gaussian laser operating in its fundamental mode with an electric field $$E(x,y,z) = \hat{e}E_0 \exp\left(-\frac{x^2+y^2}{w^2}\right)\exp[-i(kz-\omega t)].$$

traveling in the z-direction, where ê is the polarization vector. Light produced by such a source has either linear or circular polarization which are limited to the transverse (x, y) plane with no electric field component in the z-direction. The induced dipole moments of interest then are only $P_x$ and $P_y$.

A longitudinal mode along the z-direction incident on a molecule scatters light that completes the picture of the molecule's polarizability to include $P\_z$. An electric field having a z-component is a radially-polarized beam with a polarization vector $$\hat{e} = x\hat{x} + y\hat{y} = \hat{r}.$$

Figure 71:
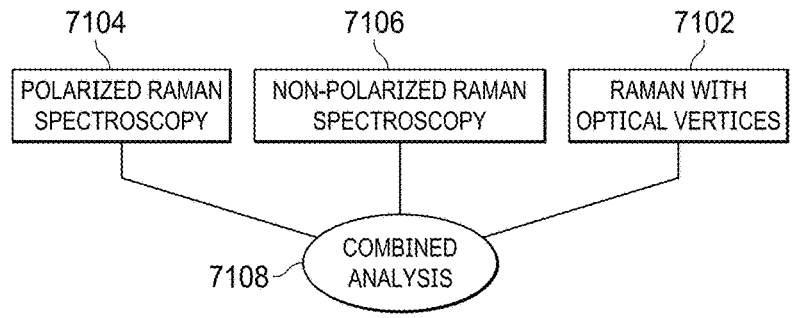
FIG. 71 illustrates a combination of polarized and non-polarized Rahman spectroscopy with optical vortices.

Several methods exist to generate radially polarized fields having longitudinal components when tightly focused. In Raman spectroscopy, the induced dipole moment, $P_z$, is the result of $E_z$ which may increase the strength of vibrational modes in addition to generating new vibrational modes previously unobserved with conventional Raman spectroscopy. As shown in FIG. 71, information gained by Raman beams endowed with optical vortices 7102 adds a third degree of spectroscopic capability when coupled with polarized 7104 and non-polarized 7106 Raman spectroscopy in a combined analysis 7108. Such Raman spectroscopy can also work in conjunction with incident photons that carry OAM.

THz Spectroscopy

Figure 72:
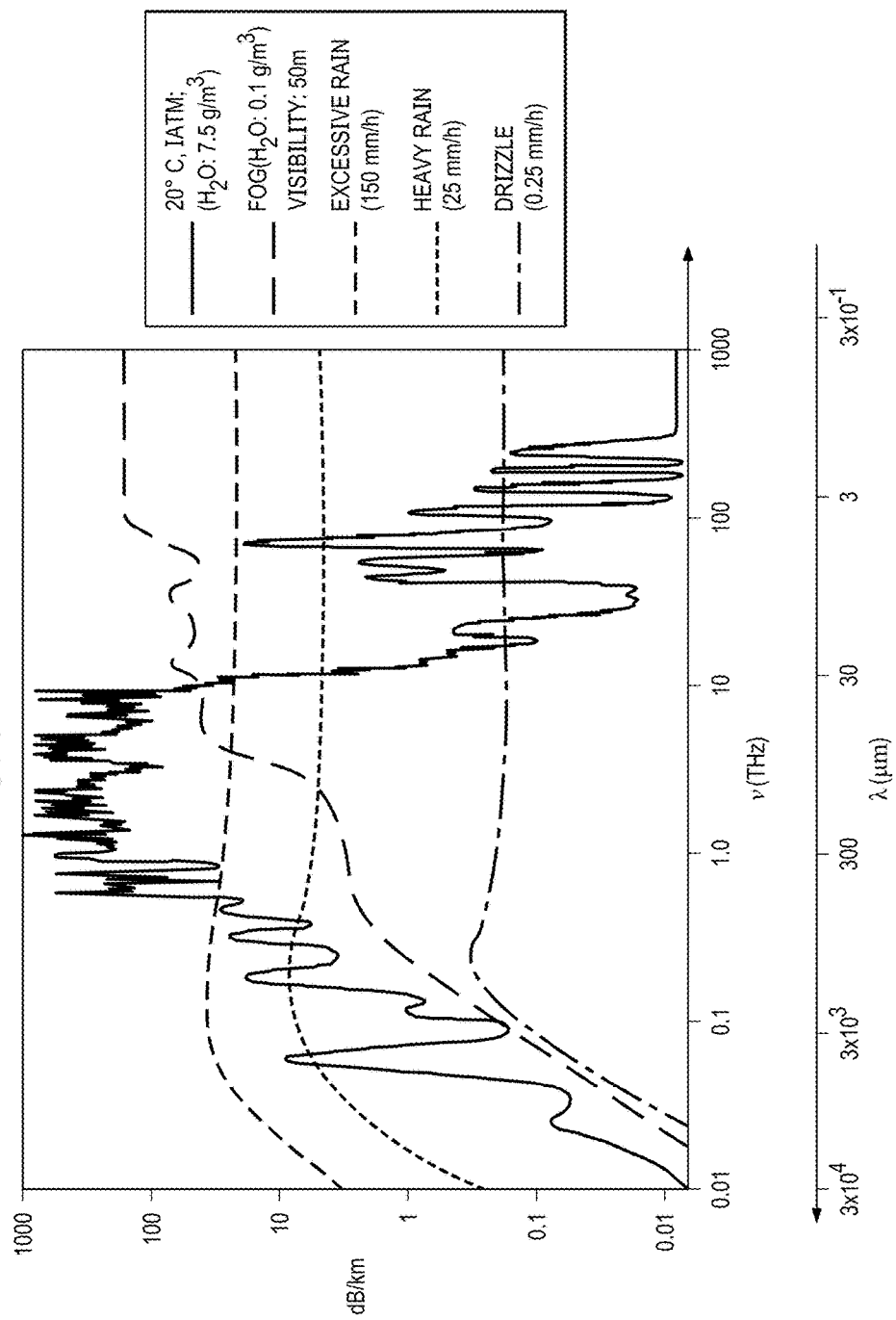
FIG. 72 illustrates the electromagnetic wave attenuation by atmospheric water versus frequency and wavelength.

Terahertz spectroscopy is conducted in the far-infrared frequency range of the electromagnetic spectrum (FIG. 61) and is therefore useful for identifying far-infrared vibrational modes in molecules. THz spectroscopy can provide a higher signal-to-noise ratio and wider dynamic range than far-infrared spectroscopy due the use of bright light sources and sensitive detectors. This provides for selective detection of weak inter- and intra-molecular vibrational modes commonly occurring in biological and chemical processes which are not active in IR-spectroscopy. THz spectroscopy may also be used in conjunction with incident photons that carry OAM. Terahertz waves pass through media that are opaque in the visible and near-IR spectra and are strongly absorbed by aqueous environments (see FIG. 72).

THz spectroscopy was historically hindered by a lack of appropriately high powered light sources. However, access to practical THz spectroscopy in the far-infrared range was permitted by the generation of THz rays based on picosecond and femtosecond laser pulses. Today, THz sources include either short pulse mode (e.g. photoconductive antennas, optical rectifiers) or continuous wave (CW) mode having a wide range of available output power (nanowatts to 10 watts).

Several different types of THz sources are used today to interrogate biological, chemical and solid state processes. Sources in the 1-3.5 THz range are frequently used in biology and medicine, for example, to investigate conformational molecular changes. THz spectroscopy is used today as frequently as Raman spectroscopy.

Terahertz Time-Domain Spectroscopy

Terahertz time-domain spectroscopy (THz-TDS) is one of the most widely used THz techniques which includes coherent emission of single-cycle THz pulses such as provided by a femtosecond laser. The detection of these pulses occurs at a repetition rate of about 100 MHz.

Two dimensional THz absorption properties of samples are characterized by a THz imaging technique. This technique was demonstrated in systems designed for THz-TDS based on picosecond pulses as well as systems utilizing continuous-wave (CW) sources such as a THz-wave parametric oscillator, quantum cascade laser, or optically pumped terahertz laser. THz spectroscopy can be used in conjunction with incident photons that carry OAM.

THz pulse imaging provides broad image frequency information between 0.1-5 THz while THz CW imaging may be performed in real-time, is frequency-sensitive, and has a higher dynamic range due to significantly higher spectral power density. In both pulse and CW THz imaging the characteristics of the light source (coherency, power, and stability) are important. A THz spectrometer may mechanically scan a sample in two dimensions, but the time of each scan scales with sample size. Real time THz imaging is often conducted with an array of THz wave detectors composed of electro-optic crystals or a pyroelectric camera. Such THz spectroscopy can be used in conjunction with incident photons that carry OAM.

THz imaging suffers from poor resolution as estimated in terms of its diffraction limit which is less than a millimeter and from low transmission through an aperture resulting in low sensitivity. To exceed the diffraction limitation near-field microscopy is used to achieve sub-wavelength resolution, though low transmission remains an issue.

Fluorescence Spectroscopy

Figure 73:
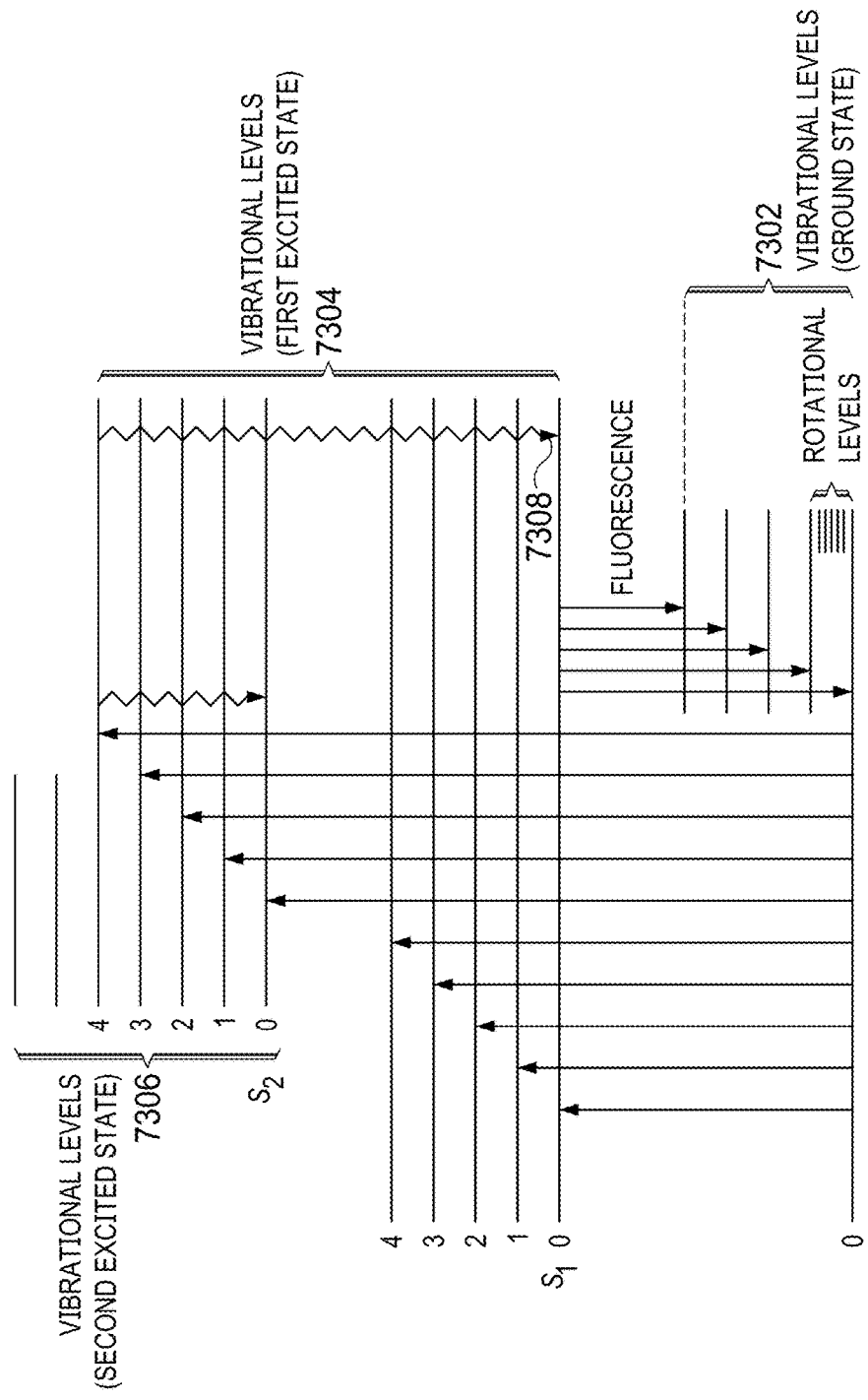
FIG. 73 illustrates the absorption and emission sequences associated with fluorescence spectroscopy.

Perturbed by incident light, electrons in molecules at room temperature are excited from the lowest vibrational energy level 7302 of the electronic ground state to either the first (S_1) 7304 or second (S_2) 7306 vibrational state (FIG. 73) and may occupy any one of several vibrational sub-levels. Each vibrational sub-level has many neighboring rotational energy levels in such close proximity that inter-sub-level energy transitions are almost indistinguishable. Consequently, most molecular compounds have broad absorption spectra with the exception of those having negligible rotational characteristics such as planar and aromatic compounds.

In fluorescence spectroscopy, molecules absorb energy from incident photons, obtain a higher vibrational energy sub-level of an excited state (S_1 or S_2), then lose their excess vibrational energy through collisions and return to the lowest vibrational sub-level of the excited state. Most molecules occupying an electronic state above S_2, experience internal conversion and decay by collision through the lowest vibrational energy sub-level of the upper state to a higher vibrational sub-level of a lower excited state having the same energy. The electrons continue to lose energy until they occupy the lowest vibrational energy sub-level of S_1 7308. The decay of the molecule into any vibrational energy sub-level of the ground state causes the emission of fluorescent photons.

If the absorption and emission process differs from this sequence, the quantum efficiency is less than unity. The "0-0" transition from the lowest vibrational ground state sub-level to the lowest vibrational S_1 sub-level 7308 is common to both the absorption and emission phenomena while all other absorption transitions occur only with more energy than any transition in the fluorescence emission. The emission spectrum subsequently overlaps the absorption spectrum at the incident photon frequency corresponding to this "0-0" transition while the rest of the emission spectrum will have less energy and equivalently occurs at a lower frequency. The "0-0" transition in the absorption and emission spectra rarely coincide exactly given a small loss of energy due to interaction of the molecule with surrounding solvent molecules.

Hence, distributions of vibrational sub-levels in S_1 and S_2 are very similar since incident photon energy doesn't significantly affect the shape of the molecule. Energy differences between bands in the emission spectrum will be similar to those in the absorption spectrum and frequently, the emission spectrum will be approximately a mirror image of the absorption spectrum. The shape of the emission spectrum is always the same despite an incident photon frequency shift from that of the incident radiation since the emission of fluorescent photons always occurs from the lowest vibrational energy sub-level of S_1. If the incident radiation intensity yielding excitation remains constant as the frequency shifts, the emission spectrum is considered a corrected excitation spectrum.

The quantum efficiency of most complex molecules is independent of the frequency of incident photons and the emission is directly correlated to the molecular extinction coefficient of the compound. In other words, the corrected excitation spectrum of a substance will be the same as its absorption spectrum. The intensity of fluorescence emission is directly proportional to the incident radiation intensity.

Figure 74A:
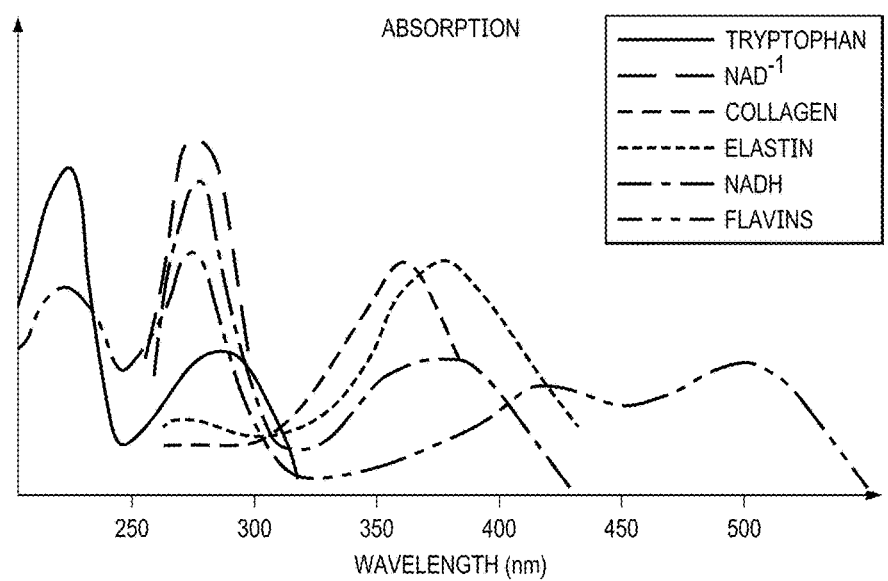
FIG. 74A illustrates the absorption spectra of various materials.
Figure 74B:
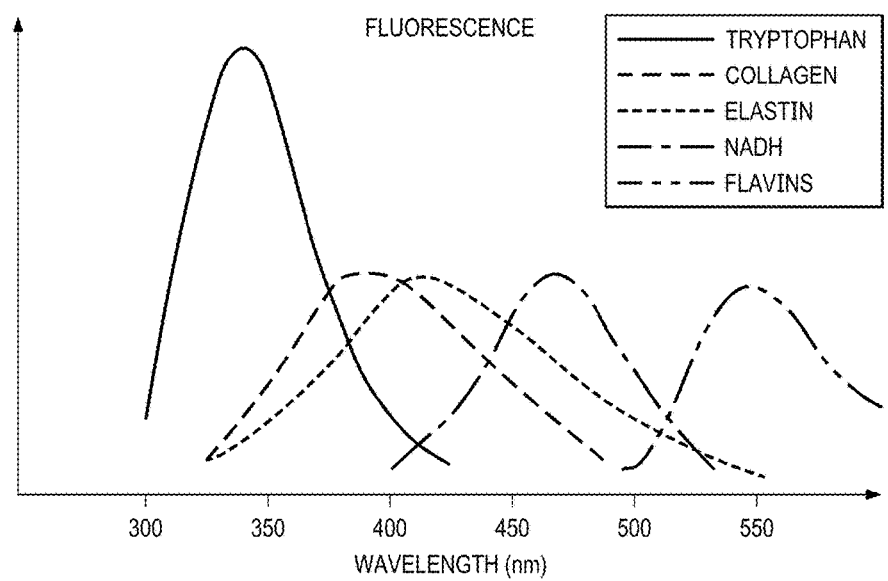
FIG. 74B illustrates the fluorescence spectra of various materials.

Fluorescence spectroscopy results in emission and excitation spectra. In emission fluoroscopy, the exciting radiation is held at a fixed wavelength and the emitted fluorescent intensity is measured as a function of emission wavelength. In excitation fluoroscopy, the emission wavelength is held fixed and the fluorescence intensity is measured as a function of the excitation wavelength. This type of fluorescence spectroscopy may also be used in conjunction with incident photons that carry OAM. Performing both emission and excitation spectra together yields a spectral map of the material under interrogation. Materials of interest may contain many fluorophores, and different excitation wavelengths are required to interrogate different molecules as shown in FIGS. 74A and 74B for the absorption and emission spectra for tryptophan, elastin, collagen, nicotinamide, adenine dinucleotide (NADH) and flavins.

Fluorescence spectrometers analyze the spectral distribution of the light emitted from a sample (the fluorescence emission spectrum) by means of either a continuously variable interference filter or a monochromator. Monochromators used in more sophisticated spectrometers select the exciting radiation and analyze the sample emission spectra. Such instruments are also capable of measuring the variation of emission intensity with exciting wavelength (the fluorescence excitation spectrum).

One advantage of fluorescence spectroscopy compared to equivalent absorption techniques is that the sample may be contained in simple test tubes rather than precision cuvettes without appreciable loss in precision because of the geometrical configuration of simple fluorimeters in which only the small central region of the cuvette is interrogated by the detector. Hence, the overall size of the cuvette is less important.

Sensitivity of fluorescence spectroscopy depends largely on the properties of the measured sample and is typically measured in parts per billion or trillion for most materials. This remarkable degree of sensitivity permits reliable detection of very small sample sizes of fluorescent materials (e.g. chlorophyll and aromatic hydrocarbons).

Fluorescence spectroscopy is exceptionally specific and less prone to interference because few materials absorb or emit light (fluoresce) and rarely emit at the same frequency as compounds in the target material.

Fluorescence measurements scale directly with sample concentration over a broad frequency range and can be performed over a range of concentrations of up to about one six orders of magnitude without sample dilution or alteration of the sample cell. Additionally, the sensitivity and specificity of fluoroscopy reduces or eliminates the need for costly and time-consuming sample preparation procedures, thus expediting the analysis. Overall, fluoroscopy represents a low-cost material identification technique owing to its high sensitivity (small sample size requirement).

Pump-Probe Spectroscopy

Pump-probe spectroscopy is used to study ultrafast phenomena in which a pump beam pulse perturbs atomic and molecular constituents of a sample and a probe beam pulse is used to interrogate the perturbed sample after an adjustable period of time. This optical technique is a type of transient spectroscopy in which the electronic and structural properties of short-lived transient states of photochemically or photophysically relevant molecules may be investigated. The resulting excited state is examined by monitoring properties related to the probe beam including its reflectivity, absorption, luminescence, and Raman scattering characteristics. Electronic and structural changes occurring within femto- to pico-second timeframes may be studied using this technique.

Generally, pump-induced states represent higher energy forms of the molecule. These higher energy molecular forms differ from their lowest ground state energy states including a redistribution of electrons and/or nuclei.

Figure 75:
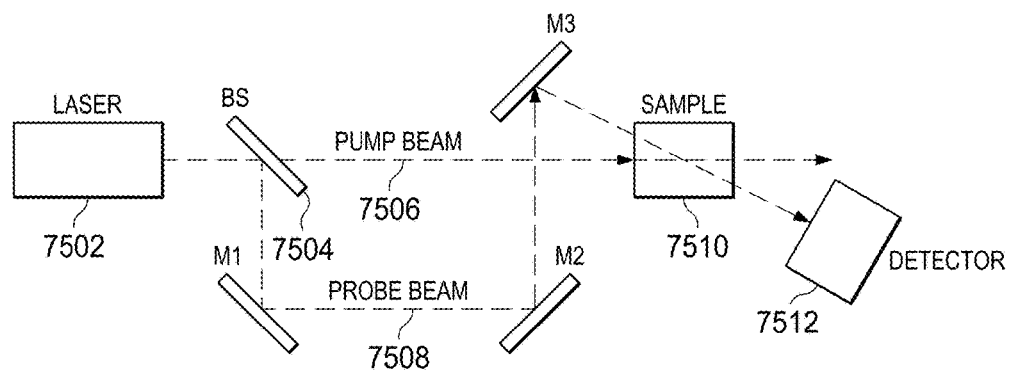
FIG. 75 illustrates a pump-probe spectroscopy set up.

A basic pump probe configuration is shown schematically in FIG. 75. A pulse train generated by a laser 7502 is split into a pump pulse 7506 and a probe pulse 7508 using a beamsplitter 7504. The pump pulse 7506 interacts with the atoms and molecules in a sample 7510. The probe pulse 7508 is used to probe the resulting changes within the sample after a short period of time between the pulse train and the probe pulse train. By changing the delay time between pulse trains with an optical delay line, a spectrum of absorption, reflectivity, Raman scattering, and luminescence of the probe beam may be acquired after the sample to study the changes made by the pump pulse train at detector 7512. It is possible to obtain information concerning the decay of the pump-induced excitation by monitoring the probe train 7508 as a function of the relative time delay. The probe train 7508 is typically averaged over many pulses and doesn't require a fast photodetector 7512. The temporal resolution of measurements in pump-probe spectroscopy is limited only by the pulse durations of each train. In general, the uncertainty in timing must be smaller than the timescale of the structural or electronic process induced by the pump train.

In two-color pump-probe spectroscopy, the pump 7506 and probe 7508 beams have different wavelengths produced by two synchronized sources. While this technique provides additional capabilities in ultrafast spectroscopy, it's essential to ensure precise source synchronization with a very low relative timing jitter.

Figure 76:
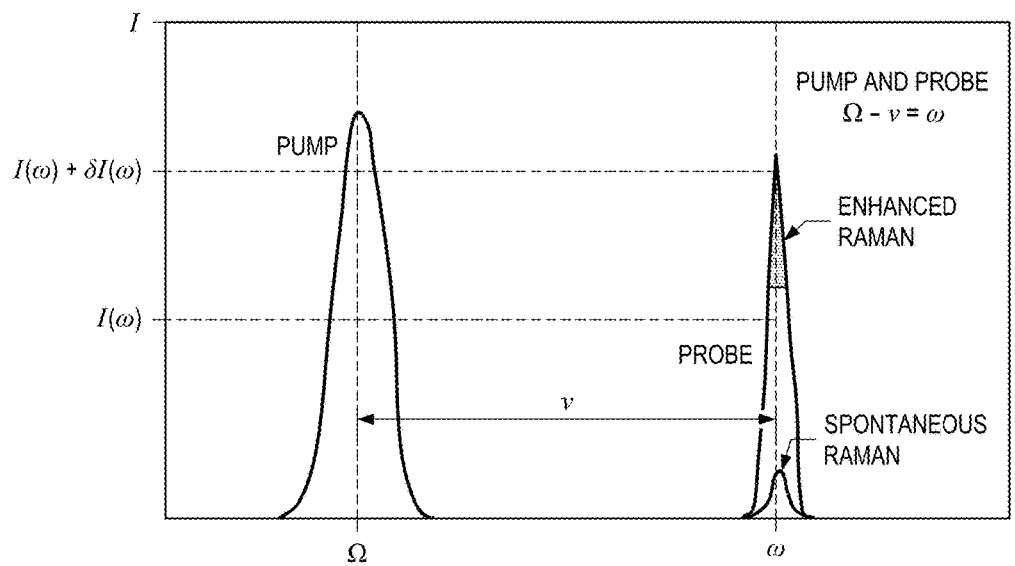
FIG. 76 illustrates an enhanced Ramen signal.

In comparison with spontaneous Raman scattering intensities, the scattered intensities provided by a pump-probe Raman spectroscopy technique may be tremendously enhanced with different pump and probe frequencies, $\Omega$ and $\omega$, as shown in FIG. 76. The frequency of the pump beam is changed, while the frequency of the probe beam is fixed. The pump beam is used to induce Raman emission, while the probe beam serves to reveal Raman modes. Both the pump and the probe beam traverse a Raman-active medium in collinearity. When the difference between the pump and probe frequencies coincide with a Raman vibrational mode frequency, $v$, of the medium, the weak spontaneous Raman light is amplified by several orders of magnitude ($10$-$10^4$) due to the pump photon flux. Gain is achieved as shown in FIG. 76.

The pump beam is essentially engineered to provide a variety of perturbative excitations within a wide range of samples. Pump-probe spectroscopy is therefore applicable to use within the context of other spectroscopy techniques including the use of a pump beam endowed with orbital angular momentum as discussed in the next section.

Orbital Angular Momentum (OAM) Spectroscopy

Chiral optics conventionally involved circularly polarized light in which a plane polarized state is understood as a superposition of circular polarizations with opposite handedness. The right- and left-handedness of circularly polarized light indicates its spin angular momentum (SAM), $\pm\hbar$ in addition to the polarization one can use the helicity of the associated electromagnetic field vectors. Its interaction with matter is enantiomerically specific. The combined techniques would have specific signatures for different materials.

As described more fully herein above, optical vortices occurring in beams of light introduce helicity in the wavefront surface of the electromagnetic fields and the associated angular momentum is considered "orbital". Orbital angular momentum (OAM) of photonic radiation is frequently called a "twisted" or "helical" property of the beam. Most studies of OAM-endowed light interactions with matter involve achiral molecules.

Delocalized OAM within solid materials associated with the envelope wavefunction in a Bloch framework, which may be spatially macroscopic in extent, may be distinguished from local OAM associated with atoms. The latter is associated with the Landé g-factor of electronic states and part of the effective spin while the former is of interest to orbitally coherent systems (e.g. quantum Hall layers, superconductors, and topological insulators). Development of these techniques represents opportunities to improve our understanding of scattering and quantum coherence of chiral electronic states, with potential implications for materials discovery and quantum information. To this end, theoretical frameworks describing the OAM-matter interaction, such as with dielectric materials are useful.

OAM-endowed beams of light have been used to induce such delocalized OAM-states in solids using a time-resolved pump-probe scheme using LG beams in which the OAM-sensitive dichroism of bulk n-doped ($3\times10^{16}$ cm$^{-3}$ Si) and undoped GaAs (held in a cryostat at 5K) is exploited. Using this method, "whirlpools" of electrons were induced and measured with a time-delayed probe beam whose OAM components were detected in a balanced photodiode bridge. The study demonstrates that time-resolved OAM decay rates (picoseconds to nanoseconds) are doping dependent, differed from spin and population lifetimes, and longer than anticipated as described in M. A. Noyan and J. M. Kikkawa, "Time-resolved orbital angular momentum spectroscopy," *Appl. Phys. Lett.* 107 032406 (2015), which is incorporated herein by reference in its entirety.

Figure 77:
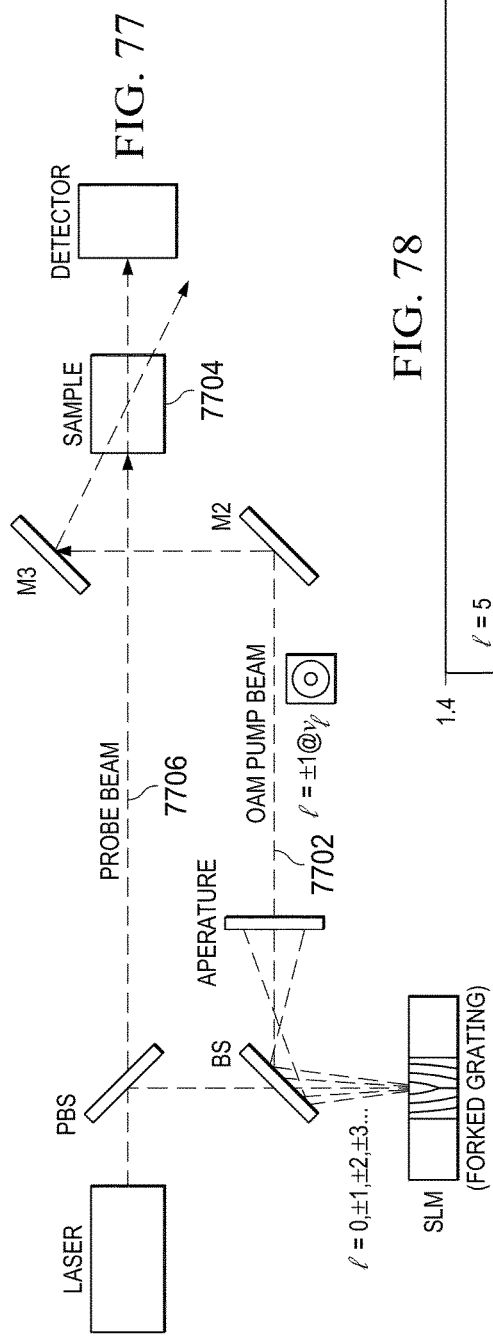
FIG. 77 illustrates a pump-probe OAM spectroscopy set up.

A simple pump-probe OAM spectroscopy instrument is shown schematically in FIG. 77 in which the OAM pump beam 7702 is an l=±1 Laguerre-Gaussian beam cycled between l=±1 and l=−1 at some frequency, v_l. The pump beam 7702 perturbs target molecules in the sample 7704 while a direct probe beam 7406 is used to interrogate the resulting perturbation. The sample may be a crystalline solid, amorphous solid, liquid, biological, or inorganic.

The interaction of light exhibiting OAM, an azimuthal photonic flow of momentum, with chiral molecules is the subject of several recent theoretical and experimental reports. On one hand, the strength of the interaction has been conjectured as negligible, while on the other hand, not only does such an interaction exist, it may be stronger than the interactions occurring in conventional polarimetry experiments in which the direction of linearly polarized light incident on a solution is rotated by some angle characteristic of the solution itself. A few limited experimental studies have suggested that the former theoretical body of work is correct—that such an interaction is negligible.

Nonetheless, a variety of light-matter interactions involving OAM-endowed optical beams indicate a broad range of possibilities in spectroscopy including OAM transfer between acoustic and photonic modes in optical fibers, OAM-endowed Raman sideband generation, and the manipulation of colloidal particles manipulation with optical OAM "tweezers".

OAM Spectroscopy of Chiral Molecules

Recent experiments using Laguerre-Gaussian (LG) beams of varying integer azimuthal order, l, traveling through a short optical path length of various concentrations of glucose, support the theoretical body of work suggesting the existence of measurable OAM light-matter interactions. These experiments suggest that not only does the interaction exist, but it appears to be stronger than with polarimetry since perturbations of the OAM beam occur within a very short optical path length (1-3 cm) than commonly required in conventional polarimetry studies (>10 cm) to obtain a measurable perturbation of the linear state of polarization.

The Gaussian beam solution to the wave equation and its extension to higher order laser modes, including Hermite-Gaussian (HG) and commonly studied in optics labs. Of particular interest, LG modes exhibit spiral, or helical, phase fronts. In addition to spin angular momentum, the propagation vector includes an orbital angular momentum (OAM) component often referred to as vorticity.

A spatial light modulator (SLM) is frequently used to realize holograms that modulate the phase front of a Gaussian beam and has renewed interest in engineered beams for a variety of purposes.

The expression for the electric field of an LG beam in cylindrical coordinates is $$u(r, \theta, z) = \left[\frac{2pl}{1 + \delta_{\sigma,m}\pi(l + p)!}\right]^{\frac{1}{2}} \exp$$

$$\left\{j(2p + l + 1)[\psi(z) - \psi_0]\right\} \cdot \frac{\sqrt{2}r}{w^2(z)} L_p^l\left(\frac{2r^2}{w^2(z)}\right) \exp\left[-jk\frac{r^2}{2q(z)} + il\theta\right]$$

with w(z) the beam spot size, q(z) a complex beam parameter comprising evolution of the spherical wavefront and spot size, and integers p and l index the radial and azimuthal modes, respectively. The exp(ilθ) term describes spiral phase fronts. A collimated beam is reflected off the SLM appropriately encoded by a phase retarding forked grating, or hologram, like the one shown in FIGS. 15A-15D. The generating equation for the forked hologram may be written as a Fourier series, $$T(r, \varphi) = \sum_{m=-\infty}^{\infty} t_m \exp\left[-im\left(\frac{2\pi}{D}r\cos\varphi - l\varphi\right)\right],$$

where r and φ are coordinates, l is the order of vorticity, and D is the rectilinear grating period far from the forked pole. Weights, t_m, of the Fourier components may be written in terms of integer-order Bessel functions, $$t_m = (-i)^m J_m(k\beta)\exp(ik\alpha).$$

where kα and kβ bias and modulate the grating phase, respectively. Only a few terms are needed to generate OAM beams, such as −1≤m≤1, $$T(r, \varphi) = \frac{1}{2} - \frac{1}{2}\sin\left(\frac{2\pi}{D}r\cos\varphi - l\varphi\right).$$

Figure 78:
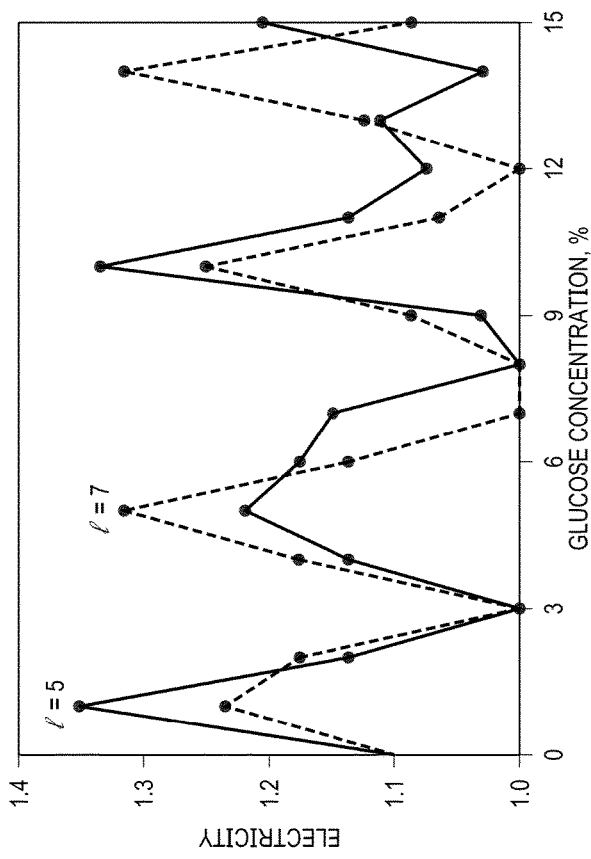
FIG. 78 illustrates measured eccentricities of OAM beams.

As shown in FIG. 78 for OAM mode orders l=5, 6, and 7 propagated through 3 cm cuvettes containing different concentrations of glucose, the OAM signature was found to be nonlinear with respect to concentration. Though this preliminary data is noisy, the trend persists over several OAM orders and was repeatable day to day and after several setup re-alignments and other changes made for convenience.

Glucose exhibits a broad optical absorption band at ~750 nm with FWHM~250 nm. A stronger OAM response was observed at 543 nm where absorbance is four times smaller than at 633 nm. This suggests an interaction based on the real part of susceptibility, $\chi'$, rather than its imaginary part, $\chi''$. In separate glucose polarimetry experiments with cuvettes as long as 20 cm, a 50% larger specific rotation was measured at 543 nm than at 633 nm. Consistent with previous OAM polarimetry studies with chiral molecules in solution no discernable polarization state changes were observed with OAM beams through 3 cm or shorter samples.

While glucose is known to have polarimetric responses at these wavelengths the concentration-path length product, cl, was too small in this OAM study to produce measurable shifts in the state of polarization. The observed topological changes reported using OAM-endowed beams suggests the interaction of OAM beams with chiral molecules is more pronounced than interactions associated with traditional polarimetry. OAM beam interactions with chiral molecules may lead to new meteorological techniques and perhaps a richer understanding of subtle light-matter interactions. Of particular interest is the interaction of light with molecules exhibiting varying degrees of chirality, a subject taken up in the next section.

Molecular Chirality

The chirality of a molecule is a geometric property of its "handedness" characterized by a variety of spatial rotation, inversion, and reflection operations. Conventionally, the degree of chirality of molecules was starkly limited to a molecule being either "chiral" or "achiral" in addition to being "left-handed" or "right-handed". However, this binary scale of chirality doesn't lend well to detailed spectroscopic studies of millions of molecular systems that may be studied. In its place, a continuous scale of 0 through 100 has been implemented for the past two decades called the Continuous Chirality Measure (CCM). Essentially, this continuous measure of chirality involves the Continuous Symmetry Measure (CSM) function, $$S'(G) = \frac{1}{n}\sum_{i=1}^{n}\|P_i - \hat{P}_i\|^2$$

where G is a particular symmetry group, $P_i$ are the points of the original configuration, $\hat{P}_i$ are the corresponding points in the nearest G-symmetric configuration, and n is the total number of configuration points.

The objective is to identify a point set, $P_i$, having a desired G-symmetry such that the total normalized displacement from the original point set $P_i$ is a minimum. The range of symmetry, $0 \leq S'(G) \leq 1$, may be expanded such that $S=100S'$. The advantages of CCM over other chiral measure schemes include its ease of application to a wide variety of chiral structures including distorted tetrahedra, helicenes, fullerenes, frozen rotamers, knots, and chiral reaction coordinates, as well as being a measured without reference to an ideal shape. Unique chirality values are made with reference to nearest symmetry groups ($\sigma$ or $S_{2n}$), thus allowing for direct comparison with a wide variety of geometric.

Yet, since the new technique described above discusses the use of Stimulated Raman or Resonant Raman spectroscopy with vector beams (i.e., beams with "twistedness" plus polarization), the technique can equally be applied to both chiral and non-chiral molecules.

Raman with Orbital Angular Momentum

Figure 79:
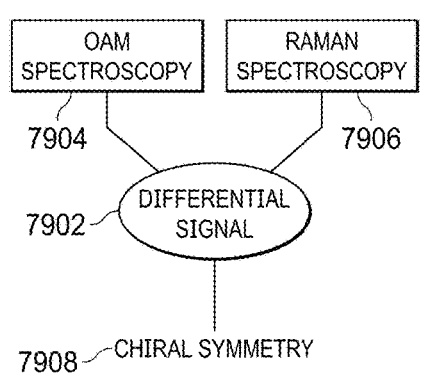
FIG. 79 illustrates a combination of OAM spectroscopy with Ramen spectroscopy for the generation of differential signals.

The effect of orbital angular momentum on the Raman scattering spectra of glucose has been investigated. Changes have been observed in the Raman spectra, in particular at 2950 cm$^{-1}$ with L=2 (helical beam) as compared to L=0 (Gaussian beam). The innovation is that if the sugar molecules possess some types of chiral symmetry 7908 than there may be a differential signal 7902 (FIG. 79) using OAM 7904 and Raman 7906 spectroscopy. The Raman spectra of glucose, sucrose and fructose have already been collected for the three laser wavelengths 488, 514.5 and 632.8 nm from argon-ion and helium neon laser sources, the signals have been tabulated and the agreement of each vibration is justified with the other two laser lines. No resonances were observed as would be expected since there is no direct electronic absorption with these energies. The Raman spectra, however, are sensitive to local and global symmetries of the molecule at any wavelength. Differential Raman signals will give fundamental information about the interaction of a chiral electromagnetic field with the sugar molecules, as well as potentially lead to a selected symmetry resonance for low level glucose detection in the blood.

The system used for these measurements is a confocal microscope attached to a 75 cm single stage spectrometer using a grating blazed at 500 nm and 1200 lines/mm groove density. The microscope objective used was 10× magnification. To generate the OAM beam with angular momentum value L=2, a Q plate was incorporated into the system.

Figure 80:
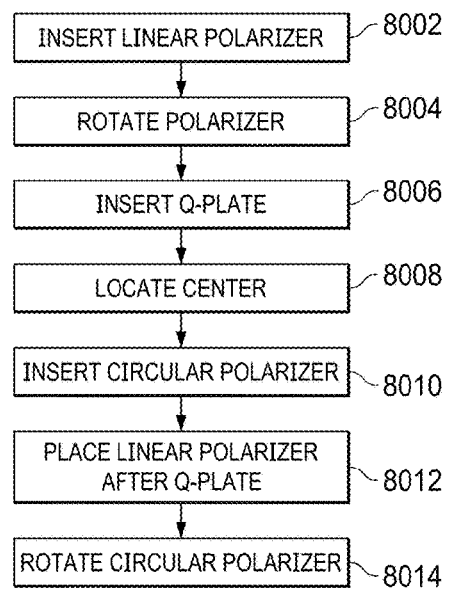
FIG. 80 illustrates a flow diagram of an alignment procedure.

Referring now to FIG. 80 there is illustrated the alignment procedure. A linear polarizer is inserted at step 8002 into the beam path and rotated at step 8004 until maximum transmission intensity is achieved. A Q-plate is inserted at step 8006 into the beam path and locates at step 8008 the center that produces the OAM beam (by observation of the donut). The circular polarizer is inserted at step 8010 before the Q-Plate. The linear polarizer is placed at step 8012 after the Q-plate to observe the 4 lobed structure. Finally, the circular polarizer is rotated at step 8014 until the output from final linear polarizer shows donut for all angles of final linear polarization. This procedure is iterative also adjusting applied voltage to Q-plate (appx 4 Volts) and the square wave driving frequency (appx 2 KHz). The measurements are taken without the final linear polarizer.

Figure 81:
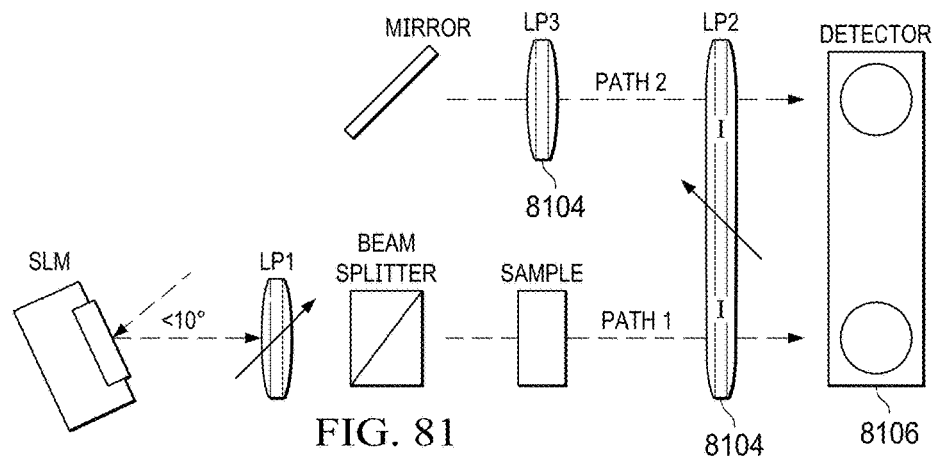
FIG. 81 illustrates a balanced detection scheme.
Figure 82:
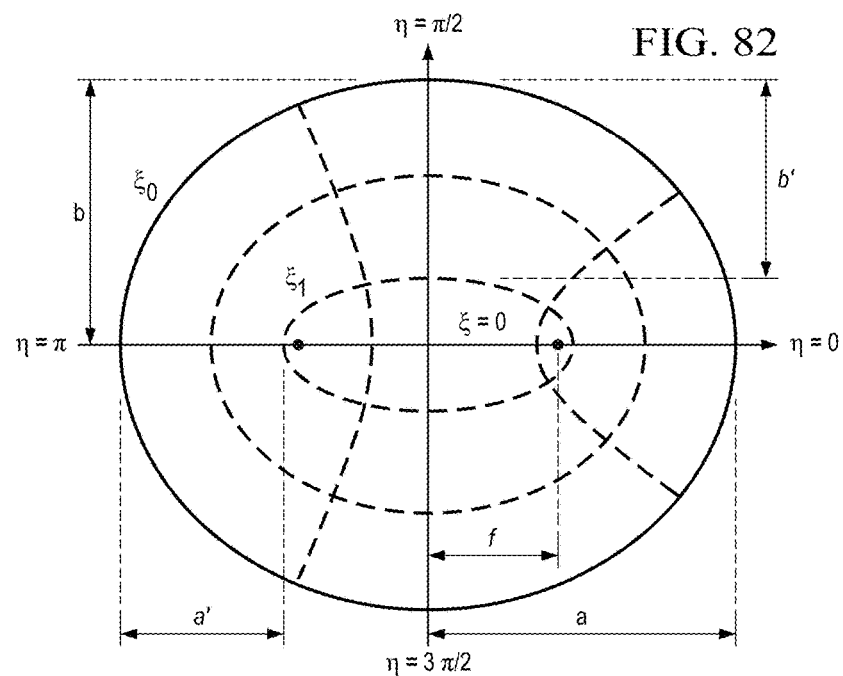
FIG. 82 illustrates an elliptical coordinate system.

The resulting spectra with L=2 along with a spectra with L=0 (no elements in the beam path) are shown in FIGS. 81 and 82, both normalized to the maximum value which for both cases is the Raman signal near 2800 cm$^{-1}$. From these measurements it does show that there are differential intensities between the two different excitations. At 400 and 550 cm$^{-1}$ there is almost a 50 percent increase in scattering intensity while the L=2 spectrum shows a few additional shoulders of each of these lines. Most pronounced is the intensity ratio of the doublet around 2950 cm$^{-1}$.

The Raman system used for these measurements is alignment restricted. The incorporation of the additional waveplates causes slight walk-off which leads to significant collection intensity drop in the confocal system. Presumably, normalization would eliminate any alignment intensity issues, however signal to noise suffers and longer integrations are required. Long integration times are not always possible or feasible.

These measurements need to be repeated for glucose and also done for fructose. Also needed to be checked is the response to pure circular polarization without OAM. We should be able to access the alignment and optimize for the Q-plate operation. Also to do is use L=1 value and L=20 values of OAM. With promising results, we will use a quarter waveplate for 488 nm as this laser produces the best spectra in the shortest acquisition times on the system.

Although the higher energy Raman signals are not unique to glucose as they represent generic carbon and carbon hydrogen bonds present in many organic systems, it may prove to be unique to chiral systems. Additionally, the lower energy modes that are more unique to glucose may show better differentiation with OAM once the system is better optimized for Q-plates.

Optical Activity with Single Crystal Rock Candy

Optical activity of sugar molecules is well studied and is a result of the chiral symmetry of the molecule which leads to the polarization of the sugar system imparting a small rotation of the incident light, therefore the final transmitted beam will have a rotation dependent on the concentration of molecules present. Experiments have been started in order to develop a versatile and sensitive system for the detection of polarization changes via transmission or reflection of materials using orbital angular momentum. This system is best suited with the use of the SLM so that any type of beam can in principle be generated. As a starting point, we have obtained rock candy which shows high crystallinity and regular cleavage planes of the samples which are few mm thick each. These candy samples can be polished to have an optical quality finish on the surfaces, however interior defects so far have prevented clean transmission measurements and the signal is collected as forward scatter. The crystals cleave into 3 pieces showing the clear symmetry of the planes of the crystal, the z-axis of the crystal is oblique to the cleavage planes. As we begin these measurements, we are also comparing data to the Q-plate outputs as well. This measurement system will become the optical system for balanced and lock-in detection for future polarization sensitive measurements and the stimulated Raman measurements.

Multiple monitor access is needed for the SLM on properly configured computers capable of running the SLM, Matlab and video capture simultaneously.

Referring now to FIG. 81, the output of a HeNe laser is chopped around 1 kHz and sent into a single mode fiber. The output is collimated with two biconvex lenses, sent through a half wave plate to adjust the polarization incident onto the Hamamatsu LCOS SLM 8102 with an angle of incidence of <10 degrees per operation specifications of SLM. The SLM 8102 displays forked diffraction grating or spiral phase pattern holograms generated using the MATLAB code in order to generate the desired OAM beam. The reflected beam carries OAM and a characteristic "donut" shape is seen, with zero intensity along the beam axis. This beam is then sent through a pair of crossed polarizers 8104 and to the detector 8106 for lock-in detection. We will also explore experimental system which incorporates the use of a balanced detector.

Experiments have shown a shift of approximately 20 degrees in the intensity curve for these polished sugar crystals. A series of measurements are taken once the detection scheme is finalized. These include:

1. Optical activity through the entire polished crystal.
2. Optical activity through each of the cleaved pieces independently to investigate if there is additive/subtractive effects of optical activity for different cleavage directions and if any of the directions are sensitive to OAM.

Raman Detection of Glycated Protein

Hb and Hb-A1c a proteins by Raman spectroscopy using OAM may also be investigated. Mammalian blood is considered as connective tissue because of its cellular composition and due to its embryonic origin and also due to the origin and presence of colloidal proteins in its plasma. Red Blood cells and Plasma proteins are the major constituents of blood. These connective tissue components are targets for metabolic stress under disease conditions and result in the chemical alterations. All the blood components are subjected to excessive metabolic stress under hyperglycemic states. Blood acts a primary transporter of nutrients, gases and wastes. Blood plasma acts as a primary carrier for glucose to the tissues. Normal pre-prandial plasma glucose levels are 80 mg/dl to 130 mg/dl and normal postprandial plasma glucose is <180 mg/dl. The Renal Threshold for Glucose (RTG) is the physiologic maximum of plasma glucose beyond which kidneys fail to reabsorb the glucose and get excreted in urine. This is a condition called glycosuria. Glycosuria is the key characteristic of Diabetes mellitus (DM). High plasma glucose in DM will cause increased levels of Glycosylated Hemoglobin also known as HbA1c. Under normal physiological conditions HbA1c levels are <7%, this also expressed as eAG which should be below 154 mg/dl in Normo-glycemic condition.

Glycation of Plasma Proteins in DM

Glycation is defined as the non-enzymatic random non-specific covalent linking of glucose or other hexose sugar moieties to the proteins. Under normal blood glucose levels in healthy individuals will have levels <7% Glycated Hemoglobin (HbA1c) in the blood, however under hyperglycemic conditions like DM, its levels will increase. Higher blood glucose levels can induce glycation of other major proteins of blood plasma like albumin.

Advantages of Measurement of Glycated Proteins in DM:

Measurements of blood glucose levels only provide the information about the glycemic status of a subject at a given moment, i.e. a diabetic person with uncontrolled blood sugar levels for several months may yield normal blood glucose level if he/she gets the test under fasting state or with low carbohydrate intake on a given day. However the measurement of Glycated hemoglobin (HbA1c) levels in blood yield the information about average blood sugar levels in patient for past 2 to 3 months. Therefore it has become a standard clinical practice since past decade to measure Glycated Hemoglobin in patients with DM with the development sensitive and reliable laboratory analyses. We propose the use of Raman spectroscopic studies on Diabetic blood and its components for the detection of specific Raman finger prints that may result from non-enzymatic glycosylation of key blood proteins Hemoglobin, plasma albumin and others in its native and altered physical states. The process of glycation in proteins induces the chemical alterations, structural modifications, conformational changes. Any or all of these can result in special Raman spectral changes which can used as a clinical marker.

Measurements were carried out with a small benchtop OceanOptics Raman system with 532 nm excitation.

Raman Spectroscopy of Tryptophan:

The Hemoglobin (tetramer) has 6 residues of Tryptophan therefore Hemoglobin is a fluorescent protein. Tryptophan can undergo glycation and result in conformational changes in Hemoglobin. The tryptophan changes can be identified by using Raman studies (Masako Na-Gai et al. Biochemistry, 2012, 51 (30), pp 59325941) which is incorporated herein by reference. In order to understand the glycation induced Raman spectral changes in Tryptophan residues Raman spectra is obtained from analytical grade amorphous Tryptophan using 532 nm OceanOptics Raman Raman Spectra of Proteins:

Solid amorphous powders of albumin and Glycated albumin samples were subjected to Raman measurements using a OceanOptic 532 nm Raman system and the confocal Raman system using 488, 514.5 and 632.8 nm. No Raman signal was observed from these samples, and therefore we need to retest in solution at a physiologic pH of 7.4.

The next steps are:

1. NIR Raman: Blood and its components have intense fluorescence in visible range so NIR Raman may help reduce fluorescence and get good Raman signals from target protein molecules.

2. OceanOptics 532 nm Raman: This can be used detect some of Glycation derivatives in blood. This needs normal and diabetic blood either from human subjects or animal models. And also Reference spectra of synthetic glycation products can be obtained by using this system, which can later be compared with the Raman signal from blood samples.

3. In Vivo Animal model: For future experiments to be successful for in vivo blood glucose and diabetes testing, the Raman measurements need to be carried out in a rat diabetes animal model.

OAM with Raman for Food Freshness, Spoilage, and Organic Detection

Another aspect that will be investigated is food safety concerns due to spoilage of meats, produce, diary, and grains and determination if labeled food is organic using Raman and OAM. Public and individual concern led to both governmental regulation and commercial requirements of quality, stability, and safety of food storage periods. Moreover, food deterioration resulting in food spoilage leads to not only health issues but also economic loss to food manufacturing and related industries. Thus, minimizing food spoilage, determining food freshness, or maximizing shelf life of food is desired.

Moreover, in 2000, the U.S. Department of Agriculture ("USDA") established guidelines and national standards for the term "organic." For example, organic food, as defined by USDA guidelines, means that food must be produced without sewer-sludge fertilizers, synthetic fertilizers and pesticides, genetic engineering, growth hormones, irradiation, and antibiotics.

The traditional physical characteristics of food spoilage, such as unpleasant smells, unpleasant tastes, color changes, texture changes, and mold growth, manifest well after biochemical processes have occurred that impair food quality or safety. As a result, they are not adequate indicators of determining acceptable criteria to use for food freshness, preservation, and spoilage.

Thus, research to date includes the identification of so-called "biomarkers" of food spoilage. This research includes identification of the biochemical mechanisms that produce certain chemical by-products that are associated with the physical characteristics of food spoilage. These mechanisms can be physical (e.g., temperature, pH, light, mechanical damage); chemical (e.g., enzymatic reaction, non-enzymatic reaction, rancidity, chemical interaction); microorganism-based (e.g., bacteria, viruses, yeasts, molds); or other (e.g., insects, rodents, animals, birds).

One aspect of the investigation is to use OAM and Raman techniques to identify these so-called biomarkers and their associated concentrations to better determine shelf life of basic food categories. Additionally, another aspect of the invention is to investigate the chemicals used that would fail to qualify foodstuffs as "organic." For example, the Table 1 below shows several researched biochemical processes and chemical by-products associated with food spoilage mechanisms associated with common food groups:

TABLE 1

| Biochemical Process | Mechanism | Food Category/ Spoilage Action | Resulting Biomarker |
|---|---|---|---|
| Oxidation | Light | Reversion Flavor of Soybean | 2-pentyl furan |
| Oxidation | Light | Sunlight flavor in milk | dimethyl disulfide, 2-butanone, ethanol, diacetyl, n-butanol |
| Oxidation | Light | Loss of Riboflavin, Vitamins D, E, and C | vitamin D-5,6 ep25 oxide |
| Oxidation | Light | Greening of Potato | alpha-solanine, alpha-chaconine |
| Oxidation | Decay | meat and diary (fats, oils, lipids) | aldehydes |
| Enzymatic | Decay | Chicken/Meat | dimethylsulfide, dimethyl disulfide, dimethyl trisulfide, dimethyl tetrasulfide, hydrogen sulfide, ethanol, 3-methyl-1-butanol, acetic acid, propanioc acid, methanethiol, free fatty acids (FFAs) |
| Enzymatic: Decarboxylation of free amino acids (natural fermentation or via contimation of microorganisms) | Decay | Fruits, Vegatables, Meat, Fish, Poultry | biogenic amines (tyraimine, putrescine, cadaverine, histamine) |
| Enzymatic | Decay | Vegatables (loss of vitamin C) | ascrbic acid, oxidase |
| Enzymatic | Decay | Milk, oils (hydrolytic rancidity) | lipase, glycerol, free fatty acids (FFAs), 3-(E)-hexenal, 2-(E)-hexenal |
| Enzymatic | Decay | Vegatables (loss of vitamin A) | lipoxygenase |
| Enzymatic | Decay | Fruits (loss of pectic substances, i.e., softing) | petic enzymes |
| Enzymatic | Decay | Fruits (browning) | peroxidases (polyphenol oxidase, o-diphenol, monophenol, o-quinone) |
| Enzymatic | Decay | Fruits, Vegetables (browning, sour flavor, vitamin loss) | melanin |
| Enzymatic | Decay | Eggs, Crab, Lobster, Flour (reduction of shelf life, overtenderization, reduction in gluten network formation) | proteases |
| Enzymatic | Decay | Meats, Fish | thiaminase |
| Microbial | Bacteria | Carbohydrates (fermentation) | alcoholic (ethanol, CO2); homofermentative lactic acid (lactic acid); heterofermentative lactic acid (lactic acid, acetic acid, ethanol, CO2); propionic acid fermentation (propionic acid, aetic acid, CO2); butyric acid fermentation (butyric acid, acetic acid, CO2, H2); mixed acid fermentation (lactic acid, acetic acid, CO2, H2, ethanol); 2,3-butanediol fermentation (CO2, ethanol, 2,3-butanediol, formic acid) |
| Microbial | Bacteria | Degradation of N-Compounds | (H2S, methyl mercaptns, indole, cadaverine, putrescine, histamine) |
| Microbial | bacteria | Fish (odor) | trimethylamine |
| Microbial | Bacteria | Lipids | aldehyde, ketones |
| Microbial | Bacteria | Pectin Degradation | polygalcturonic acid, galacturonic acid, methanol |
| Fishy Odor | Decay | Meat, Egg, Fish | trimethylamine |
| Garlic odor | Decay | Wine, Fish, Meat, Milk | dimethyl trisulfide |
| Onion odor | Decay | Wine, Fish, Meat, Milk | dimethyl disulfide |
| Cabbage odor | Decay | Wine, Fish, Meat, Milk | dimethyl sulfide |
| Fruity odor | Decay | Milk, Fish, Wine | esters |
| Potato odor | Decay | Meat, Egg, Fish | 2-methoxy-3-isopropylprazine |
| Alcoholic odor | Decay | Fruit juices, Mayonnaise | ethanol |
| Musty odor | Decay | Bread, Wine | tricholoranisole |
| Cheesy odor | Decay | Meat | diacetyl, acetoin |
| Medicinal odor | Decay | Juice, Wine | 2-methoxy phenol |
| Souring | Decay | Wine, Beer, Dairy | acetic acid, lactic acid, citric acid |
| Slime | Decay | Meat, Juices, Wine | polysaccharide |

TABLE 1-continued

| Biochemical Process | Mechanism | Food Category/ Spoilage Action | Resulting Biomarker |
|---|---|---|---|
| Curdling | Decay | Milk | lactic acid |
| Holes | Decay | Hard cheese | carbon dioxide |

A person skilled in the art would be well aware of various other mechanisms and biochemical indicators evidencing food spoilage of common foodstuffs, including other reactions or volatile or non-volatile organic compound (VOC) by-products associated with food spoilage. Likewise, a person skilled in the art would be well aware of the chemicals and additives that do not qualify food as organic, whether investigating grains, dairy, produce, or meats.

Traditional spectroscopy techniques are not adequate to identify in real-time or adequate concentration these biomarkers in any meaningful manner to determine shelf life of the food sample or organic nature of the food in question. The present investigation and invention will employ Raman and OAM techniques described above to classify, identify, and quantify the various bio-markers in the table above and the common chemicals that do not qualify food as organic as defined in federal regulations.

Such techniques are equally applicable whether the bio-marker or chemical is a chiral or non-chiral molecule. Such data can then be correlated to concentration of degradation of the sampled food group to determine minimum and maximum concentrations acceptable to food freshness, spoilage, organic quality, and safety.

Ince-Gaussian Spectroscopy

Another type of spectroscopic technique that may be combined with one or more other spectroscopic techniques is Ince-Gaussian Spectroscopy. Ince Gaussian (IG) beams are the solutions of paraxial beams in an elliptical coordinate system. IG beams are the third calls of orthogonal Eigen states and can probe the chirality structures of samples. Since IG modes have a preferred symmetry (long axis versus short axis) this enables it to probe chirality better than Laguerre Gaussian or Hermite Gaussian modes. This enables the propagation of more IG modes within an elliptical core fiber than Laguerre Gaussian modes or Hermite Gaussian modes. Thus, IG modes can be used as a program signal for spectroscopy in the same manner that Laguerre Gaussian modes or Hermite Gaussian modes are used. This enables the detection of types of materials and concentration of materials using an IG mode probe signal.

The wave equation can be represented as a Helmholtz equation in Cartesian coordinates as follows $$(\nabla^2 + k^2) E(x,y,z) = 0$$

E(x, y, z) is complex field amplitude which can be expressed in terms of its slowly varying envelope and fast varying part in z-direction.

$$E(x,y,z) = \psi(x,y,z) e^{jkz}$$

A Paraxial Wave approximation may be determined by substituting our assumption in the Helmholtz Equation.

$$(\nabla^2 + k^2) \psi \cdot e^{jkz} = 0$$

$$\frac{\delta^2 \psi}{\delta x^2} + \frac{\delta^2 \psi}{\delta y^2} + \frac{\delta^2 \psi}{\delta z^2} - j2k\frac{\delta \psi}{\delta z} = 0$$

We then make our slowly varying envelope approximation $$\left|\frac{\delta^2 \psi}{\delta z^2}\right| \ll \left|\frac{\delta^2 \psi}{\delta x^2}\right|, \left|\frac{\delta^2 \psi}{\delta y^2}\right|, 2k\left|\frac{\delta \psi}{\delta z}\right|$$

$$\nabla_t^2 \psi + j2k\frac{\delta \psi}{\delta z} = 0$$

Which comprises a Paraxial wave equation.

The elliptical-cylindrical coordinate system may be define as shown in FIG. 82.

$$x = a\cosh\xi\cos\eta$$

$$y = a\sinh\xi\sin\eta$$

$$\xi \in (0, \infty), \eta \in (0, 2\pi)$$

$$a = f(z) \text{ where } f(z) = \frac{f_0 w(z)}{w_0}$$

Figure 83:
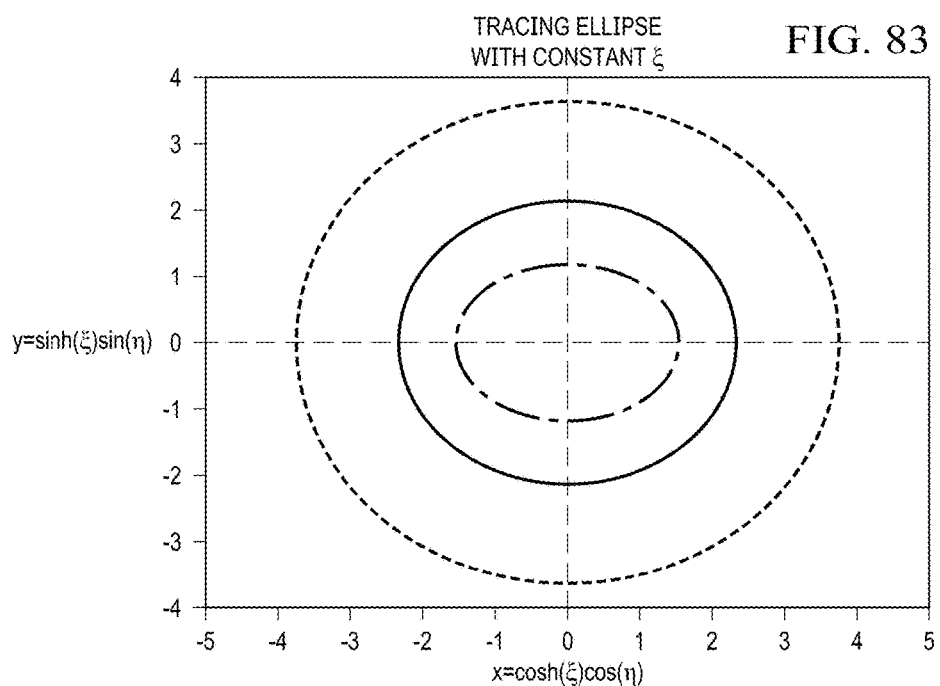
FIG. 83 illustrates a tracing the lips with constant $\xi$.

Curves of constant value of ξ trace confocal ellipses as shown in FIG. 83.

$$\frac{x^2}{a^2\cosh^2\xi} + \frac{y^2}{a^2\sinh^2\xi} = 1 \text{ (Ellipse)}$$

Figure 84:
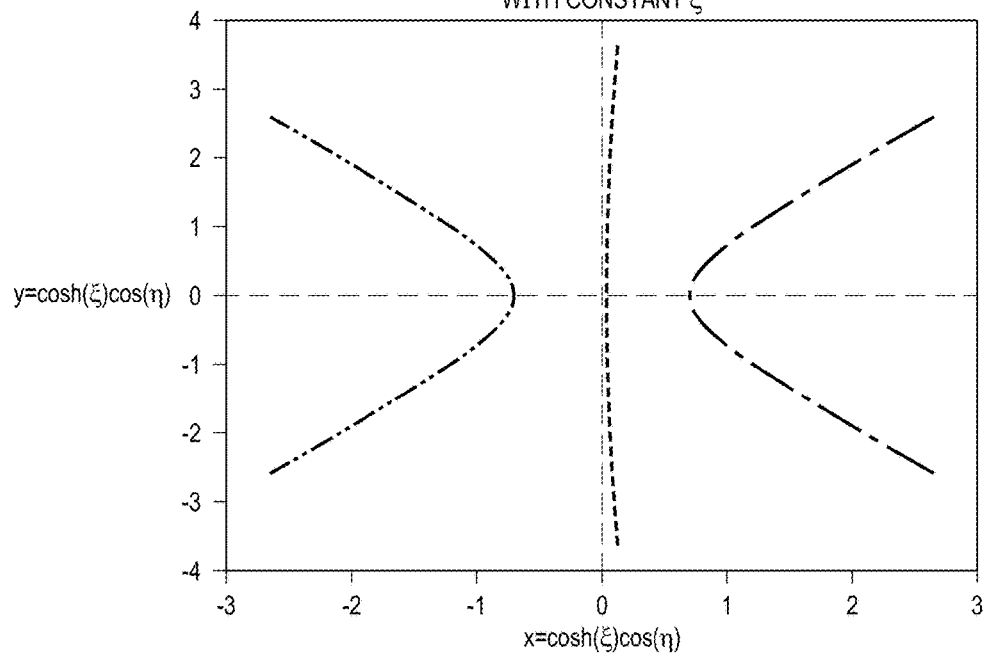
FIG. 84 illustrates tracing hyperbolas with constant $\eta$.

A constant value of η give confocal hyperbolas as shown in FIG. 84.

$$\frac{x^2}{a^2\cos^2\eta} - \frac{y^2}{a^2\sin^2\eta} = 1 \text{ (hyperbola)}$$

An elliptical-cylindrical coordinate system may then be defined in the following manner $$\nabla_t^2 = \frac{1}{h_\xi^2}\frac{\delta^2}{\delta\xi^2} + \frac{1}{h_\eta^2}\frac{\delta^2}{\delta\eta^2}$$

Where $h_\xi$, $h_\eta$ are scale factors $$h_\xi = \sqrt{\left(\frac{\delta x}{\delta \xi}\right)^2 + \left(\frac{\delta y}{\delta \xi}\right)^2}$$

$$h_\eta = \sqrt{\left(\frac{\delta x}{\delta \eta}\right)^2 + \left(\frac{\delta y}{\delta \eta}\right)^2}$$

$$h_\xi = h_\eta = a\sqrt{\sinh^2\xi + \sin^2\eta}$$

$$\nabla_t^2 = \frac{1}{a^2\sinh^2\xi\sin^2\eta}\left(\frac{\delta^2}{\delta\xi^2} + \frac{\delta^2}{\delta\eta^2}\right)$$

The solution to the paraxial wave equations may then be made in elliptical coordinates. Paraxial Wave Equation in Elliptic Cylindrical co-ordinates are defined as $$\frac{1}{a^2(\sinh^2\xi\sin^2\eta)}\left(\frac{\delta^2\psi}{\delta\xi^2} + \frac{\delta^2\psi}{\delta\eta^2}\right) - j2k\frac{\delta\psi}{\delta z} = 0$$

Assuming separable solution as modulated version of fundamental Gaussian beam.

$$IG(\vec{r}) = E(\xi)N(\eta)\exp(jZ(z))\psi_{GB}(\vec{r})$$

$$\text{Where } \psi_{GB}(\vec{r}) = \frac{w_0}{w(z)}\exp\left[-\frac{r^2}{w^2(z)} + j\frac{kr^2}{2R(z)} - j\psi_{GS}(z)\right]$$

E, N & Z are real functions. They have the same wave-fronts as $\psi_{GB}$ but different intensity distribution.

Separated differential equations are defined as $$\frac{d^2E}{d\xi^2} - \epsilon\sinh2\xi\frac{dE}{d\xi} - (a - p\epsilon\cosh2\xi)E = 0$$

$$\frac{d^2N}{d\eta^2} - \epsilon\sin2\eta\frac{dN}{d\eta} - (a - p\epsilon\cos2\eta) = 0$$

$$-\left(\frac{z^2 + z_r^2}{z_r}\right)\frac{dZ}{dz} = p$$

Where a and p are separation constants $$\epsilon = \frac{f_0 w_0}{w(z)}$$

The even solutions for the Ince-Gaussian equations are $$IG_{pm}^e(\vec{r}, \epsilon) =$$

$$\frac{Cw_0}{w(z)}C_p^m(j\xi, \epsilon)C_p^m(\eta, \epsilon)\exp\left(-\frac{r^2}{w^2(z)}\right)\times\exp j\left(kz + \frac{kr^2}{2R(z)} - (p+1)\psi_{GS}(z)\right)$$

Figure 85A:
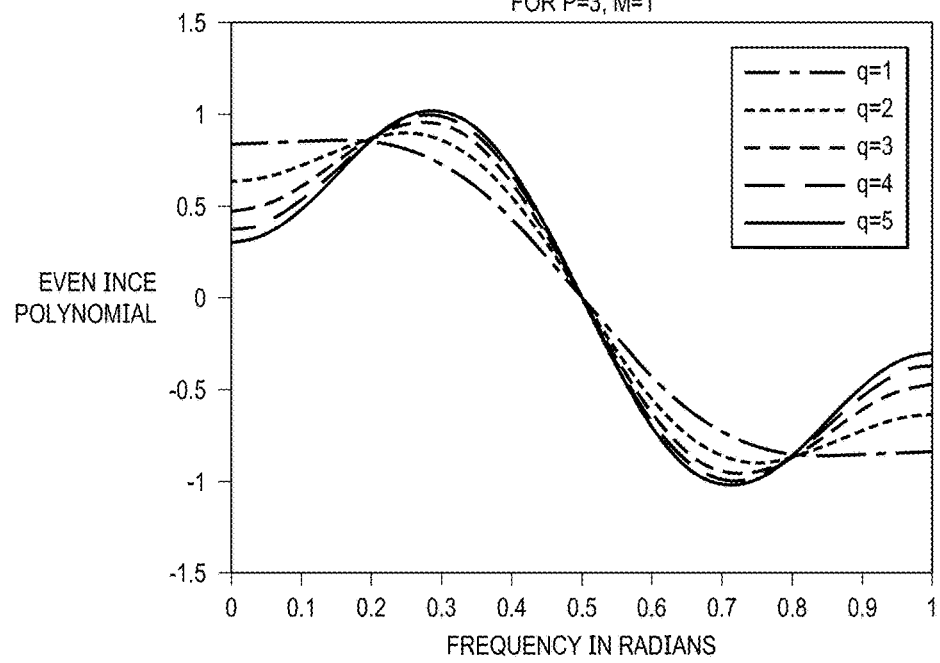
FIGS. 85A and 85B illustrates even Ince Polynomials.
Figure 85B:
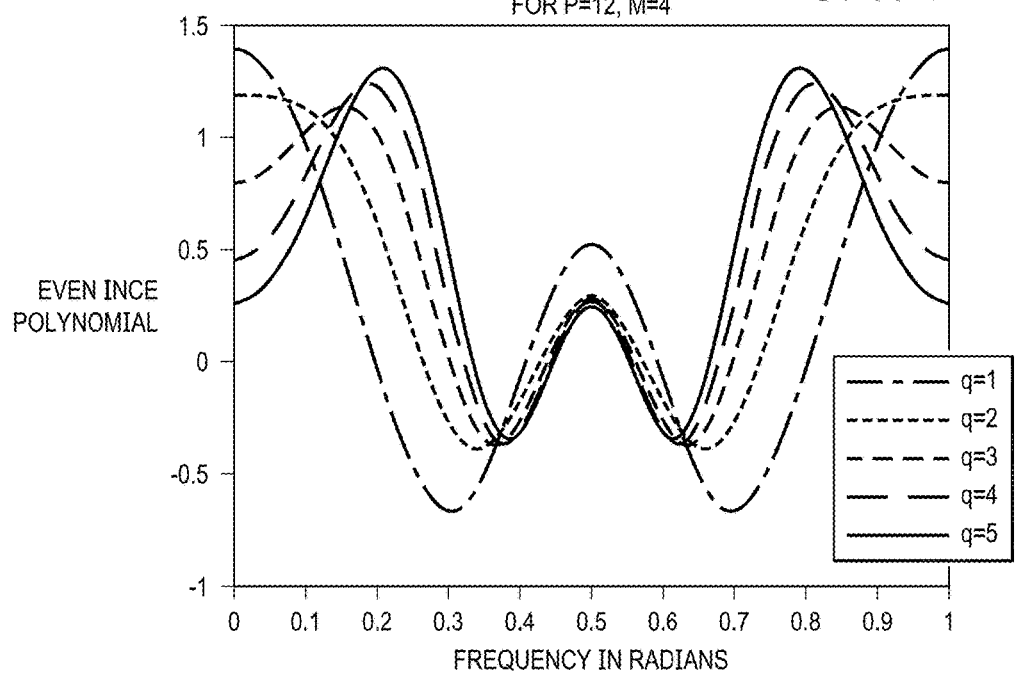
Figure 86:
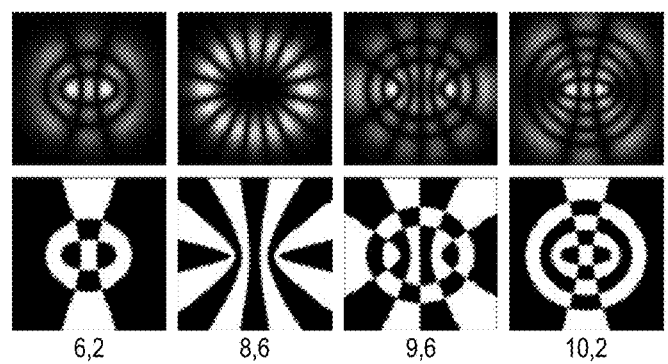
FIG. 86 illustrates modes and phases for even Ince mode.

The frequency of the even Ince Polynomials are illustrated in FIGS. 85A and 85B and the modes and their phases are illustrated in FIG. 86.

The odd solutions for the Ince-Gaussian equations are $$IG_{pm}^o(\vec{r}, \epsilon) =$$

$$\frac{sw_0}{w(z)}S_p^m(j\xi, \epsilon)S_p^m(\eta, \epsilon)\exp\left(-\frac{r^2}{w^2(z)}\right)\times\exp j\left(kz + \frac{kr^2}{2R(z)} - (p+1)\psi_{GS}(z)\right)$$

Figure 87A:
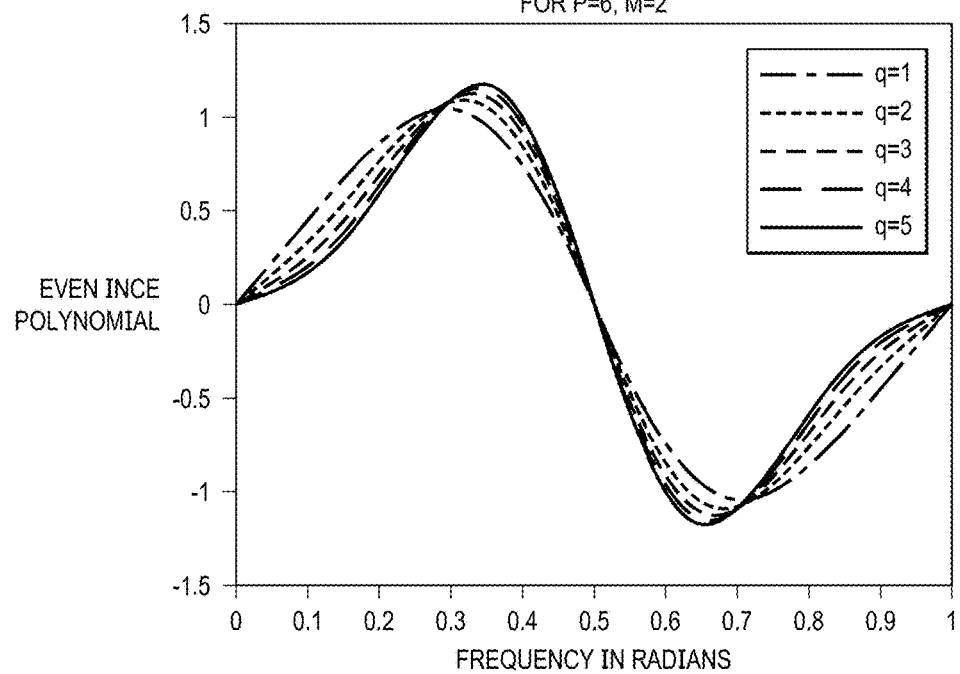
FIGS. 87A and 87B illustrates odd Ince Polynomials.
Figure 87B:
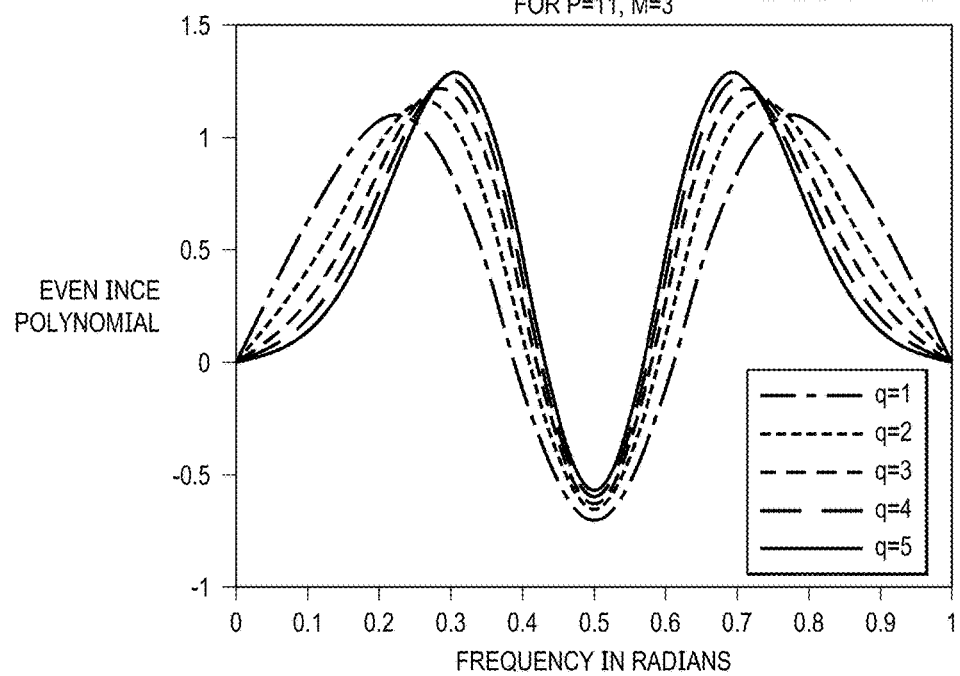
Figure 88:
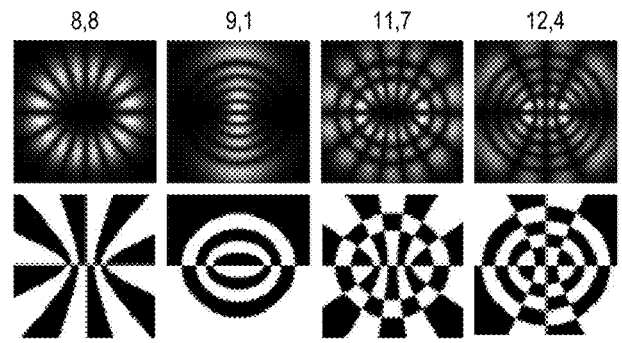
FIG. 88 illustrates modes and phases for odd Ince mode.

The frequency of the odd Ince Polynomials are illustrated in FIGS. 87A and 87B and the modes and their phases are illustrated in FIG. 88.

Thus, as previously discussed with respect to FIG. 59, by combining two or more different types of spectroscopy techniques, various types of different parameters may be monitored and used for determining types and concentrations of sample materials. The use of multiple types of spectroscopic parameter analysis enables for more accurate and detailed analysis of sample types and concentrations. Thus, any number of spectroscopic techniques such as optical spectroscopy, infrared spectroscopy, Ramen spectroscopy, spontaneous Ramen spectroscopy, simulated Ramen spectroscopy, resonance Ramen spectroscopy, polarized Ramen spectroscopy, Ramen spectroscopy with optical vortices, THz spectroscopy, terahertz time domain spectroscopy, fluorescence spectroscopy, pump probe spectroscopy, OAM spectroscopy, or Ince Gaussian spectroscopy may be used in any number of various combinations in order to provide better detection of sample types in concentrations. It should be realized that the types of spectroscopy discussed herein are not limiting in any combination of spectroscopic techniques may be utilized in the analysis of sample materials.

Multi-Parameter Dual Comb Spectroscopy with OAM

Figure 89:
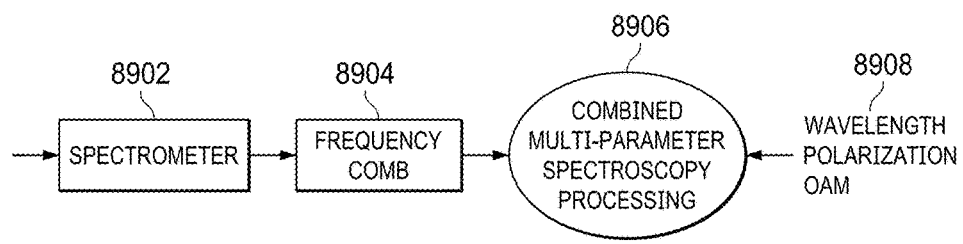
FIG. 89 illustrates dual comp spectroscopy.

One can perform precision spectroscopy with pairing optical frequency combs which can improve the results. Referring now to FIG. 89, in broadband frequency comb spectroscopy, the signal from an optical frequency comb is read by a conventional spectrometer, but in a technique called dual-comb spectroscopy, that conventional spectrometer 8902 and the instrument's limitations on speed and resolution are removed. Instead, a second frequency comb 8904 takes on the work previously done by the spectrometer 8902. The result can be dramatic gains in data acquisition speed, spectral resolution and sensitivity. These techniques can be used in conjunction with muti-parameter spectroscopy 8906 leveraging wavelength, polarization and OAM spectroscopy 8908.

Optical Frequency Combs

An optical frequency comb 8904 is a spectrum consisting of hundreds of thousands or millions of equally spaced, sharp lines-analogous having a great many continuous-wave (CW) lasers simultaneously emitting at different, equally spaced frequencies. Optical combs can be generated in many ways; the most common method uses a phase-stabilized, mode-locked ultrashort-pulse laser. In the time domain, the laser produces a pulse train at a specific repetition rate, and with a specific, increasing additional carrier-envelope phase with each successive pulse. When the repetition rate and carrier-envelope phase of the pulse train are both stabilized against radio- or optical-frequency references, a Fourier transformation of the laser's periodic pulse train shows a sharp, comb-like spectrum in the frequency domain.

If the frequency comb is well stabilized and referenced to an absolute frequency standard, such as an atomic clock, the comb spectrum becomes an extremely precise ruler for measuring optical frequencies. That ruler has found applications in a wide variety of scientific problems: high-resolution frequency measurements of atomic, ionic or molecular transitions to answer fundamental questions in physics; the detection of tiny amounts of Doppler shift; and other applications in attosecond physics, ultrapure microwave generation, time-frequency transfer over long distances, manipulation of atomic qubits, and many others.

One of the most active research areas for frequency combs is broadband molecular spectroscopy. The comb's millions of equally spaced, sharp lines offer the opportunity to measure complex broadband molecular signatures with high spectral resolution and sensitivity. Exploiting those advantages, however, requires a spectrometer of sufficiently high resolution to resolve each individual comb line. One approach can be the use of a spectrometer based on virtually imaged phased array (VIPA) disperser in combination with a diffraction grating; another common scheme uses an analytical chemistry, the Michelson-type Fourier transform spectrometer, and replaces the conventional broadband, usually incoherent light source with a frequency comb.

In this approach to frequency comb spectroscopy, the frequency comb pulse train is split into interferometer arms, one of which includes a mechanically scanned mirror, and the two pulse trains are sent through the sample to be analyzed. As the mirror is scanned, a series of interferograms is recorded with a single photo-receiver and a digitizer; Fourier transformation of the interferograms generates the spectrum, with a resolution determined by the maximum optical-path-length difference of the interferometer.

The Dual-Comb Advantage

A key drawback of doing frequency comb spectroscopy the Michelson-type setup described is speed: the scan rate of the setup, which is limited by the velocity of the scanning mirror, is commonly only on the order of Hz. Dual-comb spectroscopy eases this disadvantage by using a second frequency comb, rather than a moving mirror, to supply the delay time. The result can be a significant enhancement of the spectrometer's performance.

In the dual-comb setup, the pulse train forms a second comb, with a slightly different pulse repetition rate from the first, that is spatially combined with the train from the first comb. The combined pulse train is passed through the sample to be analyzed, and detected by a photo-receiver. The result, in the time domain, is a repeated series of cross-correlation-like interferometric signals between the pulses, with a steadily increasing time difference based on the difference in repetition rate between the two combs. The dual-comb interferograms thus have characteristics similar to those of a conventional Michelson-type Fourier transform spectrometer but because the dual-comb setup does not depend on the mechanical motion of a mirror, its scanning rate is several orders of magnitude faster than that of the Michelson-type interferometer.

Another advantage of dual-comb spectroscopy emerges in the frequency domain There, the mixing of the two optical combs, with slightly different repetition rates, results in a third, down-converted radio-frequency (RF) comb, with spacing between teeth equivalent to the repetition rate difference between the two optical combs. The sample's response is thus encoded on this down-converted RF comb, and the beat measurement between the two optical combs generates a multi-heterodyne signal that can be recovered from the RF comb. In summary, the down-converted comb inherits the coherence property of the optical frequency combs, enabling broadband spectroscopy with a high resolution and accuracy with the speed and digital signal processing advantages of RF heterodyne detection.

Small Wearable Device

Figure 90:
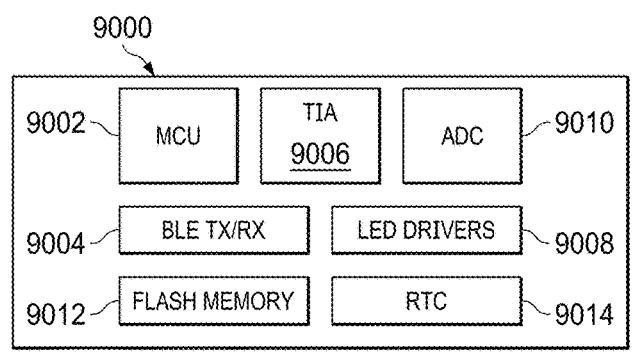
FIG. 90 illustrates a wearable multi-parameter spectroscopy device.

Compact wearable optical devices based on Raman and NIR absorption to detect changes in physiological chemical levels in the body may also be implemented. Along with the novel detection scheme, we are also developing the compact integrated electronic-photonic system (ultimately an integrated silicon-photonic system). A wearable device 9000 should include the following components as shown in FIG. 90. An MCU (microcontroller) 9002 controls overall operation of the wearable device 9000. BLE (Bluetooth low energy) transmitter/receiver 9004 transmits signals to and from the wearable device 9000. Trance-impedance amplifier (TIA) for internally amplifying signals. Drivers 9008 for driving LED/lasers within the device 9000. High resolution ADC 9010 performs analog to digital conversions. Flash memory 9012 stores data within the wearable device 9000. Real-time clock 9014 controls internal clocking operations.

The major requirement is low quiescent current for every component, ability to enter deep sleep mode, low current consumption in operating mode, low-frequency mode for real-time clock/low power operation, and single battery operation of the MCU (microcontroller) and BLE (bluetooth low energy). MCU+BLE chipsets of 2013-2015 model year provide the following component options:

a) EFM32 (MCU Silicon Laboratories)+CC2541 (BLE chip Texas Instruments) or BCM20732 (Broadcom), or b) Single chip solution form Nordic Semiconductors NRF51822 which includes similar Cortex M0 core and BLE radio, BLE stack is realized via underling Nordic proprietary OS (SoftDevice) which occupies about 100 kB of chips memory.

Either of these two solutions is used in 90% of modern BLE wearable devices. In the present case the preferred embodiment would be using the single chip solution from Nordic Semiconductor. Major characteristics are:

1) External crystal for real-time clock,
2) 256 kb of memory (256 kb–100 kb (SoftDevice)=156 kB for the program and storage)
3) Sleep mode in 1 uA range
4) Support of all standard BLE profiles and adjustable radio power up to 4 dBm.

It also supports ANT protocol which may be useful in future development.

The near infrared laser diode system provides approximately 30 controllable channels between 990 and 1600 nm, as well as an additional tunable source between 1450 and 1600.

Similar portable devices may be used with respect to other embodiments and uses described above, including the detection of proteins and food spoilage or food organic biomarkers due to the various biochemical mechanisms associated with food spoilage.

OAM Body-Imaging

Imaging through and parts of the body is critical for most biomedical optical technology. Past work has developed imaging and spectroscopy in select transmission windows in the NIR where glucose and proteins have strong absorptions while water has reduced absorption. Since optical detection of glucose or other chemical compounds will most likely need to be in a region free of strong absorptions from other molecules, and will take place with OAM beams, imaging of the body tissues, brain, bone and skin with OAM may be used. Possible routes to investigate would be phase contrast and dark field imaging, ballistic transport of OAM through scattering media in the NIR and birefringent imaging. The diode lasers available for the wearable device can also be incorporated into the NIR OAM imaging once a suitable detector is acquired and tested. Single channel detectors in the NIR are cheaper than 2D CCD arrays, however a scanning system and image construction software would be needed when imaging with a single channel detector.

Potential Applications

A compact, handheld 3D spectrometer capable of simultaneous polarization, wavelength, and OAM-spectroscopy operated in a broad electromagnetic frequency range empowers consumers with tremendous amounts of useful information about such things as their food and air quality, household biological contaminants, medicinal identification, and health-related issues such as real-time information about dental caries. This section serves as an outline of some of the potential applications of 3D spectroscopy.

Food Industry

Food substances primarily consist of water, fat, proteins, and carbohydrates. The molecular structure and concentration of food substances govern their functional properties. Quantification of these properties dictates the quality of food in terms of minimum standards of suitability for human consumption or exposure which include chemical, biological, and microbial factors that may impact such parameters as their shelf-life. Recent advances in industrialization of our food supply chains and changes in consumer eating habits have placed greater demand on the rapidity with which our food must be analyzed for safety and quality. This demand requires appropriate analytical tools such as spectroscopy.

Food spectroscopy is a desirable analysis method because it requires minimal or no sample preparation as well rapid, production-line measurements. Given the nature of spectroscopic analysis, multiple tests may be done on the sample.

Outside the industrialized production line of our food supply, novel spectroscopic techniques could be employed at the level of individual consumers. For example, an individual consumer may spectroscopically measure the sugar concentration in his foods, overall food quality, ripeness, or identify a watermelon in the local grocery store as having been spoiled using a pocket size laser-based spectrometer.

Nanoscale Material Development for Defense and National Security

Nanoscale material development for defense and national security technologies generally necessitates the binding site to recognize the target of interest. Several spectroscopic techniques are currently based on absorption, scattering, of light, such as electron absorption (UV-vis), photoluminescence (PL), infrared (IR) absorption, and Raman scattering while more advanced techniques include single molecule spectroscopy, sum frequency generation, and luminescence up-conversion. These spectroscopy technologies aid in the fabrication process of nanoscale material architectures employed as biological and chemical sensors.

Chemical Industry

Optical spectroscopy of gas sensors is useful for a variety of environmental, industrial, medical, scientific and household applications. The gas may be hazardous to human health, an atmospheric pollutant, or important in terms of its concentration for industrial or medical purposes. Aside from triggering an alarm, it is frequently desirable to measure accurate, real-time concentrations of a particular target gas, which is often in a mixture of other gases. Consumers may use household units to monitor air for biological or chemical hazards such as airborne germs or carbon monoxide as well as surfactant contaminations on and around children's play areas, toys, and bedrooms. Such units would be useful in school classrooms, business offices, and shopping malls to alert to facilities managers to potential health hazards. Further units may be useful in various industrial settings, including for example, chemical and/or petrochemical facilities, including but not limited to, using near-infrared spectroscopy. In addition to improved environmental benefits of detecting various fugitive emissions of gases, such detection presents various economic benefits for industrial operators to fix fugitive emission sources for increases in product recovery and abatement of governmental fines.

Pharmaceutical Industry

The manufacturing process of highly precise drug concentrations in pills, capsules and liquids requires strict real-time monitoring as may be performed by optical spectroscopy technologies. Once produced and distributed, consumers may readily identify pills and medication at home using an advanced, real-time spectroscopy technique integrated into a handheld device.

Medical Industry

There is strong interest in developing more sophisticated optical biopsy technologies that non-invasively detect disease. These technologies may be driven by spectroscopy that may optically biopsy tissues without the need to remove it from the patient's body. Such a technology may be developed to produce a photonics finger imager for accurate prostate checkups, breast mammograms, and other cancer-detection procedures. A pocket-sized dermatological spectrometer would give patients private, real-time information that may be combined with the patient's medical record for discussion with medical professionals.

The use of small, handheld optical spectrometers can be integrated into a patient's routine health maintenance schedule. An example is the early detection of chemicals associated with Alzheimer's disease and Parkinson's by spectroscopic detection during routine eye exams.

Dentistry

Everyday personal dental care requires small tools and instruments such as toothbrushes and dental floss. A toothbrush-size optical spectrometer would be useful to detect the onset of small dental caries (tooth decay and cavities) and alert the consumer to schedule a visit to the family dentist who may have been sent tooth-specific information before the scheduled visit.

Biomedical Photonics

These technologies can be applied to, and not limited to, neuro-imaging applications such as optical spectroscopy and correlation methods to measure oxygen and blood flow; the development of new microscopes for functional imaging to improve the quantitative interpretation of measurement of brain activities and psychology using functional near-infrared spectroscopy; the development technologies such as diffuse correlation spectroscopy to measure blood flow; and the development of multi-spectral optical imaging of cerebral hemoglobin.

Mode Crosstalk Matrix for Glycation Detection

The glycation induced changes in human hemoglobin ($HbA_1$-$a_2B_2$) are studied using absorption, fluorescence, Raman and time resolved fluorescence spectroscopic methods. The non-enzymatic glycosylation of hemoglobin that results from sustained elevated blood sugar levels changes the chemistry of its native chromophore and fluorophore moieties as a result the tertiary structure gets altered significantly. These post translational molecular modifications induce changes in optical properties of materials like absorption, fluorescence emissions, fluorescence lifetimes and Raman finger prints. Changes in the fluorescence lifetimes of native fluorospores may be used to compare normal and glycated hemoglobin to detect glycated hemoglobin levels. The optical properties of normal hemoglobin can be compared with glycated hemoglobin under non-denaturing conditions to evaluate their potential as diagnostic and/or investigative biomarkers for chronic hyperglycemic conditions such as Diabetes Mellitus Type 1 and 2. Also, using the absorption, fluorescence, Raman and time resolved fluorescence spectroscopic methods as diagnostic and/or investigative biomarkers for chronic hyperglycemic conditions such as Diabetes Mellitus Type 1 and 2.

Figure 91:
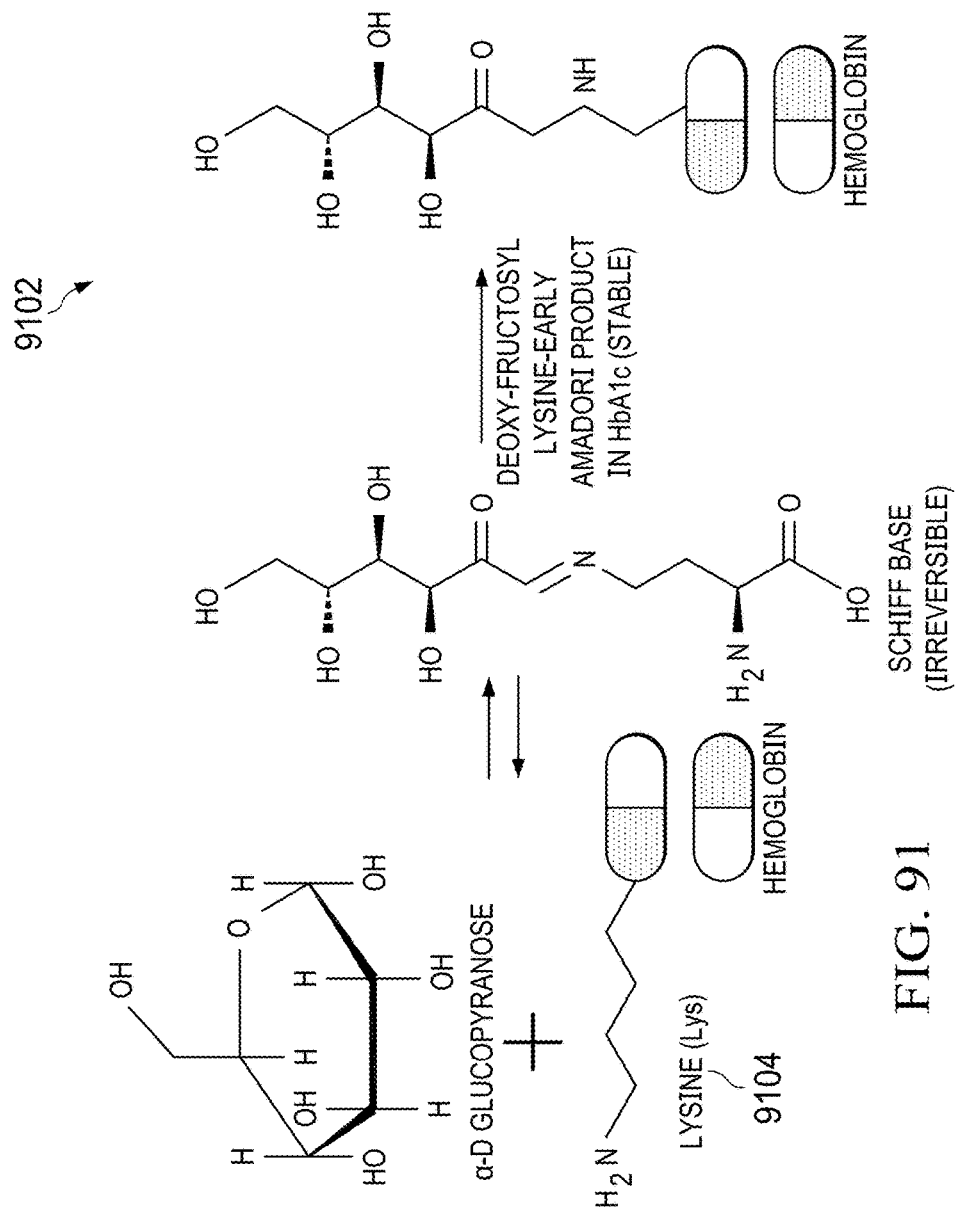
FIG. 91 illustrates glycated hemoglobin formation in hypoglycemia.
Figure 92:
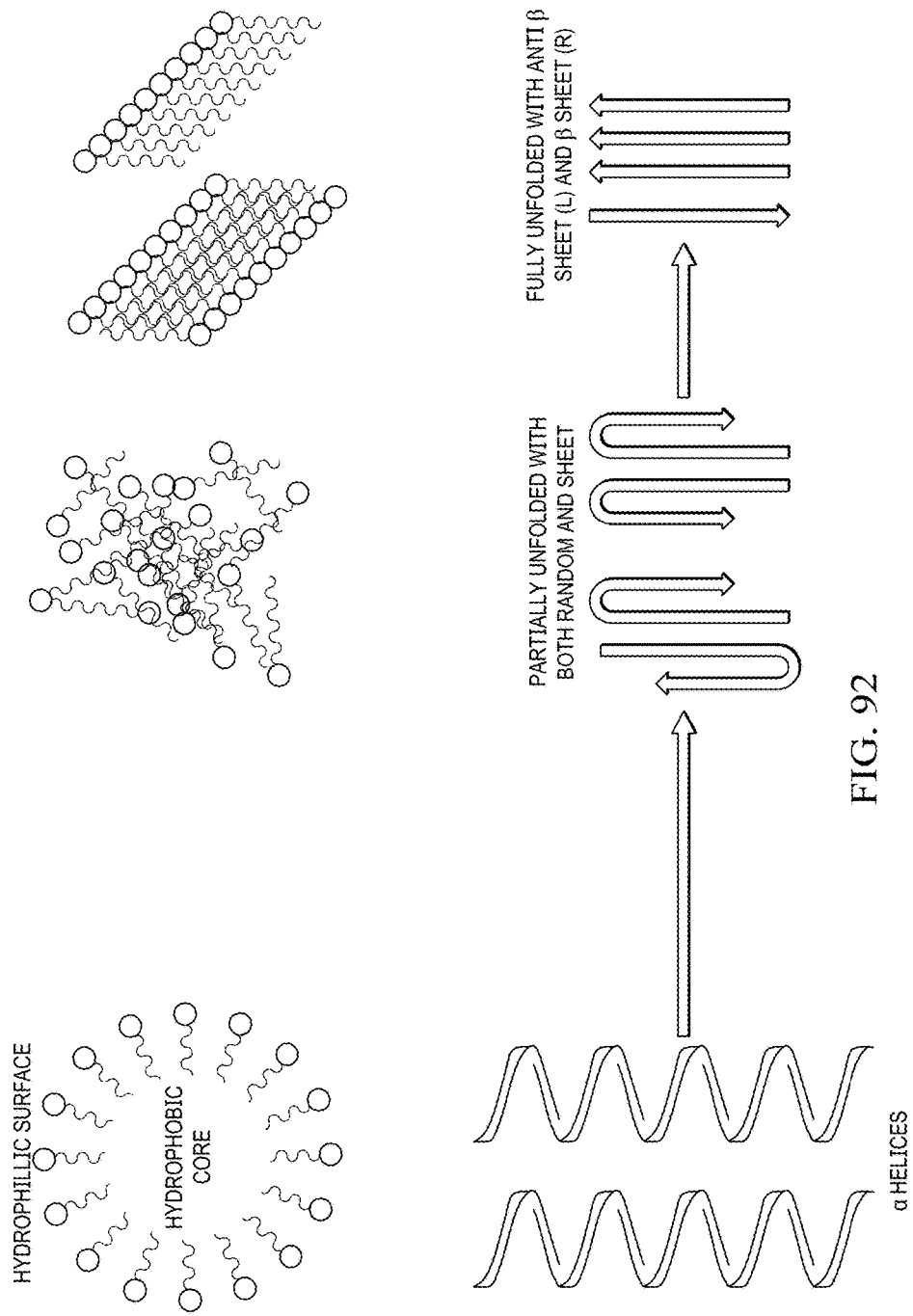
FIG. 92 illustrates the steps involved in the unfolding of a globular protein.

Referring now to FIG. 91, glycated hemoglobin 9102 is formed by non-enzymatic reaction of sugars to sidechains of amino acids usually lysine and Tryptophan 9104. Amadori reaction of lysine and Tryptophan residue form advanced glycation end products (AGEs) in Hb. Emission wavelengths of UV fluorescence of HbA1 are due to Tryptophan 9104 being altered either by Amadori reaction or due to Hb structural changes. Glycation causes loss of globular structure of Hb due to unfolding of its a Helical segments as shown in FIG. 92.

Glycated proteins have a number of differences with respect to the optical properties of the proteins when compared to normal proteins. The florescence Stokes $\Delta\lambda$. (excitation-emission) differences of the native florophores like tryptophan are different between glycated proteins and normal proteins and may be used for comparison to detect glycation levels of hemoglobin. There are also changes in the florescence lifetimes of native florophores between glycated protein and normal protein that may be used for comparing the normal and glycated protein to detect the glycated protein levels. Another difference are the changes in Raman vibrational modes of Amide 1 and 3 bands related to protein structure of glycated proteins and normal proteins. Changes in the Raman vibrational modes of the Amide 1 and Amide 3 bands may be used to detect protein structure of normal and glycated protein. Further difference between glycated proteins and normal proteins are changes in Raman vibrational modes of amino acid residues due to altered molecular orientation and symmetry of the bond vibrations and chemistry. These differences may be used to detect glycation levels within hemoglobin.

Figure 93:
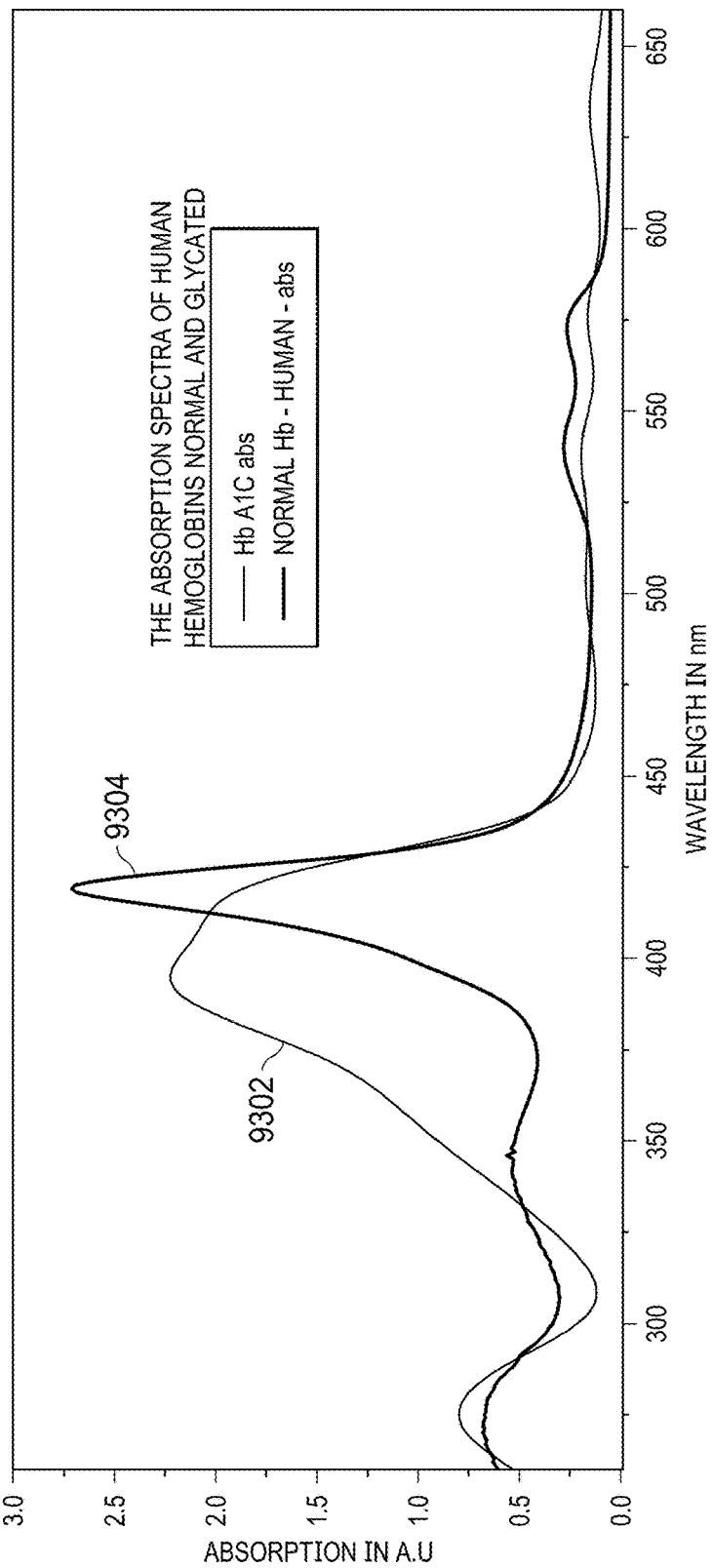
FIG. 93 illustrates a comparison of results between glycated hemoglobin and normal hemoglobin with respect to absorption data.
Figure 94:
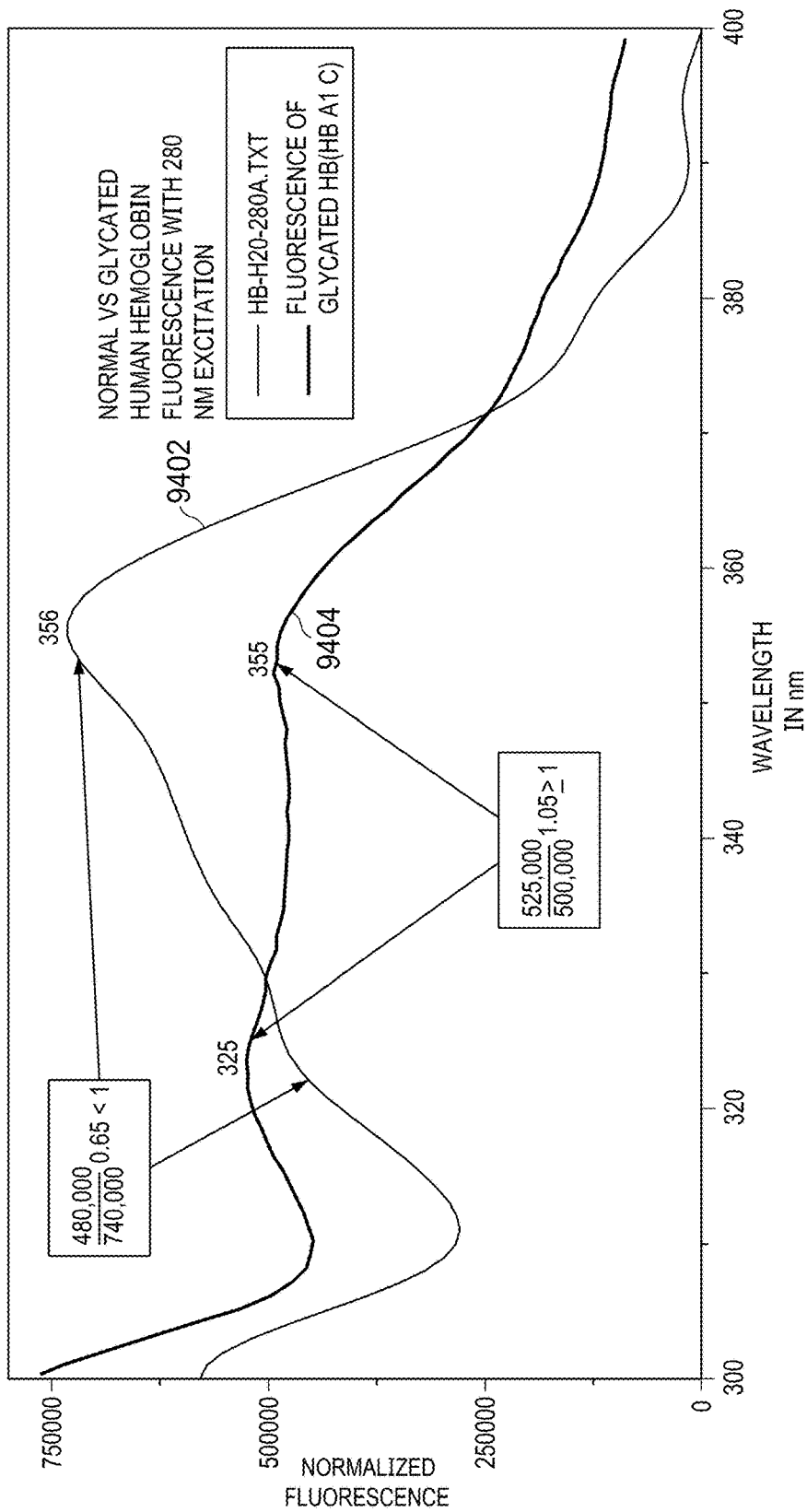
FIG. 94 illustrates a comparison of results between glycated hemoglobin and normal hemoglobin with respect to fluorescence emission data.
Figure 95:
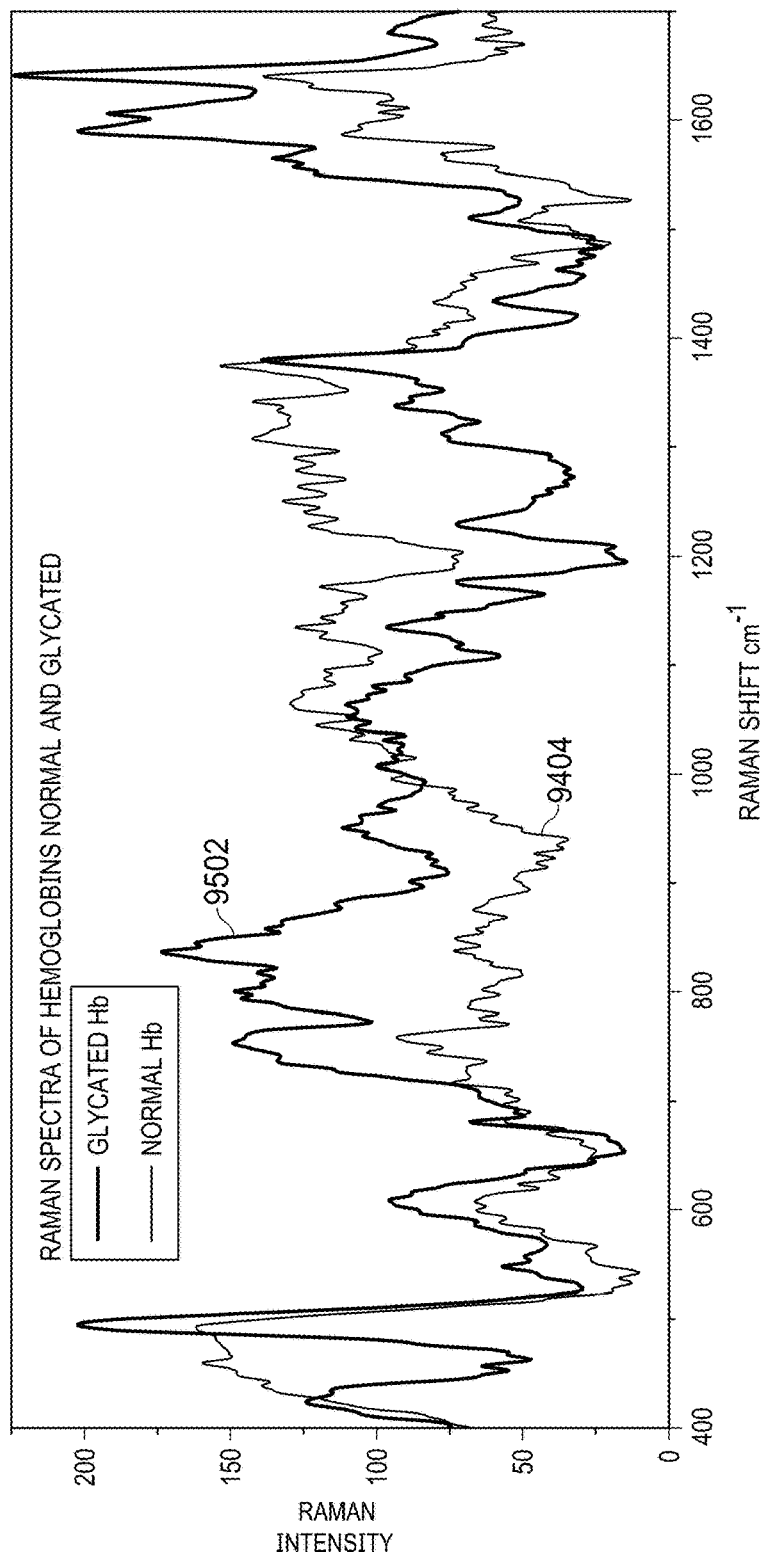
FIG. 95 illustrates a comparison of results between glycated hemoglobin and normal hemoglobin with respect to Raman data.

Referring now to FIGS. 93-95, there are illustrated comparisons of results between glycated hemoglobin and normal hemoglobin with respect to the absorption data (FIG. 93), fluorescence emission data (FIG. 94) and Raman data (FIG. 95). The analysis was run using normal and glycated human Hemoglobin. The absorption spectra was measured with a Cary absorption spectroscope. The fluorescence spectra was measured using a FluoroMax spectroscope by excitation at 280 nm. The fluorescence lifetime was measured with streak camera. The Raman spectra was measured using a Oceanoptics MicroRaman 532 nm system. The Absorption, Emission and Raman data were replotted and analyzed using Orginpro7.1 Software.

FIG. 93 illustrates the florescence emission data for normal hemoglobin 9302 and glycated hemoglobin 9304. FIG. 94 illustrates the normalized florescence spectra for normal hemoglobin 9402 and glycated hemoglobin 9404. Finally, FIG. 95 illustrates the Ramen intensity for glycated hemoglobin 9502 and normal hemoglobin 9504. As can be seen from the above illustrations with respect glycated hemoglobin and normal hemoglobin, there are spectral differences between the various optical characteristics of the materials. The fluorescence ratio of glycated hemoglobin is greater than or equal to 1, and the fluorescence ratio of normal hemoglobin is less than 1. The ratios are calculated by dividing the intensities at lower wavelengths to intensities at higher wavelengths. A further unique biomarker may be utilized for glycated hemoglobin and normal hemoglobin, as well as other materials, using correlation matrices as described hereinbelow.

Figure 96:
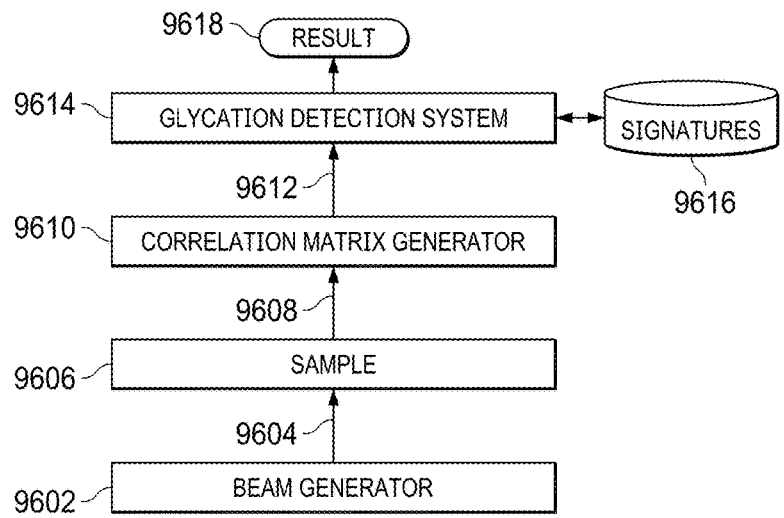
FIG. 96 illustrates a system for generating a unique biomarker for glycated material using correlation matrices.

Referring now to FIG. 96, there is illustrated a system for generating a unique biomarker for glycated material using a pair of correlation matrixes. Glycation causes major changes in physiochemical characteristics of Hemoglobin and these characteristics can be detected using fluorescence intensity matrices of two different wavelengths to use as investigative biomarkers for chronic hyperglycemic conditions. A beam generator 9602 is used for generating an optical beam 9604 having a variety of wavelengths applied thereto for transmission through a sample under test 9606. Upon passing through the sample 9606, a second beam 9608 having unique characteristics applied thereto by interaction with the sample 906 is processed by correlation matrix generation circuitry 9610. The correlation matrix generation circuitry 9610 will be more fully described hereinbelow. The correlation matrix generation circuitry 9610 generates a pair of correlation matrices 9612 that are provided to a glycation detection system 9614. The glycation detection system 9614 utilizes a generated matrix associated with the sample 9606 along with a plurality of stored signatures within a signature database 9616 to provide a more unique determination of glycation levels within the sample 9606. Responsive to the comparison of the matrix 2612 with the variety of signatures within the database 9616, glycation detection system 9614 may provide a result 9618 that indicates the glycation level determined with respect to the sample 9606.

Figure 97:
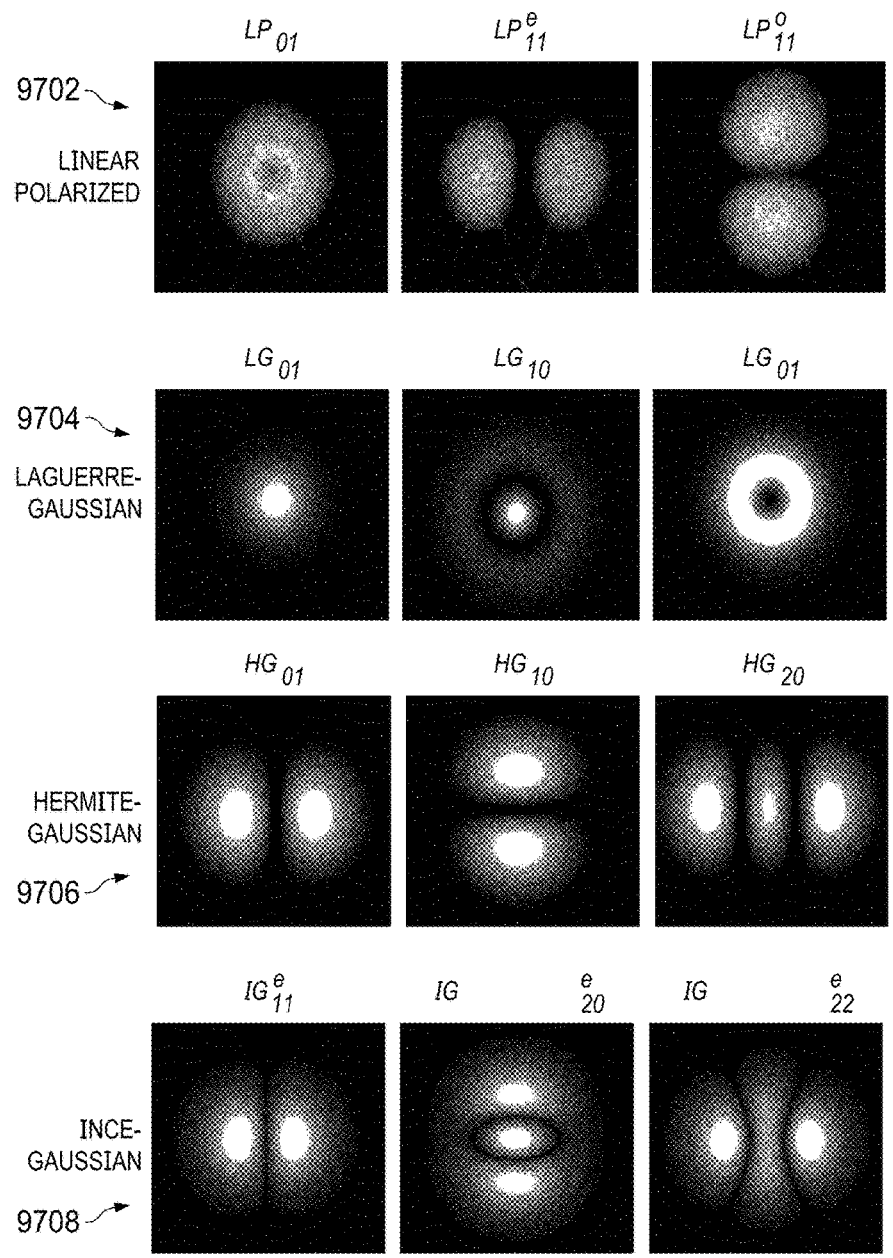
FIG. 97 illustrates intensity diagrams for various beam topologies within fibers.

The general process for the generation of correlation matrices by the correlation matrix generation circuitry 9610 is described more particularly with respect to FIGS. 97-107. Referring now to FIG. 97, there are illustrated intensity diagrams for various different types of beam topologies within fibers. Row 9702 illustrates linearly polarized signals transmitted through a fiber for various modes. Row 9704 illustrates intensity diagrams for Laguerre-Gaussian signals for $LG_{01}$ mode, $LG_{10}$ mode and $LG_{01}$ mode. Row 9706 illustrates the intensity diagrams for Hermite-Gaussian signals for $HG_{01}$ mode, $HG_{10}$ mode and $HG_{20}$ mode. Finally, row 9708 illustrates the intensity diagrams for Ince-Gaussian beams in $IG_{11}$ mode, $IG_{20}$ mode and $IG_{22}$ mode.

Figure 98:
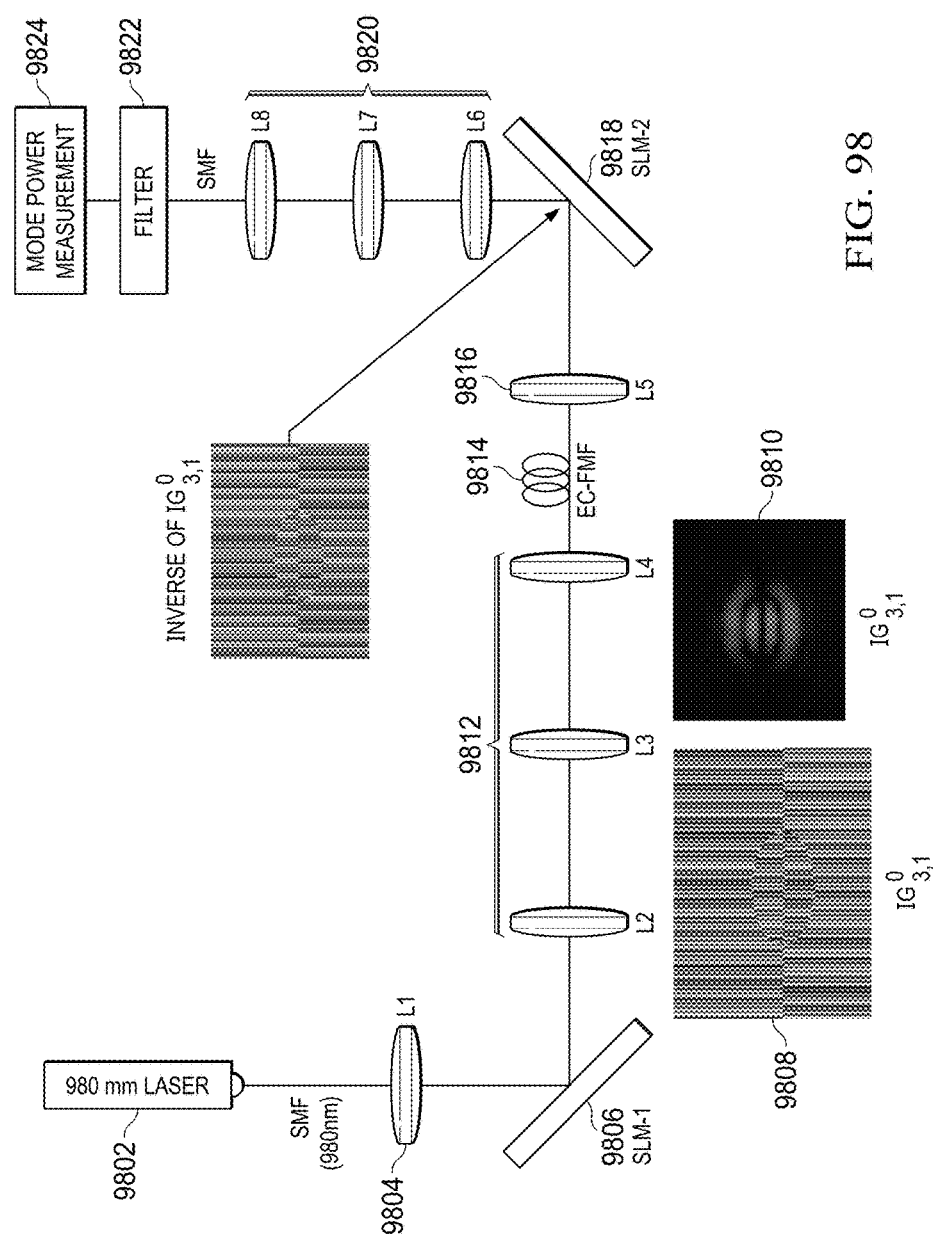
FIG. 98 illustrates a measurement technique for generating a mode crosstalk matrix.

A mode crosstalk matrix provides an illustration of the relative amount of light scattered into adjacent modes that were not launched into a fiber. Referring now to FIG. 98 there is illustrated a measurement technique for generating a mode crosstalk matrix. FIG. 99 is a flow diagram illustrating the steps of the process. A 980 nm laser 9802 generates a laser signal that is transmitted through a first lens 9804 A first spatial light modulator 9806 utilizes a hologram 9808 to generate a first Ince-Gaussian, Hermite-Gaussian, LaGuerre-Gaussian or other type of orthogonal function processed beam of a first mode having a particular intensity diagram 9810. The generated beam from the SLM 9806 passes through a series of lenses 9812 that focuses and launches the generated beam having a particular mode onto an elliptical core few mode fiber 9814 or other fiber at step 9902 (see FIG. 99). While the present embodiment discloses transmitting the signal through an elliptical core few mode fiber, other types of fibers and communications links may also be tested using the described process to populate a mode crosstalk matrix.

After passing through the fiber 9814, the output of the fiber is monitored at step 9904. The output will comprise a superposition of the various output mode components. Within the monitoring process, the output signal passes through a lens 9816 to a second spatial light modulator (SLM) 9818. For every output mode component to be measured, the SLM 9818 will imprint at step 9906 an inverse of the modes face front onto the output beam from the fiber 9814. The output of the SLM 9818 next passes through a further series of lenses 9820 before being input to a spatial filter 9822. The output mode components from the SLM 9818 to be measured will have a planar face front after the imprinting with the inverse of the Ince-Gaussian, Hermite-Gaussian, LaGuerre-Gaussian or other type of orthogonal function processed beam. The spatial filter 9822 passes the plane wave component and blocks other output mode components within the signal from the SLM 9818 at step 9910. The relative amount of power through the spatial filter 9822 is the amount of the output mode component to be measured at step 9912 by the mode power measurement circuitry 9844. By interrogating each of the adjacent mode components, the mode power measurement circuitry 9824 populates the columns of the mode crosstalk matrix for the fiber or communications link under test for a particular row associated with the mode being transmitted.

Initially, the mode output power for a first of the adjacent modes measured at step 9912 is used to populate a first column of the row associated with the row associated with the mode under test. Each of the columns is associated with one of the adjacent mode components of the mode being transmitted. After storage of the power value for the adjacent mode in the mode crosstalk matrix, inquiry step 9914 determines if there are adjacent modes for test. If so, the measurement circuitry 9824 proceeds to the next adjacent mode at step 9916 and measures at step 9912 the output power for the next adjacent mode at step 9912. After population of the matrix row associated with the current mode being transmitted through the fiber or communications link is determined to be complete at inquiry step 9914, inquiry step 9918 determines if a new mode for test exists. If so, a next mode may be launched at step 9920 into the fiber or communications link under test to complete a next row of the crosstalk matrix. The output associated with this mode is monitored at step 9904. The above process is repeated for each mode to be tested.

FIG. 100 illustrates a generated single row of the mode crosstalk matrix. The mode $HG_{11}$ has been launched into the fiber 9814 (or communications link). The power output is measured for various other adjacent modes to the transmitted mode and the values associated with the adjacent modes are stored in the columns within the row. Thus, the selectively measured output for mode $HG_{00}$ is −23.7, for mode $HG_{01}$ is −21.2, for mode $HG_{10}$ is −18.8, for mode $HG_{02}$ is −17.1 and for mode $HG_{20}$ is −20.9.

Figure 101:
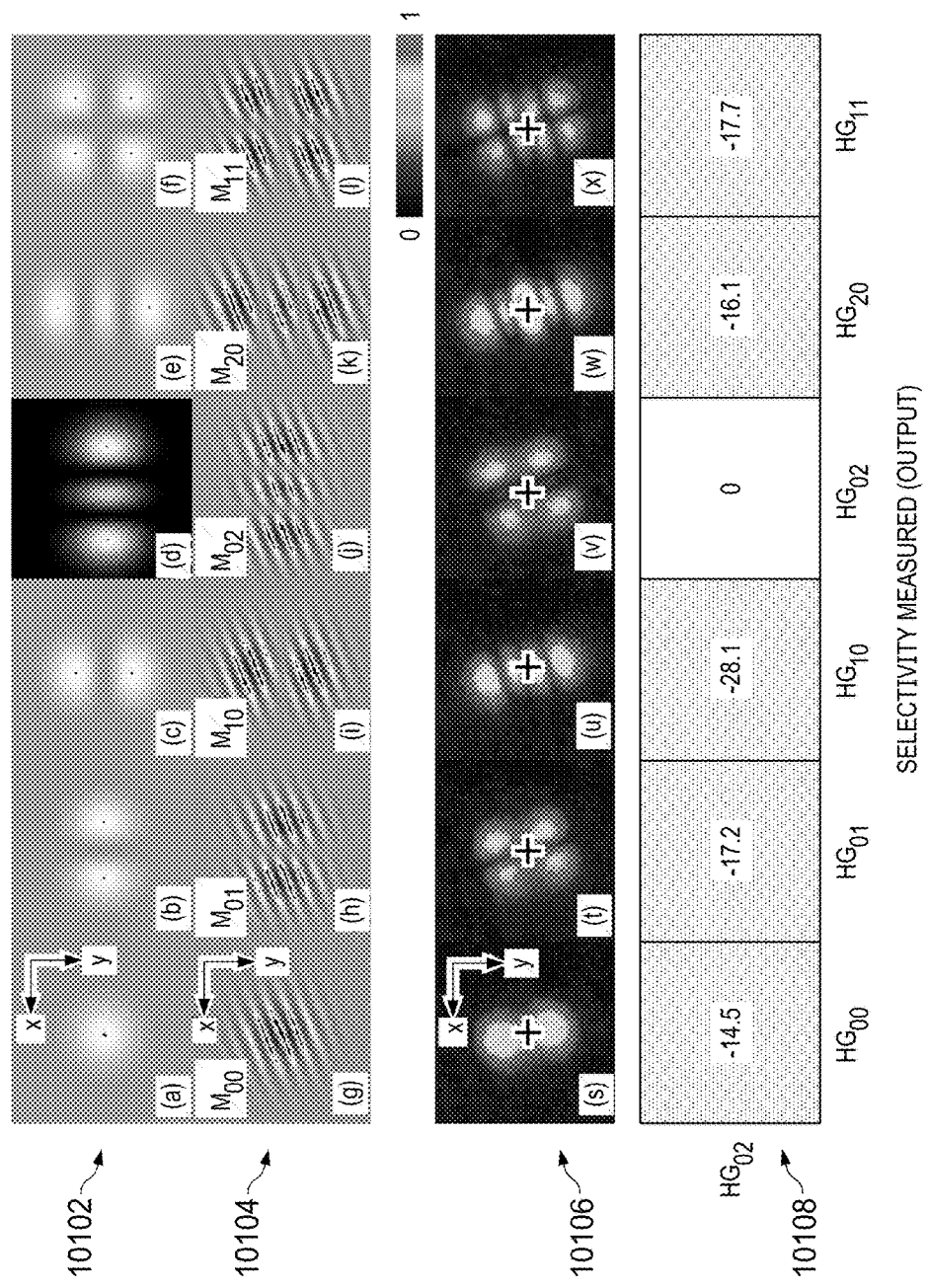
FIG. 101 illustrates the results of a comparison of selected the excited modes from an SLM.

Referring now to FIG. 101, there is illustrated the results for the comparison of each of the selectively excited modes 10102 that are calculated from the first SLM 9806. Each of the modes after passing through the fiber 9814 is measured by set of masks (holograms) 10104 using the second SLM 9818 to yield an associated set of intensity images 10106. For each of the intensity images 10106, the optical power of the light coupled into the fiber is measured using the mode power measurement circuitry 9844. These are represented for the various modes as indicated generally at 10108 from a level of −28.1 dB to −14.5 dB.

Figures 102, 103:
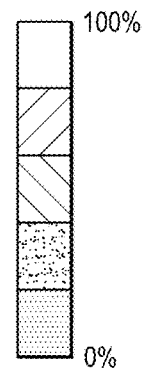
FIG. 102 illustrates a mode crosstalk matrix populated using Hermite-Gaussian modes.
FIG. 103 illustrates a mode crosstalk matrix for Laguerre-Gaussian modes.
Figure 104:
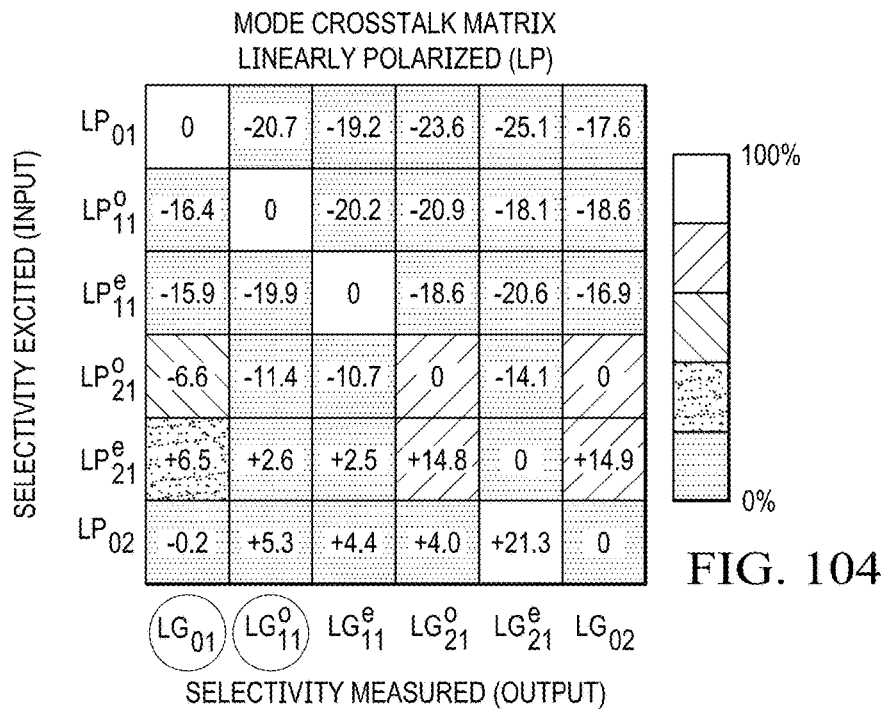
FIG. 104 illustrates a mode crosstalk matrix for linearly polarized modes.
Figure 105:
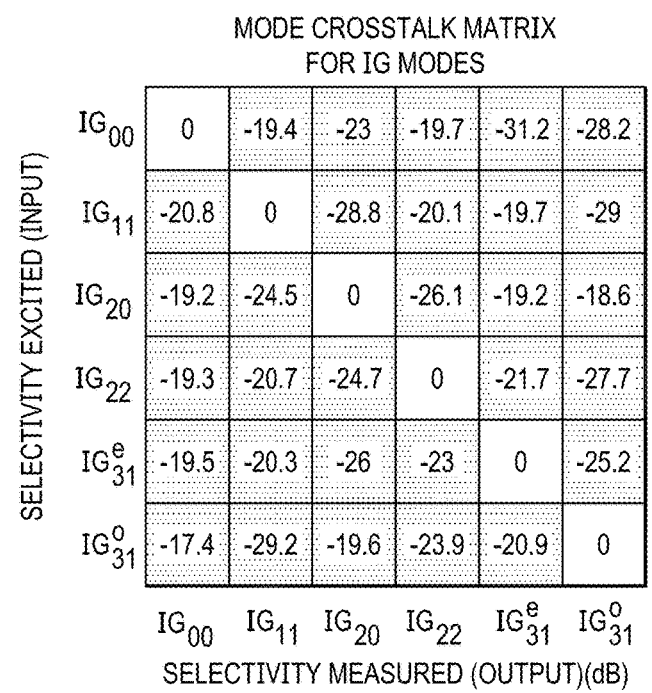
FIG. 105 illustrates a mode crosstalk matrix for Ince-Gaussian modes.

Each of the selectively measured outputs 10108 that are measured may be used to populate a mode crosstalk matrix using Hermite-Gaussian modes as illustrated in FIG. 102. The mode crosstalk matrix 10202 generates the power values for adjacent modes to a transmitted mode for provided input values according to dB→10 $\log_{10} P_{ij}/P_{ii}$ in each row and are measured for each selectively measured output by the spatial light modulator 9818 for a given selectively excited input to the fiber 9814 by the SLM 9806. The rows of the mode crosstalk matrix 10202 comprise the modes selectively excited by the spatial light modulator 9806. The columns of the mode crosstalk matrix 10202 comprise the modes selectively excited by the spatial light modulator 9818. A mode crosstalk matrix for Laguerre-Gaussian modes, linearly polarized modes and Ince-Gaussian modes are illustrated in FIGS. 103, 104 and 105, respectively.

In addition to those various orthogonal function mode techniques discussed hereinabove to which Ince Gaussian functions may be applied in a manner similar to that of Hermite Gaussian, Laguerre Gaussian or other types of orthogonal functions, Ince Gaussian orthogonal modes/functions may be applied in a number of other manners. The mode crosstalk matrix with Hermite-Gaussian, Laguerre-Gaussian and Ince-Gaussian spatial orthogonal modes may also be used with WDM and DWDM to determine a number of modes that can be multiplexed together based upon the determined crosstalk as indicated by the mode crosstalk matrix. These further include the use of Ince Gaussian orthogonal modes in fibers to perform phase estimation and carrier recovery, to perform symbol, estimation and clock recovery, to perform decision directed carrier recovery where decoded signals are compared with the closest constellation points or for dealing with amplifier nonlinearity. Ince Gaussian orthogonal modes within a fiber may also be used for adaptive power control, adaptive variable symbol rate and within adaptive equalization techniques.

Figure 106A:
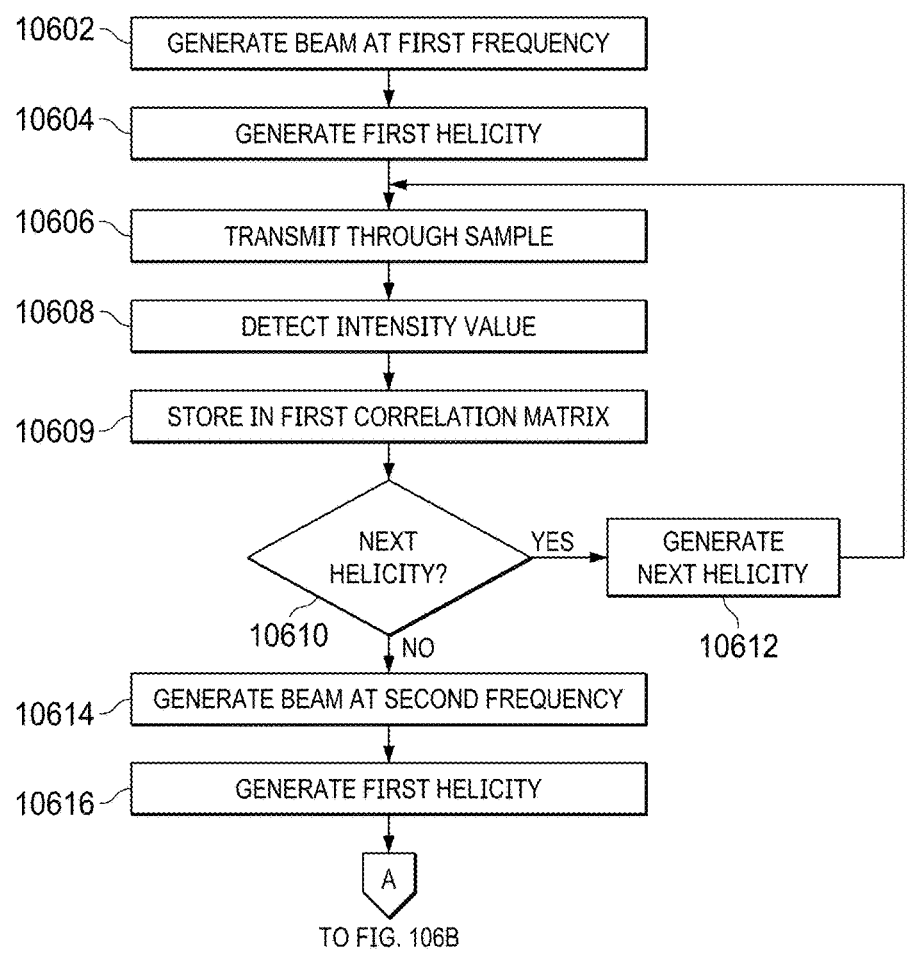
FIGS. 106A-106B illustrate a flow diagram of the process for generating a unique biomarker of a glycation level within hemoglobin.
Figure 106B:
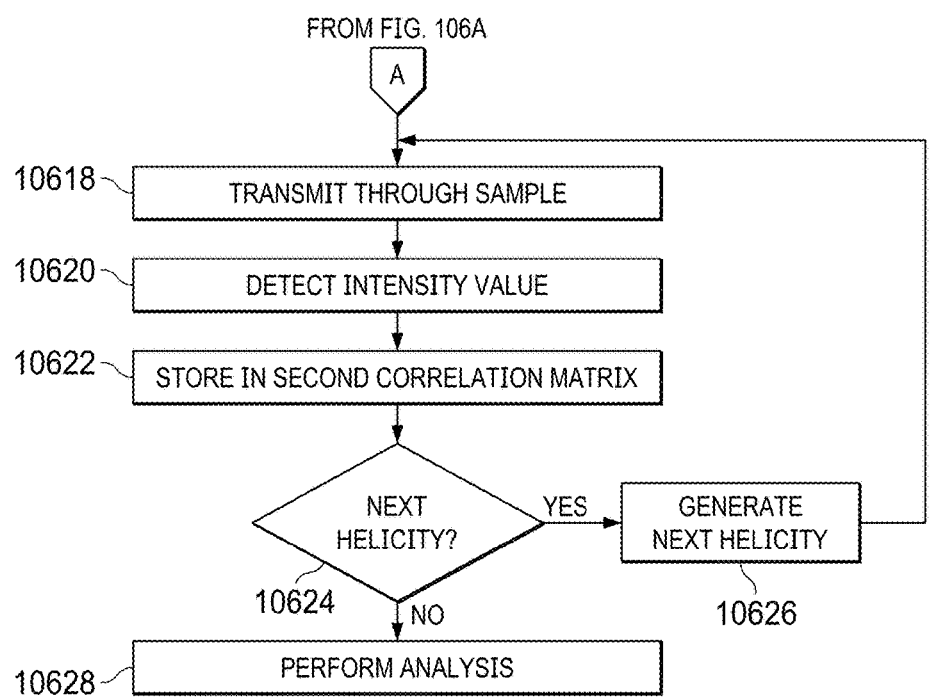

The above describes the process for generating a single correlation matrix. FIGS. 106A-106B are a flow diagram illustrating the process for generating a unique biomarker of a level of glycation within a hemoglobin sample using first and second correlation matrices generated using light beams at first and second wavelengths with the above described techniques. The beam generator 9602 generates at step 10602 a beam at a first wavelength. The beam generator 9602 additionally generates and applies a first helicity to the light beam at step 10604. While the present discussion envisions the application of differing helicity using differing Hermite Gaussian functions to the light beam, it should be realized that other types of orthogonal functions such as Laguerre Gaussian, Ince Gaussian, etc. described hereinabove may also be applied to the light beam at the first wavelength. The generated light beam is transmitted at step 10606 through the sample 9606 in order to generate a sample affected light beam 9608. The intensity of the light beam 9608 from the sample is detected at step 10608 using the correlation matrix generation circuitry 9610. The detected intensity value is stored at step 10609 by the correlation matrix generation circuitry 9610 at an entry in a first correlation matrix as described above. Inquiry step 10610 determines if a further helicity exist to be applied to the light beam in order to fill another entry within the correlation matrix. If further helicity values exist, control passes to step 10612 to generate a next helicity which is applied to the light beam and transmitted through the sample at step 10606.

If inquiry step 10610 determines that there are no further helicity values to apply to the light beam for population of another row within the correlation matrix, control passes to step 10614 wherein a next light beam is generated at a second wavelength. The first helicity is generated again at step 10616 and applied to the light beam at the second wavelength. The newly generated light beam is transmitted through the sample at step 10618. The sample affected beam is processed to detect intensity value of the beam at step 10620, and the detected intensity value is stored within a second correlation matrix associated with the second wavelength at step 10622. Inquiry step 10624 determines if additional helicity values exist to be applied to the light beam at the second wavelength and if so, the light beam having the next helicity applied thereto is generated at step 10626 and control passes back to step 106182 transmit the beam through the sample. If inquiry step 10624 determines there are no further helicity values available and the correlation matrix has been fully populated for the light beam at the second frequency, control passes to step 10628 to perform an analysis based upon the two generated correlation matrices as will be more fully described with respect to FIG. 107.

Figure 107:
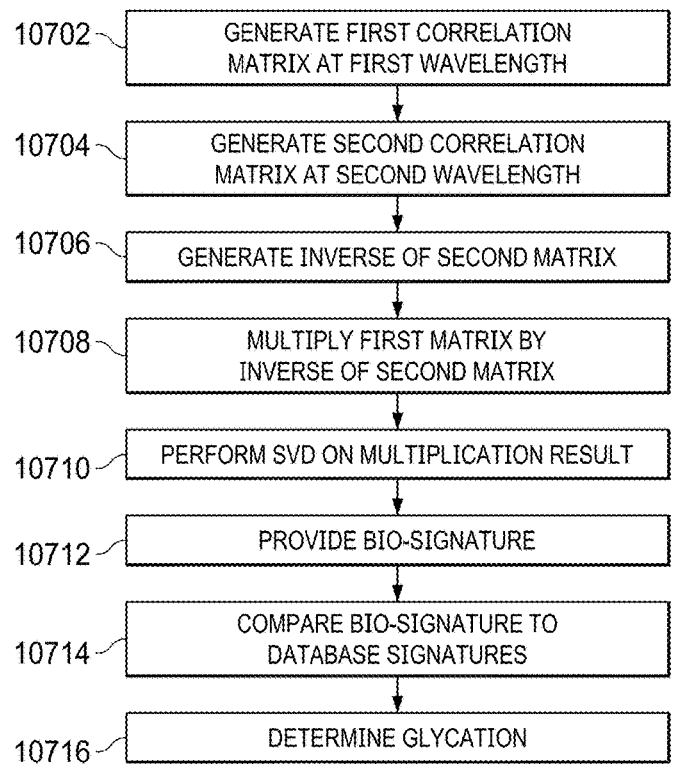
FIG. 107 illustrates a flow diagram describing the process for utilizing first and second correlation matrices to determine a glycation level within hemoglobin.

FIG. 107 illustrates a flow diagram describing the process for utilizing the first and second correlation matrices generated with respect to FIGS. 106A-106B for creating a unique biomarker signature for the hemoglobin sample being tested. Initially at steps 10702 and 10704, the first and second correlation matrices are generated at first and second wavelengths as has been previously described with respect to FIGS. 106A-106B. Referring now to FIGS. 108 and 109 there are illustrated first and second correlation matrices that have been generated at two different wavelengths. FIG. 108 illustrates the correlation matrix $A_{325}$. This correlation matrix comprises an intensity matrix of the glycated sample at a 325 nm wavelength. FIG. 109 illustrates the correlation matrix $B_{355}$. This correlation matrix comprises an intensity matrix of the glycated sample at a 355 nm wavelength. The alpha values $\alpha_n$ (intensity values) that are not along the diagonal are crosstalk from other Laguerre Gaussian modes and these values are much smaller than those located on the diagonal.

Once each of the first and second correlation matrices have been created, the inverse of the second matrix is generated at step 10706. The first correlation matrix is multiplied by the inverse of the second correlation matrix at step 10710 in accordance with the equation:

$$C=AB^{-1}$$

The generated matrix C is subjected to a singular value decomposition (SVD) that yields:

$$C=UDV$$

where D is the signature of the molecule under test.

This yields the signature matrix D as shown in FIG. 110. The signature matrix D includes a diagonal having various $\sigma_n$ on the diagonal entries of the matrix and zero values within each of the other entries. The diagonal of the matrix D is the signature of the molecule under test and is produced using singular value decomposition on matrix C.

The above described SVD provides the bio-signature generated by the sample at step 10712 as described above. The generated bio-signature is compared to the database 9616 of bio signatures at step 10714 and based upon the comparison a determination of the glycation level is made at step 10716. Each of the signatures in the database 9616 is associated with a particular glycation level of hemoglobin.

It will be appreciated by those skilled in the art having the benefit of this disclosure that the system and method for spectroscopy with correlation matrices, ratio and glycation provides an improved process for detecting glycation levels in hemoglobin. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A method for detecting glycation levels within hemoglobin, comprising:
    generating a first correlation matrix using a first light beam at a first wavelength passing through a hemoglobin sample;
    generating a second correlation matrix using a second light beam at a second wavelength passing through the hemoglobin sample;
    multiplying the first correlation matrix by an inverse of the second correlation matrix to obtain a third matrix;
    generating a fourth matrix by taking a singular value decomposition of the third matrix, wherein the fourth matrix comprises a unique biomarker for a level of glycation within the hemoglobin sample;
    determining the level of glycation within the hemoglobin sample responsive to the fourth matrix; and
    outputting an indicator identifying the determined level of glycation.

2. The method of claim 1, wherein the step of determining the level of glycation further comprises:
    comparing the fourth matrix to a plurality of matrices stored within a database, each of the plurality of matrices associated with a particular level of glycation within hemoglobin;
    determining a stored matrix of the plurality of matrices that matches the fourth matrix; and
    identifying the level of glycation within the hemoglobin sample based upon the level of glycation associated with the determined stored matrix that matches the fourth matrix.

3. The method of claim 1, wherein the step of generating the first correlation matrix further comprise the steps of:
    generating the first light beam at the first wavelength;
    applying each of a plurality of different orthogonal functions to the first light beam;
    shining the first light beam through the hemoglobin sample as each of the plurality of different orthogonal functions is applied thereto to generate a third light beam exiting the hemoglobin sample;
    measuring an intensity value of the third light beam exiting the hemoglobin sample for each of the plurality of different orthogonal functions; and
    storing the measured intensity values of the third light beam for each of the different orthogonal functions within the first correlation matrix.

4. The method of claim 3, wherein the step of generating the second correlation matrix further comprise the steps of:
    generating the second light beam at the second wavelength;
    applying each of the plurality of different orthogonal functions to the second light beam;
    shining the second light beam through the hemoglobin sample as each of the plurality of different orthogonal functions is applied thereto to generate a fourth light beam exiting the hemoglobin sample;
    measuring an intensity value of the fourth light beam exiting the hemoglobin sample for each of the plurality of different orthogonal functions; and
    storing the measured intensity values of the fourth light beam for each of the different orthogonal functions within the second correlation matrix.

5. The method of claim 4, wherein the plurality of different orthogonal functions comprise a plurality of different Hermite-Gaussian functions for applying a different helicity to the first and the second light beams.

6. The method of claim 1, wherein the step of multiplying further comprises the step of inverting the second correlation matrix to create the inverse of the second correlation matrix.

7. The method of claim 1, wherein the unique biomarker comprises at least one of fluorescence lifetimes of native fluorophores, Raman vibrational modes of Amide 1 and 3 bands; florescence Stokes $\Delta\lambda$ (excitation-emission) differences and Raman vibrational modes of amino acids residues.

8. A system for detecting glycation levels within hemoglobin, comprising:
    a database containing a plurality of matrices, each of the plurality of matrices associated with a particular level of glycation within hemoglobin;
    a processor;
    a memory coupled to the processor, the memory storing a plurality of instructions for execution by the processor, the plurality of instructions including:
        instructions for generating a first correlation matrix using a first light beam at a first wavelength passing through a hemoglobin sample;

instructions for generating a second correlation matrix using a second light beam at a second wavelength passing through the hemoglobin sample;

instructions for multiplying the first correlation matrix by an inverse of the second correlation matrix to obtain a third matrix;

instructions for generating a fourth matrix by taking a singular value decomposition of the third matrix, wherein the fourth matrix comprises a unique biomarker for a level of glycation within the hemoglobin sample;

instructions for determining the level of glycation within the hemoglobin sample responsive to the fourth matrix; and instructions for outputting an indicator identifying the determined level of glycation.

9. The system of claim 8, wherein the instructions for determining the level of glycation further include:

instructions for comparing the fourth matrix to a plurality of matrices stored within a database, each of the plurality of matrices associated with a particular level of glycation within hemoglobin;

instructions for determining a stored matrix of the plurality of matrices that matches the fourth matrix; and instructions for identifying the level of glycation within the hemoglobin sample based upon the level of glycation associated with the determined stored matrix that matches the fourth matrix.

10. The system of claim 8, wherein the instructions for generating the first correlation matrix further include:

instructions for generating the first light beam at the first wavelength;

instructions for applying each of a plurality of different orthogonal functions to the first light beam;

instructions for shining the first light beam through the hemoglobin sample as each of the plurality of different orthogonal functions is applied thereto to generate a third light beam exiting the hemoglobin sample;

instructions for measuring an intensity value of the third light beam exiting the hemoglobin sample for each of the plurality of different orthogonal functions; and instructions for storing the measured intensity values of the third light beam for each of the different orthogonal functions within the first correlation matrix.

11. The system of claim 10, wherein the instructions for generating the second correlation matrix further include:

instructions for generating the second light beam at the second wavelength;

instructions for applying each of the plurality of different orthogonal functions to the second light beam;

instructions for shining the second light beam through the hemoglobin sample as each of the plurality of different orthogonal functions is applied thereto to generate a fourth light beam exiting the hemoglobin sample;

instructions for measuring an intensity value of the fourth light beam exiting the hemoglobin sample for each of the plurality of different orthogonal functions; and instructions for storing the measured intensity values of the fourth light beam for each of the plurality of different orthogonal functions within the second correlation matrix.

12. The system of claim 11, wherein the plurality of different orthogonal functions comprise a plurality of different Hermite-Gaussian functions for applying a different helicity to the first and the second light beams.

13. The system of claim 8, wherein the instructions for multiplying further comprise instructions for inverting the second correlation matrix to create the inverse of the second correlation matrix.

14. The system of claim 8, wherein the unique biomarker comprises at least one of fluorescence lifetimes of native fluorophores, Raman vibrational modes of Amide 1 and 3 bands; florescence Stokes $\Delta\lambda$ (excitation-emission) differences and Raman vibrational modes of amino acids residues.

15. A system for detecting glycation levels within hemoglobin, comprising:

a database containing a plurality of matrices, each of the plurality of matrices associated with a particular level of glycation within hemoglobin;

a beam generator for generating a light beam at a first wavelength and a second wavelength having one of a plurality of orthogonal functions applied thereto and directing the light beam through a hemoglobin sample;

a correlation matrix generator for generating a first correlation matrix using a first light beam from the beam generator at the first wavelength passing through the hemoglobin sample and for generating a second correlation matrix using a second light beam at the second wavelength passing through the hemoglobin sample; and a glycation detection system for multiplying the first correlation matrix by an inverse of the second correlation matrix to obtain a third matrix, for generating a fourth matrix by taking a singular value decomposition of the third matrix, wherein the fourth matrix comprises a unique biomarker for a level of glycation within the hemoglobin sample, for determining the level of glycation within the hemoglobin sample responsive to the fourth matrix and the plurality of matrices within the database and for outputting an indicator identifying the determined level of glycation of the hemoglobin sample.

16. The system of claim 15, wherein the glycation detection system further compares the fourth matrix to the plurality of matrices stored within the database, determines a stored matrix of the plurality of matrices that matches the fourth matrix and identifies the level of glycation within the hemoglobin sample based upon the level of glycation associated with the determined stored matrix that matches the fourth matrix.

17. The system of claim 15, wherein the correlation matrix generator further generates the first light beam at the first wavelength, applies each of a plurality of different orthogonal functions to the first light beam and shines the first light beam through the hemoglobin sample as each of the plurality of different orthogonal functions is applied thereto to generate a third light beam exiting the hemoglobin sample, further wherein the correlation matrix generator measures an intensity value of the third light beam exiting the hemoglobin sample for each of the plurality of different orthogonal functions and stores the measured intensity values of the third light beam for each of the different orthogonal functions within the first correlation matrix.

18. The system of claim 17, wherein the correlation matrix generator further generates the second light beam at the second wavelength, applies each of the plurality of different orthogonal functions to the second light beam and shines the second light beam through the hemoglobin sample as each of the plurality of different orthogonal functions is applied thereto to generate a fourth light beam exiting the hemoglobin sample, further wherein the correlation matrix generator generates an intensity value of the fourth light beam exiting the hemoglobin sample for each of the plurality of different orthogonal functions and stores the measured intensity values of the fourth light beam for each of the different orthogonal functions within the second correlation matrix.

19. The system of claim 18, wherein the plurality of different orthogonal functions comprise a plurality of different Hermite-Gaussian functions for applying a different helicity to the first and the second light beams.

20. The system of claim 15, wherein the correlation matrix generator further inverts the second correlation matrix to create the inverse of the second correlation matrix.

21. The system of claim 15, wherein the unique biomarker comprises at least one of fluorescence lifetimes of native fluorophores, Raman vibrational modes of Amide 1 and 3 bands; florescence Stokes Δλ (excitation-emission) differences and Raman vibrational modes of amino acids residues.

22. A method for detecting glycation levels within hemoglobin, comprising:
   generating a first correlation matrix using a first light beam at a first wavelength passing through a hemoglobin sample;
   generating a second correlation matrix using a second light beam at a second wavelength passing through the hemoglobin sample;
   multiplying the first correlation matrix by an inverse of the second correlation matrix to obtain a third matrix;
   generating a fourth matrix by taking a singular value decomposition of the third matrix, wherein the fourth matrix comprises a unique biomarker for a level of glycation within the hemoglobin sample;
   comparing the fourth matrix to a plurality of matrices stored within a database, each of the plurality of matrices associated with a particular level of glycation within hemoglobin;
   determining a stored matrix of the plurality of matrices that matches the fourth matrix;
   identifying the level of glycation within the hemoglobin sample based upon the level of glycation associated with the determined stored matrix that matches the fourth matrix; and
   outputting an indicator identifying the level of glycation.

23. The method of claim 22, wherein the step of generating the first correlation matrix further comprise the steps of:
   generating the first light beam at the first wavelength;
   applying each of a plurality of different orthogonal functions to the first light beam;
   shining the first light beam through the hemoglobin sample as each of the plurality of different orthogonal functions is applied thereto to generate a third light beam exiting the hemoglobin sample;
   measuring an intensity value of the third light beam exiting the hemoglobin sample for each of the plurality of different orthogonal functions; and
   storing the measured intensity values of the third light beam for each of the different orthogonal functions within the first correlation matrix;
   wherein the step of generating the second correlation matrix further comprise the steps of:
   generating the second light beam at the second wavelength;
   applying each of the plurality of different orthogonal functions to the second light beam; and
   shining the second light beam through the hemoglobin sample as each of the plurality of different orthogonal functions is applied thereto to generate a fourth light beam exiting the hemoglobin sample.

* * * * *